(12) United States Patent
Williams et al.

(10) Patent No.: US 11,041,866 B2
(45) Date of Patent: Jun. 22, 2021

(54) PANCREATIC CANCER BIOMARKERS AND USES THEREOF

(71) Applicant: SomaLogic, Inc., Boulder, CO (US)

(72) Inventors: Stephen Alaric Williams, Boulder, CO (US); Michael Riel-Mehan, Louisville, CO (US); Rachel M. Ostroff, Westminster, CO (US)

(73) Assignee: SomaLogic, Inc., Boulder, CO (US)

( * ) Notice: Subject to any disclaimer, the term of this patent is extended or adjusted under 35 U.S.C. 154(b) by 113 days.

(21) Appl. No.: 15/679,643

(22) Filed: Aug. 17, 2017

(65) Prior Publication Data

US 2018/0045739 A1 Feb. 15, 2018

Related U.S. Application Data

(63) Continuation of application No. 14/020,334, filed on Sep. 6, 2013, now abandoned, which is a continuation of application No. 13/208,903, filed on Aug. 12, 2011, now abandoned.

(60) Provisional application No. 61/482,480, filed on May 4, 2011, provisional application No. 61/482,347, filed on May 4, 2011, provisional application No. 61/418,689, filed on Dec. 1, 2010, provisional application No. 61/373,687, filed on Aug. 13, 2010.

(51) Int. Cl.
| | | |
|---|---|---|
| *G01N 33/53* | (2006.01) | |
| *G01N 33/68* | (2006.01) | |
| *G01N 33/574* | (2006.01) | |
| *G16B 20/00* | (2019.01) | |

(52) U.S. Cl.
CPC ... *G01N 33/6893* (2013.01); *G01N 33/57438* (2013.01); *G16B 20/00* (2019.02)

(58) Field of Classification Search
CPC ......... G01N 33/6893; G01N 33/57438; G16B 20/00; G06F 19/00; G06F 19/18; G06F 19/30
See application file for complete search history.

(56) References Cited

U.S. PATENT DOCUMENTS

| | | | |
|---|---|---|---|
| 5,660,985 A | 8/1997 | Pieken et al. | |
| 6,004,267 A | 12/1999 | Tewari et al. | |
| 6,335,170 B1 | 1/2002 | Orntoft et al. | |
| 6,631,330 B1 | 10/2003 | Poynard | |
| 7,081,340 B2 | 7/2006 | Baker et al. | |
| 7,090,983 B1 | 8/2006 | Muramatsu et al. | |
| 7,189,507 B2 | 3/2007 | Mack et al. | |
| 7,521,195 B1 | 4/2009 | Joseloff et al. | |
| 7,526,387 B2 | 4/2009 | Baker et al. | |
| 7,569,345 B2 | 8/2009 | Cobleigh et al. | |
| 7,582,441 B1 | 9/2009 | Ruben et al. | |
| 7,622,251 B2 | 11/2009 | Baker et al. | |
| 7,695,913 B2 | 4/2010 | Cowens et al. | |
| 7,723,033 B2 | 5/2010 | Baker et al. | |
| 7,767,391 B2 | 8/2010 | Scott et al. | |
| 7,807,392 B1 | 10/2010 | Domon | |
| 7,838,224 B2 | 11/2010 | Baker et al. | |
| 7,858,304 B2 | 12/2010 | Baker et al. | |
| 7,862,995 B2 | 1/2011 | Bacus et al. | |
| 7,871,769 B2 | 1/2011 | Baker et al. | |
| 7,888,019 B2 | 2/2011 | Kiefer et al. | |
| 7,892,760 B2 | 2/2011 | Birse et al. | |
| 7,930,104 B2 | 4/2011 | Baker et al. | |
| 7,939,261 B2 | 5/2011 | Baker et al. | |
| 7,947,447 B2 | 5/2011 | Zichi et al. | |
| 8,008,003 B2 | 8/2011 | Baker et al. | |

(Continued)

FOREIGN PATENT DOCUMENTS

| | | |
|---|---|---|
| CA | 2648382 | 4/2008 |
| CN | 101283106 A | 10/2008 |

(Continued)

OTHER PUBLICATIONS

Ostroff et al. Journal of Proteomics, 2010, vol. 73, pp. 649-666.*
ADAPT website by the Patterson Institute for Cancer Research, probesets for MMP7, printed May 22, 2013.
ADAPT website, The Paterson Institute for Cancer Research, probesets for VEGF, printed Jan. 29, 2014.
Amonkar et al. (2009) PLoS. One, 4(2):e4599, "Development and preliminary evaluation of a multivariate index assay for ovarian cancer".
Aspinall-O'Dea et al. (2007) Proteomics Clin. Appl. 1:1066-1079 "The pancreatic cancer proteome—recent advances and future promise".

(Continued)

*Primary Examiner* — David C Thomas
(74) *Attorney, Agent, or Firm* — Leydig, Voit & Mayer, Ltd.

(57) ABSTRACT

The present disclosure includes biomarkers, methods, devices, reagents, systems, and kits for the detection and diagnosis of cancer generally and pancreatic cancer specifically. In one aspect, the disclosure provides biomarkers that can be used alone or in various combinations to diagnose cancer generally or pancreatic cancer specifically. In another aspect, methods are provided for diagnosing pancreatic cancer in an individual, where the methods include detecting, in a biological sample from an individual, at least one biomarker value corresponding to at least one biomarker selected from the group of biomarkers provided in Table 1, wherein the individual is classified as having pancreatic cancer, or the likelihood of the individual having pancreatic cancer is determined, based on the at least one biomarker value. In a further aspect, methods are provided for diagnosing cancer generally in an individual, where the methods include detecting, in a biological sample from an individual, at least one biomarker value corresponding to at least one biomarker selected from the group of biomarkers provided in Table 19, wherein the individual is classified as having cancer generally, or the likelihood of the individual having cancer is determined, based on the at least one biomarker value.

8 Claims, 16 Drawing Sheets

(56) References Cited

U.S. PATENT DOCUMENTS

| | | | |
|---|---|---|---|
| 8,014,957 | B2 | 9/2011 | Radich et al. |
| 8,019,552 | B2 | 9/2011 | Dai et al. |
| 8,026,060 | B2 | 9/2011 | Watson et al. |
| 8,029,995 | B2 | 10/2011 | Watson et al. |
| 8,034,565 | B2 | 10/2011 | Cobleigh et al. |
| 8,067,178 | B2 | 11/2011 | Baker et al. |
| 8,071,286 | B2 | 12/2011 | Baker et al. |
| 8,450,069 | B2 | 5/2013 | Goix et al. |
| 8,632,983 | B2 | 1/2014 | Haab et al. |
| 10,024,857 | B2* | 7/2018 | Pastural .......... G01N 33/57438 |
| 2003/0134343 | A1 | 7/2003 | Batra et al. |
| 2003/0144476 | A1 | 7/2003 | Agarwal et al. |
| 2003/0215895 | A1 | 11/2003 | Wennerberg et al. |
| 2004/0009489 | A1 | 1/2004 | Golub et al. |
| 2004/0219572 | A1 | 11/2004 | Chen et al. |
| 2004/0241653 | A1 | 12/2004 | Feinstein et al. |
| 2005/0069963 | A1 | 3/2005 | Loskin et al. |
| 2005/0095611 | A1 | 5/2005 | Chan et al. |
| 2005/0181375 | A1 | 8/2005 | Aziz et al. |
| 2005/0214826 | A1 | 9/2005 | Mor et al. |
| 2005/0260639 | A1 | 11/2005 | Nakamura et al. |
| 2005/0260697 | A1 | 11/2005 | Wang et al. |
| 2006/0019256 | A1 | 1/2006 | Clarke et al. |
| 2006/0223127 | A1 | 10/2006 | Yip et al. |
| 2007/0099209 | A1 | 5/2007 | Clarke et al. |
| 2007/0105142 | A1 | 5/2007 | Wilhelm et al. |
| 2007/0178108 | A1 | 8/2007 | Dillion et al. |
| 2007/0178504 | A1 | 8/2007 | Colpitts et al. |
| 2007/0212721 | A1 | 9/2007 | Fischer et al. |
| 2007/0275422 | A1 | 11/2007 | Lowe et al. |
| 2008/0057590 | A1 | 3/2008 | Urdea et al. |
| 2008/0090258 | A1 | 4/2008 | Lokshin |
| 2008/0171319 | A1 | 7/2008 | Urdea et al. |
| 2008/0274481 | A1 | 11/2008 | Fung et al. |
| 2008/0305962 | A1 | 12/2008 | Wirtz et al. |
| 2009/0005268 | A1 | 1/2009 | Berlin |
| 2009/0023149 | A1 | 1/2009 | Knudsen et al. |
| 2009/0042229 | A1 | 2/2009 | Folkman et al. |
| 2009/0053189 | A1 | 2/2009 | Glimcher et al. |
| 2009/0068690 | A1 | 3/2009 | Fisher et al. |
| 2009/0104617 | A1 | 4/2009 | Gordon et al. |
| 2009/0176228 | A1 | 7/2009 | Birse et al. |
| 2009/0197285 | A1 | 8/2009 | Hirschowitz et al. |
| 2009/0233286 | A1 | 9/2009 | Segara et al. |
| 2010/0009386 | A1 | 1/2010 | Streeper et al. |
| 2010/0070191 | A1 | 3/2010 | Gold et al. |
| 2010/0086948 | A1 | 4/2010 | Gold et al. |
| 2010/0130527 | A1 | 5/2010 | Lehrer et al. |
| 2010/0131432 | A1 | 5/2010 | Kennedy et al. |
| 2010/0184034 | A1 | 7/2010 | Bankaitis-Davis et al. |
| 2010/0221752 | A2 | 9/2010 | Gold et al. |
| 2010/0267041 | A1 | 10/2010 | Shuber et al. |
| 2010/0279419 | A1 | 11/2010 | Streckfus et al. |
| 2011/0003707 | A1 | 1/2011 | Goix et al. |
| 2011/0015865 | A1 | 1/2011 | Rosenberg et al. |
| 2011/0059103 | A1 | 1/2011 | Briessen et al. |
| 2011/0144914 | A1 | 6/2011 | Harrington et al. |
| 2011/0150080 | A1* | 6/2011 | Watanabe .......... H04N 19/117 375/240.03 |
| 2011/0171633 | A1 | 7/2011 | Cowens et al. |
| 2011/0236903 | A1 | 9/2011 | McClelland et al. |
| 2012/0077695 | A1 | 3/2012 | Ostroff et al. |
| 2012/0101002 | A1 | 4/2012 | Riel-Mehan et al. |
| 2012/0143805 | A1 | 6/2012 | Gold et al. |
| 2012/0165217 | A1 | 6/2012 | Gold et al. |
| 2012/0178111 | A1 | 7/2012 | Diamandis et al. |
| 2012/0252039 | A1 | 10/2012 | Cho et al. |
| 2013/0065782 | A1 | 3/2013 | Ostroff et al. |
| 2013/0085079 | A1 | 4/2013 | Gill et al. |
| 2014/0073521 | A1 | 3/2014 | Ostroff et al. |
| 2018/0201641 | A1 | 7/2018 | Rohloff et al. |
| 2018/0275143 | A1 | 9/2018 | Wilcox et al. |

FOREIGN PATENT DOCUMENTS

| | | |
|---|---|---|
| CN | 102084253 A | 6/2011 |
| CN | 102209968 A | 10/2011 |
| CN | 102762743 A | 10/2012 |
| JP | 2005-527180 A | 9/2005 |
| JP | 2006-53113 A | 2/2006 |
| JP | 2011-510297 | 3/2011 |
| SG | 187045 | 2/2013 |
| WO | WO-2002/073204 | 9/2002 |
| WO | WO 2002/086443 | 10/2002 |
| WO | WO 2004/031412 | 4/2004 |
| WO | WO 2004/074510 | 9/2004 |
| WO | WO 2004/075713 | 9/2004 |
| WO | WO 2004/099432 | 11/2004 |
| WO | WO 2005/005601 | 1/2005 |
| WO | WO 2005/043163 | 5/2005 |
| WO | WO 2005/083446 | 9/2005 |
| WO | WO 2005/103281 | 11/2005 |
| WO | WO 2006/022643 | 3/2006 |
| WO | WO 2006/022895 | 3/2006 |
| WO | WO 2007/013665 | 2/2007 |
| WO | WO 2007/045996 | 4/2007 |
| WO | WO 2007/109571 | 9/2007 |
| WO | WO 2008/046911 | 4/2008 |
| WO | WO 2008/048371 | 4/2008 |
| WO | WO 2008/063413 | 5/2008 |
| WO | WO 2008/117067 | 10/2008 |
| WO | WO 2008/144034 | 11/2008 |
| WO | WO 2009/036123 | 3/2009 |
| WO | WO 2009/091581 | 7/2009 |
| WO | WO 2009/103542 | 8/2009 |
| WO | WO 2010/030697 | 3/2010 |
| WO | WO 2010/042525 | 4/2010 |
| WO | WO 2010/049538 | 5/2010 |
| WO | WO 2010/142713 | 12/2010 |
| WO | WO 2010/144358 | 12/2010 |
| WO | 2011/022552 | 2/2011 |
| WO | WO 2011/031344 | 3/2011 |
| WO | WO 2011/043840 | 4/2011 |
| WO | WO 2011/050328 | 4/2011 |
| WO | WO 2011/059721 | 5/2011 |
| WO | WO 2011/068839 | 6/2011 |
| WO | WO 2011/072177 | 6/2011 |
| WO | WO 2011/094483 | 8/2011 |
| WO | WO 2011/100472 | 8/2011 |
| WO | WO 2011/100483 | 8/2011 |
| WO | 2011/109440 | 9/2011 |
| WO | 2011/127219 | 10/2011 |
| WO | WO 2012/021795 | 2/2012 |
| WO | WO 2012/149550 | 11/2012 |
| WO | WO 2013/049674 | 4/2013 |
| WO | WO/2013/142114 | 9/2013 |

OTHER PUBLICATIONS

Balasenthil et al. (2011) Cancer Prev Res 4:137-149 "A Migration Signature and Plasma Biomarker Panel for Pancreatic Adenocarcinoma".

Baron et al. (1999) Cancer Epidemiology; Biomarkers & Prevention 8:129-137, "Serum sErB1 and Epidermal Growth Factor Levels as Tumor Biomarkers in Women with Stage III or IV Epithelial Ovarian Cancer".

Bast et al. (2003) J. Clinical Oncology 21:200s-205s, "Status of Tumor Markers in Ovarian Cancer Screening".

Bignotti et al. (2006) Gynecol. Oncol.103:405-416, "Differential gene expression profiles between tumor biopsies and short-term primary cultures of ovarian serous carcinomas: Identification of novel molecular biomarkers for early diagnosis and therapy".

Bock et al. (2004) Proteomics 4(3):609-618 "Photoaptamer arrays applied to multiplexed proteomic analysis".

Borrebaeck (2006) Expert Opin. Biol. Ther. 6(8):833-838 "Antibody microarray-based oncoproteomics".

Brand et al. (2007) Gut 56:1460-1469 "Advances in counselling and surveillance of patients at risk for pancreatic cancer".

Brody and Gold (2005) Reviews in Molecular Biotechnology 74:5-13, "Aptamers as therapeutic and diagnostic agents".

(56) References Cited

OTHER PUBLICATIONS

Bünger et al. (2010) J Cancer Res Clin Oncol "Serum biomarkers for improved diagnostic of pancreatic cancer: a current overview".
Burgess (2008) Proteomics Clin. Appl 2:1223-1233 "Prostate cancer serum biomarker discovery through proteomic analysis of alpha-2 macroglobulin protein complexes".
Cecconi et al. (2011) Proteomics 11:816-828 "Proteomics in pancreatic cancer research".
Chaturvedi et al. (2010) Journal of Clinical Oncology 28(16):2719-2726 "C-Reactive Protein and Risk of Lung Cancer".
Chen et al. (2002) Molecular and Cellular Proteomics 1:304-323 "Discordant Protein and mRNA Expression in Lung Adenocarcinomas*".
Chang et al. (Dec. 2009) Journal of Translational Medicine, 7(1):105, "Identification of a biomarker panel using a multiplex proximity ligation assay improves accuracy of pancreatic cancer diagnosis".
Chen et al. (2005) Gastroenterology 129:1187-1197 "Pancreatic Cancer Proteome: The Proteins That Underlie Invasion, Metastasis, and Immunologic Escape".
Chen, et al. (2008) Proteome. Sci. 6:20, pp. 1-11, "Profiling of serum and tissue high abundance acute-phase proteins of patients with epithelial and germ line ovarian carcinoma".
Chu et al. (2011) Cancer Biology & Therapy 11(12):995-1000 "Diagnostic values of SCC, CEA, Cyfra21-1 and NSE for lung cancer in patients with suspicious pulmonary masses".
Diamandis, et al. (2000) Clin. Biochem. 33(7):579-583, "Human Kallikrein 6 (Zyme/Protease M/Neurosin): A new serum biomarker of ovarian carcinoma".
Douglas et al. (2010) Cancer Epidemiol Biomarkers Prev 19(9):2298-2306 "Serum IGF-I, IGF-II, IGFBP-3, and IGF-I/IGFBP-3 Molar Ratio and Risk of Pancreatic Cancer in the Prostate, Lung, Colorectal, and Ovarian Cancer Screening Trial".
Dowling et al. (2007) Electrophoresis 28(23):4302-4310 "2D difference gel electrophoresis of the lung squamous cell carcinoma versus normal sera demonstrates consistent alterations in the levels of ten specific proteins".
Ehmann et al. (2007) Pancreas 34:205-214 "Identification of Potential Markers for the Detection of Pancreatic Cancer Through Comparative Serum Protein Expression Profiling".
Erdogan et al. (2007) APMIS, 115, 204-209, "C-kit protein expression in uterine and ovarian mesenchymal tumours".
European Partial Search Report dated Nov. 26, 2014 in EP 11817097.6.
European Search Report dated May 7, 2012 in EP 09819761.9.
European Search Report dated Mar. 24, 2015 in EP 11817097.6.
Fredriksson et al (Mar. 2008) Clinical Chemistry, 54:582-589, "Multiplexed Proximity Ligation Assays to Profile Putative Plasma Biomarkers Relevant to Pancreatic and Ovarian Cancer".
Fuji et al. (2004) Journal of Proteome Research 3:712-718 "Multidimensional Protein Profiling Technology and Its Application to Human Plasma Proteome".
Gao et al. (2005) BMC Cancer 5:110 (internet pp. 1-10) "Distinctive serum protein profiles involving abundant proteins in lung cancer patients based upon antibody microarray analysis".
Gold et al. (2010) Cancer Epidemiol Biomarkers Prev 19(11):2786-94 "Detection of Early-Stage Pancreatic Adenocarcinoma".
Gold, L., et al. (2010) PLoS One, 5(12): p. e15004, "Aptamer-based multiplexed proteomic technology for biomarker discovery".
Gortzak-Uzan et al. (2008) J. Proteome. Res., 7:339-351, "A proteome resource of ovarian cancer ascites: Integrated proteomic and bioinformatic analyses to identify putative biomarkers".
Granville et al. (2005) Am. J. Respir. Cell. Mol. Biol. 32:169-176, "An Overview of Lung Cancer Genomics and Proteomics".
Gray et al. (2009) J Thorac Oncoll 4(3):411-425, "In arrayed ranks: array technology in the study of mesothelioma".
Greenbaum (2001) Genome Research, Cold Spring Harbor Laboratory 11(9):1463-1468, "Interrelating different types of genomic data, from proteome to secretome: 'Oming in on function'".
Grønborg et al. (2004) Journal of Proteome Research 3:1042-1055 "Comprehensive Proteomic Analysis of Human Pancreatic Juice".
Havrilesky et al. (2008) Gynecol. Oncol. 110:374-382, "Evaluation of biomarker panels for early stage ovarian cancer detection and monitoring for disease recurrence".
Heo et al. (2007) Proteomics. 7(23):4292-4302, "Identification of putative serum glycoprotein biomarkers for human lung adenocarcinoma by multilectin affinity chromatography and LC-MS/MS".
Herszényl et al. (2008) European Journal of Cancer Prevention 17(5):438-445 "Serum cathepsin B and plasma urokinase-type plasminogen activator levels in gastrointestinal tract cancers".
Honda et al. (2013) Jpn J Clin Oncol 43(2)103-109, "Proteomic Approaches to the Discovery of Cancer Biomarkers for Early Detection and Personalized Medicine".
Hongsachart (2009) Electrophoresis 30:1206-1220, "Glycoproteomic analysis of WGA-bound glycoprotein biomarkers in sera from patents with lung adenocarcinoma".
Hough et al. (2001) Cancer Research 61:3869-3876, "Coordinately Up-Regulated Genes in Ovarian Cancer".
HUGO Gene Nomenclature Committee, Symbol Report for "MMP7", printed May 2015.
Ingvarsson et al. (2008) Proteomics 8:2211-2219 "Detection of pancreatic cancer using antibody microarray-based serum protein profiling".
International Search Report and Written Opinion dated Nov. 20, 2009 in PCT/US2009/056399.
International Search Report and Written Opinion dated Jan. 13, 2010 in PCT/US2009/059706.
International Search Report and Written Opinion dated Apr. 30, 2010 in PCT/US2010/026439.
International Search Report and Written Opinion dated May 18, 2010 in PCT/US2010/0029878.
International Preliminary Report on Patentability dated Sep. 30, 2010 in PCT/US2009/056399.
International Search Report and Written Opinion dated Feb. 23, 2012 in PCT/US2011/047570.
International Preliminary Report on Patentability dated Aug. 8, 2013 in PCT/US2011/047570.
Jackson et al. (2007) Clin. Cancer Res. 13(24), "Proteomic Profiling Identifies Afamin as a Potential Biomarker for ovarian cancer".
Jäger et al. (2002) British Journal of Cancer 86:858-863, "Serum levels of the angiogenic factor pleiotrophin in relation to disease stage in lung cancer patients".
Jamieson et al. (2011) Clin Cancer Res 17:3316-3331 "Tissue Biomarkers for Prognosis in Pancreatic Ductal Adenocarcinoma: A Systematic Review and Meta-analysis".
Johansen et al. (2010) Cancer Epidemiol Biomarkers Prev 19(9):2307-17 "Metabolic Factors and the Risk of Pancreatic Cancer: A Prospective Analysis of almost 580,000 Men and Women in the Metabolic Syndrome and Cancer Project".
Katz et al. (2005) Pancreatology 5:576-590 "An Evidence-Based Approach to the Diagnosis and Staging of Pancreatic Cancer".
Kim et al. (2006) J. Korean Med. Sci., 21:81-85, "Expression and mutational analysis of c-kit in ovarian surface epithelial tumors".
Kioi et al. (2006) Cancer 107(6):1407-1418, "Interleukin-13 receptor alpha2 chain: a potential biomarker and molecular target for ovarian cancer therapy".
Kojima et al. (2008) J Gastrointest Surg 12:1683-1690, "Applying Proteomic-Based Biomarker Tools for the Accurate Diagnosis of Pancreatic Cancer".
Kosanam et al. (2011) Proteomics 11:4551-4558 "Mining the malignant ascites proteome for pancreatic cancer biomarkers".
Kuhlmann et al. (2007) Cancer Epidemiol Biomarkers Prev 16(5):886-91 "Evaluation of Matrix Metalloproteinase 7 in Plasma and Pancreatic Juice as a Biomarker for Pancreatic Cancer".
Kuk et al. (2009) Mol. Cell Proteomics 8:661-669, "Mining the ovarian cancer ascites proteome for potential ovarian cancer biomarkers".
Lassus et al. (2004) Br. J. Cancer, 91:2048-2055, "Genetic alterations and protein expression of KIT and PDGFRA in serous ovarian carcinoma".
Lemos-González (2007) British Journal of Cancer 96:1569-1578, "Alteration of the serum levels of the epidermal growth factor receptor and its ligands in patients with non-small cell lung cancer and head and neck carcinoma".

(56) References Cited

OTHER PUBLICATIONS

Leto et al. (1997) Pancreas 14(1):22-27 "Lysosomal aspartic and cysteine proteinases serum levels in patients with pancreatic cancer or pancreatitis".
Li et al (2006) Journal of Clinical Oncology, 24:1754-1760, "Serum Circulating Human mRNA Profiling and Its Utility for Oral Cancer Detection".
Louhimo et al. (2004) Oncology 66:126-131 "Serum HCGβ and CA 72-4 Are Stronger Prognostic Factors than CEA, CA 19-9 and CA 242 in Pancreatic Canter".
Lowe et al. (2007) PLoS ONE 2(3):e323 "Gene Expression Patterns in Pancreatic Tumors, Cells and Tissues".
Lu et al. (May 2004) Clinical Cancer Research 10:3291-3300, "Selection of Potential Markers for Epithelial Ovarian Cancer with Gene Expression Arrays and Recursive Descent Partition Analysis".
Maciel et al. (2005) J. Exp. Ther. Oncol. 5:31-38, "Differential proteomic serum pattern of low molecular weight proteins expressed by adenocarcinoma lung cancer patients".
McCauley et al. (2003) Analytical Biochemistry 319:244-250 "Aptamer-based biosensor arrays for detection and quantification of biological macromolecules".
Mcintosh (Annual Report for US Army Medical Research and Material Command, Fort Detrick, MD, Award No. W81 XWH 06-1-01 00; Dec. 2006, 12 pages) "Affinity-Based Serum Proteomics for Ovarian Cancer Early Diagnosis".
Mercer (1990) Immunol. Ser., 1990;53:39-54, "Use of Multiple Markers to Enhance Clinical Utility".
Mikolajczyk et al. (2004) Clinical Biochemistry 37:519-528, "Are multiple markers the future of prostate cancer diagnostics?".
Miller et al. (2003) Proteomics 3:56-63, "Antibody microarray profiling of human prostate cancer sera: Antibody screening and identification of potential biomarkers".
Mithani et al. (2011) Melanoma Res. 21(4):298-307 "Use of integrative epigenetic and cytogenetic analyses to identify novem tumor suppressor genes in malignant melanoma".
Mohr et al. (2004) Biochim Biophys Acta. 1688(1):43-60, "Cell protection, resistance and invasiveness of two malignant mesotheliomas as assessed by 10K-microarray".
Moore et al. (2008) Gynecol. Oncol.108:402-408, "The use of multiple novel tumor biomarkers for the detection of ovarian carcinoma in patients with a pelvic mass".
Mor et al. (2005) PNAS 102(21):7677-7682, "Serum protein markers for early detection of ovarian cancer".
Niedergethmann et al. (2004) Pancreas 29(3):204-211 "Prognostic Impact of Cysteine Proteases Cathepsin B and Cathepsin L in Pancreatic Adenocarcinoma".
Nolen et al. (2009) Gynecol. Oncol. 112(1):47-54, "A serum based analysis of ovarian epithelial tumorigenesis".
Ogata et al. (2006) J. Proteome.Res. 5:3318-3325, "Elevated levels of phosphorylated fibrinogen-alpha-isoforms and differential expression of other post-translationally modified proteins in the plasma of ovarian cancer patients".
Ohta et al. (1994) Br. J. Cancer, 69:152-156 "Pancreatic trypsinogen and cathepsin B in human pancreatic carcinomas and associated metastatic lesions".
Ohta et al. (1995) Gallbladder and Pancreas, 16(5):407-412 "Activation Mechanism and Inhibition of Matrix Degrading Enzymes in Pancreatic Cancer".
Ohta et al. (1995) Gallbladder and Pancreas 16(5):407-412 "Mechanism and Control of Metastasis of Pancreatic Cancer—New Discovery".
Okada et al. (2006) Clin Cancer Res 12(1): 191-197 "A Novel Cancer Testis Antigen That Is Frequently Expressed in Pancreatic, Lung, and Endometrial Cancers".
Olchovsky et al. (2002) Acta Oncologica 41(2):182-187, "Elevated Insulin-Like Growth Factor-1 and Insulin-Line Growth Factor Binding Protein-2 in Malignant Pleural Effusion".
Orchekowski (2005) Cancer Res 65(23):11193-11202 "Antibody Microarray Profiling Reveals Individual and Combined Serum Proteins Associated with Pancreatic Cancer".
Orchekowski (2005) Cancer Res 65(23) Supplemental "Antibody Microarray Profiling Reveals Individual and Combined Serum Proteins Associated with Pancreatic Cancer".
Ostroff, R. (2010) Clin Cancer Res-American Assoc. for Cancer Research Journals 16(A3) "Detection of rare cancers with aptamer proteomic technology".
Ostroff et al., (2010)Journal of Proteomics pp. 649-666, "The stability of the circulating human proteome to variations in sample collection and handling procedures measured with an aptamer-based proteomics array".
Ostroff et al. (2010) Nature "Unlocking biomarker discovery: Large scale application of aptamer proteomic technology for early detection of lung cancer".
Palmer et al. (2008) PLoS. One., 3(7):e2633, "Systematic evaluation of candidate blood markers for detecting ovarian cancer".
Park et al. (2008) Journal of Proteome Research 7:1138-1150, "Proteomic Profiling of Endothelial Cells in Human Lung Cancer".
Patz et al. (2007) Journal of Clinical Oncology, 25(35):5578-5583, "Panel of Serum Biomarkers for the Diagnosis of Lung Cancer".
Planque et al. (2008) Clin. Cancer Res. 14(5):1355-1362, "A Multiparametric Serum Kallikrein Panel for Diagnosis of Non-Small Cell Lung Carcinoma".
Polanski et al. (2006) Biomark. Insights. 1-48, "A list of candidate cancer biomarkers for targeted proteomics".
Polanski et al. (2006) Supplement—Biomark. Insights. 1-48, "A list of candidate cancer biomarkers for targeted proteomics".
Pouniotis et al. (2005) British Society for Immunology, Clinical and Experimental Immunology 143:363-372, "Alveolar macrophage function is altered in patients with lung cancer".
Ranshoff (2005) Journal of the National Cancer Institute 97(4):315-319, "Lessons from Controversy: Ovarian Cancer Screening and Serum Proteomics".
Rosen et al. (2005) Gynecol. Oncol. 99:267-277, "Potential markers that complement expression of CA125 in epithelial ovarian cancer".
Rosty et al. (2002) Cancer Research 62:1868-1875 "Identification of Hepatocarcinoma-Intestine-Pancreas/Pancreatitis-associated Protein I as a Biomarker for Pancreatic Ductal Adenocarcinoma by Protein Biochip Technology".
Salam et al. (2009) Med. Oncol. 26:161-166, "Serum levels of epidermal growth factor and HER-2 neu in non small-cell lung cancer: prognostic correlation".
Santin et al. (2004) Int. J. Cancer 112:14-25, "Gene Express Profiles in Primary Ovarian Serous papillary Tumors and Normal Ovarian Epithelium: Identification of Candidate Molecule Markers for Ovarian Cancer Diagnosis and Therapy".
Schwartz (1995) Clinica Chimica Acta 237:67-78 "Tissue cathepsins as tumor markers" [abstract only].
Shah et al. (Apr. 2010) J. Thorac. Cardiovasc. Surg. 139(4):984-990, "Differential matrix metalloproteinase levels in adenocarcionoma and squamous cell carcinoma of the lung".
Shen (2004) Cancer Research 64:9018-9026 "Protein Expression Profiles in Pancreatic Adenocarcinoma Compared with Normal Pancreatic Tissue and Tissue Affected by Pancreatitis as Detected by Two-Dimensional Gel Electrophoresis and Mass Spectrometry".
Shen et al. (2006) Cancer Res 2006:66(23):11194-11206, "Identification and Validation of Differences in Protein Levels in Normal, Premalignant, and Malignant Lung Cells and Tissues Using High-Throughput Western Array and Immunohisochemistry."
Shih et al. (2007) Gynecol. Oncol. 105:501-507, "Ovarian cancer specific kallikrein profile in effusions".
Stearman et al., (2008) Cancer Research, 68(1):34-43, "A Macrophage Gene Expression Signature Defines a Field Effect in the Lung Tumor Microenvironment".
Suzuki et al. (2002) Lung Cancer 35(1): 29-34, "Serum endostatin correlates with progression and prognosis of non-small cell lung cancer".
Swidzińska et al. (2005) Rocz. Akad. Med. Bialymst 50:197-2000, "Serum endostatin levels in patients with lung carcinoma" (abstract only).
Tamura et al. (2002) The International Journal of Biological Markers 17(4):275-279, "Diagnostic value of plasma vascular endothelial growth factor as a tumor marker in patients with non-small cell lung cancer".

(56) References Cited

OTHER PUBLICATIONS

Tchagang et al. (2008) Mol. Cancer Ther. 7(1):27-37, "Early detection of ovarian cancer using group biomarkers".
Thakur et al. (Jan. 24, 2008) Mol Cancer 7:11, "Gene expression profiles in primary pancreatic tumors and metastatic lesions of Ela-c-myc transgenic mice" doi:10.1186/1476-4598-7-11.
Tonary et al. (2000) Int. J. Cancer, 89:242-250, "Lack of expression of c-KIT in ovarian cancers is associated with poor prognosis".
Tong et al. (2007) Diabetologia 50:439-442 "Plasma pancreatic polypeptide levels are associated with differences in body fat distribution in human subjects".
Tsukishiro et al. (2005) Gynecol.Oncol. 96:516-519, "Use of serum secretory leukocyte protease inhibitor levels in patients to improve specificity of ovarian cancer diagnosis".
Tumminello et al. (1996) Int'l Institute of Anticancer Research 16(4B):2315-2319 "Cathepsin D, B and L circulating levels as prognostic markers of malignant progression".
Welsh et al. (2003) PNAS 100(6):3410-3415, "Large-scale delineation of secreted protein biomarkers overexpressed in cancer tissue and serum".
Xue et al. (Jun. 2010) British Journal of Cancer 103(3):391-400, "Discovery of serum biomarkers for pancreatic adenocarcinoma using proteomic analysis".
Xu et al. (2010) PLoS ONE 5(1):e13696 "A Comparative Analysis of Gene-Expression Data of Multiple Cancer Types".
Yaziji et al. (Apr. 2006) Modern pathology 19(4):514-523, "Evaluation of 12 antibodies for distinguishing epithelioid mesothelioma from adenocarcinoma: identification of a three-antibody immunohistochemical panel with maximal sensitivity and specificity".
Yue et al. (2011) Proteomics 11:3665-3674 "Identification of blood-protein carriers of the CA 19-9 antigen and characterization of prevalence in pancreatic diseases".
Zeh (2005) Cancer Biomarkers 1:259-269 "Multianalyte profiling of serum cytokines for detection of pancreatic cancer".
Zelan et al. (2008) The Practical Journal of Cancer 23(4) "Common tumor biomarkers and researches on their use in detecting and diagnosing non-small cell lung cancer" [in Chinese].
Zhonghua (2006) Yi Xue Za Zhi. 86(27):1916-18, "The value of serum endostatin level in early diagnosis of lung cancer" (abstract only).
Zelan et al. (2008) The Practical Journal of Cancer 23(4) "Status Quo of Researches on Diagnosis of Non-Small Cell Lung Cancer with Common Tumor markers and Combined-Detection thereof" [English translation] previously entitled: "Common tumor biomarkers and researches on their use in detecting and diagnosing non-small cell lung cancer".
Acosta et al. (2000) PNAS 97(10):5450-5455 "Molecular basis for a link between complement and the vascular complications of diabetes".
Boroumand et al., (2011) "Association between angiographically assessed coronary artery disease and serum levels of prostate specific antigen", PSA and CAD, Abstract, Clin.Lab. 57(11-12):975-81.
Chelbi et al. (2012) Human Molecular Genetics 21(9):1968-1978 "Genetic and epigenetic mechanisms collaborate to control SERPINA3 expression and its association with placental diseases".
Chiao et al., (2010) "In vivo Matrix Metalloproteinase-7 Substrates Identified in the Left Ventricle Post-Myocardial Infarction Using Proteomics", J Proteome Res. 9(5):2649-2657.
Chieng-Yane et al., (2010) "Protease activated Receptor-1 antagonist, F 16618 reduces arterial restenosis by down-regulation of TNFα and MMP7 expression, and migration and proliferation of vascular smooth muscle cells", JPET #175182.
Clark et al. (2001) American Heart Journal 141(4):684-690 "Serum complement activation in congestive heart failure".
de Weger et al., (2011) "Proteomic profiling of the human failing heart after left ventricular assist device support", The Journal of Heart and Lung Transplantation, 30(5):497-506.

Fischetti et al. (2006) Autoimmunity 39(5):417-428 "Cross-talk between the complement system and endothelial cells in physiologic conditions and in vascular diseases".
Gronski et al. (1997) The Journal of Biological Chemistry 272(18):12189-12194 "Hydrolysis of a Broad Spectrum of Extracellular Matrix Proteins by Human Macrophage Elastase".
Hak et al. (2001) The Journal of Clinical Endocrinology & Metabolism 86(9): 4398-4405 "Markers of Inflammation and Cellular Adhesion Molecules in Relation to Insulin Resistance in Nondiabetic Elderly: The Rotterdam Study".
Halberg et al. (2008) Endocrinol. Metab. Clin. North Am. 37(3):1-15 "The Adipocyte as an Endocrine Cell".
Haskard et al. (2008) Current Opinion in Lipidology 19:478-482 "The role of complement in atherosclerosis".
Hanash et al. (2008) Nature 452:571-579 "Mining the plasma proteome for cancer biomarkers".
Invitrogen (2009) Immune Response Biomarker Profiling Service Report, p. 1-33, "Immune Response Biomarker Profiling on ProtoArray Human Protein Microarrays for Our Favorite Customer".
Jguirim-Souissi et al. (2007) American Journal of Cardiology 100:23-27 "Plasma Metalloproteinase-12 and Tissue Inhibitor of Metalloproteinase-1 Levels and Presence, Severity, and Outcome of Coronary Artery Disease".
Keefe et al. (2010) Nature Reviews Drug Discovery 9:537-550 "Aptamers as therapeutics".
Kim et al. (2006) Clinical Immunology 118:127-136 "Membrane complement regulatory proteins".
Kraaijeveld et al. (2007) Circulation 116:1931-1941 "CC Chemokine Ligand-5 (CCL5/RANTES) and CC Chemokine Ligand-18 (CCL18/PARC) Are Specific Markers of Refractory Unstable Angina Pectoris and Are Transiently Raised During Severe Ischemic Symptoms".
Langeggen et al. (2000) Clin. Exp. Immunol. 121:69-76 "The endothelium is an extrahepatic site of synthesis of the seventh component of the complement system".
Lee et al., (2011) "Simvastatin suppresses expression of angiogenic factors in the retinas of rats with streptozotocin-induced diabetes", Graefes Arch Clin Exp Ophthalmol 249:389-397.
Liang et al. (2006) Circulation 113:1993-2001 "Macrophage Metalloelastase Accelerates the Progression of Atherosclerosis in Transgenic Rabbits".
Mason et al. (2002) Circulation Research 91:696-703 "Statin-Induced Expression of Decay-Accelerating Factor Protects Vascular Endothelium Against Complement-Mediated Injury".
McNeill et al. (2010) Clinical Science 118:641-655 "Inflammatory cell recruitment in cardiovascular disease: murine models and potential clinical applications".
McPherron (2010) Immunol. Endocr. Metab. Agents Med. Chem. 10(4):217-231 "Metabolic Functions of Myostatin and GDF11".
Meltzer et al. (2010) Blood 116(1):113-121 "Venous thrombosis risk associated with plasma hypofibrinolysis is explained by elevated plasma levels of TAFI and PAI-1".
Meltzer et al., (2010) "Plasma levels of fibrinolytic proteins and the risk of myocardial infarction in men", Blood, The American Society of Hematology, 116:529-536).
Monahan et al. (1980) The Journal of Biological Chemistry 255(22):10579-10582 "Binding of the Eighth Component of Human Complement to the Soluble Cytolytic Complex Is Mediated by Its β Subunit".
Nagase et al. (2006) Cardiovascular Research 69:562-573 "Structure and function of matrix metalloproteinases and TIMPs".
Nomura et al. (2008) BBRC 365:863-869 "Skeletal muscle-derived progenitors capable of differentiating into cardiomyocytes proliferate through myostatin-independent TGF-β family signaling".
Okamoto et al. (2002) The FASEB Journal 10 Angiogenesis induced by advanced glycation end products and its prevention by cerivastatin.
Page-McCaw et al. (2007) Molecular Cell Biology 8:221-233 "Matrix metalloproteinases and the regulation of tissue remodelling".
Peden et al., (2011) "A genome-wide association study in Europeans and South Asians identifies five new loci for coronary artery disease", Nature Genetics 43(4) 339-44.

(56) References Cited

OTHER PUBLICATIONS

Podack et al. (1978) The Journal of Immunology 120(6):1841-1848 "The C5b-6 Complex: Formation, Isolation, and Inhibition of its Activity by Lipoprotein and the S-Protein of Human Serum".
ProtoArray (2009) Human ProtoArray 2.0 Content List, 1.
Raitoharju et al., (2011) "miR-21, miR-210, miR-34a, and miR-146a/b are up-regulated in human atherosclerotic plaques in the Tampere Vascular Study", Atherosclerosis 219:211-217.
Raitoharju et al., (2011) Supplementary tables "miR-21, miR-210, miR-34a, and miR-146a/b are up-regulated in human atherosclerotic plaques in the Tampere Vascular Study", Atherosclerosis 219:211-217.
Razuvaev et al., (2011) "Correlations Between Clinical Variables and Gene-expression Profiles in Carotid Plaque Instability", Eur. J. Vasc. Endovasc. Surg. 42:722-730.
Reape et al. (1999) American Journal of Pathology 154(2):365-374 "Expression and Cellular Localization of the CC Chemokines PARC and ELC in Human Atherosclerotic Plaques".
Rivera et al., (2009) "Platelet receptors and signaling in the dynamics of thrombus formation", Haematologica 94(5):700-711.
Robertson et al. (2012) BBRC 427:568-573 "Synexpression group analyses identify new functions of FSTL3, a TGFβ ligand inhibitor".
Rohatgi et al., (2009) "Differential Associations between Soluble Cellular Adhesion Molecules and Atherosclerosis in the Dallas Heart Study: a Distinct Role for Soluble Endothelial Cell-Selective Adhesion Molecule", Arterioscler. Thromb. Vasc. Biol. 29(10):1684-1690.
Scholtes et al. (2012) J. Am. Heart Assoc. 1-12 "Carotid Atherosclerotic Plaque Matrix Metalloproteinase—12-Postive Macrophage Subpopulation Predicts Adverse Outcome After Endarterectomy".
Scholz et al. (2011) Blood 118(18):5050-5059 "Angiopoietin-2 promotes myeloid cell infiltration in a β2-integrin-dependent manner".
Siddiqui et al., (2004) "Simvastatin enhances myocardial angiogenesis induced by vascular endothelial growth factor gene transfer", Journal of Molecular and Cellular Cardiology 37:1235-1244.
Somasunderam et al. (2011) Translational Medicine S1:001, p. 1-5 "Aptamers as Novel Reagents for Biomarker Discovery Applications" doi:10.4172/2161-1025.S1-001.
Souza et al. (2008) Molecular Endocrinology 22(12):2689-2702 "Proteomic Identification and Functional Validation of Activins and Bone Morphogenetic Protein 11 as Candidate Novel Muscle Mass Regulators".
Speidl et al. (2011) Journal of Thrombosis and Haemostasis 9:428-440 "Complement in atherosclerosis: friend or foe?".
Swinnen et al., (2009) "Absence of Thrombospondin-2 Causes Age-Related Dilated Cardiomyopathy", Circulation, Journal of the American Heart Association 120:1585-1597.
Takahaski et al. (2012) Heart Vessels 27:337-343 "Prospective, randomized, single-blind comparison of effects of 6 months' treatment with atorvastatin versus pravastatin on leptin and angiogenic factors in patients with coronary artery disease".
Talmud et al. (2008) Thromb. Vasc. Biol. 28:2319-2325 "ANGPTL4 E40K and T266M Effects on Plasma Triglyceride and HDL Levels, Postprandial Responses, and CHD Risk".
Tedesco et al. (1997) J. Exp. Med 185(9):1619-1627 "The Cytolytically Inactive Terminal Complement Complex Activates Endothelial Cells to Express Adhesion Molecules and Tissue Factor Procoagulant Activity".
Théroux et al. (2006) Can. J. Cardiol. 22(Suppl B):18B-24B "Complement activity and pharmacological inhibition in cardiovascular disease".
Ulrich et al. (2009) Cytometry Part A 75A(9):727-733 "Disease-specific biomarker discovery by aptamers".
van Almen et al., (2011) "Absence of thromospondin-2 increases cardiomyocyte damage and matrix disruption in doxorubicin-induced cardiomyopathy", Journal of Molecular and Cellular Cardiology 51:318-328.
Wagsater et al. (2012) International Journal of Molecular Medicine 30:288-294 "Serine protease inhibitor A3 in atherosclerosis and aneurysm disease".
Wang et al. (2011) Biomedicine & Pharmacotherapy 65:118-122 "The effect of atorvastatin on mRNA levels of inflammatory genes expression in human peripheral blood lymphocytes by DNA microarray".
Wang et al. (2012) Biomarkers 17(8):745-749 "Changes and significance of serum angiopoietin-2 levels in patients with coronary heart disease".
Wang et al., (2009) "Matrix Metalloproteinase-7 and ADAM-12 (a Disintegrin and Metalloproteinase-12) Define a Signaling Axis in Agonist-Induced Hypertension and Cardiac Hypertrophy", Circulation, Journal of the American Heart Association 119:2480-2489.
Wang et al., (2009) MMP-7 and ADAM 12 define a signalling axis in agonist-induced hypertension and cardiac hypertrophy, Supplemental Material.
Wang et al., (2010) "Common polymorphisms in ITGA2, PON1 and THBS2 are associated with coronary atherosclerosis in a candidate gene association study of the Chinese Han population", Journal of Human Genetics 55:490-494.
Yasojima et al. (2001) American Journal of Pathology 158(3): 1039-1051 "Generation of C-Reactive Protein and Complement Components in Atherosclerotic Plaques".
Yasojima et al., (2001) "Complement Components, but Not Complement Inhibitors, Are Upregulated in Atherosclerotic Plaques", Arterioscler Thromb Vasc Biol. 21:1214-1219.
Gold et al. (Posted Jun. 2010) Nature Proceedings "Aptamer-based multiplexed proteomic technology for biomarker discovery," Available online at http://precedings.nature.com/documents/4538/version/1/files/npre20104538-1.pdf, 77 pp.
Shlipak et al. (2008) Am. J. Med. 121(1):50-57 "Biomarkers to Predict Recurrent Cardiovascular Disease: The Heart and Soul Study.".
Tanner et al. (2011) Plos One 6(8), e23609: 1-12 "Pharmacogenetic Associations of MMP9 and MMP12 Variants with Cardiovascular Disease in Patients with Hypertension.".

* cited by examiner

PANCREATIC CANCER BIOMARKERS AND USES THEREOF

RELATED APPLICATIONS

This application is a continuation application of U.S. application Ser. No. 14/020,334, filed Sep. 6, 2013, which is a continuation application of U.S. application Ser. No. 13/208,903, filed Aug. 12, 2011, now abandoned, which claims the benefit of U.S. Provisional Application Ser. No. 61/373,687, filed Aug. 13, 2010. U.S. Provisional Application Ser. No. 61/418,689, filed Dec. 1, 2010. U.S. Provisional Application Ser. No. 61/482,347, filed May 4, 2011, and U.S. Provisional Application Ser. No. 61/482,480, filed May 4, 2011, each of which is incorporated herein by reference in its entirety.

FIELD OF THE INVENTION

The present application relates generally to the detection of biomarkers and the diagnosis of cancer in an individual and, more specifically, to one or more biomarkers, methods, devices, reagents, systems, and kits for diagnosing cancer, more particularly pancreatic cancer, in an individual.

BACKGROUND

The following description provides a summary of information relevant to the present application and is not an admission that any of the information provided or publications referenced herein is prior art to the present application.

Pancreatic cancer is the fourth leading cause of cancer-related death in the USA. While the 5-year survival is only 5%, this has been shown to increase with early surgical intervention: in the 20% of subjects eligible for a "curative" resection the survival increases to 15-20%. At the time of diagnosis, more than half the patients have distant disease and another 25% have regional spread. This is because the disease is notoriously difficult to diagnose in its early stages. About 20 percent of patients with "operable" disease [stage IIb or less] undergo a "curative" resection and the 5-year survival increases from less than 5% to 15-20%.

Pancreatic cancers can arise from both the exocrine and endocrine portions of the pancreas. Of pancreatic tumors, 95% develop from the exocrine portion of the pancreas, including the ductal epithelium, acinar cells, connective tissue, and lymphatic tissue. Approximately 75% of all pancreatic carcinomas occur within the head or neck of the pancreas, 15-20% occur in the body of the pancreas, and 5-10% occur in the tail.

Recurrence can be local (in or near the same place it started) or distant (spread to organs such as the liver, lungs, or bone). When pancreatic exocrine cancer recurs, it is essentially treated the same way as metastatic cancer, and is likely to include chemotherapy if the patient can tolerate it. Typically, pancreatic cancer first metastasizes to regional lymph nodes, then to the liver, and, less commonly, to the lungs. It can also directly invade surrounding visceral organs such as the duodenum, stomach, and colon or metastasize to any surface in the abdominal cavity via peritoneal spread. Ascites may result, and this has an ominous prognosis. Pancreatic cancer may spread to the skin as painful nodular metastases. Pancreatic cancer uncommonly metastasizes to bone.

Two clinical applications for a blood based pancreatic cancer test are for preclinical diagnosis in the asymptomatic, high-risk population and differential diagnosis in the symptomatic population. The clinical utility for both of these indications is outlined below.

Screening in an asymptomatic, high risk population: There were an estimated 43,140 new cases of pancreatic cancer in the USA in 2010, and 36,800 deaths. Genetics, family history, chronic pancreatitis, smoking and high alcohol consumption increase the risk of pancreatic cancer, as does cystic fibrosis. The increase in risk has been reported as:

Cigarette smoking: <25 per day is 2× risk, >25 per day is 3× risk
Alcohol: more than 3 drinks per day gives a 1.6 fold risk increase
Family history: a first degree relative with the disease gives a 5× increase
Adults with cystic fibrosis: 31× risk
BRCA2 genetic mutations: 10× risk In the asymptomatic but at-risk population in the absence of an effective screening paradignl the cancer is simply detected at the time of symptomatic presentation. This is likely to be late. The existence of an early detection test would increase the proportion of patients eligible for curative surgery. The current cure rate of 20% in the 20% c of early detection subjects is only 4% of the total population. If the eligibility for curative surgery increased—by early detection in the asymptomatic population—from the current 20%, then the curable total would increase, as would the number of lives saved per year. Since pancreatic cancer is a low prevalence disease, even in this high-risk population, high specificity is an important attribute of a screening test. A low false positive rate is essential to reduce the cost incurred by unnecessary follow-up procedures and reduce anxiety for the patient.

Differential diagnosis in the symptomatic patient. Pancreatic cancer may be difficult to distinguish from benign conditions such as pancreatitis or gastro-intestinal disorders. The differential diagnosis of a primary exocrine pancreatic cancer includes chronic pancreatitis, pancreatic endocrine tumors, autoimmune pancreatitis, lymphoma, and a variety of other rare conditions. Common but non-specific symptoms associated with pancreatic cancer include:

Abdominal pain—particularly when radiating to the back
Obstructive jaundice
Sudden unexplained diabetes
Weight loss
Anorexia, fatigue
Nausea, vomiting
Acute or chronic pancreatitis The table below shows the numbers of patients presenting to emergency rooms and to hospitals with at least two of these relevant symptoms; the first symptom is any one of the listed symptoms, and the second symptom is the one listed in the table. The emergency room data was from: (http://hcupnet.ahrq.gov/) while the ambulatory data was from the CDC 2008 National Ambulatory Medical Care Survey 2006 (number 8).

| | Relevant Symptoms by Age | | | | |
|---|---|---|---|---|---|
| | | Emergency Dept | | All Ambulatory | |
| | Per-centage | 64-84 | 45-84 | 64-84 | 45-84 |
| Abdominal pain | 10.6% | 39,922 | 142,188 | 106,458 | 379,168 |
| Jaundice | 11.0% | 1,405 | 3,429 | 3,746 | 9,145 |

-continued

Relevant Symptoms by Age

| | Per-centage | Emergency Dept | | All Ambulatory | |
|---|---|---|---|---|---|
| | | 64-84 | 45-84 | 64-84 | 45-84 |
| Weight loss | 11.0% | 5,465 | 9,860 | 14,574 | 26,294 |
| Malaise and fatigue | 4.1% | 18,200 | 32,241 | 48,533 | 85,977 |
| Acute pancreatitis | 18.6% | 9,807 | 31,080 | 26,152 | 82,879 |
| Chronic pancreatitis | 43.2% | 1,061 | 7,966 | 2,829 | 21,242 |
| All | | 75,860 | 226,765 | 202,293 | 604,705 |

Sensitive detection of resectable disease is essential for the clinical utility of this indication. Prompt detection of pancreatic cancer increases the chances of diagnosis of curable disease. The diagnosis of pancreatic cancer is typically made radiographically by the finding of a mass within the pancreas, which often obstructs the pancreatic duct or biliary tree. However, imaging can be invasive and costly. A blood test that determines which patients require follow-up, including diagnostic imaging, would benefit the patients and simplify the diagnosis.

Biomarker selection for a specific disease state involves first the identification of markers that have a measurable and statistically significant difference in a disease population compared to a control population for a specific medical application. Biomarkers can include secreted or shed molecules that parallel disease development or progression and readily diffuse into the blood stream from pancreatic cancer tissue or from surrounding tissues and circulating cells in response to a tumor. The biomarker or set of biomarkers identified are generally clinically validated or shown to be a reliable indicator for the original intended use for which it was selected. Biomarkers can include small molecules, peptides, proteins, and nucleic acids. Some of the key issues that affect the identification of biomarkers include over-fitting of the available data and bias in the data.

A variety of methods have been utilized in an attempt to identify biomarkers and diagnose disease. For protein-based markers, these include two-dimensional electrophoresis, mass spectrometry, and immunoassay methods. For nucleic acid markers, these include mRNA expression profiles, microRNA profiles. FISH, serial analysis of gene expression (SAGE), and large scale gene expression arrays.

The utility of two-dimensional electrophoresis is limited by low detection sensitivity; issues with protein solubility, charge, and hydrophobicity; gel reproducibility; and the possibility of a single spot representing multiple proteins. For mass spectrometry, depending on the format used, limitations revolve around the sample processing and separation, sensitivity to low abundance proteins, signal to noise considerations, and inability to immediately identify the detected protein. Limitations in immunoassay approaches to biomarker discovery are centered on the inability of antibody-based multiplex assays to measure a large number of analytes. One might simply print an array of high-quality antibodies and, without sandwiches, measure the analytes bound to those antibodies. (This would be the formal equivalent of using a whole genome of nucleic acid sequences to measure by hybridization all DNA or RNA sequences in an organism or a cell. The hybridization experiment works because hybridization can be a stringent for identity. Even very good antibodies are not stringent enough in selecting their binding partners to work in the context of blood or even cell extracts because the protein ensemble in those matrices have extremely different abundances.) Thus, one must use a different approach with immunoassay-based approaches to biomarker discovery—one would need to use multiplexed ELISA assays (that is, sandwiches) to get sufficient stringency to measure many analytes simultaneously to decide which analytes are indeed biomarkers. Sandwich immunoassays do not scale to high content, and thus biomarker discovery using stringent sandwich immunoassays is not possible using standard array formats. Lastly, antibody reagents are subject to substantial lot variability and reagent instability. The instant platform for protein biomarker discovery overcomes this problem.

Many of these methods rely on or require some type of sample fractionation prior to the analysis. Thus the sample preparation required to run a sufficiently powered study designed to identify and discover statistically relevant biomarkers in a series of well-defined sample populations is extremely difficult, costly, and time consuming. During fractionation, a wide range of variability can be introduced into the various samples. For example, a potential marker could be unstable to the process, the concentration of the marker could be changed, inappropriate aggregation or disaggregation could occur, and inadvertent sample contamination could occur and thus obscure the subtle changes anticipated in early disease.

It is widely accepted that biomarker discovery and detection methods using these technologies have serious limitations for the identification of diagnostic biomarkers. These limitations include an inability to detect low-abundance biomarkers, an inability to consistently cover the entire dynamic range of the proteome, irreproducibility in sample processing and fractionation, and overall irreproducibility and lack of robustness of the method. Further, these studies have introduced biases into the data and not adequately addressed the complexity of the sample populations, including appropriate controls, in terms of the distribution and randomization required to identify and validate biomarkers within a target disease population.

Although efforts aimed at the discovery of new and effective biomarkers have gone on for several decades, the efforts have been largely unsuccessful. Biomarkers for various diseases typically have been identified in academic laboratories, usually through an accidental discovery while doing basic research on some disease process. Based on the discovery and with small amounts of clinical data, papers were published that suggested the identification of a new biomarker. Most of these proposed biomarkers, however, have not been confirmed as real or useful biomarkers, primarily because the small number of clinical samples tested provide only weak statistical proof that an effective biomarker has in fact been found. That is, the initial identification was not rigorous with respect to the basic elements of statistics. In each of the years 1994 through 2003, a search of the scientific literature shows that thousands of references directed to biomarkers were published. During that same time frame, however, the FDA approved for diagnostic use, at most, three new protein biomarkers a year, and in several years no new protein biomarkers were approved.

Based on the history of failed biomarker discovery efforts, mathematical theories have been proposed that further promote the general understanding that biomarkers for disease are rare and difficult to find. Biomarker research based on 2D gels or mass spectrometry supports these notions. Very few useful biomarkers have been identified through these approaches. However, it is usually overlooked that 2D gel and mass spectrometry measure proteins that are present in blood at approximately 1 nM concentrations and higher, and that this ensemble of proteins may well be the least likely to change with disease. Other than the instant biomarker discovery platform, proteomic biomarker discovery platforms that are able to accurately measure protein expression levels at much lower concentrations do not exist.

Much is known about biochemical pathways for complex human biology. Many biochemical pathways culminate in or are started by secreted proteins that work locally within the pathology, for example growth factors are secreted to stimulate the replication of other cells in the pathology, and other factors are secreted to ward off the immune system, and so on. While many of these secreted proteins work in a paracrine fashion, some operate distally in the body. One skilled in the art with a basic understanding of biochemical pathways would understand that many pathology-specific proteins ought to exist in blood at concentrations below (even far below) the detection limits of 2D gels and mass spectrometry. What must precede the identification of this relatively abundant number of disease biomarkers is a proteomic platform that can analyze proteins at concentrations below those detectable by 2D gels or mass spectrometry.

Accordingly, a need exists for biomarkers, methods, devices, reagents, systems, and kits that enable (a) the differentiation of pancreatic cancer from benign conditions; (b) screening of asymnptomatic, high risk individuals for pancreatic cancer; (c) the detection of pancreatic cancer biomarkers; and (d) the diagnosis of pancreatic cancer.

SUMMARY

The present application includes biomarkers, methods, reagents, devices, systems, and kits for the detection and diagnosis of cancer and more particularly, pancreatic cancer. The biomarkers of the present application were identified using a multiplex aptamer-based assay which is described in detail in Example 1. By using the aptamer-based biomarker identification method described herein, this application describes a surprisingly large number of pancreatic cancer biomarkers that are useful for the detection and diagnosis of pancreatic cancer as well as a large number of cancer biomarkers that are useful for the detection and diagnosis of cancer more generally. In identifying these biomarkers, over 800 proteins from hundreds of individual samples were measured, some of which were at concentrations in the low femtomolar range. This is about four orders of magnitude lower than biomarker discovery experiments done with 2D gels and/or mass spectrometry.

While certain of the described pancreatic cancer biomarkers are useful alone for detecting and diagnosing pancreatic cancer, methods are described herein for the grouping of multiple subsets of the pancreatic cancer biomarkers that are useful as a panel of biomarkers. Once an individual biomarker or subset of biomarkers has been identified, the detection or diagnosis of pancreatic cancer in an individual can be accomplished using any assay platform or format that is capable of measuring differences in the levels of the selected biomarker or biomarkers in a biological sample.

However, it was only by using the aptamer-based biomarker identification method described herein, wherein over 800 separate potential biomarker values were individually screened from a large number of individuals having previously been diagnosed either as having or not having pancreatic cancer that it was possible to identify the pancreatic cancer biomarkers disclosed herein. This discovery approach is in stark contrast to biomarker discovery from conditioned media or lysed cells as it queries a more patient-relevant system that requires no translation to human pathology.

Thus, in one aspect of the instant application, one or more biomarkers are provided for use either alone or in various combinations to diagnose pancreatic cancer or permit the differential diagnosis of pancreatic cancer from benign gastrointestinal (GI) conditions such as acute or chronic pancreatitis (or both), pancreatic obstruction, GERD, gallstones, or abnormal imaging later found to be benign. Exemplary embodiments include the biomarkers provided in Table 1, Col. 2, which as noted above, were identified using a multiplex aptamer-based assay, as described generally in Example 1 and more specifically in Example 2. The markers provided in Table 1 are useful in diagnosing pancreatic cancer in a high risk, asymptomatic population and for distinguishing acute or chronic pancreatitis (or both), pancreatic obstruction, GERD, gallstones, or abnormal imaging later found to be benign from pancreatic cancer.

While certain of the described pancreatic cancer biomarkers are useful alone for detecting and diagnosing pancreatic cancer, methods are also described herein for the grouping of multiple subsets of the pancreatic cancer biomarkers that are each useful as a panel of two or more biomarkers. Thus, various embodiments of the instant application provide combinations comprising N biomarkers, wherein N is at least two biomarkers. In other embodiments, N is selected to be any number from 2-65 biomarkers.

In yet other embodiments, N is selected to be any number from 2-7, 2-10, 2-15, 2-20, 2-25, 2-30, 2-35, 2-40, 2-45, 2-50, 2-55, or 2-65. In other embodiments, N is selected to be any number from 3-7, 3-10, 3-15, 3-20, 3-25, 3-30, 3-35, 3-40, 3-45, 3-50, 3-55, or 3-65. In other embodiments, N is selected to be any number from 4-7, 4-10, 4-15, 4-20, 4-25, 4-30, 4-35, 4-40, 4-45, 4-50, 4-55, or 4-65. In other embodiments. N is selected to be any number from 5-7, 5-10, 5-15, 5-20, 5-25, 5-30, 5-35, 5-40, 5-45, 5-50, 5-55, or 5-65. In other embodiments, N is selected to be any number from 6-10, 6-15, 6-20, 6-25, 6-30, 6-35, 6-40, 6-45, 6-50, 6-55, or 6-65. In other embodiments, N is selected to be any number from 7-10, 7-15, 7-20, 7-25, 7-30, 7-35, 7-40, 7-45, 7-50, 7-55, or 7-65. In other embodiments, N is selected to be any number from 8-10, 8-15, 8-20, 8-25, 8-30, 8-35, 8-40, 8-45, 8-50, 8-55, or 8-65. In other embodiments, N is selected to be any number from 9-15, 9-20, 9-25, 9-30, 9-35, 9-40, 9-45, 9-50, 9-55, or 9-65. In other embodiments, N is selected to be any number from 10-15, 10-20, 10-25, 10-30, 10-35, 10-40, 10-45, 10-50, 10-55, or 10-65. It will be appreciated that N can be selected to encompass similar, but higher order, ranges.

In another aspect, a method is provided for diagnosing pancreatic cancer in an individual, the method including detecting, in a biological sample from an individual, at least one biomarker value corresponding to at least one biomarker selected from the group of biomarkers provided in Table 1, Col. 2, wherein the individual is classified as having pancreatic cancer based on the at least one biomarker value.

In another aspect, a method is provided for diagnosing pancreatic cancer in an individual, the method including detecting, in a biological sample from an individual, biomarker values that each correspond to one of at least N biomarkers selected from the group of biomarkers set forth in Table 1, Col. 2, wherein the likelihood of the individual having pancreatic cancer is determined based on the biomarker values.

In another aspect, a method is provided for diagnosing pancreatic cancer in an individual, the method including detecting, in a biological sample from an individual, biomarker values that each correspond to one of at least N biomarkers selected from the group of biomarkers set forth in Table 1, Col. 2, wherein the individual is classified as having pancreatic cancer based on the biomarker values, and wherein N=2-10.

In another aspect, a method is provided for diagnosing pancreatic cancer in an individual, the method including detecting, in a biological sample from an individual, biomarker values that each correspond to one of at least N biomarkers selected from the group of biomarkers set forth in Table 1, Col. 2, wherein the likelihood of the individual having pancreatic cancer is determined based on the biomarker values, and wherein N=2-10.

In another aspect, a method is provided for diagnosing that an individual does not have pancreatic cancer, the method including detecting, in a biological sample from an individual, at least one biomarker value corresponding to at least one biomarker selected from the group of biomarkers set forth in Table 1, Col. 2, wherein the individual is classified as not having pancreatic cancer based on the at least one biomarker value.

In another aspect, a method is provided for diagnosing that an individual does not have pancreatic cancer, the method including detecting, in a biological sample from an individual, biomarker values that each corresponding to one of at least N biomarkers selected from the group of biomarkers set forth in Table 1, Col. 2, wherein the individual is classified as not having pancreatic cancer based on the biomarker values, and wherein N=2-10.

In another aspect, a method is provided for diagnosing pancreatic cancer, the method including detecting, in a biological sample from an individual, biomarker values that each correspond to a biomarker on a panel of N biomarkers, wherein the biomarkers are selected from the group of biomarkers set forth in Table 1, Col. 2, wherein a classitication of the biomarker values indicates that the individual has pancreatic cancer, and wherein N=3-10.

In another aspect, a method is provided for diagnosing pancreatic cancer, the method including detecting, in a biological sample from an individual, biomarker values that each correspond to a biomarker on a panel of N biomarkers, wherein the biomarkers are selected from the group of biomarkers set forth in Table 1, Col. 2, wherein a classitication of the biomarker values indicates that the individual has pancreatic cancer, and wherein N=3-10.

In another aspect, a method is provided for diagnosing pancreatic cancer, the method including detecting, in a biological sample from an individual, biomarker values that each correspond to a biomarker on a panel of biomarkers selected from the group of panels set forth in Tables 2-11, wherein a classification of the biomarker values indicates that the individual has pancreatic cancer.

In another aspect, a method is provided for diagnosing an absence of pancreatic cancer, the method including detecting, in a biological sample from an individual, biomarker values that each correspond to a biomarker on a panel of N biomarkers, wherein the biomarkers are selected from the group of biomarkers set forth in Table 1, Col. 2, wherein a classification of the biomarker values indicates an absence of pancreatic cancer in the individual, and wherein N=3-10.

In another aspect, a method is provided for diagnosing an absence of pancreatic cancer, the method including detecting, in a biological sample from an individual, biomarker values that each correspond to a biomarker on a panel of N biomarkers, wherein the biomarkers are selected from the group of biomarkers set forth in Table 1, Col. 2, wherein a classification of the biomarker values indicates an absence of pancreatic cancer in the individual, and wherein N=3-10.

In another aspect, a method is provided for diagnosing an absence of pancreatic cancer, the method including detecting, in a biological sample from an individual, biomarker values that each correspond to a biomarker on a panel of biomarkers selected from the group of panels provided in Tables 2-11, wherein a classification of the biomarker values indicates an absence of pancreatic cancer in the individual.

In another aspect, a method is provided for diagnosing pancreatic cancer in an individual, the method including detecting, in a biological sample from an individual, biomarker values that correspond to one of at least N biomarkers selected from the group of biomarkers set forth in Table 1, Col. 2, wherein the individual is classified as having pancreatic cancer based on a classification score that deviates from a predetermined threshold, and wherein N=2-10.

In another aspect, a method is provided for diagnosing an absence of pancreatic cancer in an individual, the method including detecting, in a biological sample from an individual, biomarker values that correspond to one of at least N biomarkers selected from the group of biomarkers set forth in Table 1, Col. 2, wherein said individual is classified as not having pancreatic cancer based on a classification score that deviates from a predetermined threshold, and wherein N=2-10.

In another aspect, a computer-implemented method is provided for indicating a likelihood of pancreatic cancer. The method comprises: retrieving on a computer biomarker information for an individual, wherein the biomarker information comprises biomarker values that each correspond to one of at least N biomarkers, wherein N is as defined above, selected from the group of biomarkers set forth in Table 1, Col. 2; performing with the computer a classification of each of the biomarker values; and indicating a likelihood that the individual has pancreatic cancer based upon a plurality of classifications.

In another aspect, a computer-implemented method is provided for classifying an individual as either having or not having pancreatic cancer. The method comprises: retrieving on a computer biomarker information for an individual, wherein the biomarker information comprises biomarker values that each correspond to one of at least N biomarkers selected from the group of biomarkers provided in Table 1, Col. 2; performing with the computer a classification of each of the biomarker values; and indicating whether the individual has pancreatic cancer based upon a plurality of classifications.

In another aspect, a computer program product is provided for indicating a likelihood of pancreatic cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers, wherein N is as defined above, in the biological sample selected from the group of biomarkers set forth in Table 1, Col. 2; and code that executes a classification method that indicates a likelihood that the individual has pancreatic cancer as a function of the biomarker values.

In another aspect, a computer program product is provided for indicating a pancreatic cancer status of an individual. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 1, Col. 2; and code that executes a classification method that indicates a pancreatic cancer status of the individual as a function of the biomarker values.

In another aspect, a computer-implemented method is provided for indicating a likelihood of pancreatic cancer. The method comprises retrieving on a computer biomarker information for an individual, wherein the biomarker information comprises a biomarker value corresponding to a biomarker selected from the group of biomarkers set forth in Table 1, Col. 2; performing with the computer a classification of the biomarker value; and indicating a likelihood that the individual has pancreatic cancer based upon the classification.

In another aspect, a computer-implemented method is provided for classifying an individual as either having or not having pancreatic cancer. The method comprises retrieving from a computer biomarker information for an individual, wherein the biomarker information comprises a biomarker value corresponding to a biomarker selected from the group of biomarkers provided in Table 1, Col. 2; performing with the computer a classification of the biomarker value; and indicating whether the individual has pancreatic cancer based upon the classification.

In still another aspect, a computer program product is provided for indicating a likelihood of pancreatic cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers set forth in Table 1, Col. 2; and code that executes a classification method that indicates a likelihood that the individual has pancreatic cancer as a function of the biomarker value.

In still another aspect, a computer program product is provided for indicating a pancreatic cancer status of an individual. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 1, Col. 2; and code that executes a classification method that indicates a pancreatic cancer status of the individual as a function of the biomarker value.

While certain of the described cancer biomarkers are useful alone for detecting and diagnosing cancer, methods are described herein for the grouping of multiple subsets of the cancer biomarkers that are useful as a panel of biomarkers. Once an individual biomarker or subset of biomarkers has been identified, the detection or diagnosis of cancer in an individual can be accomplished using any assay platform or format that is capable of measuring differences in the levels of the selected biomarker or biomarkers in a biological sample.

However, it was only by using the aptamer-based biomarker identification method described herein, wherein over 800 separate potential biomarker values were individually screened from a large number of individuals having previously been diagnosed either as having or not having cancer that it was possible to identify the cancer biomarkers disclosed herein. This discovery approach is in stark contrast to biomarker discovery from conditioned media or lysed cells as it queries a more patient-relevant system that requires no translation to human pathology.

Thus, in one aspect of the instant application, one or more biomarkers are provided for use either alone or in various combinations to diagnose cancer. Exemplary embodiments include the biomarkers provided in Table 19, which were identified using a multiplex aptamer-based assay, as described generally in Example 1 and more specifically in Example 7. The markers provided in Table 19 are useful in distinguishing individuals who have cancer from those who do not have cancer.

While certain of the described cancer biomarkers are useful alone for detecting and diagnosing cancer, methods are also described herein for the grouping of multiple subsets of the cancer biomarkers that are each useful as a panel of three or more biomarkers. Thus, various embodiments of the instant application provide combinations comprising N biomarkers, wherein N is at least three biomarkers. In other embodiments, N is selected to be any number from 3-65 biomarkers.

In yet other embodiments, N is selected to be any number from 3-7, 3-10, 3-15, 3-20, 3-25, 3-30, 3-35, 3-40, 3-45, 3-50, 3-55, 3-60, or 3-65. In other embodiments, N is selected to be any number from 4-7, 4-10, 4-15, 4-20, 4-25, 4-30, 4-35, 4-40, 4-45, 4-50, 4-55, 4-60, or 4-65. In other embodiments, N is selected to be any number from 5-7, 5-10, 5-15, 5-20, 5-25, 5-30, 5-35, 5-40, 5-45, 5-50, 5-55, 5-60, or 5-65. In other embodiments, N is selected to be any number from 6-10, 6-15, 6-20, 6-25, 6-30, 6-35, 6-40, 6-45, 6-50, 6-55, 6-60, or 6-65. In other embodiments, N is selected to be any number from 7-10, 7-15, 7-20, 7-25, 7-30, 7-35, 7-40, 7-45, 7-50, 7-55, 7-60, or 7-65. In other embodiments, N is selected to be any number from 8-10, 8-15, 8-20, 8-25, 8-30, 8-35, 8-40, 8-45, 8-50, 8-55, 8-60, or 8-65. In other embodiments, N is selected to be any number from 9-15, 9-20, 9-25, 9-30, 9-35, 9-40, 9-45, 9-50, 9-55, 9-60, or 9-65. In other embodiments, N is selected to be any number from 10-15, 10-20, 10-25, 10-30, 10-35, 10-40, 10-45, 10-50, 10-55, 10-60, or 10-65. It will be appreciated that N can be selected to encompass similar, but higher order, ranges.

In another aspect, a method is provided for diagnosing cancer in an individual, the method including detecting, in a biological sample from an individual, at least one biomarker value corresponding to at least one biomarker selected from the group of biomarkers provided in Table 19, wherein the individual is classified as having cancer based on the at least one biomarker value.

In another aspect, a method is provided for diagnosing cancer in an individual, the method including detecting, in a biological sample from an individual, biomarker values that each correspond to one of at least N biomarkers selected from the group of biomarkers set forth in Table 19, wherein the likelihood of the individual having cancer is determined based on the biomarker values.

In another aspect, a method is provided for diagnosing cancer in an individual, the method including detecting, in a biological sample from an individual, biomarker values that each correspond to one of at least N biomarkers selected from the group of biomarkers set forth in Table 19, wherein the individual is classified as having cancer based on the biomarker values, and wherein N=3-10.

In another aspect, a method is provided for diagnosing cancer in an individual, the method including detecting, in a biological sample from an individual, biomarker values that each correspond to one of at least. N biomarkers selected from the group of biomarkers set forth in Table 19, wherein the likelihood of the individual having cancer is determined based on the biomarker values, and wherein N=3-10.

In another aspect, a method is provided for diagnosing that an individual does not have cancer, the method including detecting, in a biological sample from an individual, at least one biomarker value corresponding to at least one biomarker selected from the group of biomarkers set forth in Table 19, wherein the individual is classified as not having cancer based on the at least one biomarker value.

In another aspect, a method is provided for diagnosing that an individual does not have cancer, the method including detecting, in a biological sample from an individual, biomarker values that each corresponding to one of at least N biomarkers selected from the group of biomarkers set forth in Table 19, wherein the individual is classified as not having cancer based on the biomarker values, and wherein N=3-10.

In another aspect, a method is provided for diagnosing cancer, the method including detecting, in a biological sample from an individual, biomarker values that each correspond to a biomarker on a panel of N biomarkers, wherein the biomarkers are selected from the group of biomarkers set forth in Table 19, wherein a classification of the biomarker values indicates that the individual has cancer, and wherein N=3-10.

In another aspect, a method is provided for diagnosing cancer, the method including detecting, in a biological sample from an individual, biomarker values that each correspond to a biomarker on a panel of N biomarkers, wherein the biomarkers are selected from the group of biomarkers set forth in Table 19, wherein a classification of the biomarker values indicates that the individual has cancer, and wherein N=3-10.

In another aspect, a method is provided for diagnosing cancer, the method including detecting, in a biological sample from an individual, biomarker values that each correspond to a biomarker on a panel of biomarkers selected from the group of panels set forth in Tables 20-29 wherein a classification of the biomarker values indicates that the individual has cancer.

In another aspect, a method is provided for diagnosing an absence of cancer, the method including detecting, in a biological sample from an individual, biomarker values that each correspond to a biomarker on a panel of N biomarkers, wherein the biomarkers are selected from the group of biomarkers set forth in Table 19, wherein a classification of the biomarker values indicates an absence of cancer in the individual, and wherein N=3-10.

In another aspect, a method is provided for diagnosing an absence of cancer, the method including detecting, in a biological sample from an individual, biomarker values that each correspond to a biomarker on a panel of N biomarkers, wherein the biomarkers are selected from the group of biomarkers set forth in Table 19, wherein a classification of the biomarker values indicates an absence of cancer in the individual, and wherein N=3-10.

In another aspect, a method is provided for diagnosing an absence of cancer, the method including detecting, in a biological sample from an individual, biomarker values that each correspond to a biomarker on a panel of biomarkers selected from the group of panels provided in Tables 20-29, wherein a classification of the biomarker values indicates an absence of cancer in the individual.

In another aspect, a method is provided for diagnosing cancer in an individual, the method including detecting, in a biological sample from an individual, biomarker values that correspond to one of at least N biomarkers selected from the group of biomarkers set forth in Table 19, wherein the individual is classified as having cancer based on a classification score that deviates from a predetermined threshold, and wherein N=3-10.

In another aspect, a method is provided for diagnosing an absence of cancer in an individual, the method including detecting, in a biological sample from an individual, biomarker values that correspond to one of at least N biomarkers selected from the group of biomarkers set forth in Table 19, wherein said individual is classified as not having cancer based on a classification score that deviates from a predetermined threshold, and wherein N=3-10.

In another aspect, a computer-implemented method is provided for indicating a likelihood of cancer. The method comprises: retrieving on a computer biomarker information for an individual, wherein the biomarker information comprises biomarker values that each correspond to one of at least N biomarkers, wherein N is as defined above, selected from the group of biomarkers set forth in Table 19; performing with the computer a classification of each of the biomarker values; and indicating a likelihood that the individual has cancer based upon a plurality of classifications.

In another aspect, a computer-implemented method is provided for classifying an individual as either having or not having cancer. The method comprises: retrieving on a computer biomarker information for an individual, wherein the biomarker information comprises biomarker values that each correspond to one of at least N biomarkers selected from the group of biomarkers provided in Table 19; performing with the computer a classification of each of the biomarker values; and indicating whether the individual has cancer based upon a plurality of classifications.

In another aspect, a computer program product is provided for indicating a likelihood of cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers, wherein N is as defined above, in the biological sample selected from the group of biomarkers set forth in Table 19; and code that executes a classification method that indicates a likelihood that the individual has cancer as a function of the biomarker values.

In another aspect, a computer program product is provided for indicating a cancer status of an individual. The computer program product includes a computer readable medium embodying program code executable by a processor of a computing device or system, the program code comprising: code that retrieves data attributed to a biological sample from an individual, wherein the data comprises biomarker values that each correspond to one of at least. N biomarkers in the biological sample selected from the group of biomarkers provided in Table 19; and code that executes a classification method that indicates a cancer status of the individual as a function of the biomarker values.

In another aspect, a computer-implemented method is provided for indicating a likelihood of cancer. The method comprises retrieving on a computer biomarker information for an individual, wherein the biomarker information comprises a biomarker value corresponding to a biomarker selected from the group of biomarkers set forth in Table 19;

performing with the computer a classification of the biomarker value; and indicating a likelihood that the individual has cancer based upon the classification.

In another aspect, a computer-implemented method is provided for classifying an individual as either having or not having cancer. The method comprises retrieving from a computer biomarker information for an individual, wherein the biomarker information comprises a biomarker value corresponding to a biomarker selected from the group of biomarkers provided in Table 19; performing with the computer a classification of the biomarker value; and indicating whether the individual has cancer based upon the classification.

In still another aspect, a computer program product is provided for indicating a likelihood of cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers set forth in Table 19; and code that executes a classification method that indicates a likelihood that the individual has cancer as a function of the biomarker value.

In still another aspect, a computer program product is provided for indicating a cancer status of an individual. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 19; and code that executes a classification method that indicates a cancer status of the individual as a function of the biomarker value.

In still another aspect, a method is provided for diagnosing pancreatic cancer, the method including detecting, in a biological sample from an individual, the tumor marker CA 19-9 in addition to biomarker values that each correspond to a biomarker on a panel of biomarkers selected from the group of panels set forth in Table 1 wherein a classification of the combined CA 19-9 and biomarker values indicates that the individual has pancreatic cancer.

BRIEF DESCRIPTION OF THE DRAWINGS

In FIG. 17A, sets of ten biomarkers were randomly selected from all 10 analytes present in all 3 cancer studies that were not selected by the greedy procedure. In FIG. 17B, the same procedure as 17A was used; however, the sampling was restricted to the remaining 55 biomarkers from Table 1 that were not selected by the greedy procedure.

DETAILED DESCRIPTION

Figure 1A:
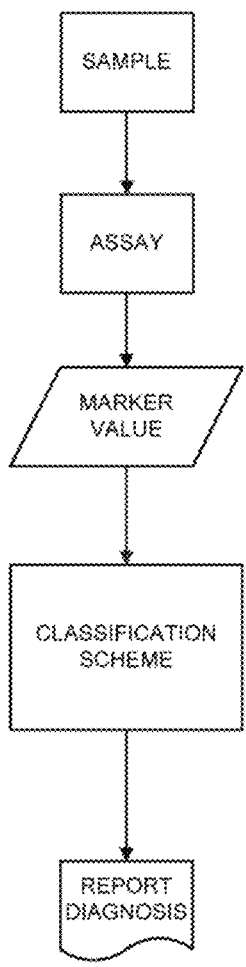
FIG. 1A is a flowchart for an exemplary method for detecting pancreatic cancer in a biological sample.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the term "about" represents an insignificant modification or variation of the numerical value such that the basic function of the item to which the numerical value relates is unchanged.

As used herein, the terms "comprises," "comprising," "includes," "including." "cotains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The present application includes biomarkers, methods, devices, reagents, systems, and kits for the detection and diagnosis of pancreatic cancer and cancer more generally.

In one aspect, one or more biomarkers are provided for use either alone or in various combinations to diagnose pancreatic cancer, permit the differential diagnosis of pancreatic cancer from non-malignant GI conditions including acute or chronic pancreatitis (or both), pancreatic obstruction, GERD, gallstones, or abnormal imaging later found to be benign, monitor pancreatic cancer recurrence, or address other clinical indications. As described in detail below, exemplary embodiments include the biomarkers provided in Table 1, Col. 2, which were identified using a multiplex aptamer-based assay that is described generally in Example 1 and more specifically in Example 2.

Table 1, Col. 2 sets forth the findings obtained from analyzing hundreds of individual blood samples from pancreatic cancer cases, and hundreds of equivalent individual blood samples from GI and normal controls. The GI and normal controls group was designed to match the populations with which a pancreatic cancer diagnostic test can have the most benefit, including asymptomatic individuals and symptomatic individuals. The normal control group represents asymptomatic individuals with a high risk of pancreatic cancer. High risk for pancreatic cancer includes family history of pancreatic cancer, obesity, smoking, diabetes, cystic fibrosis, chronic or hereditary pancreatitis, BRCA mutation carrier, p16 mutation, and Peutz-Jeghers syndrome (Brand E et al. Gut 2007:56:1.160). The GI control group includes nonspecific abdominal symptoms such as acute or chronic pancreatitis (or both), pancreatic obstruction, GERD, gallstones, or abnormal imaging later found to be benign. Samples from the normal controls were combined with the GI controls to discover biomarkers useful for both screening high risk asymptomatic individuals and differential diagnosis in symptomatic individuals. The potential biomarkers were measured in individual samples rather than pooling the disease and control blood; this allowed a better understanding of the individual and group variations in the phenotypes associated with the presence and absence of disease (in this case pancreatic cancer). Since 823 protein measurements were made on each sample, and several hundred samples from each of the disease and the control populations were individually measured, Table 1, Col. 2 resulted from an analysis of an uncommonly large set of data. The measurements were analyzed using the methods described in the section, "Classification of Biomarkers and Calculation of Disease Scores" herein. Table 1, Col. 2 lists the 65 biomarkers found to be useful in distinguishing samples obtained from individuals with pancreatic cancer from "control" samples obtained from GI and normal controls. GI controls include subjects with acute or chronic pancreatitis (or both), pancreatic obstruction, GERD, gallstones, or abnormal imaging later found to be benign.

While certain of the described pancreatic cancer biomarkers are useful alone for detecting and diagnosing pancreatic cancer, methods are also described herein for the grouping of multiple subsets of the pancreatic cancer biomarkers, where each grouping or subset selection is useful as a panel of three or more biomarkers, interchangeably referred to herein as a "biomarker panel" and a panel. Thus, various embodiments of the instant application provide combinations comprising N biomarkers, wherein N is at least two biomarkers. In other embodiments, N is selected from 2-65 biomarkers.

In yet other embodiments, N is selected to be any number from 2-7, 2-10, 2-15, 2-20, 2-25, 2-30, 2-35, 2-40, 2-45, 2-50, 2-55, or 2-65. In other embodiments, N is selected to be any number from 3-7, 3-10, 3-15, 3-20, 3-25, 3-30, 3-35, 3-40, 3-45, 3-50, 3-55, or 3-65. In other embodiments, N is selected to be any number from 4-7, 4-10, 4-15, 4-20, 4-25, 4-30, 4-35, 4-40, 4-45, 4-50, 4-55, or 4-65. In other embodiments, N is selected to be any number from 5-7, 5-10, 5-15, 5-20, 5-25, 5-30, 5-35, 5-40, 5-45, 5-50, 5-55, or 5-65. In other embodiments, N is selected to be any number from 6-10, 6-15, 6-20, 6-25, 6-30, 6-35, 6-40, 6-45, 6-50, 6-55, or 6-65. In other embodiments. N is selected to be any number from 7-10, 7-15, 7-20, 7-25, 7-30, 7-35, 7-40, 7-45, 7-50, 7-55, or 7-65. In other embodiments, N is selected to be any number from 8-10, 8-15, 8-20, 8-25, 8-30, 8-35, 8-40, 8-45, 8-50, 8-55, or 8-65. In other embodiments, N is selected to be any number from 9-15, 9-20, 9-25, 9-30, 9-35, 9-40, 9-45, 9-50, 9-55, or 9-65. In other embodiments, N is selected to be any number from 10-15, 10-20, 10-25, 10-30, 10-35, 10-40, 10-45, 10-50, 10-55, or 10-65. It will be appreciated that N can be selected to encompass similar, but higher order, ranges.

In one embodiment, the number of biomarkers useful for a biomarker subset or panel is based on the sensitivity and specificity value for the particular combination of biomarker values. The terms "sensitivity" and "specificity" are used herein with respect to the ability to correctly classify an individual, based on one or more biomarker values detected in their biological sample, as having pancreatic cancer or not having pancreatic cancer. "Sensitivity" indicates the performance of the biomarker(s) with respect to correctly classifying individuals that have pancreatic cancer. "Specificity" indicates the performance of the biomarker(s) with respect to correctly classifying individuals who do not have pancreatic cancer. For example, 85% specificity and 90% sensitivity for a panel of markers used to test a set of control samples and pancreatic cancer samples indicates that 85% of the control samples were correctly classified as control samples by the panel, and 90% of the pancreatic cancer samples were correctly classified as pancreatic cancer samples by the panel. The desired or preferred minimum value can be determined as described in Example 3. Representative panels are set forth in Tables 4-11, which set forth a series of 100 different panels of 3-10 biomarkers, which have the indicated levels of specificity and sensitivity for each panel. The total number of occurrences of each marker in each of these panels is indicated at the bottom of each Table.

In one aspect, pancreatic cancer is detected or diagnosed in an individual by conducting an assay on a biological sample from the individual and detecting biomarker values that each correspond to at least one of the biomarkers CTSB, C5a or C5 and at least N additional biomarkers selected from the list of biomarkers in Table 1, Col. 2, wherein N equals 2, 3, 4, 5, 6, 7, 8, or 9. In a further aspect, pancreatic cancer is detected or diagnosed in an individual by conducting an assay on a biological sample from the individual and detecting biomarker values that each correspond to the biomarkers CTSB, C5a or C5 and one of at least N additional biomarkers selected from the list of biomarkers in Table 1, Col. 2, wherein N equals 1, 2, 3, 4, 5, 6, or 7. In a further aspect, pancreatic cancer is detected or diagnosed in an individual by conducting an assay on a biological sample from the individual and detecting biomarker values that each correspond to the biomarker CTSB and one of at least N additional biomarkers selected from the list of biomarkers in Table 1, Col. 2, wherein N equals 2, 3, 4, 5, 6, 7, 8, or 9. In a further aspect, pancreatic cancer is detected or diagnosed in an individual by conducting an assay on a biological sample from the individual and detecting biomarker values that each correspond to the biomarker C5a and one of at least N additional biomarkers selected from the list of biomarkers in Table 1, Col. 2, wherein N equals 2, 3, 4, 5, 6, 7, 8, or 9. In a further aspect, pancreatic cancer is detected or diagnosed in an individual by conducting an assay on a biological sample from the individual and detecting biomarker values that each correspond to the biomarker C5 and one of at least. N additional biomarkers selected from the list of biomarkers in Table 1, Col. 2, wherein N equals 2, 3, 4, 5, 6, 7, 8, or 9.

The pancreatic cancer biomarkers identified herein represent a relatively large number of choices for subsets or panels of biomarkers that can be used to effectively detect or diagnose pancreatic cancer. Selection of the desired number of such biomarkers depends on the specific combination of biomarkers chosen. It is important to remember that panels of biomarkers for detecting or diagnosing pancreatic cancer may also include biomarkers not found in Table 1, Col. 2, and that the inclusion of additional biomarkers not found in Table 1, Col. 2 may reduce the number of biomarkers in the particular subset or panel that is selected from Table 1, Col. 2. The number of biomarkers from Table 1, Col. 2 used in a subset or panel may also be reduced if additional biomedical information is used in conjunction with the biomarker values to establish acceptable sensitivity and specificity values for a given assay.

Another factor that can affect the number of biomarkers to be used in a subset or panel of biomarkers is the procedures used to obtain biological samples from individuals who are being diagnosed for pancreatic cancer. In a carefully controlled sample procurement environment, the number of biomarkers necessary to meet desired sensitivity and specificity values will be lower than in a situation where there can be more variation in sample collection, handling and storage. In developing the list of biomarkers set forth in Table 1, Col. 2, multiple sample collection sites were utilized to collect data for classifier training. This provides for more robust biomarkers that are less sensitive to variations in sample collection, handling and storage, but can also require that the number of biomarkers in a subset or panel be larger than if the training data were all obtained under very similar conditions.

Figure 1B:
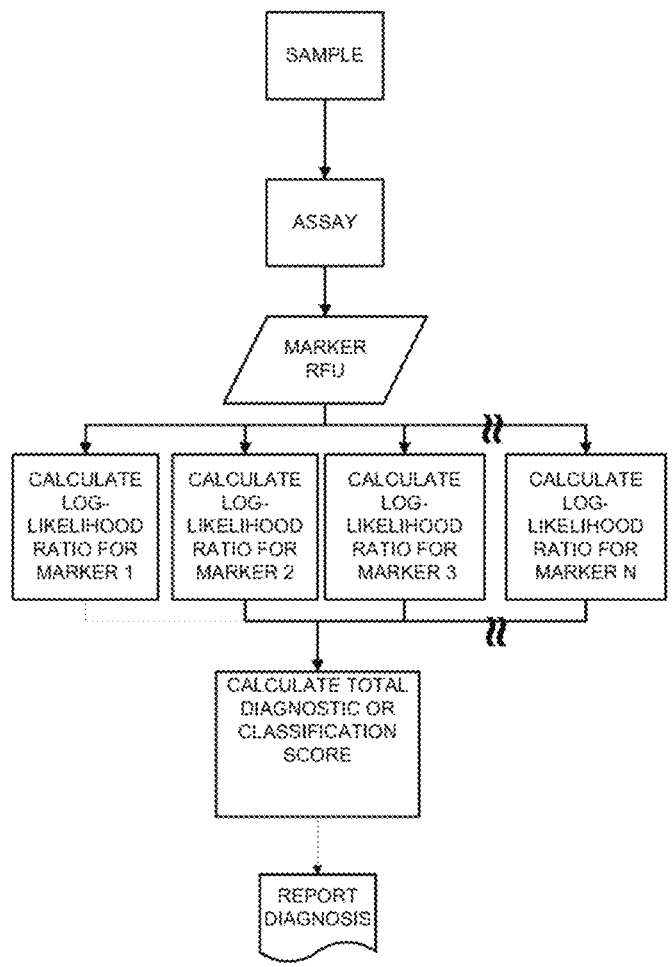
FIG. 1B is a flowchart for an exemplary method for detecting pancreatic cancer in a biological sample using a naïve Bayes classification method.

One aspect of the instant application can be described generally with reference to FIGS. 1A and 1B. A biological sample is obtained from an individual or individuals of interest. The biological sample is then assayed to detect the presence of one or more (N) biomarkers of interest and to determine a biomarker value for each of said N biomarkers (referred to in FIG. 1B as marker RFU). Once a biomarker has been detected and a biomarker value assigned each marker is scored or classified as described in detail herein. The marker scores are then combined to provide a total diagnostic score, which indicates the likelihood that the individual from whom the sample was obtained has pancreatic cancer.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, peritoneal washings, ascites, cystic fluid, meningeal fluid, amniotic fluid, glandular fluid, pancreatic fluid, lymph fluid, pleural fluid, nipple aspirate, bronchial aspirate, bronchial brushing, synovial fluid, joint aspirate, organ secretions, cells, a cellular extract, and cerebrospinal fluid. This also includes experimentally separated fractions of all of the preceding. For example, a blood sample can be fractionated into serum, plasma or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, lung washes, BAL (bronchoalveolar lavage), thyroid, breast, pancreas and liver. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

Further, it should be realized that a biological sample can be derived by taking biological samples from a number of individuals and pooling them or pooling an aliquot of each individual's biological sample. The pooled sample can be treated as a sample from a single individual and if the presence of cancer is established in the pooled sample, then each individual biological sample can be re-tested to determine which individual/s have pancreatic cancer.

For purposes of this specification, the phrase "data attributed to a biological sample from an individual" is intended to mean that the data in some form derived from, or were generated using, the biological sample of the individual. The data may have been reformatted, revised, or mathematically altered to some degree after having been generated, such as by conversion from units in one measurement system to units in another measurement system; but, the data are understood to have been derived from, or were generated using, the biological sample.

"Target", "target molecule", and "analyte" are used interchangeably herein to refer to any molecule of interest that may be present in a biological sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" is a set of copies of one type or species of molecule or multi-molecular structure. "Target molecules", "targets", and "analytes" refer to more than one such set of molecules. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing.

As used herein, "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains. Also included within the definition are preproteins and intact mature proteins; peptides or polypeptides derived from a mature protein; fragments of a protein; splice variants; recombinant forms of a protein; protein variants with amino acid modifications, deletions, or substitutions; digests; and post-translational modifications, such as glycosylation, acetylation, phosphorylation, and the like.

As used herein, "marker" and "biomarker" are used interchangeably to refer to a target molecule that indicates or is a sign of a normal or abnormal process in an individual or of a disease or other condition in an individual. More specifically, a "marker" or "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. When a biomarker is a protein, it is also possible to use the expression of the corresponding gene as a surrogate measure of the amount or presence or absence of the corresponding protein biomarker in a biological sample or methylation state of the gene encoding the biomarker or proteins that control expression of the biomarker.

As used herein, "biomarker value", "value", "biomarker level", and "level" are used interchangeably to refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "value" or "level" depends on the specific design and components of the particular analytical method employed to detect the biomarker.

When a biomarker indicates or is a sign of an abnormal process or a disease or other condition in an individual, that biomarker is generally described as being either over-expressed or under-expressed as compared to an expression level or value of the biomarker that indicates or is a sign of a normal process or an absence of a disease or other condition in an individual. "Up-regulation". "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The term "differential gene expression" and "differential expression" are used interchangeably to refer to a gene (or its corresponding protein expression product) whose expression is activated to a higher or lower level in a subject suffering from a specific disease, relative to its expression in a normal or control subject. The terms also include genes (or the corresponding protein expression products) whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a variety of changes including mRNA levels, surface expression, secretion or other partitioning of a polypeptide. Differential gene expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a gene or its expression products among, for example, normal and diseased cells, or among cells which have undergone different disease events or disease stages.

As used herein, "individual" refers to a test subject or patient. The individual can be a mammal or a non-mammal. In various embodiments, the individual is a mammal. A mammalian individual can be a human or non-human. In various embodiments, the individual is a human. A healthy or normal individual is an individual in which the disease or condition of interest (including, for example, pancreatic diseases, pancreatic-associated diseases, or other pancreatic conditions) is not detectable by conventional diagnostic methods.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual. The diagnosis of pancreatic cancer includes distinguishing individuals who have cancer from individuals who do not. It further includes distinguishing GI and normal controls from pancreatic cancer.

"Prognose", "prognosing", "prognlosis", and variations thereof refer to the prediction of a future course of a disease or condition in an individual who has the disease or condition (e.g., predicting patient survival), and such terms encompass the evaluation of disease response after the administration of a treatment or therapy to the individual.

"Evaluate", "evaluating", "evaluation", and variations thereof encompass both "diagnose" and "prognose" and also encompass determinations or predictions about the future course of a disease or condition in an individual who does not have the disease as well as determinations or predictions regarding the likelihood that a disease or condition will recur in an individual who apparently has been cured of the disease. The term "evaluate" also encompasses assessing an individual's response to a therapy, such as, for example, predicting whether an individual is likely to respond favorably to a therapeutic agent or is unlikely to respond to a therapeutic agent (or will experience toxic or other undesirable side effects, for example), selecting a therapeutic agent for administration to an individual, or monitoring or determining an individual's response to a therapy that has been administered to the individual. Thus, "evaluating" pancreatic cancer can include, for example, any of the following: prognosing the future course of pancreatic cancer in an individual; predicting the recurrence of pancreatic cancer in an individual who apparently has been cured of pancreatic cancer; or determining or predicting an individual's response to a pancreatic cancer treatment or selecting a pancreatic cancer treatment to administer to an individual based upon a determination of the biomarker values derived from the individual's biological sample.

Any of the following examples may be referred to as either "diagnosing" or "evaluating" pancreatic cancer: initially detecting the presence or absence of pancreatic cancer; determining a specific stage, type or sub-type, or other classification or characteristic of pancreatic cancer; determining whether a suspicious mass is a benign lesion or a malignant pancreatic tumor; or detecting/monitoring pancreatic cancer progression (e.g., monitoring tumor growth or metastatic spread), remission, or recurrence.

As used herein, "additional biomedical information" refers to one or more evaluations of an individual, other than using any of the biomarkers described herein, that are associated with cancer risk or, more specifically, pancreatic cancer risk. "Additional biomedical information" includes any of the following: physical descriptors of an individual, including a pancreatic mass observed by any of contrast-enhanced multislice (multidetector) helical computed tomography (CT) scanning with three dimensional reconstruction, transcutaneous or endoscopic ultrasound (US or EUS), endoscopic retrograde cholangiopancreatography (ERCP), magnetic resonance imaging (MRI), MR cholangiopancreatography (MRCP), or abdominal ultrasound; the height and/or weight of an individual; change in weight; the ethnicity of an individual; occupational history; family history of pancreatic cancer (or other cancer); the presence of a genetic marker(s) correlating with a higher risk of pancreatic cancer (or other cancer) in the individual or a family member; the presence or absence of a pancreatic mass or other abdominal mass; size of mass; location of mass; morphology of mass and associated abdominal region (e.g., as observed through imaging); clinical symptoms such as abdominal pain, weight loss, anorexia, early satiety, diarrhea, or steatorrhea, jaundice, recent onset of atypical diabetes mellitus, a history of recent but unexplained thrombophlebitis, or previous attack of pancreatitis, and the like; gene expression values; physical descriptors of an individual, including physical descriptors observed by radiologic imaging; the height and/or weight of an individual; the gender of an individual; the ethnicity of an individual; smoking history; alcohol use history; occupational history; exposure to known carcinogens (e.g., exposure to any of asbestos, radon gas, chemicals, smoke from fires, and air pollution, which can include emissions from stationary or mobile sources such as industrial/factory or auto/marine/aircraft emissions); exposure to second-hand smoke; and family history of pancreatic cancer or other cancer. Testing of biomarker levels in combination with an evaluation of any additional biomedical information, including other laboratory tests (e.g., CA 19-9 testing, serum bilirubin concentration, alkaline phosphatase activity, presence of anemia), may, for example, improve sensitivity, specificity, and/or AUC for detecting pancreatic cancer (or other pancreatic cancer-related uses) as compared to biomarker testing alone or evaluating any particular item of additional biomedical information alone (e.g., ultrasound imaging alone). Additional biomedical information can be obtained from an individual using routine techniques known in the art, such as from the individual themselves by use of a routine patient questionnaire or health history questionnaire, etc., or from a medical practitioner, etc. Testing of biomarker levels in combination with an evaluation of any additional biomedical information may, for example, improve sensitivity, specificity, and/or AUC for detecting pancreatic cancer (or other pancreatic cancer-related uses) as compared to biomarker testing alone or evaluating any particular item of additional biomedical information alone (e.g., CT imaging alone).

Cancer associated antigen 19-9 (CA 19-9) is a known blood marker for pancreatic cancer. The reported sensitivity and specificity of CA 19-9 for pancreatic cancer are 80 to 90 percent, respectively. However, these values are closely related to tumor size. The accuracy of CA 19-9 to identify patients with small surgically resectable cancers is limited. CA 19-9 requires the presence of the Lewis blood group antigen (a glycosyl transferase) to be expressed. Among individuals with a Lewis-negative phenotype (an estimated 5 to 10 percent of the population). CA 19-9 levels are not a useful tumor marker. The specificity of CA 19-9 is also limited. CA 19-9 is frequently elevated in patients with various benign pancreaticobiliary disorders. The degree of elevation of CA 19-9 (both at initial presentation and in the postoperative setting) is associated with long-term prognosis. Furthermore, in patients who appear to have potentially resectable disease, the magnitude of the CA 19-9 level can also help to predict the presence of radiographically occult metastatic disease as well. Serial monitoring of CA 19-9 levels is useful to follow patients after potentially curative surgery and for those who are receiving chemotherapy for advanced disease. Rising CA 19-9 levels usually precede the radiographic appearance of recurrent disease, but confirmation of disease progression should be pursued with imaging studies and/or biopsy. Testing of biomarker levels in combination with CA 19-9 may, for example, improve improve sensitivity, specificity, and/or AUC for detecting pancreatic cancer (or other pancreatic cancer-related uses) as compared to CA 19-9 alone.

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., pancreatic cancer samples and normal or control samples). ROC curves are useful for plotting the performance of a particular feature (e.g., any of the biomarkers described herein and/or any item of additional biomedical information) in distinguishing between two populations (e.g., cases having pancreatic cancer and controls without pancreatic cancer). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

As used herein, "detecting" or "determining" with respect to a biomarker value includes the use of both the instrument required to observe and record a signal corresponding to a biomarker value and the material/s required to generate that signal. In various embodiments, the biomarker value is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly) vinylidenefluoride, polycarbonate, and polymethylpentene. Suitable solid support particles that can be used include, e.g., encoded particles, such as Luminex-type encoded particles, magnetic particles, and glass particles.

Exemplary Uses of Biomarkers

In various exemplary embodiments, methods are provided for diagnosing pancreatic cancer in an individual by detecting one or more biomarker values corresponding to one or more biomarkers that are present in the circulation of an individual, such as in serum or plasma, by any number of analytical methods, including any of the analytical methods described herein. These biomarkers are, for example, differentially expressed in individuals with pancreatic cancer as compared to individuals without pancreatic cancer. Detection of the differential expression of a biomarker in an individual can be used, for example, to permit the early diagnosis of pancreatic cancer, to distinguish between a benign and malignant mass (such as, for example, a mass observed on a computed tomography (CT) scan, MRI or ultrasound), to monitor pancreatic cancer recurrence, or for differential diagnosis from other clinical conditions such as acute or chronic pancreatitis (or both), pancreatic obstruction, GERD, gallstones, or abnormal imaging later found to be benign.

Any of the biomarkers described herein may be used in a variety of clinical indications for pancreatic cancer, including any of the following: detection of pancreatic cancer (such as in a high-risk individual or population); characterizing pancreatic cancer (e.g., determining pancreatic cancer type, sub-type, or stage), such as by distinguishing between pancreatic cancer (pancreatic cancer) and acute or chronic pancreatitis (or both), pancreatic obstruction, GERD, gallstones, or abnormal imaging later found to be benign and/or between adenocarcinoma and other malignant cell types (or otherwise facilitating histopathology); determining whether a pancreatic mass is benign or a malignant pancreatic tumor; determining pancreatic cancer prognosis; monitoring pancreatic cancer progression or remission; monitoring for pancreatic cancer recurrence; monitoring metastasis; treatment selection; monitoring response to a therapeutic agent or other treatment; stratification of individuals for endoscopic ultrasound (EUS) screening (e.g., identifying those individuals at greater risk of pancreatic cancer and thereby most likely to benefit from radiologic screening, thus increasing the positive predictive value of EUS); combining biomarker testing with additional biomedical information, such as smoking or alcohol history, etc., or CA 19-9 level, the presence of a genetic marker(s) indicating a higher risk for pancreatic cancer, etc., or with mass size, morphology, presence of ascites, etc. (such as to provide an assay with increased diagnostic performance compared to CA 19-9 testing or other biomarker testing or with mass size, morphology, etc.); facilitating the diagnosis of an abdominal mass as malignant or benign; facilitating clinical decision making once an abdominal mass is observed on CT, MRI, PET or EUS (e.g., ordering repeat radiologic scans if the abdominal mass is deemed to be low risk, such as if a biomarker-based test is negative, with or without categorization of mass size, or considering biopsy if the mass is deemed medium to high risk, such as if a biomarker-based test is positive, with or without categorization of mass size or extent of tissue invasion); and facilitating decisions regarding clinical follow-up (e.g., whether to implement repeat radiologic imaging scans, fine needle biopsy, or surgery after observing an abdominal mass on imaging). Biomarker testing may improve positive predictive value (PPV) over EUS screening of high risk individuals alone. In addition to their utilities in conjunction with EUS screening, the biomarkers described herein can also be used in conjunction with any other imaging modalities used for pancreatic cancer, such as CT, MRI or PET scan. Furthermore, the described biomarkers may also be useful in permitting certain of these uses before indications of pancreatic cancer are detected by imaging modalities or other clinical correlates, or before symptoms appear. It further includes distinguishing acute or chronic pancreatitis (or both), pancreatic obstruction, GERD, gallstones, or abnormal imaging later found to be benign from pancreatic cancer.

As an example of the manner in which any of the biomarkers described herein can be used to diagnose pancreatic cancer, differential expression of one or more of the described biomarkers in an individual who is not known to have pancreatic cancer may indicate that the individual has pancreatic cancer, thereby enabling detection of pancreatic cancer at an early stage of the disease when treatment is most effective, perhaps before the pancreatic cancer is detected by other means or before symptoms appear. Overexpression of one or more of the biomarkers during the course of pancreatic cancer may be indicative of pancreatic cancer progression, e.g., a pancreatic tumor is growing and/or metastasizing (and thus indicate a poor prognosis), whereas a decrease in the degree to which one or more of the biomarkers is differentially expressed (i.e., in subsequent biomarker tests, the expression level in the individual is moving toward or approaching a "normal" expression level) may be indicative of pancreatic cancer remission, e.g., a pancreatic tumor is shrinking (and thus indicate a good or better prognosis). Similarly, an increase in the degree to which one or more of the biomarkers is differentially expressed (i.e., in subsequent biomarker tests, the expression level in the individual is moving further away from a "normal" expression level) during the course of pancreatic cancer treatment may indicate that the pancreatic cancer is progressing and therefore indicate that the treatment is ineffective, whereas a decrease in differential expression of one or more of the biomarkers during the course of pancreatic cancer treatment may be indicative of pancreatic cancer remission and therefore indicate that the treatment is working successfully. Additionally, an increase or decrease in the differential expression of one or more of the biomarkers after an individual has apparently been cured of pancreatic cancer may be indicative of pancreatic cancer recurrence. In a situation such as this, for example, the individual can be re-started on therapy (or the therapeutic regimen modified such as to increase dosage amount and/or frequency, if the individual has maintained therapy) at an earlier stage than if the recurrence of pancreatic cancer was not detected until later. Furthermore, a differential expression level of one or more of the biomarkers in an individual may be predictive of the individual's response to a particular therapeutic agent. In monitoring for pancreatic cancer recurrence or progression, changes in the biomarker expression levels may indicate the need for repeat imaging (e.g., repeat EUS), such as to determine pancreatic cancer activity or to determine the need for changes in treatment.

Detection of any of the biomarkers described herein may be particularly useful following, or in conjunction with, pancreatic cancer treatment, such as to evaluate the success of the treatment or to monitor pancreatic cancer remission, recurrence, and/or progression (including metastasis) following treatment. Pancreatic cancer treatment may include, for example, administration of a therapeutic agent to the individual, performance of surgery (e.g., surgical resection of at least a portion of a pancreatic tumor or removal of pancreatic and surrounding tissue), administration of radiation therapy, or any other type of pancreatic cancer treatment used in the art, and any combination of these treatments. For example, any of the biomarkers may be detected at least once after treatment or may be detected multiple times after treatment (such as at periodic intervals), or may be detected both before and after treatment. Differential expression levels of any of the biomarkers in an individual over time may be indicative of pancreatic cancer progression, remission, or recurrence, examples of which include any of the following: an increase or decrease in the expression level of the biomarkers after treatment compared with the expression level of the biomarker before treatment; an increase or decrease in the expression level of the biomarker at a later time point after treatment compared with the expression level of the biomarker at an earlier time point after treatment; and a differential expression level of the biomarker at a single time point after treatment compared with normal levels of the biomarker.

As a specific example, the biomarker levels for any of the biomarkers described herein can be determined in pre-surgery and post-surgery (e.g., 2-8 weeks after surgery) serum or plasma samples. An increase in the biomarker expression level(s) in the post-surgery sample compared with the pre-surgery sample can indicate progression of pancreatic cancer (e.g., unsuccessful surgery), whereas a decrease in the biomarker expression level(s) in the post-surgery sample compared with the pre-surgery sample can indicate regression of pancreatic cancer (e.g., the surgery successfully removed the pancreatic tumor). Similar analyses of the biomarker levels can be carried out before and after other forms of treatment, such as before and after radiation therapy or administration of a therapeutic agent or cancer vaccine.

In addition to testing biomarker levels as a stand-alone diagnostic test, biomarker levels can also be done in conjunction with determination of SNPs or other genetic lesions or variability that are indicative of increased risk of susceptibility of disease. (See, e.g., Amos et al., Nature Genetics 40, 616-622 (2009)).

In addition to testing biomarker levels as a stand-alone diagnostic test, biomarker levels can also be done in conjunction with radiologic screening. In addition to testing biomarker levels as a stand-alone diagnostic test, biomarker levels can also be done in conjunction with relevant symptoms or genetic testing. Detection of any of the biomarkers described herein may be useful after pancreatic mass has been observed through imaging to aid in the diagnosis of pancreatic cancer and guide appropriate clinical care of the individual, including care by an appropriate surgical specialist or by palliative therapy in the unresectable patient. In addition to testing biomarker levels in conjunction with relevant symptoms or risk factors, information regarding the biomarkers can also be evaluated in conjunction with other types of data, particularly data that indicates an individual's risk for pancreatic cancer (e.g., patient clinical history, symptoms, family history of pancreatic cancer, history of smoking or alcohol use, sudden onset of diabetes mellitus, jaundice, risk factors such as the presence of a genetic marker(s), and/or status of other biomarkers, etc.). These various data can be assessed by automated methods, such as a computer program/software, which can be embodied in a computer or other apparatus/device.

In addition to testing biomarker levels in conjunction with radiologic screening in high risk individuals (e.g., assessing biomarker levels in conjunction with size or other characteristics of a pancreatic mass observed on an imaging scan), information regarding the biomarkers can also be evaluated in conjunction with other types of data, particularly data that indicates an individual's risk for pancreatic cancer (e.g., patient clinical history, symptoms, family history of cancer, risk factors such as whether or not the individual is a smoker, heavy alcohol user and/or status of other biomarkers, etc.). These various data can be assessed by automated methods, such as a computer program/software, which can be embodied in a computer or other apparatus/device.

Any of the described biomarkers may also be used in imaging tests. For example, an imaging agent can be coupled to any of the described biomarkers, which can be used to aid in pancreatic cancer diagnosis, to monitor disease progression/remission or metastasis, to monitor for disease recurrence, or to monitor response to therapy, among other uses.

Detection and Determination of Biomarkers and Biomarker Values

A biomarker value for the biomarkers described herein can be detected using any of a variety of known analytical methods. In one embodiment, a biomarker value is detected using a capture reagent. As used herein, a "capture agent" or "capture reagent" refers to a molecule that is capable of binding specifically to a biomarker. In various embodiments, the capture reagent can be exposed to the biomarker in solution or can be exposed to the biomarker while the capture reagent is immobilized on a solid support. In other embodiments, the capture reagent contains a feature that is reactive with a secondary feature on a solid support. In these embodiments, the capture reagent can be exposed to the biomarker in solution, and then the feature on the capture reagent can be used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, imprinted polymers, avimers, peptidomimetics, a hormone receptor, a cytokine receptor, and synthetic receptors, and modifications and fragments of these.

In some embodiments, a biomarker value is detected using a biomarker/capture reagent complex.

In other embodiments, the biomarker value is derived from the biomarker/capture reagent complex and is detected indirectly, such as, for example, as a result of a reaction that is subsequent to the biomarker/capture reagent interaction, but is dependent on the formation of the biomarker/capture reagent complex.

In some embodiments, the biomarker value is detected directly from the biomarker in a biological sample.

In one embodiment, the biomarkers are detected using a multiplexed format that allows for the simultaneous detection of two or more biomarkers in a biological sample. In one embodiment of the multiplexed format, capture reagents are immobilized, directly or indirectly, covalently or non-covalently, in discrete locations on a solid support. In another embodiment, a multiplexed format uses discrete solid supports where each solid support has a unique capture reagent associated with that solid support, such as, for example quantum dots. In another embodiment, an individual device is used for the detection of each one of multiple biomarkers to be detected in a biological sample. Individual devices can be configured to permit each biomarker in the biological sample to be processed simultaneously. For example, a microtiter plate can be used such that each well in the plate is used to uniquely analyze one of multiple biomarkers to be detected in a biological sample.

In one or more of the foregoing embodiments, a fluorescent tag can be used to label a component of the biomarker/capture complex to enable the detection of the biomarker value. In various embodiments, the fluorescent label can be conjugated to a capture reagent specific to any of the biomarkers described herein using known techniques, and the fluorescent label can then be used to detect the corresponding biomarker value. Suitable fluorescent labels include rare earth chelates, fluorescein and its derivatives, rhodamine and its derivatives, dansyl, allophycocyanin, PBXL-3, Qdot 605, Lissamine, phycoerythrin, Texas Red, and other such compounds.

In one embodiment, the fluorescent label is a fluorescent dye molecule. In some embodiments, the fluorescent dye molecule includes at least one substituted indolium ring system in which the substituent on the 3-carbon of the indolium ring contains a chemically reactive group or a conjugated substance. In some embodiments, the dye molecule includes an AlexFluor molecule, such as, for example, AlexaFluor 488, AlexaFluor 532, AlexaFluor 647, AlexaFluor 680, or AlexaFluor 700. In other embodiments, the dye molecule includes a first type and a second type of dye molecule, such as, e.g., two different AlexaFluor molecules. In other embodiments, the dye molecule includes a first type and a second type of dye molecule, and the two dye molecules have different emission spectra.

Fluorescence can be measured with a variety of instrumentation compatible with a wide range of assay formats. For example, spectrofluorimeters have been designed to analyze microtiter plates, microscope slides, printed arrays, cuvettes, etc. See Principles of Fluorescence Spectroscopy, by J. R. Lakowicz, Springer Science+Business Media, Inc., 2004. See Bioluminescence & Chemiluminescence: Progress & Current Applications; Philip E. Stanley and Larry J. Kricka editors, World Scientific Publishing Company, January 2002.

In one or more of the foregoing embodiments, a chemiluminescence tag can optionally be used to label a component of the biomarker/capture complex to enable the detection of a biomarker value. Suitable chemiluminescent materials include any of oxalyl chloride, Rodamin 6G, Ru(bipy)32+, TMAE (tetrakis(dimethylamino)ethylene), Pyrogallol (1,2,3-trihydroxibenzene), Lucigenin, peroxyoxalates, Aryl oxalates. Acridinium esters, dioxetanes, and others.

In yet other embodiments, the detection method includes an enzyme/substrate combination that generates a detectable signal that corresponds to the biomarker value. Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In yet other embodiments, the detection method can be a combination of fluorescence, chemiluminescence, radionuclide or enzyme/substrate combinations that generate a measurable signal. Multimodal signaling could have unique and advantageous characteristics in biomarker assay formats.

More specifically, the biomarker values for the biomarkers described herein can be detected using known analytical methods including, singleplex aptamer assays, multiplexed aptamer assays, singleplex or multiplexed immunoassays, mRNA expression profiling, miRNA expression profiling, mass spectrometric analysis, histological/cytological methods, etc. as detailed below.

Determination of Biomarker Values Using Aptamer-Based Assays

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands"; see also, e.g., U.S. Pat. Nos. 6,242,246, 6,458,543, and 6,503,715, each of which is entitled "Nucleic Acid Ligand Diagnostic Biochip". Once the microarray is contacted with a sample, the aptamers bind to their respective target molecules present in the sample and thereby enable a determination of a biomarker value corresponding to a biomarker.

As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

As used herein, a "SOMAmer" or Slow Off-Rate Modified Aptamer refers to an aptamer having improved off-rate characteristics. SOMAmers can be generated using the improved SELEX methods described in U.S. Publication No. 2009/0004667, entitled "Method for Generating Aptamers with Improved Off-Rates."

The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH2), 2'-fluoro (2'-F), and/or 2'-O-methyl (2'-OMe). See also, U.S. Patent Application Publication 20090098549, entitled "SELEX and PHOTOSELEX", which describes nucleic acid libraries having expanded physical and chemical properties and their use in SELEX and photoSELEX.

SELEX can also be used to identify aptamers that have desirable off-rate characteristics. See U.S. Patent Application Publication 20090004667, entitled "Method for Generating Aptamers with Improved Off-Rates", which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers with improved off-rate performance.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers. In this manner, the assay enables the detection of a biomarker value corresponding to a biomarker in the test sample.

In both of these assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Aptamer assays that permit an aptamer to capture its target in solution and then employ separation steps that are designed to remove specific components of the aptamer-target mixture prior to detection have also been described (see U.S. Patent Application Publication 20090042206, entitled "Multiplexed Analyses of Test Samples"). The described aptamer assay methods enable the detection and quantification of a non-nucleic acid target (e.g., a protein target) in a test sample by detecting and quantifying a nucleic acid (i.e., an aptamer). The described methods create a nucleic acid surrogate (i.e. the aptamer) for detecting and quantifying a non-nucleic acid target, thus allowing the wide variety of nucleic acid technologies, including amplification, to be applied to a broader range of desired targets, including protein targets.

Aptamers can be constructed to facilitate the separation of the assay components from an aptamer biomarker complex (or photoaptamer biomarker covalent complex) and permit isolation of the aptamer for detection and/or quantification. In one embodiment, these constructs can include a cleavable or releasable element within the aptamer sequence. In other embodiments, additional functionality can be introduced into the aptamer, for example, a labeled or detectable component, a spacer component, or a specific binding tag or immobilization element. For example, the aptamer can include a tag connected to the aptamer via a cleavable moiety, a label, a spacer component separating the label, and the cleavable moiety. In one embodiment, a cleavable element is a photocleavable linker. The photocleavable linker can be attached to a biotin moiety and a spacer section, can include an NHS group for derivatization of amines, and can be used to introduce a biotin group to an aptamer, thereby allowing for the release of the aptamer later in an assay method.

Homogenous assays, done with all assay components in solution, do not require separation of sample and reagents prior to the detection of signal. These methods are rapid and easy to use. These methods generate signal based on a molecular capture or binding reagent that reacts with its specific target. For pancreatic cancer, the molecular capture reagents would be an aptamer or an antibody or the like and the specific target would be a pancreatic cancer biomarker of Table 1, Col. 2.

In one embodiment, a method for signal generation takes advantage of anisotropy signal change due to the interaction of a fluorophore-labeled capture reagent with its specific biomarker target. When the labeled capture reacts with its target, the increased molecular weight causes the rotational motion of the fluorophore attached to the complex to become much slower changing the anisotropy value. By monitoring the anisotropy change, binding events may be used to quantitatively measure the biomarkers in solutions. Other methods include fluorescence polarization assays, molecular beacon methods, time resolved fluorescence quenching, chemiluminescence, fluorescence resonance energy transfer, and the like.

An exemplary solution-based aptamer assay that can be used to detect a biomarker value corresponding to a biomarker in a biological sample includes the following: (a) preparing a mixture by contacting the biological sample with an aptamer that includes a first tag and has a specific affinity for the biomarker, wherein an aptamer affinity complex is formed when the biomarker is present in the sample; (b) exposing the mixture to a first solid support including a first capture element, and allowing the first tag to associate with the first capture element; (c) removing any components of the mixture not associated with the first solid support; (d) attaching a second tag to the biomarker component of the aptamer affinity complex; (e) releasing the aptamer affinity complex from the first solid support; (f) exposing the released aptamer affinity complex to a second solid support that includes a second capture element and allowing the second tag to associate with the second capture element; (g) removing any non-complexed aptamer from the mixture by partitioning the non-complexed aptamer from the aptamer affinity complex; (h) eluting the aptamer from the solid support; and (i) detecting the biomarker by detecting the aptamer component of the aptamer affinity complex.

Any means known in the art can be used to detect a biomarker value by detecting the aptamer component of an aptamer affinity complex. A number of different detection methods can be used to detect the aptamer component of an affinity complex, such as, for example, hybridization assays, mass spectroscopy, or QPCR. In some embodiments, nucleic acid sequencing methods can be used to detect the aptamer component of an aptamer affinity complex and thereby detect a biomarker value. Briefly, a test sample can be subjected to any kind of nucleic acid sequencing method to identify and quantify the sequence or sequences of one or more aptamers present in the test sample. In some embodiments, the sequence includes the entire aptamer molecule or any portion of the molecule that may be used to uniquely identify the molecule. In other embodiments, the identifying sequencing is a specific sequence added to the aptamer; such sequences are often referred to as "tags," "barcodes," or "zipcodes." In some embodiments, the sequencing method includes enzymatic steps to amplify the aptamer sequence or to convert any kind of nucleic acid, including RNA and DNA that contain chemical modifications to any position, to any other kind of nucleic acid appropriate for sequencing.

In some embodiments, the sequencing method includes one or more cloning steps. In other embodiments the sequencing method includes a direct sequencing method without cloning.

In some embodiments, the sequencing method includes a directed approach with specific primers that target one or more aptamers in the test sample. In other embodiments, the sequencing method includes a shotgun approach that targets all aptamers in the test sample.

In some embodiments, the sequencing method includes enzymatic steps to amplify the molecule targeted for sequencing. In other embodiments, the sequencing method directly sequences single molecules. An exemplary nucleic acid sequencing-based method that can be used to detect a biomarker value corresponding to a biomarker in a biological sample includes the following: (a) converting a mixture of aptamers that contain chemically modified nucleotides to unmodified nucleic acids with an enzymatic step; (b) shotgun sequencing the resulting unmodified nucleic acids with a massively parallel sequencing platform such as, for example, the 454 Sequencing System (454 Life Sciences/Roche), the Illumina Sequencing System (Illumina), the ABI SOLiD Sequencing System (Applied Biosystems), the HeliScope Single Molecule Sequencer (Helicos Biosciences), or the Pacific Biosciences Real Time Single-Molecule Sequencing System (Pacific BioSciences) or the Polonator G Sequencing System (Dover Systems); and (c) identifying and quantifying the aptamers present in the mixture by specific sequence and sequence count.

Determination of Biomarker Values Using Immunoassays

Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes (I125) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Determination of Biomarker Values using Gene Expression Profiling

Measuring mRNA in a biological sample may be used as a surrogate for detection of the level of the corresponding protein in the biological sample. Thus, any of the biomarkers or biomarker panels described herein can also be detected by detecting the appropriate RNA.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols. Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve wide-spread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Detection of Biomarkers Using In Vivo Molecular Imaging Technologies

Any of the described biomarkers (see Table 1, Col. 2) may also be used in molecular imaging tests. For example, an imaging agent can be coupled to any of the described biomarkers, which can be used to aid in pancreatic cancer diagnosis, to monitor disease progression/remission or metastasis, to monitor for disease recurrence, or to monitor response to therapy, among other uses.

In vivo imaging technologies provide non-invasive methods for determining the state of a particular disease in the body of an individual. For example, entire portions of the body, or even the entire body, may be viewed as a three dimensional image, thereby providing valuable information concerning morphology and structures in the body. Such technologies may be combined with the detection of the biomarkers described herein to provide information concerning the cancer status, in particular the pancreatic cancer status, of an individual.

The use of in vivo molecular imaging technologies is expanding due to various advances in technology. These advances include the development, of new contrast agents or labels, such as radiolabels and/or fluorescent labels, which can provide strong signals within the body; and the development of powerful new imaging technology, which can detect and analyze these signals from outside the body, with sufficient sensitivity and accuracy to provide useful information. The contrast agent can be visualized in an appropriate imaging system, thereby providing an image of the portion or portions of the body in which the contrast agent is located. The contrast agent may be bound to or associated with a capture reagent, such as an aptamer or an antibody, for example, and/or with a peptide or protein, or an oligonucleotide (for example, for the detection of gene expression), or a complex containing any of these with one or more macromolecules and/or other particulate forms.

The contrast agent may also feature a radioactive atom that is useful in imaging. Suitable radioactive atoms include tecmetium-99 ml or iodine-123 for scintigraphic studies. Other readily detectable moieties include, for example, spin labels for magnetic resonance imaging (MRI) such as, for example, iodine-123 again, iodine-131, indium-111, fluorine-19, carbon-13, nitrogen-15, oxygen-17, gadolinium, manganese or iron. Such labels are well known in the art and could easily be selected by one of ordinary skill in the art.

Standard imaging techniques include but are not limited to magnetic resonance imaging, computed tomography scanning, positron emission tomography (PET), single photon emission computed tomography (SPECT), and the like. For diagnostic in vivo imaging, the type of detection instrument available is a major factor in selecting a given contrast agent, such as a given radionuclide and the particular biomarker that it is used to target (protein, mRNA, and the like). The radionuclide chosen typically has a type of decay that is detectable by a given type of instrument. Also, when selecting a radionuclide for in vivo diagnosis, its half-life should be long enough to enable detection at the time of maximum uptake by the target tissue but short enough that deleterious radiation of the host is minimized.

Exemplary imaging techniques include but are not limited to PET and SPECT, which are imaging techniques in which a radionuclide is synthetically or locally administered to an individual. The subsequent uptake of the radiotracer is measured over time and used to obtain information about the targeted tissue and the biomarker. Because of the high-energy (gamma-ray) emissions of the specific isotopes employed and the sensitivity and sophistication of the instruments used to detect them, the two-dimensional distribution of radioactivity may be inferred from outside of the body.

Commonly used positron-emitting nuclides in PET include, for example, carbon-11, nitrogen-13, oxygen-15, and fluorine-18. Isotopes that decay by electron capture and/or gamma-emission are used in SPECT and include, for example iodine-123 and technetium-99m. An exemplary method for labeling amino acids with technetium-99m is the reduction of pertechnetate ion in the presence of a chelating precursor to form the labile technetium-99m-precursor complex, which, in turn, reacts with the metal binding group of a bifunctionally modified chemotactic peptide to form a technetium-99m-chemnotactic peptide conjugate.

Antibodies are frequently used for such in vivo imaging diagnostic methods. The preparation and use of antibodies for in vivo diagnosis is well known in the art. Labeled antibodies which specifically bind any of the biomarkers in Table 1, Col. 2 can be injected into an individual suspected of having a certain type of cancer (e.g., pancreatic cancer), detectable according to the particular biomarker used, for the purpose of diagnosing or evaluating the disease status of the individual. The label used will be selected in accordance with the imaging modality to be used, as previously described. Localization of the label permits determination of the spread of the cancer. The amount of label within an organ or tissue also allows determination of the presence or absence of cancer in that organ or tissue.

Similarly, aptamers may be used for such in vivo imaging diagnostic methods. For example, an aptamer that was used to identify a particular biomarker described in Table 1, Col. 2 (and therefore binds specifically to that particular biomarker) may be appropriately labeled and injected into an individual suspected of having pancreatic cancer, detectable according to the particular biomarker, for the purpose of diagnosing or evaluating the pancreatic cancer status of the individual. The label used will be selected in accordance with the imaging modality to be used, as previously described. Localization of the label permits determination of the spread of the cancer. The amount of label within an organ or tissue also allows determination of the presence or absence of cancer in that organ or tissue. Aptamer-directed imaging agents could have unique and advantageous characteristics relating to tissue penetration, tissue distribution, kinetics, elimination, potency, and selectivity as compared to other imaging agents.

Such techniques may also optionally be performed with labeled oligonucleotides, for example, for detection of gene expression through imaging with antisense oligonucleotides. These methods are used for in situ hybridization, for example, with fluorescent molecules or radionuclides as the label. Other methods for detection of gene expression include, for example, detection of the activity of a reporter gene.

Another general type of imaging technology is optical imaging, in which fluorescent signals within the subject are detected by an optical device that is external to the subject. These signals may be due to actual fluorescence and/or to bioluminescence. Improvements in the sensitivity of optical detection devices have increased the usefulness of optical imaging for in vivo diagnostic assays.

The use of in vivo molecular biomarker imaging is increasing, including for clinical trials, for example, to more rapidly measure clinical efficacy in trials for new cancer therapies and/or to avoid prolonged treatment with a placebo for those diseases, such as multiple sclerosis, in which such prolonged treatment may be considered to be ethically questionable.

For a review of other techniques, see N. Blow, Nature Methods, 6, 465-469, 2009.

Determination of Biomarker Values Using Histology/Cytology Methods

For evaluation of pancreatic cancer, a variety of tissue samples may be used in histological or cytological methods. Sample selection depends on the primary tumor location and sites of metastases. For example, tissue samples (forceps biopsy, fine needle aspiration (FNA), and/or brush cytology) collected at the time of endoscopic retrograde cholangiopancreatography (ERCP), or endoscopic ultrasound (EUS)-guided FNA can be used for histology. Ascites or peritoneal washings or pancreatic fluid can be used for cyotology. Any of the biomarkers identified herein that were shown to be up-regulated (ee Table 1. Col. 6) in the individuals with pancreatic can be used to stain a histological specimen as an indication of disease.

In one embodiment, one or more capture reagent/s specific to the corresponding biomarker/s are used in a cytological evaluation of a pancreatic cell sample and may include one or more of the following: collecting a cell sample, fixing the cell sample, dehydrating, clearing, immobilizing the cell sample on a microscope slide, permeabilizing the cell sample, treating for analyte retrieval, staining, destaining, washing, blocking, and reacting with one or more capture reagent/s in a buffered solution. In another embodiment, the cell sample is produced from a cell block.

In another embodiment, one or more capture reagent/s specific to the corresponding biomarkers are used in a histological evaluation of a pancreatic tissue sample and may include one or more of the following: collecting a tissue specimen, fixing the tissue sample, dehydrating, clearing, immobilizing the tissue sample on a microscope slide, permeabilizing the tissue sample, treating for analyte retrieval, staining, destaining, washing, blocking, rehydrating, and reacting with capture reagent/s in a buffered solution. In another embodiment, fixing and dehydrating are replaced with freezing.

In another embodiment, the one or more aptamer/s specific to the corresponding biomarker/s are reacted with the histological or cytological sample and can serve as the nucleic acid target in a nucleic acid amplification method. Suitable nucleic acid amplification methods include, for example, PCR, q-beta replicase, rolling circle amplification, strand displacement, helicase dependent amplification, loop mediated isothermal amplification, ligase chain reaction, and restriction and circularization aided rolling circle amplification.

In one embodiment, the one or more capture reagent/s specific to the corresponding biomarkers for use in the histological or cytological evaluation are mixed in a buffered solution that can include any of the following: blocking materials, competitors, detergents, stabilizers, carrier nucleic acid, polyanionic materials, etc.

A "cytology protocol" generally includes sample collection, sample fixation, sample immobilization, and staining. "Cell preparation" can include several processing steps after sample collection, including the use of one or more slow off-rate aptamers for the staining of the prepared cells.

Sample collection can include directly placing the sample in an untreated transport container, placing the sample in a transport container containing some type of media, or placing the sample directly onto a slide (immobilization) without any treatment or fixation.

Sample immobilization can be improved by applying a portion of the collected specimen to a glass slide that is treated with polylysine, gelatin, or a silane. Slides can be prepared by smearing a thin and even layer of cells across the slide. Care is generally taken to minimize mechanical distortion and drying artifacts. Liquid specimens can be processed in a cell block method. Or, alternatively, liquid specimens can be mixed 1:1 with the fixative solution for about 10 minutes at room temperature.

Cell blocks can be prepared from residual effusions, sputum, urine sediments, gastrointestinal fluids, cell scraping, or fine needle aspirates. Cells are concentrated or packed by centrifugation or membrane filtration. A number of methods for cell block preparation have been developed. Representative procedures include the fixed sediment, bacterial agar, or membrane filtration methods. In the fixed sediment method, the cell sediment is mixed with a fixative like Bouins, picric acid, or buffered formalin and then the mixture is centrifuged to pellet the fixed cells. The supernatant is removed, drying the cell pellet as completely as possible. The pellet is collected and wrapped in lens paper and then placed in a tissue cassette. The tissue cassette is placed in a jar with additional fixative and processed as a tissue sample. Agar method is very similar but the pellet is removed and dried on paper towel and then cut in half. The cut side is placed in a drop of melted agar on a glass slide and then the pellet is covered with agar making sure that no bubbles form in the agar. The agar is allowed to harden and then any excess agar is trimmed away. This is placed in a tissue cassette and the tissue process completed. Alternatively, the pellet may be directly suspended in 2% liquid agar at 65° C. and the sample centrifuged. The agar cell pellet is allowed to solidify for an hour at 4° C. The solid agar may be removed from the centrifuge tube and sliced in half. The agar is wrapped in filter paper and then the tissue cassette. Processing from this point forward is as described above. Centrifugation can be replaced in any these procedures with membrane filtration. Any of these processes may be used to generate a "cell block sample".

Cell blocks can be prepared using specialized resin including Lowicryl resins, LR White, LR Gold, Unicryl, and MonoStep. These resins have low viscosity and can be polymerized at low temperatures and with ultra violet (UV) light. The embedding process relies on progressively cooling the sample during dehydration, transferring the sample to the resin, and polymerizing a block at the final low temperature at the appropriate UV wavelength.

Cell block sections can be stained with hematoxylin-eosin for cytomorphological examination while additional sections are used for examination for specific markers.

Whether the process is cytologoical or histological, the sample may be fixed prior to additional processing to prevent sample degradation. This process is called "fixation" and describes a wide range of materials and procedures that may be used interchangeably. The sample fixation protocol and reagents are best selected empirically based on the targets to be detected and the specific cell/tissue type to be analyzed. Sample fixation relies on reagents such as ethanol, polyethylene glycol, methanol, formalin, or isopropanol. The samples should be fixed as soon after collection and affixation to the slide as possible. However, the fixative selected can introduce structural changes into various molecular targets making their subsequent detection more difficult. The fixation and immobilization processes and their sequence can modify the appearance of the cell and these changes must be anticipated and recognized by the cytotechnologist. Fixatives can cause shrinkage of certain cell types and cause the cytoplasm to appear granular or reticular. Many fixatives function by crosslinking cellular components. This can damage or modify specific epitopes, generate new epitopes, cause molecular associations, and reduce membrane permeability. Formalin fixation is one of the most common cytological/histological approaches. Formalin forms methyl bridges between neighboring proteins or within proteins. Precipitation or coagulation is also used for fixation and ethanol is frequently used in this type of fixation. A combination of crosslinking and precipitation can also be used for fixation. A strong fixation process is best at preserving morphological information while a weaker fixation process is best for the preservation of molecular targets.

A representative fixative is 50% absolute ethanol. 2 mM polyethylene glycol (PEG), 1.85% formaldehyde. Variations on this formulation include ethanol (50% to 95%), methanol (20%-50%), and formalin (formaldehyde) only. Another common fixative is 2% PEG 1500, 50% ethanol, and 3% methanol. Slides are place in the fixative for about 10 to 15 minutes at room temperature and then removed and allowed to dry. Once slides are fixed they can be rinsed with a buffered solution like PBS.

A wide range of dyes can be used to differentially highlight and contrast or "stain" cellular, sub-cellular, and tissue features or morphological structures. Hematoylin is used to stain nuclei a blue or black color. Orange G-6 and Eosin Azure both stain the cell's cytoplasm. Orange G stains keratin and glycogen containing cells yellow. Eosin Y is used to stain nucleoli, cilia, red blood cells, and superficial epithelial squamous cells. Romanowsky stains are used for air dried slides and are useful in enhancing pleomorphism and distinguishing extracellular from intracytoplasmic material.

The staining process can include a treatment to increase the permeability of the cells to the stain. Treatment of the cells with a detergent can be used to increase permeability. To increase cell and tissue permeability, fixed samples can be further treated with solvents, saponins, or non-ionic detergents. Enzymatic digestion can also improve the accessibility of specific targets in a tissue sample.

After staining, the sample is dehydrated using a succession of alcohol rinses with increasing alcohol concentration. The final wash is done with xylene or a xylene substitute, such as a citrus terpene, that has a refractive index close to that of the coverslip to be applied to the slide. This final step is referred to as clearing. Once the sample is dehydrated and cleared, a mounting medium is applied. The mounting medium is selected to have a refractive index close to the glass and is capable of bonding the coverslip to the slide. It will also inhibit the additional drying, shrinking, or fading of the cell sample.

Regardless of the stains or processing used, the final evaluation of the pancreatic cytological specimen is made by some type of microscopy to permit a visual inspection of the morphology and a determination of the marker's presence or absence. Exemplary microscopic methods include brightfield, phase contrast, fluorescence, and differential interference contrast.

If secondary tests are required on the sample after examination, the coverslip may be removed and the slide destained. Destaining involves using the original solvent systems used in staining the slide originally without the added dye and in a reverse order to the original staining procedure. Destaining may also be completed by soaking the slide in an acid alcohol until the cells are colorless. Once colorless the slides are rinsed well in a water bath and the second staining procedure applied.

In addition, specific molecular differentiation may be possible in conjunction with the cellular morphological analysis through the use of specific molecular reagents such as antibodies or nucleic acid probes or aptamers. This improves the accuracy of diagnostic cytology. Micro-dissection can be used to isolate a subset of cells for additional evaluation, in particular, for genetic evaluation of abnormal chromosomes, gene expression, or mutations.

Preparation of a tissue sample for histological evaluation involves fixation, dehydration, infiltration, embedding, and sectioning. The fixation reagents used in histology are very similar or identical to those used in cytology and have the same issues of preserving morphological features at the expense of molecular ones such as individual proteins. Time can be saved if the tissue sample is not fixed and dehydrated but instead is frozen and then sectioned while frozen. This is a more gentle processing procedure and can preserve more individual markers. However, freezing is not acceptable for long term storage of a tissue sample as sub-cellular information is lost due to the introduction of ice crystals. Ice in the frozen tissue sample also prevents the sectioning process from producing a very thin slice and thus some microscopic resolution and imaging of subcellular structures can be lost. In addition to formalin fixation, osmium tetroxide is used to fix and stain phospholipids (membranes).

Dehydration of tissues is accomplished with successive washes of increasing alcohol concentration. Clearing employs a material that is miscible with alcohol and the embedding material and involves a stepwise process starting at 50:50 alcohol:clearing reagent and then 100% clearing agent (xylene or xylene substitute). Infiltration involves incubating the tissue with a liquid form of the embedding agent (warm wax, nitrocellulose solution) first at 50:50 embedding agent: clearing agent and the 100% embedding agent. Embedding is completed by placing the tissue in a mold or cassette and filling with melted embedding agent such as wax, agar, or gelatin. The embedding agent is allowed to harden. The hardened tissue sample may then be sliced into thin section for staining and subsequent examination.

Prior to staining, the tissue section is dewaxed and rehydrated. Xylene is used to dewax the section, one or more changes of xylene may be used, and the tissue is rehydrated by successive washes in alcohol of decreasing concentration. Prior to dewax, the tissue section may be heat immobilized to a glass slide at about 80° C. for about 20 minutes.

Laser capture micro-dissection allows the isolation of a subset of cells for further analysis from a tissue section.

As in cytology, to enhance the visualization of the microscopic features, the tissue section or slice can be stained with a variety of stains. A large menu of commercially available stains can be used to enhance or identify specific features.

To further increase the interaction of molecular reagents with cytological/histological samples, a number of techniques for "analyte retrieval" have been developed. The first such technique uses high temperature heating of a fixed sample. This method is also referred to as heat-induced epitope retrieval or HIER. A variety of heating techniques have been used, including steam heating, microwaving, autoclaving, water baths, and pressure cooking or a combination of these methods of heating. Analyte retrieval solutions include, for example, water, citrate, and normal saline buffers. The key to analyte retrieval is the time at high temperature but lower temperatures for longer times have also been successfully used. Another key to analyte retrieval is the pH of the heating solution. Low pH has been found to provide the best immunostaining but also gives rise to backgrounds that frequently require the use of a second tissue section as a negative control. The most consistent benefit (increased immunostaining without increase in background) is generally obtained with a high pH solution regardless of the buffer composition. The analyte retrieval process for a specific target is empirically optimized for the target using heat, time. pH, and buffer composition as variables for process optimization. Using the microwave analyte retrieval method allows for sequential staining of different targets with antibody reagents. But the time required to achieve antibody and enzyme complexes between staining steps has also been shown to degrade cell membrane analytes. Microwave heating methods have improved in situ hybridization methods as well.

To initiate the analyte retrieval process, the section is first dewaxed and hydrated. The slide is then placed in 10 mM sodium citrate buffer pH 6.0 in a dish or jar. A representative procedure uses an 1100W microwave and microwaves the slide at 100% power for 2 minutes followed by microwaving the slides using 20% power for 18 minutes after checking to be sure the slide remains covered in liquid. The slide is then allowed to cool in the uncovered container and then rinsed with distilled water. HIER may be used in combination with an enzymatic digestion to improve the reactivity of the target to immunochemical reagents.

One such enzymatic digestion protocol uses proteinase K. A 20 g/ml concentration of proteinase K is prepared in 50 mM Tris Base, 1 mM EDTA, 0.5% Triton X-100, pH 8.0 buffer. The process first involves dewaxing sections in 2 changes of xylene, 5 minutes each. Then the sample is hydrated in 2 changes of 100% ethanol for 3 minutes each, 95% and 80% ethanol for 1 minute each, and then rinsed in distilled water. Sections are covered with Proteinase K working solution and incubated 10-20 minutes at 37 C in humidified chamber (optimal incubation time may vary depending on tissue type and degree of fixation). The sections are cooled at room temperature for 10 minutes and then rinsed in PBS Tween 20 for 2×2 min. If desired, sections can be blocked to eliminate potential interference from endogenous compounds and enzymes. The section is then incubated with primary antibody at appropriate dilution in primary antibody dilution buffer for 1 hour at room temperature or overnight at 4 C. The section is then rinsed with PBS Tween 20 for 2×2 min. Additional blocking can be performed, if required for the specific application, followed by additional rinsing with PBS Tween 20 for 3×2 min and then finally the immunostaining protocol completed.

A simple treatment with 1% SDS at room temperature has also been demonstrated to improve immunohistochemical staining. Analyte retrieval methods have been applied to slide mounted sections as well as free floating sections. Another treatment option is to place the slide in a jar containing citric acid and 0.1 Nonident. P40 at pH 6.0 and heating to 95° C. The slide is then washed with a buffer solution like PBS.

For immunological staining of tissues it may be useful to block non-specific association of the antibody with tissue proteins by soaking the section in a protein solution like serum or non-fat dry milk.

Blocking reactions may include the need to reduce the level of endogenous biotin; eliminate endogenous charge effects; inactivate endogenous nucleases; and/or inactivate endogenous enzymes like peroxidase and alkaline phosphatase. Endogenous nucleases may be inactivated by degradation with proteinase K, by heat treatment, use of a chelating agent such as EDTA or EGTA, the introduction of carrier DNA or RNA, treatment with a chaotrope such as urea, thiourea, guanidine hydrochloride, guanidine thiocyanate, lithium perchlorate, etc, or diethyl pyrocarbonate. Alkaline phosphatase may be inactivated by treated with 0.1N HCl for 5 minutes at room temperature or treatment with 1 mM levamisole. Peroxidase activity may be eliminated by treatment with 0.03% hydrogen peroxide. Endogenous biotin may be blocked by soaking the slide or section in an avidin (streptavidin, neutravidin may be substituted) solution for at least 15 minutes at room temperature. The slide or section is then washed for at least 10 minutes in buffer. This may be repeated at least three times. Then the slide or section is soaked in a biotin solution for 10 minutes. This may be repeated at least three times with a fresh biotin solution each time. The buffer wash procedure is repeated. Blocking protocols should be minimized to prevent damaging either the cell or tissue structure or the target or targets of interest but one or more of these protocols could be combined to "block" a slide or section prior to reaction with one or more slow off-rate aptamers. See Basic Medical Histology: the Biology of Cells, Tissues and Organs, authored by Richard G. Kessel, Oxford University Press. 1998.

Determination of Biomarker Values Using Mass Spectrometry MethOds

A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Conunon ion sources are, for example, electrospray, including nanospray and microspray or nmatrix-assisted laser desorption. Common mass analyzers include a quadrupole mass filter, ion trap mass analyzer and time-of-flight mass analyzer. Additional mass spectrometry methods are well known in the art (see Burlingame et al. Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight. (TOF/TOF) technology, called ultraflex III TOF/TOF, atmospheric pressure chemical ionization mass spectrometry (APCI-MS), APCI-MS/MS, APCI-(MS)N, atmospheric pressure photoionization mass spectrometry (APPI-MS), APPI-MS/MS, and APPI-(MS)N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')2 fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

Determination of Biomarker Values Using a Proximity Ligation Assay

A proximity ligation assay can be used to determine biomarker values. Briefly, a test sample is contacted with a pair of affinity probes that may be a pair of antibodies or a pair of aptamers, with each member of the pair extended with an oligonucleotide. The targets for the pair of affinity probes may be two distinct determinates on one protein or one determinate on each of two different proteins, which may exist as homo- or hetero-multimeric complexes. When probes bind to the target determinates, the free ends of the oligonucleotide extensions are brought into sufficiently close proximity to hybridize together. The hybridization of the oligonucleotide extensions is facilitated by a common connector oligonucleotide which serves to bridge together the oligonucleotide extensions when they are positioned in sufficient proximity. Once the oligonucleotide extensions of the probes are hybridized, the ends of the extensions are joined together by enzymatic DNA ligation.

Each oligonucleotide extension comprises a primer site for PCR amplification. Once the oligonucleotide extensions are ligated together, the oligonucleotides form a continuous DNA sequence which, through PCR amplification, reveals information regarding the identity and amount of the target protein, as well as, information regarding protein-protein interactions where the target determinates are on two different proteins. Proximity ligation can provide a highly sensitive and specific assay for real-time protein concentration and interaction information through use of real-time PCR. Probes that do not bind the determinates of interest do not have the corresponding oligonucleotide extensions brought into proximity and no ligation or PCR amplification can proceed, resulting in no signal being produced.

The foregoing assays enable the detection of biomarker values that are useful in methods for diagnosing pancreatic cancer, where the methods comprise detecting, in a biological sample from an individual, at least N biomarker values that each correspond to a biomarker selected from the group consisting of the biomarkers provided in Table 1, Col. 2, wherein a classification, as described in detail below, using the biomarker values indicates whether the individual has pancreatic cancer. While certain of the described pancreatic cancer biomarkers are useful alone for detecting and diagnosing pancreatic cancer, methods are also described herein for the grouping of multiple subsets of the pancreatic cancer biomarkers that are each useful as a panel of three or more biomarkers. Thus, various embodiments of the instant application provide combinations comprising N biomarkers, wherein N is at least three biomarkers. In other embodiments, N is selected to be any number from 2-65 biomarkers. It will be appreciated that N can be selected to be any number from any of the above described ranges, as well as similar, but higher order, ranges. In accordance with any of the methods described herein, biomarker values can be detected and classified individually or they can be detected and classified collectively, as for example in a multiplex assay format.

In another aspect, methods are provided for detecting an absence of pancreatic cancer, the methods comprising detecting, in a biological sample from an individual, at least N biomarker values that each correspond to a biomarker selected from the group consisting of the biomarkers provided in Table 1, Col. 2, wherein a classification, as described in detail below, of the biomarker values indicates an absence of pancreatic cancer in the individual. While certain of the described pancreatic cancer biomarkers are useful alone for detecting and diagnosing the absence of pancreatic cancer, methods are also described herein for the grouping of multiple subsets of the pancreatic cancer biomarkers that are each useful as a panel of three or more biomarkers. Thus, various embodiments of the instant application provide combinations comprising N biomarkers, wherein N is at least three biomarkers. In other embodiments, N is selected to be any number from 2-65 biomarkers. It will be appreciated that N can be selected to be any number from any of the above described ranges, as well as similar, but higher order, ranges. In accordance with any of the methods described herein, biomarker values can be detected and classified individually or they can be detected and classified collectively, as for example in a multiplex assay format.

Classification of Biomarkers and Calculation of Disease Scores

A biomarker "signature" for a given diagnostic test contains a set of markers, each marker having different levels in the populations of interest. Different levels, in this context, may refer to different means of the marker levels for the individuals in two or more groups, or different variances in the two or more groups, or a combination of both. For the simplest form of a diagnostic test, these markers can be used to assign an unknown sample from an individual into one of two groups, either diseased or not diseased. The assignment of a sample into one of two or more groups is known as classification, and the procedure used to accomplish this assignment is known as a classifier or a classification method. Classification methods may also be referred to as scoring methods. There are many classification methods that can be used to construct a diagnostic classifier from a set of biomarker values. In general, classification methods are most easily performed using supervised learning techniques where a data set is collected using samples obtained from individuals within two (or more, for multiple classification states) distinct groups one wishes to distinguish. Since the class (group or population) to which each sample belongs is known in advance for each sample, the classification method can be trained to give the desired classification response. It is also possible to use unsupervised learning techniques to produce a diagnostic classifier.

Common approaches for developing diagnostic classifiers include decision trees; bagging, boosting, forests and random forests; rule inference based learning; Parzen Windows; linear models; logistic; neural network methods; unsupervised clustering; K-means; hierarchical ascending/descending; semi-supervised learning; prototype methods; nearest neighbor; kernel density estimation; support vector machines; hidden Markov models; Boltzmann Learning; and classifiers may be combined either simply or in ways which minimize particular objective functions. For a review, see, e.g., Pattern Classification, R. O. Duda, et al., editors, John Wiley & Sons. 2nd edition, 2001; see also, The Elements of Statistical Learning—Data Mining, Inference, and Prediction, T. Iastie, et al., editors, Springer Science+Business Media, LLC, 2nd edition, 2009; each of which is incorporated by reference in its entirety.

To produce a classifier using supervised learning techniques, a set of samples called training data are obtained. In the context of diagnostic tests, training data includes samples from the distinct groups (classes) to which unknown samples will later be assigned. For example, samples collected from individuals in a control population and individuals in a particular disease population can constitute training data to develop a classifier that can classify unknown samples (or, more particularly, the individuals from whom the samples were obtained) as either having the disease or being free from the disease. The development of the classifier from the training data is known as training the classifier. Specific details on classifier training depend on the nature of the supervised learning technique. For purposes of illustration, an example of training a naïve Bayesian classifier will be described below (see, e.g., Pattern Classification, R. O. Duda, et al., editors, John Wiley & Sons, 2nd edition, 2001; see also, The Elements of Statistical Learning—Data Mining. Inference, and Prediction, T. Hastie. et al., editors, Springer Science+Business Media, LLC, 2nd edition, 2009).

Since typically there are many more potential biomarker values than samples in a training set, care must be used to avoid over-fitting. Over-fitting occurs when a statistical model describes random error or noise instead of the underlying relationship. Over-fitting can be avoided in a variety of way, including, for example, by limiting the number of markers used in developing the classifier, by assuming that the marker responses are independent of one another, by limiting the complexity of the underlying statistical model employed, and by ensuring that the underlying statistical model conforms to the data.

An illustrative example of the development of a diagnostic test using a set of biomarkers includes the application of a naïve Bayes classifier, a simple probabilistic classifier based on Bayes theorem with strict independent treatment of the biomarkers. Each biomarker is described by a class-dependent probability density function (pdf) for the measured RFU values or log RFU (relative fluorescence units) values in each class. The joint pdfs for the set of markers in one class is assumed to be the product of the individual class-dependent pdfs for each biomarker. Training a naïve Bayes classifier in this context amounts to assigning parameters ("parameterization") to characterize the class dependent pdfs. Any underlying model for the class-dependent pdfs may be used, but the model should generally conform to the data observed in the training set.

Specifically, the class-dependent probability of measuring a value $x_i$ for biomarker i in the disease class is written as $p(x_i|d)$ and the overall naïve Bayes probability of observing n markers with values $\tilde{x}=(x_1, x_2, \ldots, x_n)$ is written as $p(\tilde{x}|d)=\Pi_{i=1}^{n}p(x_i|d)$ where the individual $x_i$s are the measured biomarker levels in RFU or log RFU. The classification assignment for an unknown is facilitated by calculating the probability of being diseased $p(d|\tilde{x})$ having measured $\tilde{x}$ compared to the probability of being disease free (control) $p(c|\tilde{x})$ for the same measured values. The ratio of these probabilities is computed from the class-dependent pdfs by application of Bayes theorem, i.e., $\frac{p(d|\tilde{x})}{p(c|\tilde{x})} = \frac{p(\tilde{x}|d)p(d)}{p(\tilde{x}|c)(1-p(d))}$ where p(d) is the prevalence of the disease in the population appropriate to the test. Taking the logarithm of both sides of this ratio and substituting the naïve Bayes class-dependent probabilities from above gives $$\ln\left(\frac{p(d|\tilde{x})}{p(c|\tilde{x})}\right) = \sum_{i=1}^{n} \ln\left(\frac{p(x_i|d)}{p(x_i|c)}\right) + \ln\left(\frac{p(d)}{1-p(d)}\right).$$

This form is known as the log likelihood ratio and simply states that the log likelihood of being free of the particular disease versus having the disease and is primarily composed of the sum of individual log likelihood ratios of the n individual biomarkers. In its simplest form, an unknown sample (or, more particularly, the individual from whom the sample was obtained) is classified as being free of the disease if the above ratio is greater than zero and having the disease if the ratio is less than zero.

In one exemplary embodiment, the class-dependent biomarker pdfs $p(x_i|c)$ and $p(x_i|d)$ are assumed to be normal or log-normal distributions in the measured RFU values $x_i$, i.e. $p(x_i|c) = \frac{1}{\sqrt{2\pi}\,\sigma_{c,i}} \exp\left(-\frac{(x_i - \mu_{c,i})^2}{2\sigma_{c,i}^2}\right),$ with a similar expression for with and. Parameterization of the model requires estimation of two parameters for each class-dependent pdf, a mean $\mu$ and a variance $\sigma^2$, from the training data. This may be accomplished in a number of ways, including, for example, by maximum likelihood estimates, by least-squares, and by any other methods known to one skilled in the art. Substituting the normal distributions for and into the log-likelihood ratio defined above gives the following expression:

$$\ln\left(\frac{p(d|\tilde{x})}{p(c|\tilde{x})}\right) =$$

$$\sum_{i=1}^{n} \ln\left(\frac{\sigma_{c,i}}{\sigma_{d,i}}\right) - \frac{1}{2}\sum_{i=1}^{n}\left[\left(\frac{x_i - \mu_{d,i}}{\sigma_{d,i}}\right)^2 - \left(\frac{x_i - \mu_{c,i}}{\sigma_{c,i}}\right)^2\right] + \ln\left(\frac{p(d)}{1-p(d)}\right)$$

Once a set of $\mu$s and $\sigma^2$s have been defined for each pd in each class from the training data and the disease prevalence in the population is specified, the Bayes classifier is fully determined and may be used to classify unknown samples with measured values $\tilde{x}$.

The performance of the naïve Bayes classifier is dependent upon the number and quality of the biomarkers used to construct and train the classifier. A single biomarker will perform in accordance with its KS-distance (Kolmogorov-Smirnov), as defined in Example 3, below. If a classifier performance metric is defined as the area under the receiver operator characteristic curve (AUC), a perfect classifier will have a score of 1 and a random classifier, on average, will have a score of 0.5. The definition of the KS-distance between two sets A and B of sizes n and m is the value, $D_{n,m} = \sup_x |F_{A,n}(x) - F_{B,m}(x)|$, which is the largest difference between two empirical cumulative distribution functions (cdf). The empirical cdf for a set A of n observations $X_i$ is defined as, $$F_{A,n}(x) = \frac{1}{n}\sum_{i=1}^{n} I_{X_i \leq x},$$

where $I_{X_i \leq x}$ is the indicator function which is equal to 1 if $X_i < x$ and is otherwise equal to 0. By definition, this value is bounded between 0 and 1, where a KS-distance of 1 indicates that the emperical distributions do not overlap.

The addition of subsequent markers with good KS distances (>0.3, for example) will, in general, improve the classification performance if the subsequently added markers are independent of the first marker. Using the sensitivity plus specificity as a classifier score, it is straightforward to generate many high scoring classifiers with a variation of a greedy algorithm. (A greedy algorithm is any algorithm that follows the problem solving metaheuristic of making the locally optimal choice at each stage with the hope of finding the global optimum.)

The algorithm approach used here is described in detail in Example 4. Briefly, all single analyte classifiers are generated from a table of potential biomarkers and added to a list. Next, all possible additions of a second analyte to each of the stored single analyte classifiers is then performed, saving a predetermined number of the best scoring pairs, say, for example, a thousand, on a new list. All possible three marker classifiers are explored using this new list of the best two-marker classifiers, again saving the best thousand of these. This process continues until the score either plateaus or begins to deteriorate as additional markers are added. Those high scoring classifiers that remain after convergence can be evaluated for the desired performance for an intended use. For example, in one diagnostic application, classifiers with a high sensitivity and modest specificity may be more desirable than modest sensitivity and high specificity. In another diagnostic application, classifiers with a high specificity and a modest sensitivity may be more desirable. The desired level of performance is generally selected based upon a trade-off that must be made between the number of false positives and false negatives that can each be tolerated for the particular diagnostic application. Such trade-offs generally depend on the medical consequences of an error, either false positive or false negative.

Various other techniques are known in the art and may be employed to generate many potential classifiers from a list of biomarkers using a naïve Bayes classifier. In one embodiment, what is referred to as a genetic algorithm can be used to combine different markers using the fitness score as defined above. Genetic algorithms are particularly well suited to exploring a large diverse population of potential classifiers. In another embodiment, so-called ant colony optimization can be used to generate sets of classifiers. Other strategies that are known in the art can also be employed, including, for example, other evolutionary strategies as well as simulated annealing and other stochastic search methods. Metaheuristic methods, such as, for example, harmony search may also be employed.

Figure 2:
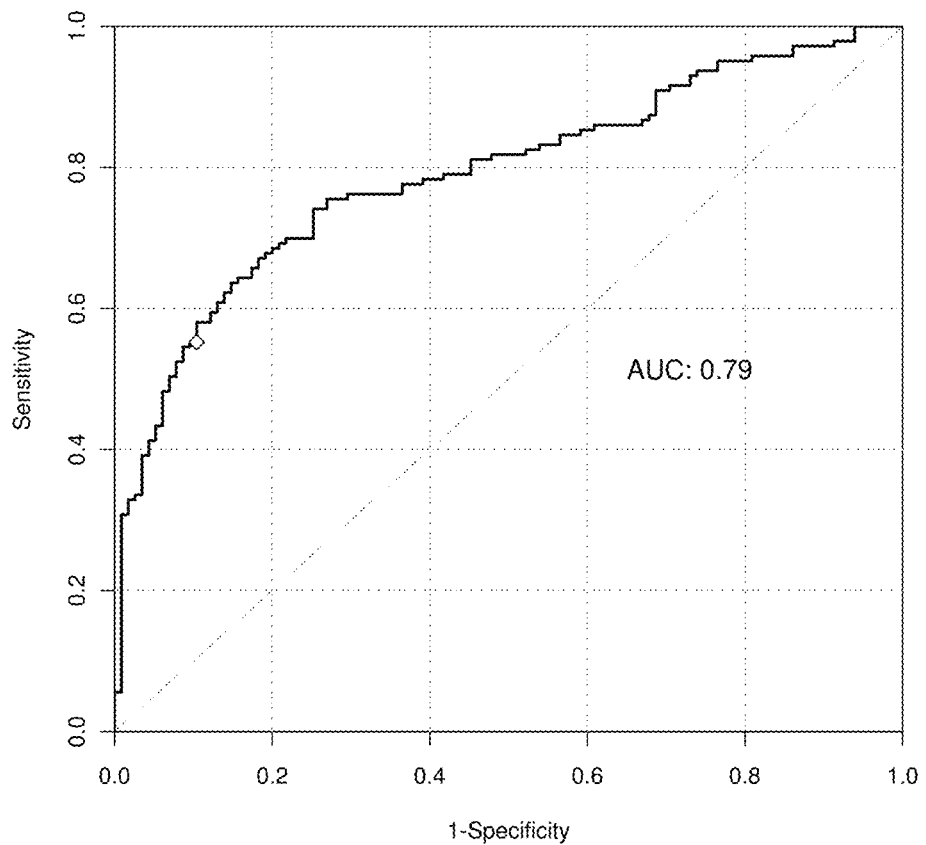
FIG. 2 shows a ROC curve for a single biomarker, CTSB, using a naïve Bayes classifier for a test that detects pancreatic cancer.

Exemplary embodiments use any number of the pancreatic cancer biomarkers listed in Table 1, Col. 2 in various combinations to produce diagnostic tests for detecting pancreatic cancer (see Example 2 for a detailed description of how these biomarkers were identified). In one embodiment, a method for diagnosing pancreatic cancer uses a naïve Bayes classification method in conjunction with any number of the pancreatic cancer biomarkers listed in Table 1, Col. 2. In an illustrative example (Example 3), the simplest test for detecting pancreatic cancer from a population of GI and normal controls can be constructed using a single biomarker, for example, CTSB which is differentially expressed in pancreatic cancer with a KS-distance of 0.52. Using the parameters, $\mu_{c,i}$, $\sigma_{c,i}$, $\mu_{d,i}$, and, $\sigma_{d,i}$, for CTSB from Table 16 and the equation for the log-likelihood described above, a diagnostic test with an AUC of 0.79 can be derived, see Table 15. The ROC curve for this test is displayed in FIG. 2.

Figure 3:
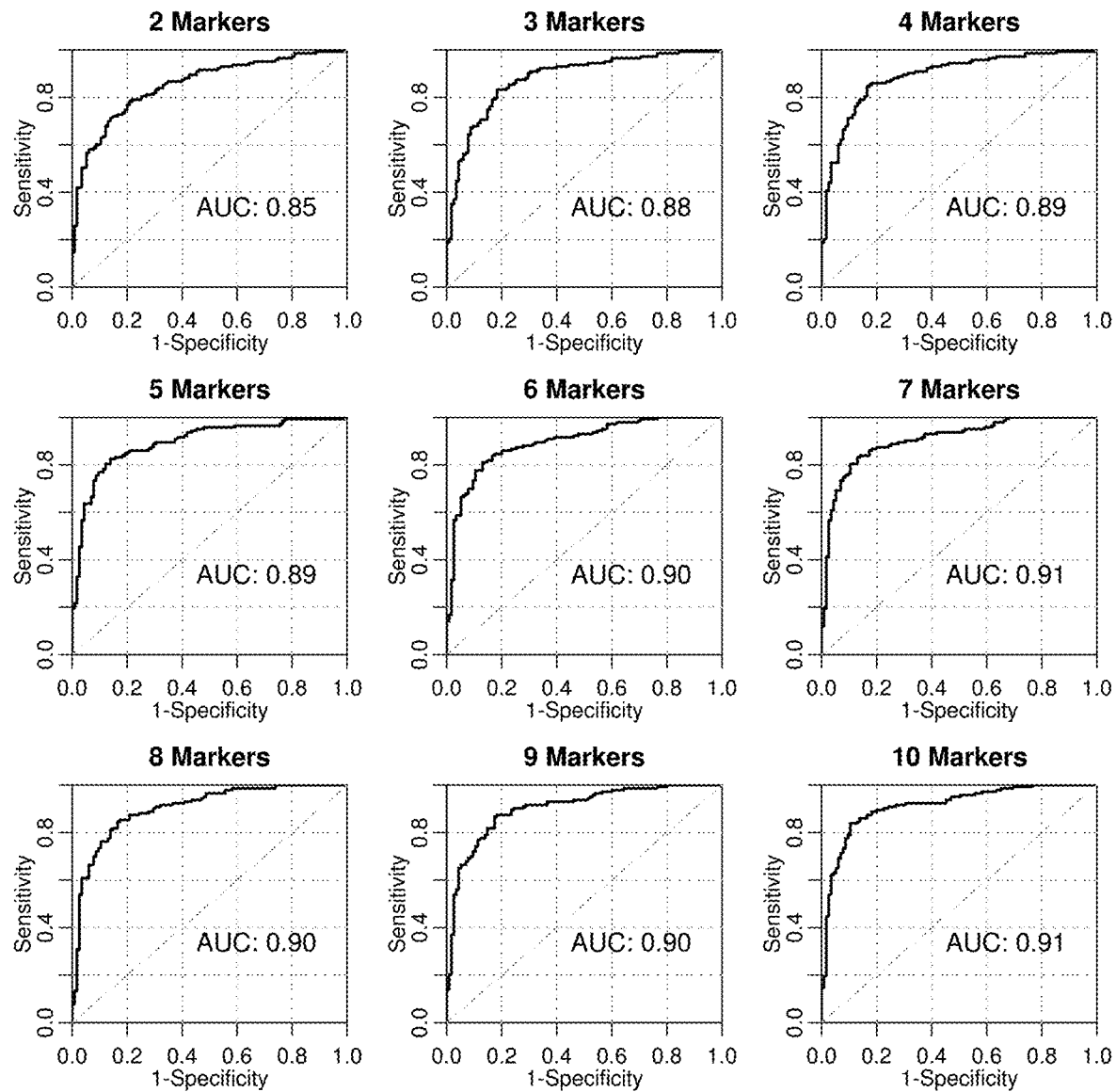
FIG. 3 shows ROC curves for biomarker panels of from two to ten biomarkers using naïve Bayes classifiers for a test that detects pancreatic cancer.
Figure 4:
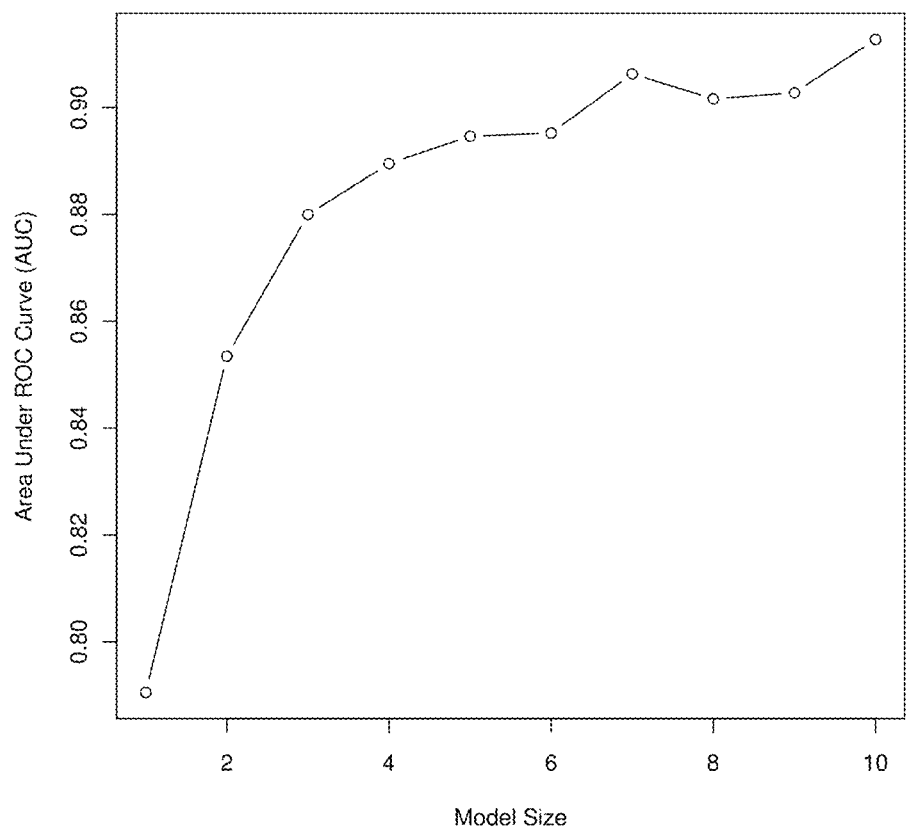
FIG. 4 illustrates the increase in the classification score (AUC) as the number of biomarkers is increased from one to ten using naïve Bayes classification for a pancreatic cancer panel.

Addition of biomarker C5a, for example, with a KS-distance of 0.40, significantly improves the classifier performance to an AUC of 0.85. Note that the score for a classifier constructed of two biomarkers is not a simple sum of the KS-distances; KS-distances are not additive when combining biomarkers and it takes many more weak markers to achieve the same level of performance as a strong marker. Adding a third marker, C5, for example, boosts the classifier performance to an AUC of 0.88. Adding additional biomarkers, such as, for example, CCL18, CSF1R, KLK7, ETHE1, C5-C6, KLK8, and VEGFA, produces a series of pancreatic cancer tests summarized in Table 15 and displayed as a series of ROC curves in FIG. 3. The score of the classifiers as a function of the number of analytes used in classifier construction is displayed in FIG. 4. The AUC of this exemplary ten-marker classifier is 0.91.

The markers listed in Table 1, Col. 2 can be combined in many ways to produce classifiers for diagnosing pancreatic cancer. In some embodiments, panels of biomarkers are comprised of different numbers of analytes depending on a specific diagnostic performance criterion that is selected. For example, certain combinations of biomarkers will produce tests that are more sensitive (or more specific) than other combinations.

Once a panel is defined to include a particular set of biomarkers from Table 1, Col. 2 and a classifier is constructed from a set of training data, the definition of the diagnostic test is complete. In one embodiment, the procedure used to classify an unknown sample is outlined in FIG. 1A. In another embodiment the procedure used to classify an unknown sample is outlined in FIG. 1B. The biological sample is appropriately diluted and then run in one or more assays to produce the relevant quantitative biomarker levels used for classification. The measured biomarker levels are used as input for the classification method that outputs a classification and an optional score for the sample that reflects the confidence of the class assignment.

Table 1 identifies 65 biomarkers that are useful for diagnosing pancreatic cancer. This is a surprisingly larger number than expected when compared to what is typically found during biomarker discovery efforts and may be attributable to the scale of the described study, which encompassed over 800 proteins measured in hundreds of individual samples, in some cases at concentrations in the low femtomolar range. Presumably, the large number of discovered biomarkers reflects the diverse biochemical pathways implicated in both tumor biology and the body's response to the tumor's presence; each pathway and process involves many proteins. The results show that no single protein of a small group of proteins is uniquely informative about such complex processes; rather, that multiple proteins are involved in relevant processes, such as apoptosis or extracellular matrix repair, for example.

Given the numerous biomarkers identified during the described study, one would expect to be able to derive large numbers of high-performing classifiers that can be used in various diagnostic methods. To test this notion, tens of thousands of classifiers were evaluated using the biomarkers in Table 1. As described in Example 4, many subsets of the biomarkers presented in Table 1 can be combined to generate useful classifiers. By way of example, descriptions are provided for classifiers containing 1, 2, and 3 biomarkers for detection of pancreatic cancer. As described in Example 4, all classifiers that were built using the biomarkers in Table 1 perform distinctly better than classifiers that were built using "non-markers".

The performance of classifiers obtained by randomly excluding some of the markers in Table 1, which resulted in smaller subsets from which to build the classifiers, was also tested. As described in Example 4, Part 3, the classifiers that were built from random subsets of the markers in Table 1 performed similarly to optimal classifiers that were built using the full list of markers in Table 1.

The performance of ten-marker classifiers obtained by excluding the "best" individual markers from the ten-marker aggregation was also tested. As described in Example 4, Part 3, classifiers constructed without the "best" markers in Table 1 also performed well. Many subsets of the biomarkers listed in Table 1 performed close to optimally, even after removing the top 15 of the markers listed in the Table. This implies that the performance characteristics of any particular classifier are likely not due to some small core group of biomarkers and that the disease process likely impacts numerous biochemical pathways, which alters the expression level of many proteins.

The results from Example 4 suggest certain possible conclusions: First, the identification of a large number of biomarkers enables their aggregation into a vast number of classifiers that offer similarly high performance. Second, classifiers can be constructed such that particular biomarkers may be substituted for other biomarkers in a manner that reflects the redundancies that undoubtedly pervade the complexities of the underlying disease processes. That is to say, the information about the disease contributed by any individual biomarker identified in Table 1 overlaps with the information contributed by other biomarkers, such that it may be that no particular biomarker or small group of biomarkers in Table 1 must be included in any classifier.

Exemplary embodiments use naïve Bayes classifiers constructed from the data in Table 16 to classify an unknown sample. The procedure is outlined in FIGS. 1A and 1B. In one embodiment, the biological sample is optionally diluted and run in a multiplexed aptamer assay. The data from the assay are normalized and calibrated as outlined in Example 3, and the resulting biomarker levels are used as input to a Bayes classification scheme. The log-likelihood ratio is computed for each measured biomarker individually and then summed to produce a final classification score, which is also referred to as a diagnostic score. The resulting assignment as well as the overall classification score can be reported. Optionally, the individual log-likelihood risk factors computed for each biomarker level can be reported as well. The details of the classification score calculation are presented in Example 3.

Kits

Any combination of the biomarkers of Table 1. Col. 2 (as well as additional biomedical information) can be detected using a suitable kit, such as for use in performing the methods disclosed herein. Furthermore, any kit can contain one or more detectable labels as described herein, such as a fluorescent moiety, etc.

In one embodiment, a kit includes (a) one or more capture reagents (such as, for example, at least one aptamer or antibody) for detecting one or more biomarkers in a biological sample, wherein the biomarkers include any of the biomarkers set forth in Table 1, Col. 2, and optionally (b) one or more software or computer program products for classifying the individual from whom the biological sample was obtained as either having or not having pancreatic cancer or for determining the likelihood that the individual has pancreatic cancer, as further described herein. Alternatively, rather than one or more computer program products, one or more instructions for manually performing the above steps by a human can be provided.

The combination of a solid support with a corresponding capture reagent and a signal generating material is referred to herein as a "detection device" or "kit". The kit can also include instructions for using the devices and reagents, handling the sample, and analyzing the data. Further the kit may be used with a computer system or software to analyze and report the result of the analysis of the biological sample.

The kits can also contain one or more reagents (e.g., solubilization buffers, detergents, washes, or buffers) for processing a biological sample. Any of the kits described herein can also include, e.g., buffers, blocking agents, mass spectrometry matrix materials, antibody capture agents, positive control samples, negative control samples, software and information such as protocols, guidance and reference data.

In one aspect, the invention provides kits for the analysis of pancreatic cancer status. The kits include PCR primers for one or more biomarkers selected from Table 1. Col. 2. The kit may further include instructions for use and correlation of the biomarkers with pancreatic cancer. The kit may also include a DNA array containing the complement of one or more of the biomarkers selected from Table 1, Col. 2, reagents, and/or enzymes for amplifying or isolating sample DNA. The kits may include reagents for real-time PCR, for example, TaqMan probes and/or primers, and enzymes.

For example, a kit can comprise (a) reagents comprising at least capture reagent for quantifying one or more biomarkers in a test sample, wherein said biomarkers comprise the biomarkers set forth in Table 1, Col. 2, or any other biomarkers or biomarkers panels described herein, and optionally (b) one or more algorithms or computer programs for performing the steps of comparing the amount of each biomarker quantified in the test sample to one or more predetermined cutoffs and assigning a score for each biomarker quantified based on said comparison, combining the assigned scores for each biomarker quantified to obtain a total score, comparing the total score with a predetermined score, and using said comparison to determine whether an individual has pancreatic cancer. Alternatively, rather than one or more algorithms or computer programs, one or more instructions for manually performing the above steps by a human can be provided.

Computer Methods and Software

Once a biomarker or biomarker panel is selected, a method for diagnosing an individual can comprise the following: 1) collect or otherwise obtain a biological sample; 2) perform an analytical method to detect and measure the biomarker or biomarkers in the panel in the biological sample; 3) perform any data normalization or standardization required for the method used to collect biomarker values; 4) calculate the marker score; 5) combine the marker scores to obtain a total diagnostic score; and 6) report the individual's diagnostic score. In this approach, the diagnostic score may be a single number determined from the sum of all the marker calculations that is compared to a preset threshold value that is an indication of the presence or absence of disease. Or the diagnostic score may be a series of bars that each represent a biomarker value and the pattern of the responses may be compared to a pre-set pattern for determination of the presence or absence of disease.

Figure 6:
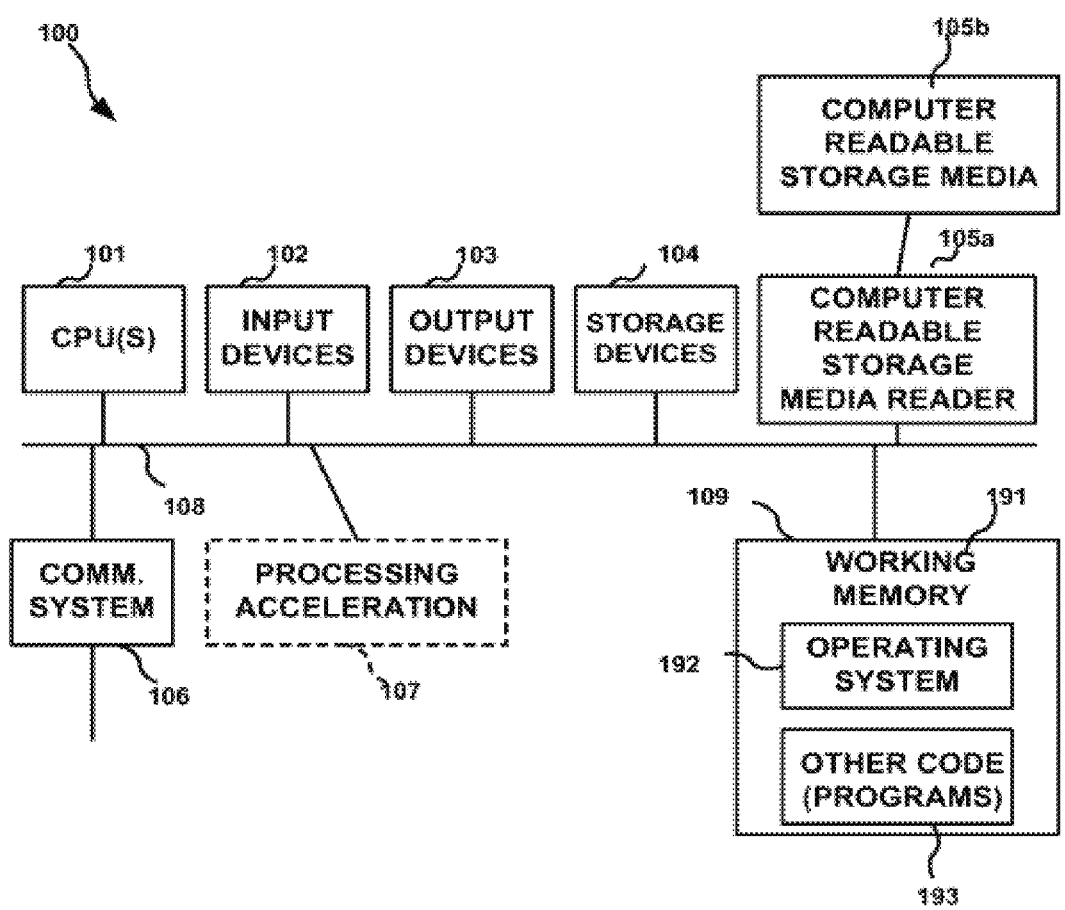
FIG. 6 illustrates an exemplary computer system for use with various computer-implemented methods described herein.

At least some embodiments of the methods described herein can be implemented with the use of a computer. An example of a computer system 100 is shown in FIG. 6. With reference to FIG. 6, system 100 is shown comprised of hardware elements that are electrically coupled via bus 108, including a processor 101, input device 102, output device 103, storage device 104, computer-readable storage media reader 105a, communications system 106 processing acceleration (e.g., DSP or special-purpose processors) 107 and memory 109. Computer-readable storage media reader 105a is further coupled to computer-readable storage media 105b, the combination comprehensively representing remote, local, fixed and/or removable storage devices plus storage media, memory, etc. for temporarily and/or more permanently containing computer-readable information, which can include storage device 104, memory 109 and/or any other such accessible system 100 resource. System 100 also comprises software elements (shown as being currently located within working memory 191) including an operating system 192 and other code 193, such as programs, data and the like.

With respect to FIG. 6, system 100 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 100 component. (e.g., within communications system 106). Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system can comprise a database containing features of biomarkers characteristic of pancreatic cancer. The biomarker data (or biomarker information) can be utilized as an input to the computer for use as part of a computer implemented method. The biomarker data can include the data as described herein.

In one aspect, the system further comprises one or more devices for providing input data to the one or more processors.

The system further comprises a memory for storing a data set of ranked data elements.

In another aspect, the device for providing input data comprises a detector for detecting the characteristic of the data element, e.g., such as a mass spectrometer or gene chip reader.

The system additionally may comprise a database management system. User requests or queries can be formatted in an appropriate language understood by the database management system that processes the query to extract the relevant information from the database of training sets.

The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests.

The system may include an operating system (e.g., UNIX or Linux) for executing instructions from a database management system. In one aspect, the operating system can operate on a global communications network, such as the internet, and utilize a global communications network server to connect to such a network.

The system may include one or more devices that comprise a graphical display interface comprising interface elements such as buttons, pull down menus, scroll bars, fields for entering text, and the like as are routinely found in graphical user interfaces known in the art. Requests entered on a user interface can be transmitted to an application program in the system for formatting to search for relevant information in one or more of the system databases. Requests or queries entered by a user may be constructed in any suitable database language.

The graphical user interface may be generated by a graphical user interface code as part of the operating system and can be used to input data and/or to display inputted data. The result of processed data can be displayed in the interface, printed on a printer in communication with the system, saved in a memory device, and/or transmitted over the network or can be provided in the form of the computer readable medium.

The system can be in communication with an input device for providing data regarding data elements to the system (e.g., expression values). In one aspect, the input device can include a gene expression profiling system including, e.g., a mass spectrometer, gene chip or array reader, and the like.

The methods and apparatus for analyzing pancreatic cancer biomarker information according to various embodiments may be implemented in any suitable manner, for example, using a computer program operating on a computer system. A conventional computer system comprising a processor and a random access memory, such as a remotely-accessible application server, network server, personal computer or workstation may be used. Additional computer system components may include memory devices or information storage systems, such as a mass storage system and a user interface, for example a conventional monitor, keyboard and tracking device. The computer system may be a stand-alone system or part of a network of computers including a server and one or more databases.

The pancreatic cancer biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the pancreatic cancer biomarkers. The computer program may comprise multiple modules performing various functions or operations, such as a processing module for processing raw data and generating supplemental data and an analysis module for analyzing raw data and supplemental data to generate a pancreatic cancer status and/or diagnosis. Diagnosing pancreatic cancer status may comprise generating or collecting any other information, including additional biomedical information, regarding the condition of the individual relative to the disease, identifying whether further tests may be desirable, or otherwise evaluating the health status of the individual.

Figure 7:
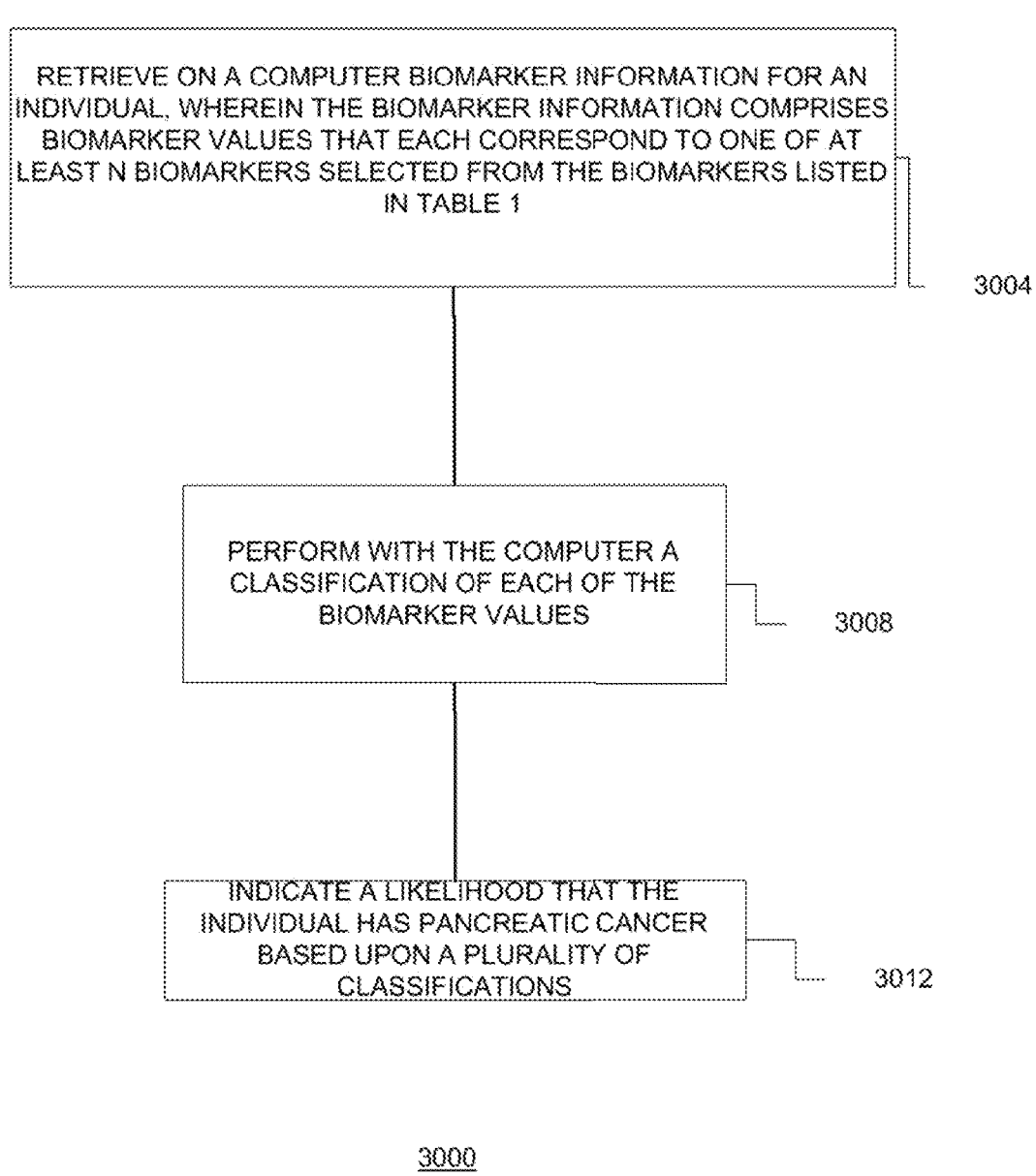
FIG. 7 is a flowchart for a method of indicating the likelihood that an individual has pancreatic cancer in accordance with one embodiment.

Referring now to FIG. 7, an example of a method of utilizing a computer in accordance with principles of a disclosed embodiment can be seen. In FIG. 7, a flowchart 3000 is shown. In block 3004, biomarker information can be retrieved for an individual. The biomarker information can be retrieved from a computer database, for example, after testing of the individual's biological sample is performed. The biomarker information can comprise biomarker values that each correspond to one of at least N biomarkers selected from a group consisting of the biomarkers provided in Table 1. Col. 2, wherein N=2-65. In block 3008, a computer can be utilized to classify each of the biomarker values. And, in block 3012, a determination can be made as to the likelihood that an individual has pancreatic cancer based upon a plurality of classifications. The indication can be output to a display or other indicating device so that it is viewable by a person. Thus, for example, it can be displayed on a display screen of a computer or other output device.

Figure 8:
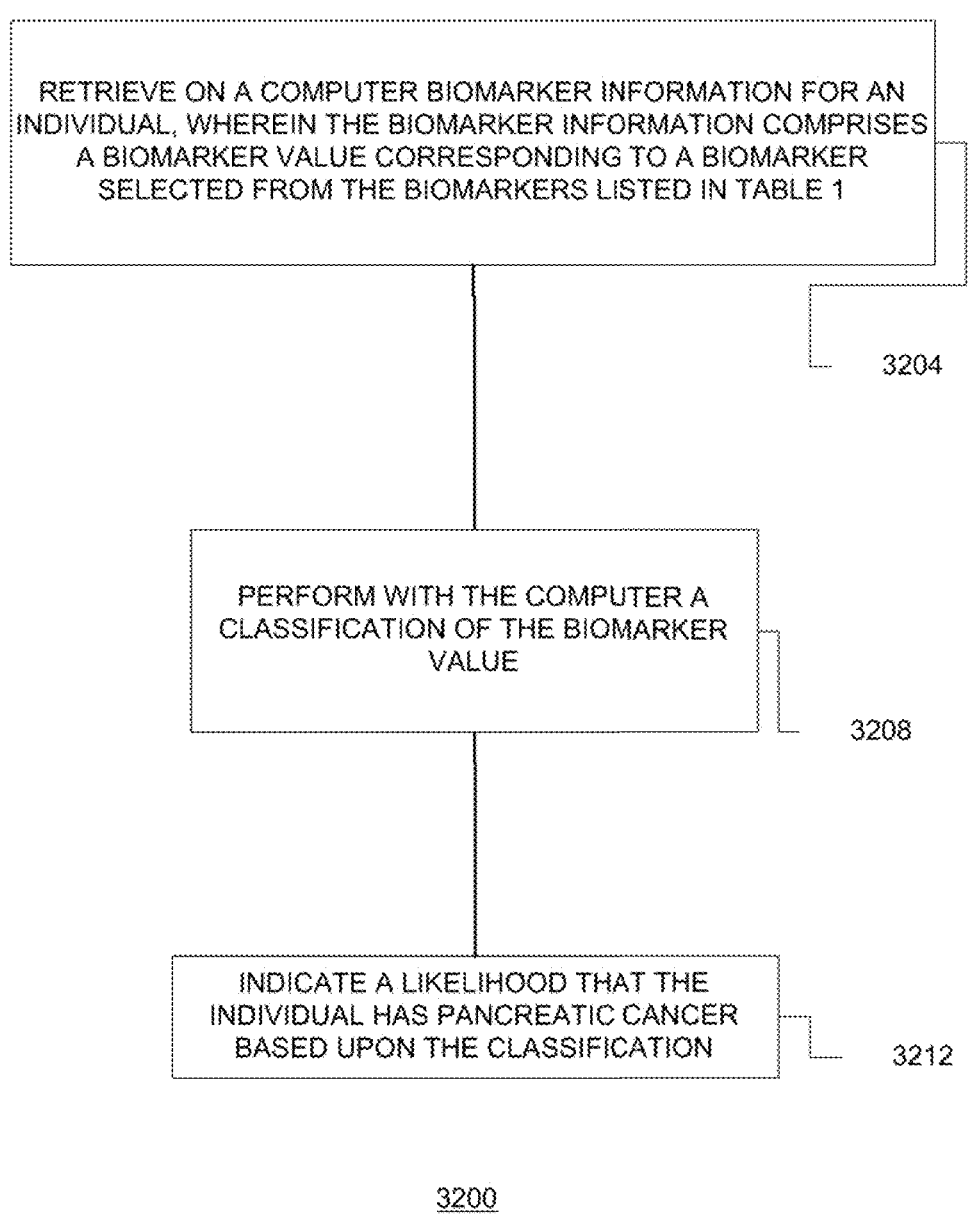
FIG. 8 is a flowchart for a method of indicating the likelihood that an individual has pancreatic cancer in accordance with one embodiment.

Referring now to FIG. 8, an alternative method of utilizing a computer in accordance with another embodiment can be illustrated via flowchart 3200. In block 3204, a computer can be utilized to retrieve biomarker information for an individual. The biomarker information comprises a biomarker value corresponding to a biomarker selected from the group of biomarkers provided in Table 1, Col. 2. In block 3208, a classification of the biomarker value can be performed with the computer. And, in block 3212, an indication can be made as to the likelihood that the individual has pancreatic cancer based upon the classification. The indication can be output to a display or other indicating device so that it is viewable by a person. Thus, for example, it can be displayed on a display screen of a computer or other output device.

Some embodiments described herein can be implemented so as to include a computer program product. A computer program product may include a computer readable medium having computer readable program code embodied in the medium for causing an application program to execute on a computer with a database.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided for indicating a likelihood of pancreatic cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 1, Col. 2, wherein N=2-65; and code that executes a classification method that indicates a pancreatic cancer status of the individual as a function of the biomarker values.

In still another aspect, a computer program product is provided for indicating a likelihood of pancreatic cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 1, Col. 2; and code that executes a classification method that indicates a pancreatic cancer status of the individual as a function of the biomarker value.

While various embodiments have been described as methods or apparatuses, it should be understood that embodiments can be implemented through code coupled with a computer, e.g., code resident on a computer or accessible by the computer. For example, software and databases could be utilized to implement many of the methods discussed above. Thus, in addition to embodiments accomplished by hardware, it is also noted that these embodiments can be accomplished through the use of an article of manufacture comprised of a computer usable medium having a computer readable program code embodied therein, which causes the enablement of the functions disclosed in this description. Therefore, it is desired that embodiments also be considered protected by this patent in their program code means as well. Furthermore, the embodiments may be embodied as code stored in a computer-readable memory of virtually any kind including, without limitation, RAM, ROM, magnetic media, optical media, or magneto-optical media. Even more generally, the embodiments could be implemented in software, or in hardware, or any combination thereof including, but not limited to, software running on a general purpose processor, microcode, PLAs, or ASICs.

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

The biomarker identification process, the utilization of the biomarkers disclosed herein, and the various methods for determining biomarker values are described in detail above with respect to pancreatic cancer. However, the application of the process, the use of identified biomarkers, and the methods for determining biomarker values are fully applicable to other specific types of cancer, to cancer generally, to any other disease or medical condition, or to the identification of individuals who may or may not be benefited by an ancillary medical treatment. Except when referring to specific results related to pancreatic cancer, as is clear from the context, references herein to pancreatic cancer may be understood to include other types of cancer, cancer generally, or any other disease or medical condition.

EXAMPLES

The following examples are provided for illustrative purposes only and are not intended to limit the scope of the application as defined by the appended claims. All examples described herein were carried out using standard techniques, which are well known and routine to those of skill in the art. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Example 1

Multiplexed Aptamer Analysis of Samples

Figure 9:
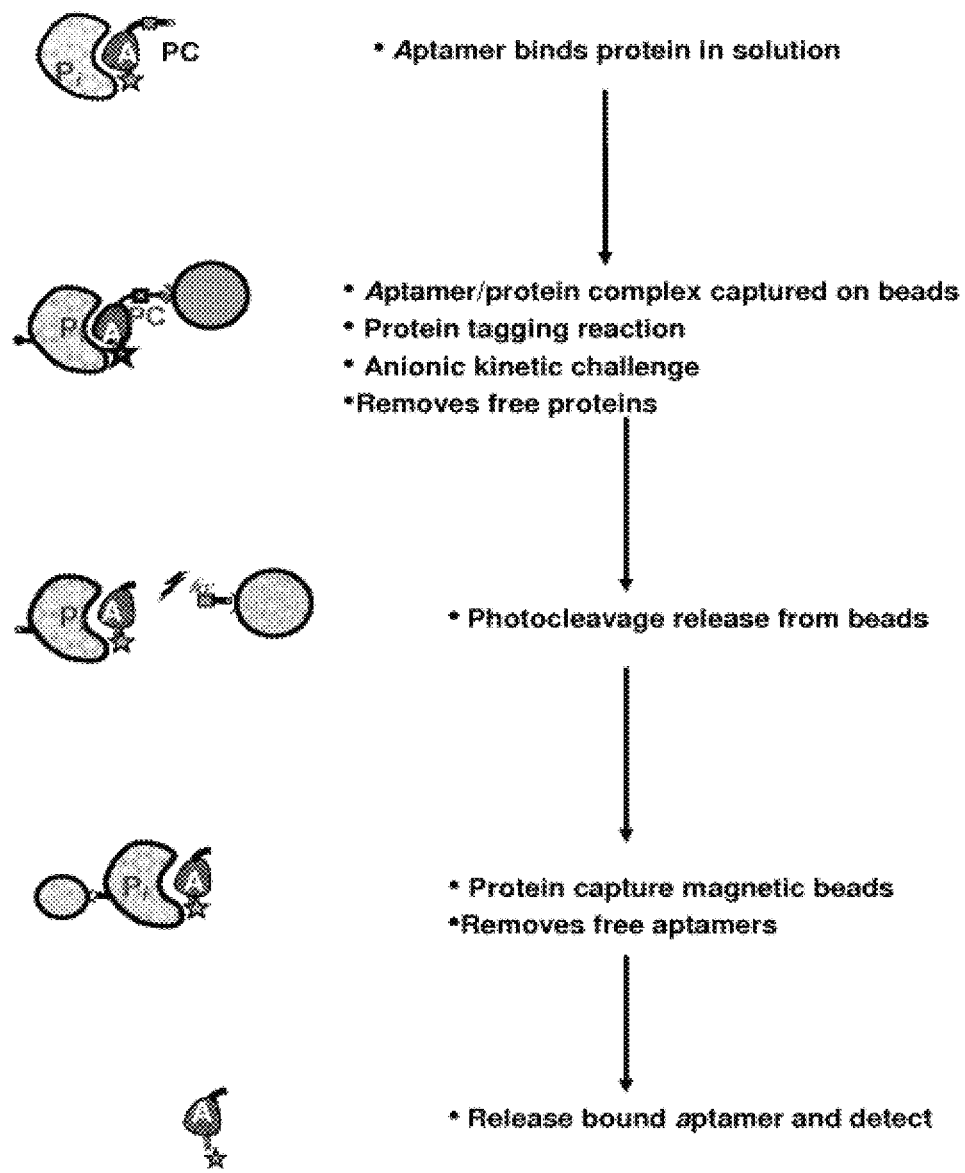
FIG. 9 illustrates an exemplary aptamer assay that can be used to detect one or more pancreatic cancer biomarkers in a biological sample.

This example describes the multiplex aptamer assay used to analyze the samples and controls for the identification of the biomarkers set forth in Table 1, Col. 2 (see FIG. 9) and the identification of the cancer biomarkers set forth in Table 19. For the pancreatic cancer, lung cancer, and mesothelioma studies, the multiplexed analysis utilized 823 aptamers, each unique to a specific target.

In this method, pipette tips were changed for each solution addition.

Also, unless otherwise indicated, most solution transfers and wash additions used the 96-well head of a Beckman Biomek FxP. Method steps manually pipetted used a twelve channel P200 Pipetteman (Rainin Instruments, LLC. Oakland, Calif.), unless otherwise indicated. A custom buffer referred to as SB17 was prepared in-house, comprising 40 mM HEPES, 100 mM NaCl, 5 mM KCl, 5 mM MgCl2, 1 mM EDTA at pH 7.5. A custom buffer referred to as SB18 was prepared in-house, comprising 40 mM HEPES, 100 mM NaCl, 5 mM KCl. 5 mM MgCl2 at pH 7.5. All steps were performed at room temperature unless otherwise indicated.

1. Preparation of Aptamer Stock Solution

For aptamers without a photo-cleavable biotin linker, custom stock aptamer solutions for 10%, 1% and 0.03% plasma were prepared at 8× concentration in 1×SB17, 0.05% Tween-20 with appropriate photo-cleavable, biotinylated primers, where the resultant primer concentration was 3 times the relevant aptamer concentration. The primers hybridized to all or part of the corresponding aptamer.

Each of the 3, 8× aptamer solutions were diluted separately 1:4 into 1×SB17, 0.05% Tween-20 (1500 µL of 8× stock into 4500 µL of 1×SB17, 0.05% Tween-20) to achieve a 2× concentration. Each diluted aptamer master mix was then split, 1500 µL each, into 4 2 mL screw cap tubes and brought to 95° C. for 5 minutes, followed by a 37° C. incubation for 15 minutes. After incubation the 4 2 mL tubes corresponding to a particular aptamer master mix were combined into a reagent trough, and 55 µL of a 2x aptamer mix (for all three mixes) was manually pipetted into a 96-well Hybaid plate and the plate foil sealed. The final result was 3, 96-well, foil-sealed Hybaid plates. The individual aptamer concentration was 0.5 nM.

2. Assay Sample Preparation

Frozen aliquots of 100% plasma, stored at −80° C., were placed in 25° C. water bath for 10 minutes. Thawed samples were placed on ice, gently vortexed (set on 4) for 8 seconds and then replaced on ice.

A 20% sample solution was prepared by transferring 16 µL of sample using a 50 µL 8-channel spanning pipettor into 96-well Hybaid plates, each well containing 64 µL of the appropriate sample diluent at 4° C. (0.8x SB18, 0.05%

Tween-20, 2 µM Z-block_2, 0.6 mM MgCl2 for plasma). This plate was stored on ice until the next sample dilution steps were initiated.

To commence sample and aptamer equilibration, the 20% sample plate was briefly centrifuged and placed on the Beckman FX where it was mixed by pipetting up and down with the 96-well pipettor. A 2% sample was then prepared by diluting 10 µL of the 20% sample into 90 µL of 1×SB17, 0.05% Tween-20. Next, dilution of 6 µL of the resultant 2% sample into 194 µL of 1×SB17, 0.05% Tween-20 made a 0.06% sample plate. Dilutions were done on the Beckman Biomek FxP. After each transfer, the solutions were mixed by pipetting up and down. The 3 sample dilution plates were then transferred to their respective aptamer solutions by adding 55 µL of the sample to 55 µL of the appropriate 2× aptamer mix. The sample and aptamer solutions were mixed on the robot by pipetting up and down.

3. Sample Equilibration Binding

The sample/aptamer plates were foil sealed and placed into a 37° C. incubator for 3.5 hours before proceeding to the Catch 1 step.

4. Preparation of Catch 2 Bead Plate

An 5.5 mL aliquot of MyOne (Invitrogen Corp., Carlsbad, Calif.) Streptavidin C1 beads (10 mg/mL) was washed 2 times with equal volumes of 20 mM NaOH (5 minute incubation for each wash), 3 times with equal volumes of 1×SB17, 0.05% Tween-20 and resuspended in 5.5 mL 1×SB17, 0.05% Tween-20. Using a 12-span multichannel pipettor, 50 µL of this solution was manually pipetted into each well of a 96-well Hybaid plate. The plate was then covered with foil and stored at 4° C. for use in the assay.

5. Preparation of Catch 1 Bead Plates

Three 0.45 µm Millipore HV plates (Durapore membrane, Cat# MAHVN4550) were equilibrated with 100 µL of 1×SB17, 0.05% e Tween-20 for at least 10 minutes. The equilibration buffer was then filtered through the plate and 133.3 µL of a 7.5% streptavidin-agarose bead slurry (in 1×SB17, 0.05% Tween-20) was added into each well. To keep the streptavidin-agarose beads suspended while transferring them into the filter plate, the bead solution was manually mixed with a 200 µL, 12-channel pipettor, 15 times. After the beads were distributed across the 3 filter plates, a vacuum was applied to remove the bead supernatant. Finally, the beads were washed in the filter plates with 200 µL 1×SB17, 0.05% Tween-20 and then resuspended in 200 µL 1×SB17, 0.05% Tween-20. The bottoms of the filter plates were blotted and the plates stored for use in the assay.

6. Loading the Cytomat.

The cytomat was loaded with all tips, plates, all reagents in troughs (except NHSbiotin reagent which was prepared fresh right before addition to the plates), 3 prepared Catch 1 filter plates and 1 prepared MyOne plate.

7. Catch 1

After a 3.5 hour equilibration time, the sample/aptamer plates were removed from the incubator, centrifuged for about 1 minute, foil removed, and placed on the deck of the Beckman Biomek FxP. The Beckman Biomek FxP program was initiated. All subsequent steps in Catch 1 were performed by the Beckman Biomek FxP robot unless otherwise noted. Within the program, the vacuum was applied to the Catch 1 filter plates to remove the bead supernatant. One hundred microleters of each of the 10%, 1% and 0.03% equilibration binding reactions were added to their respective Catch 1 filtration plates, and each plate was mixed using an on-deck orbital shaker at 800 rpm for 10 minutes.

Unbound solution was removed via vacuum filtration. The Catch 1 beads were washed with 190 µL of 100 µM biotin in 1×SB17, 0.05% Tween-20 followed by 190 µL of 1×SB17, 0.05% Tween-20 by dispensing the solution and immediately drawing a vacuum to filter the solution through the plate.

Next, 190 µL 1×SB17, 0.05% Tween-20 was added to the Catch 1 plates. Plates were blotted to remove droplets using an on-deck blot station and then incubated with orbital shakers at 800 rpm for 10 minutes at 25° C.

The robot removed this wash via vacuum filtration and blotted the bottom of the filter plate to remove droplets using the on-deck blot station.

8. Tagging

A NHS-PEO4-biotin aliquot was thawed at 37° C. for 6 minutes and then diluted 1:100 with tagging buffer (SB17 at pH=7.25 0.05% Tween-20). The NHS-PEO4-biotin reagent was dissolved at 100 mM concentration in anhydrous DMSO and had been stored frozen at −20° C. Upon a robot prompt, the diluted NHS-PEO4-biotin reagent was manually added to an on-deck trough and the robot program was manually re-initiated to dispense 100 µL of the NHS-PEO4-biotin into each well of each Catch 1 filter plate. This solution was allowed to incubate with Catch 1 beads shaking at 800 rpm for 5 minutes on the orbital shakers.

9. Kinetic Challenge and Photo-cleavage

The tagging reaction was quenched by the addition of 150 µL of 20 mM glycine in 1×SB17, 0.05% Tween-20 to the Catch 1 plates while still containing the NHS tag. The plates were then incubated for 1 minute on orbital shakers at 800 rpm. The NHS-tag/glycine solution was removed via vacuum filtration. Next, 190 µL 20 mM glycine (1×SB17, 0.05% Tween-20) was added to each plate and incubated for 1 minute on orbital shakers at 800 rpm before removal by vacuum filtration.

190 µL of 1×SB17, 0.05% Tween-20 was added to each plate and removed by vacuum filtration.

The wells of the Catch 1 plates were subsequently washed three times by adding 190 µL 1×SB17, 0.05% Tween-20, placing the plates on orbital shakers for 1 minute at 800 rpm followed by vacuum filtration. After the last wash the plates were placed on top of a 1 mL deep-well plate and removed from the deck. The Catch 1 plates were centrifuged at 1000 rpm for 1 minute to remove as much extraneous volume from the agarose beads before elution as possible.

The plates were placed back onto the Beckman Biomek FxP and 85 µL of 10 mM DxSO4 in 1×SB17, 0.05%% Tween-20 was added to each well of the filter plates.

The filter plates were removed from the deck, placed onto a Variomag Thermoshaker (Thermo Fisher Scientific, Inc., Waltham, Mass.) under the BlackRay (Ted Pella. Inc., Redding, Calif.) light sources, and irradiated for 10 minutes while shaking at 800 rpm.

The photocleaved solutions were sequentially eluted from each Catch 1 plate into a common deep well plate by first placing the 10%% Catch 1 filter plate on top of a 1 mL deep-well plate and centrifuging at 1000 rpm for 1 minute. The 1% and 0.03% Catch 1 plates were then sequentially centrifuged into the same deep well plate.

10. Catch 2 Bead Capture

The 1 mL deep well block containing the combined eluates of Catch 1 was placed on the deck of the Beckman Biomek FxP for Catch 2.

The robot transferred all of the photo-cleaved eluate from the 1 mL deep-well plate onto the Hybaid plate containing the previously prepared Catch 2 MyOne magnetic beads (after removal of the MyOne buffer via magnetic separation).

The solution was incubated while shaking at 1350 rpm for 5 minutes at 25° C. on a Variomag Thermoshaker (Thermo Fisher Scientific, Inc., Waltham, Mass.).

The robot transferred the plate to the on deck magnetic separator station. The plate was incubated on the magnet for 90 seconds before removal and discarding of the supernatant.

11. 37° C. 30% Glycerol Washes

The Catch 2 plate was moved to the on-deck thermal shaker and 75 μL of 1×SB17, 0.05% Tween-20 was transferred to each well. The plate was mixed for 1 minute at 1350 rpm and 37° C. to resuspend and warm the beads. To each well of the Catch 2 plate, 75 μL of 60% glycerol at 37° C. was transferred and the plate continued to mix for another minute at 1350 rpm and 37° C. The robot transferred the plate to the 37° C. magnetic separator where it was incubated on the magnet for 2 minutes and then the robot removed and discarded the supernatant. These washes were repeated two more times.

After removal of the third 30% glycerol wash from the Catch 2 beads, 150 μL of 1×SB17, 0.05% Tween-20 was added to each well and incubated at 37° C., shaking at 1350 rpm for 1 minute, before removal by magnetic separation on the 37° C. magnet.

The Catch 2 beads were washed a final time using 150 μL 1×SB19, 0.05% Tween-20 with incubation for 1 minute while shaking at 1350 rpm at 25° C. prior to magnetic separation.

12. Catch 2 Bead Elution and Neutralization

The aptamers were eluted from Catch 2 beads by adding 105 μL of 100 mM CAPSO with 1 M NaCl, 0.05% Tween-20 to each well. The beads were incubated with this solution with shaking at 1350 rpm for 5 minutes.

The Catch 2 plate was then placed onto the magnetic separator for 90 seconds prior to transferring 90 μL of the eluate to a new 96-well plate containing 10 μL of 500 mM HCl, 500 mM HEPES, 0.05% Tween-20 in each well. After transfer, the solution was mixed robotically by pipetting 90 μL up and down five times.

13. Hybridization

The Beckman Biomek FxP transferred 20 μL of the neutralized Catch 2 eluate to a fresh Hybaid plate, and 5 μL of 10x Agilent Block, containing a 10x spike of hybridization controls, was added to each well. Next, 25 μL of 2x Agilent. Hybridization buffer was manually pipetted to the each well of the plate containing the neutralized samples and blocking buffer and the solution was mixed by manually pipetting 25 μL up and down 15 times slowly to avoid extensive bubble formation. The plate was spun at 1000 rpm for 1 minute.

A gasket slide was placed into an Agilent hybridization chamber and 40 μL of each of the samples containing hybridization and blocking solution was manually pipetted into each gasket. An 8-channel variable spanning pipettor was used in a manner intended to minimize bubble formation. Custom Agilent microarray slides (Agilent Technologies, Inc., Santa Clara, Calif.), with their Number Barcode facing up, were then slowly lowered onto the gasket slides (see Agilent manual for detailed description).

The top of the hybridization chambers were placed onto the slide/backing sandwich and clamping brackets slid over the whole assembly. These assemblies were tightly clamped by turning the screws securely.

Each slide/backing slide sandwich was visually inspected to assure the solution bubble could move freely within the sample. If the bubble did not move freely the hybridization chamber assembly was gently tapped to disengage bubbles lodged near the gasket.

The assembled hybridization chambers were incubated in an Agilent hybridization oven for 19 hours at 60° C. rotating at 20 rpm.

14. Post Hybridization Washing

Approximately 400 mL Agilent Wash Buffer 1 was placed into each of two separate glass staining dishes. One of the staining dishes was placed on a magnetic stir plate and a slide rack and stir bar were placed into the buffer.

A staining dish for Agilent. Wash 2 was prepared by placing a stir bar into an empty glass staining dish.

A fourth glass staining dish was set aside for the final acetonitrile wash.

Each of six hybridization chambers was disassembled. One-by-one, the slide/backing sandwich was removed from its hybridization chamber and submerged into the staining dish containing Wash 1. The slide/backing sandwich was pried apart using a pair of tweezers, while still submerging the microarray slide. The slide was quickly transferred into the slide rack in the Wash 1 staining dish on the magnetic stir plate.

The slide rack was gently raised and lowered 5 times. The magnetic stirrer was turned on at a low setting and the slides incubated for 5 minutes.

When one minute was remaining for Wash 1, Wash Buffer 2 pre-warmed to 37° C. in an incubator was added to the second prepared staining dish. The slide rack was quickly transferred to Wash Buffer 2 and any excess buffer on the bottom of the rack was removed by scraping it on the top of the stain dish. The slide rack was gently raised and lowered 5 times. The magnetic stirrer was turned on at a low setting and the slides incubated for 5 minutes.

The slide rack was slowly pulled out of Wash 2, taking approximately 15 seconds to remove the slides from the solution.

With one minute remaining in Wash 2 acetonitrile (ACN) was added to the fourth staining dish. The slide rack was transferred to the acetonitrile stain dish. The slide rack was gently raised and lowered 5 times. The magnetic stirrer was turned on at a low setting and the slides incubated for 5 minutes.

The slide rack was slowly pulled out of the ACN stain dish and placed on an absorbent towel. The bottom edges of the slides were quickly dried and the slide was placed into a clean slide box.

15. Microarray Imaging

The microarray slides were placed into Agilent scanner slide holders and loaded into the Agilent Microarray scanner according to the manufacturers instructions.

The slides were imaged in the Cy3-channel at 5 μm resolution at the 100% PMT setting and the XRD option enabled at 0.05. The resulting tiff images were processed using Agilent feature extraction software version 10.5.

Example 2

Biomarker Identification

The identification of potential pancreatic cancer biomarkers was performed for diagnosis of pancreatic cancer in asymptomatic individuals and symptomatic individuals with acute or chronic pancreatitis (or both), pancreatic obstruction, GERD, gallstones, or abnormal imaging later found to be benign, collectively the GI and normal controls. Enrollment criteria for this study were age 18 or older, able to give informed consent, and plasma sample and documented diagnosis of pancreatic cancer or benign findings. For cases, blood samples collected prior to treatment or surgery and subsequently diagnosed with pancreatic cancer. Exclusion criteria included prior diagnosis or treatment of cancer (excluding squamous cell carcinoma of the skin) within 5 years of the blood draw. Plasma samples were collected from 2 different sites and included 143 pancreatic cancer samples and 115 control group samples. The multiplexed aptamer affinity assay as described in Example 1 was used to measure and report the RFU value for 823 analytes in each of these 258 samples. Since the plasma samples were obtained from 2 independent studies and sites under similar protocols, an examination of site differences prior to the analysis for biomarkers discovery was performed.

Each of the case and control populations were separately compared by generating class-dependent cumulative distribution functions (cdfs) for each of the 823 analytes. The KS-distance (Kolmogorov-Smirnov statistic) between values from two sets of samples is a non parametric measurement of the extent to which the empirical distribution of the values from one set (Set A) differs from the distribution of values from the other set (Set B). For any value of a threshold T some proportion of the values from Set A will be less than T, and some proportion of the values from Set B will be less than T. The KS-distance measures the maximum (unsigned) difference between the proportion of the values from the two sets for any choice of T.

This set of potential biomarkers can be used to build classifiers that assign samples to either a control or disease group. In fact, many such classifiers were produced from these sets of biomarkers and the frequency with which any biomarker was used in good scoring classifiers determined. Those biomarkers that occurred most frequently among the top scoring classifiers were the most useful for creating a diagnostic test. In this example, Bayesian classifiers were used to explore the classification space but many other supervised learning techniques may be employed for this purpose. The scoring fitness of any individual classifier was gauged by the area under the receiver operating characterisic curve (AUC of the ROC) of the classifier at the Bayesian surface assuming a disease prevalence of 0.5. This scoring metric varies from zero to one, with one being an error-free classifier. The details of constructing a Bayesian classifier from biomarker population measurements are described in Example 3.

Figure 10:
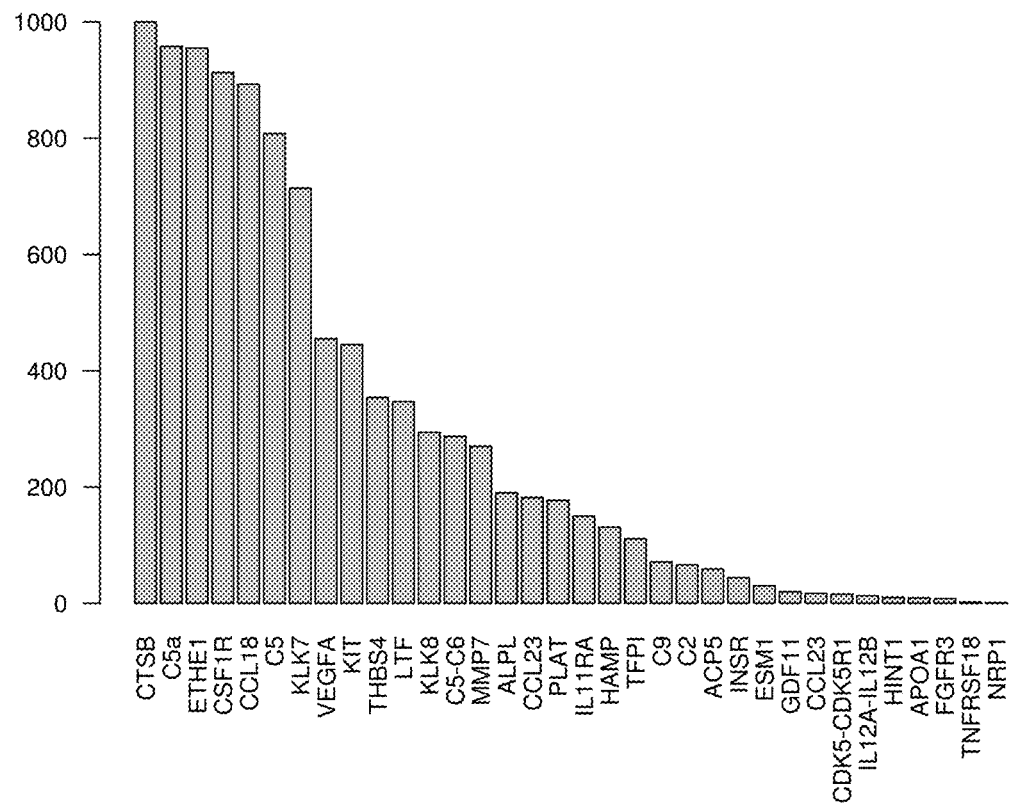
FIG. 10 shows a histogram of frequencies for which biomarkers were used in building classifiers to distinguish between pancreatic cancer and the GI and normal controls from an aggregated set of potential biomarkers.

Using the 65 analytes in Table 1, a total of 973 10-analyte classifiers were found with an AUC of 0.90 for diagnosing pancreatic cancer from the control group. From this set of classifiers, a total of 11 biomarkers were found to be present in 30% or more of the high scoring classifiers. Table 13 provides a list of these potential biomarkers and FIG. 10 is a frequency plot for the identified biomarkers.

Example 3

Naïve Bayesian Classification for Pancreatic Cancer

Figure 5:
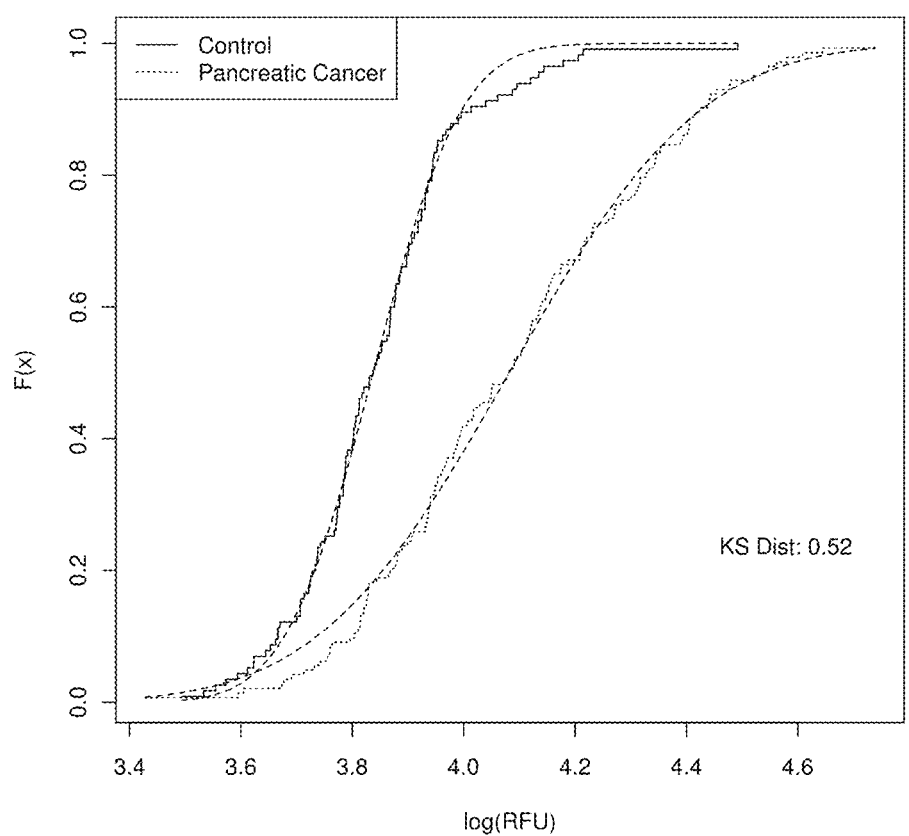
FIG. 5 shows the measured biomarker distributions for CTSB as a cumulative distribution function (cdf) in log-transformed RFU for the GI and normal controls combined (solid line) and the pancreatic cancer disease group (dotted line) along with their curve fits to a normal cdf (dashed lines) used to train the naïve Bayes classifiers.

From the list of biomarkers identified as useful for discriminating between pancreatic cancer and controls, a panel of ten biomarkers was selected and a naïve Bayes classifier was constructed, see Table 16. The class-dependent probability density functions (pdfs), $p(x_i|c)$ and $p(x_i|d)$, where $x_i$ is the log of the measured RFU value for biomarker i, and c and d refer to the control and disease populations, were modeled as log-normal distribution functions characterized by a mean $\mu$ and variance $\sigma^2$. The parameters for pdfs of the ten biomarkers are listed in Table 16 and an example of the raw data along with the model fit to a normal pdf is displayed in FIG. 5. The underlying assumption appears to fit the data quite well as evidenced by FIG. 5.

The naïve Bayes classification for such a model is given by the following equation, where p(d) is the prevalence of the disease in the population, $$\ln\left(\frac{p(d|\tilde{x})}{p(c|\tilde{x})}\right) = \sum_{i=1}^{n} \ln\left(\frac{\sigma_{c,i}}{\sigma_{d_i}}\right) - \frac{1}{2}\sum_{i=1}^{n}\left[\left(\frac{x_i - \mu_{d,i}}{\sigma_{d,i}}\right)^2 - \left(\frac{x_i - \mu_{c,i}}{\sigma_{c,i}}\right)^2\right] + \ln\left(\frac{p(d)}{1-p(d)}\right),$$

appropriate to the test and n=10. Each of the terms in the summation is a log-likelihood ratio for an individual marker and the total log-likelihood ratio of a sample $\tilde{x}$ being free from the disease of interest (i.e. in this case, pancreatic cancer) versus having the disease is simply the sum of these individual terms plus a term that accounts for the prevalence of the disease. For simplicity, we assume $$p(d) = 0.5 \text{ so that } \ln\left(\frac{p(d)}{1-p(d)}\right) = 0.$$

Given an unknown sample measurement in log(RFU for each of the ten biomarkers of 6.3, 9.3, 8.7, 10.8, 7.4, 11.4, 11.7, 9.0, 8.0, 7.3, the calculation of the classification is detailed in Table 16. The individual components comprising the log likelihood ratio for disease versus control class are tabulated and can be computed from the parameters in Table 16 and the values of $\tilde{x}$. The sum of the individual log likelihood ratios is $-3.0414$, or a likelihood of being free from the disease versus having the disease of 21, where likelihood $e^{3.444}=21$. The first 3 biomarker values have likelihoods more consistent with the disease group (log likelihood >0) but the remaining 7 biomarkers are all consistently found to favor the control group. Multiplying the likelihoods together gives the same results as that shown above; a likelihood of 21 that the unknown sample is free from the disease. In fact, this sample came from the control population in the training set.

Example 4

Greedy Algorithm for Selecting Biomarker Panels for Classifiers

This example describes the selection of biomarkers from Table 1 to form panels that can be used as classifiers in any of the methods described herein. Subsets of the biomarkers in Table 1 were selected to construct classifiers with good performance. This method was also used to determine which potential markers were included as biomarkers in Example 2.

The measure of classifier performance used here is the AUC; a performance of 0.5 is the baseline expectation for a random (coin toss) classifier, a classifier worse than random would score between 0.0 and 0.5, a classifier with better than random performance would score between 0.5 and 1.0. A perfect classifier with no errors would have a sensitivity of 1.0 and a specificity of 1.0. One can apply the methods described in Example 4 to other common measures of performance such as the F-measure, the sum of sensitivity and specificity, or the product of sensitivity and specificity. Specifically one might want to treat sensitivity and specificity with differing weight, so as to select those classifiers which perform with higher specificity at the expense of some sensitivity, or to select those classifiers which perform with higher sensitivity at the expense of some specificity. Since the method described here only involves a measure of "performance", any weighting scheme which results in a single performance measure can be used. Different applications will have different benefits for true positive and true negative findings, and also different costs associated with false positive findings from false negative findings. For example, screening asymptomatic high risk individuals and the differential diagnosis of pancreatic cancer from benign GI symptoms will not in general have the same optimal trade-off between specificity and sensitivity. The different demands of the two tests will in general require setting different weighting to positive and negative misclassifications, reflected in the performance measure. Changing the performance measure will in general change the exact subset of markers selected from Table 1, Col. 2 for a given set of data.

For the Bayesian approach to the discrimination of pancreatic cancer samples from control samples described in Example 3, the classifier was completely parameterized by the distributions of biomarkers in the disease and benign training samples, and the list of biomarkers was chosen from Table 1; that is to say, the subset of markers chosen forinclusion determined a classifier in a one-to-one manner given a set of training data.

The greedy method employed here was used to search for the optimal subset of markers from Table 1. For small numbers of markers or classifiers with relatively few markers, every possible subset of markers was enumerated and evaluated in terms of the performance of the classifier constructed with that particular set of markers (see Example 4, Part 2). (This approach is well known in the field of statistics as "best subset selection"; see, e.g., Hastie et al). However, for the classifiers described herein, the number of combinations of multiple markers can be very large, and it was not feasible to evaluate every possible set of 10 markers, as there are 30,045,015 possible combinations that can be generated from a list of only 30 total analytes. Because of the impracticality of searching through every subset of markers, the single optimal subset may not be found; however, by using this approach, many excellent subsets were found, and, in many cases, any of these subsets may represent an optimal one.

Instead of evaluating every possible set of markers, a "greedy" forward stepwise approach may be followed (see, e.g., Dabney A R, Storey J D (2007) Optimality Driven Nearest Centroid Classification from Genomic Data. PLoS ONE 2(10): e1002. doi:10.1371/journal.pone.0001002). Using this method, a classifier is started with the best single marker (based on KS-distance for the individual markers) and is grown at each step by trying, in turn, each member of a marker list that is not currently a member of the set of markers in the classifier. The one marker which scores best in combination with the existing classifier is added to the classifier. This is repeated until no further improvement in performance is achieved. Unfortunately, this approach may miss valuable combinations of markers for which some of the individual markers are not all chosen before the process stops.

The greedy procedure used here was an elaboration of the preceding forward stepwise approach, in that, to broaden the search, rather than keeping just a single candidate classifier (marker subset) at each step, a list of candidate classifiers was kept. The list was seeded with every single marker subset (using every marker in the table on its own). The list was expanded in steps by deriving new classifiers (marker subsets) from the ones currently on the list and adding them to the list. Each marker subset currently on the list was extended by adding any marker from Table 1 not already part of that classifier, and which would not, on its addition to the subset, duplicate an existing subset (these are termed "permissible markers"). Every existing marker subset was extended by every permissible marker from the list. Clearly, such a process would eventually generate every possible subset, and the list would run out of space. Therefore, all the generated classifiers were kept only while the list was less than some predetermined size (often enough to hold all three marker subsets). Once the list reached the predetermined size limit, it became elitist; that is, only those classifiers which showed a certain level of performance were kept on the list, and the others fell off the end of the list and were lost. This was achieved by keeping the list sorted in order of classifier performance; new classifiers which were at least as good as the worst classifier currently on the list were inserted, forcing the expulsion of the current bottom underachiever. One further implementation detail is that the list was completely replaced on each generational step; therefore, every classifier on the list had the same number of markers, and at each step the number of markers per classifier grew by one.

Since this method produced a list of candidate classifiers using different combinations of markers, one may ask if the classifiers can be combined in order to avoid errors which might be made by the best single classifier, or by minority groups of the best classifiers. Such "ensemble" and "committee of experts" methods are well known in the fields of statistical and machine learning and include, for example, "Averaging", "Voting", "Stacking", "Bagging" and "Boosting" (see, e.g., Hastie et al.). These combinations of simple classifiers provide a method for reducing the variance in the classifications due to noise in any particular set of markers by including several different classifiers and therefore information from a larger set of the markers from the biomarker table, effectively averaging between the classifiers. An example of the usefulness of this approach is that it can prevent outliers in a single marker from adversely affecting the classification of a single sample. The requirement to measure a larger number of signals may be impractical in conventional "one marker at a time" antibody assays but has no downside for a fully multiplexed aptamer assay. Techniques such as these benefit from a more extensive table of biomarkers and use the multiple sources of information concerning the disease processes to provide a more robust classification.

The biomarkers selected in Table 1 gave rise to classifiers which perform better than classifiers built with "non-markers" (i.e., proteins having signals that did not meet the criteria for inclusion in Table 1 (as described in Example 2)).

For classifiers containing only one, two, and three markers, all possible classifiers obtained using the biomarkers in Table 1 were enumerated and examined for the distribution of performance compared to classifiers built from a similar table of randomly selected non-markers signals.

In FIG. 11, the AUC was used as the measure of performance; a performance of 0.5 is the baseline expectation for a random (coin toss) classifier. The histogram of classifier performance was compared with the histogram of performance from a similar exhaustive enumeration of classifiers built from a "non-marker" table of 65 non-marker signals; the 65 signals were randomly chosen from aptamers that did not demonstrate differential signaling between control and disease populations.

Figure 11A:
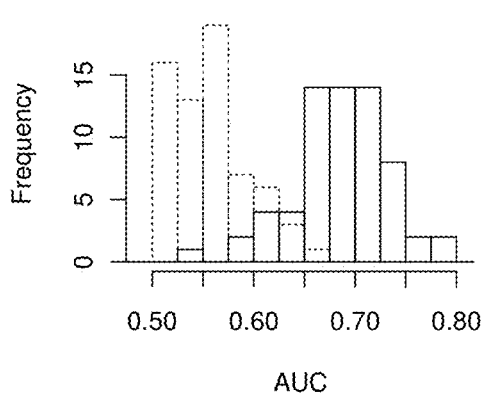
FIG. 11A shows a pair of histograms summarizing all possible single protein naïve Bayes classifier scores (AUC) using the biomarkers set forth in Table 1 (solid) and a set of random markers (dotted).
Figure 11B:
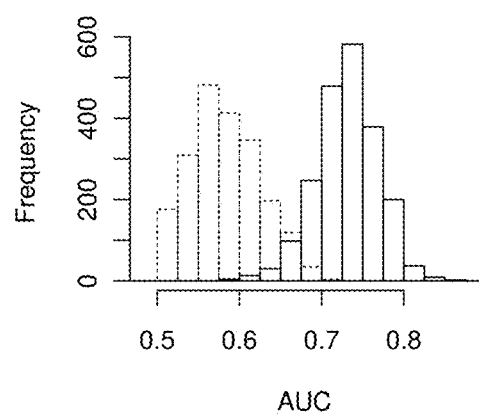
FIG. 11B shows a pair of histograms summarizing all possible two-protein protein naïve Bayes classifier scores (AUC) using the biomarkers set forth in Table 1 (solid) and a set of random markers (dotted).
Figure 11C:
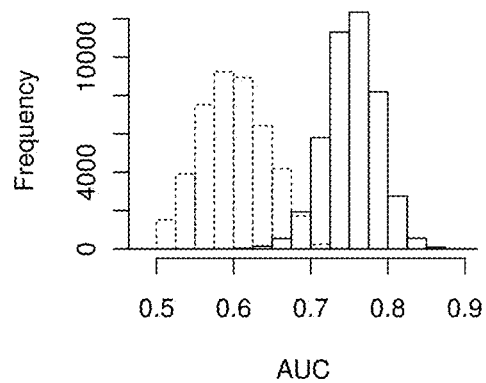
FIG. 11C shows a pair of histograms summarizing all possible three-protein naïve Bayes classifier scores (AUC) using the biomarkers set forth in Table 1 (solid) and a set of random markers (dotted).

FIG. 11 shows histograms of the performance of all possible one, two, and three-marker classifiers built from the biomarker parameters in Table 14 for biomarkers that can discriminate between the control group and pancreatic cancer and compares these classifiers with all possible one, two, and three-marker classifiers built using the 65 "non-marker" aptamer RFU signals. FIG. 11A shows the histograms of single marker classifier performance, FIG. 11B shows the histogram of two marker classifier performance, and FIG. 11C shows the histogram of three marker classifier performance.

In FIG. 11, the solid lines represent the histograms of the classifier performance of all one, two, and three-marker classifiers using the biomarker data for GI and normal controls and pancreatic cancer in Table 14. The dotted lines are the histograms of the classifier performance of all one, two, and three-marker classifiers using the data for controls and pancreatic cancer but using the set of random non-marker signals.

The classifiers built from the markers listed in Table 1 form a distinct histogram, well separated from the classifiers built with signals from the "non-markers" for all one-marker, two-marker, and three-marker comparisons. The performance and AUC score of the classifiers built from the biomarkers in Table 1 also increase faster with the number of markers than do the classifiers built from the non-markers, the separation increases between the marker and non-marker classifiers as the number of markers per classifier increases. All classifiers built using the biomarkers listed in Table 14 perform distinctly better than classifiers built using the "non-markers".

Figure 12:
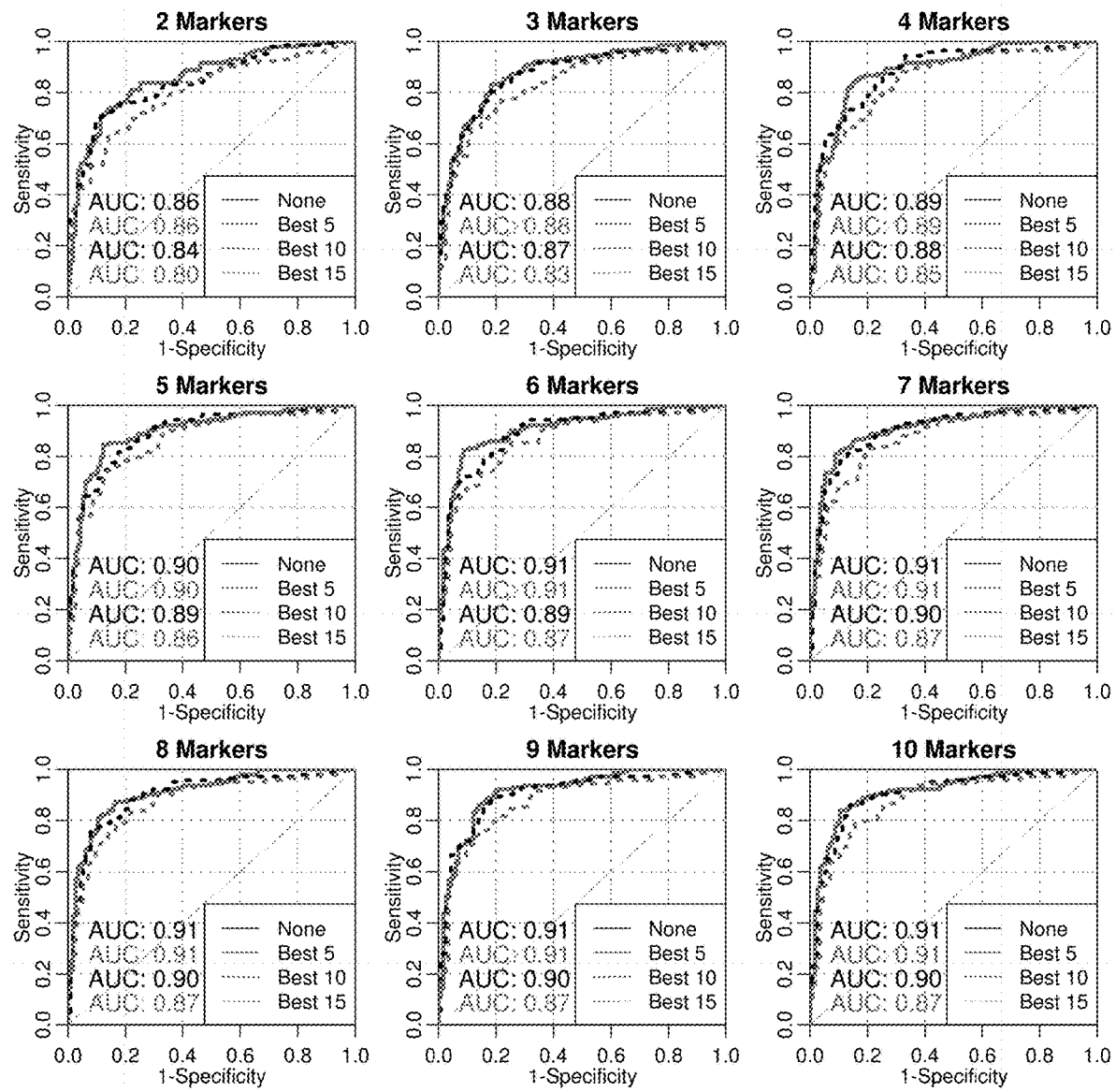
FIG. 12 shows the AUC for naïve Bayes classifiers using rom 2-10 markers selected from the full panel (diamond) and the scores obtained by dropping the best 5, 10, and 15 markers during classifier generation.

The distributions of classifier performance show that there are many possible multiple-marker classifiers that can be derived from the set of analytes in Table 1. Although some biomarkers are better than others on their own, as evidenced by the distribution of classifier scores and AUCs for single analytes, it was desirable to determine whether such biomarkers are required to construct high performing classifiers. To make this determination, the behavior of classifier performance was examined by leaving out some number of the best biomarkers. FIG. 12 compares the performance of classifiers built with the full list of biomarkers in Table 1 with the performance of classifiers built with subsets of biomarkers from Table 1 that excluded top-ranked markers.

FIG. 12 demonstrates that classifiers constructed without the best markers perform well, implying that the performance of the classifiers was not due to some small core group of markers and that the changes in the underlying processes associated with disease are reflected in the activities of many proteins. Many subsets of the biomarkers in Table 1 performed close to optimally, even after removing the top 15 of the 65 markers from Table 1. After dropping the 15 top-ranked markers (ranked by KS-distance) from Table 1, the classifier performance increased with the number of markers selected from the table to reach an AUC of almost 0.87, close to the performance of the optimal classifier score of 0.91 selected from the full list of biomarkers.

Figure 16A:
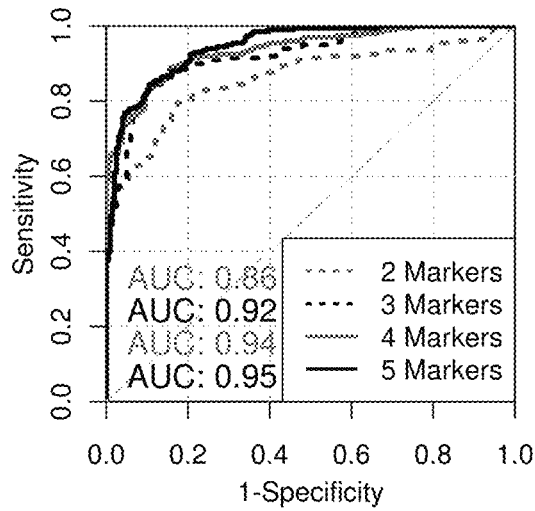
FIG. 16A shows a set of ROC curves modeled from the data in Table 14 for panels of from one to five markers.
Figure 16B:
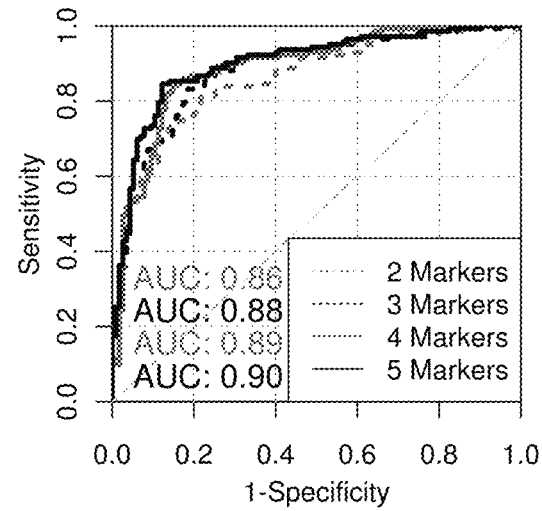
FIG. 16B shows a set of ROC curves computed from the training data for panels of from one to five markers as in FIG. 12A.

Finally, FIG. 16 shows how the ROC performance of typical classifiers constructed from the list of parameters in Table 14 according to Example 3. A five analyte classifier was constructed with CTSB, C5a, C5, CCL18, and CSF1R. FIG. 16A shows the performance of the model, assuming independence of these markers, as in Example 3, and FIG. 16B shows the empirical ROC curves generated from the study data set used to define the parameters in Table 14. It can be seen that the performance for a given number of selected markers was qualitatively in agreement, and that quantitative agreement was generally quite good, as evidenced by the AUCs, although the model calculation tends to overestimate classifier performance. This is consistent with the notion that the information contributed by any particular biomarker concerning the disease processes is redundant with the information contributed by other biomarkers provided in Table 1 while the model calculation assumes complete independence. FIG. 16 thus demonstrates that Table 1 in combination with the methods described in Example 3 enable the construction and evaluation of a great many classifiers useful for the discrimination of pancreatic cancer from the control group.

Example 5

Incorporating CA19-9

Cancer associated antigen 19-9 (CA 19-9) is a known serum marker for pancreatic cancer. The reported sensitivity and specificity of CA 19-9 for pancreatic cancer are 80 to 90 percent, respectively. However, the accuracy of CA 19-9 to identify patients with small surgically resectable cancers is limited. The specificity of CA 19-9 is also limited; CA 19-9 is frequently elevated in patients with various benign pancreaticobiliary disorders.

The degree of elevation of CA 19-9 in pancreatic cancer is associated with long-term prognosis. Furthermore, in patients who appear to have potentially resectable disease, the magnitude of the CA 19-9 level can also help to predict the presence of radiographically occult metastatic disease. Serial monitoring of CA 19-9 levels is useful to follow patients after potentially curative surgery and for those who are receiving chemotherapy for advanced disease. Rising CA 19-9 levels usually precede the radiographic appearance of recurrent disease, but confirmation of disease progression should be pursued with imaging studies and/or biopsy. Testing of biomarker levels in combination with CA 19-9 may improve sensitivity, specificity, and/or AUC for detecting pancreatic cancer (or other pancreatic cancer-related uses) as compared to CA 19-9 alone.

An elevated level of CA19-9 is considered to be 35-40 U/ml in serum.

We received clinical CA19-9 measurements for a subset of the training samples. Of the original 100 cases and 69 controls, we had CA19-9 measurements for 99 cases and 52 controls. Therefore, we trained a new set of random forest models on this subset of samples using subsets of the SOMAmers in Table 1. We also trained new classifiers which incorporated the CA19-9 measurement with our SOMAmer panel (combined panel).

Figure 13:
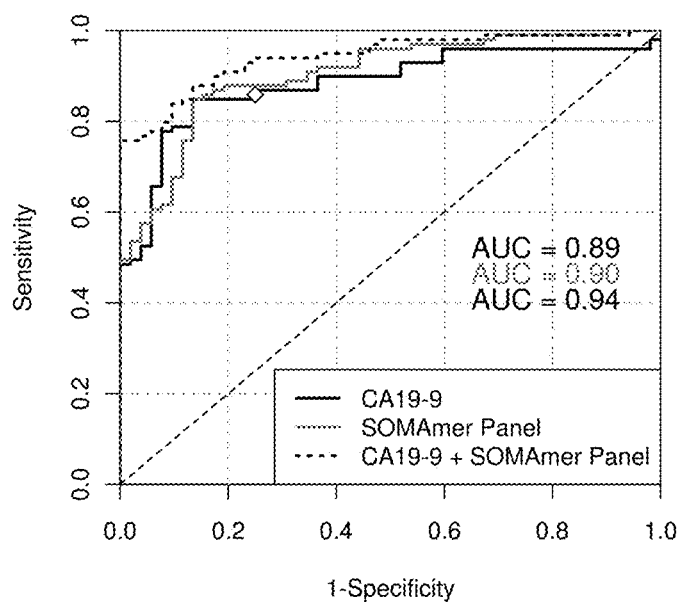
FIG. 13 shows the performance of three different classifiers: CA19-9 alone, the SOMAmer panel and the combination of SOMAmers and CA19-9.

The classifier performance of the three different approaches (SOMAmer, CA19-9, and a combined panel) is shown in FIG. 13. The SOMAmer panel and CA19-9 perform similarly, however when the two are combined into a single classifier the performance improves dramatically. For a specificity of 100%, the SOMAmer panel and CA19-9 have a sensitivity Just under 50%, whereas the combined classifier has a sensitivity of around 75%.

Figure 14A:
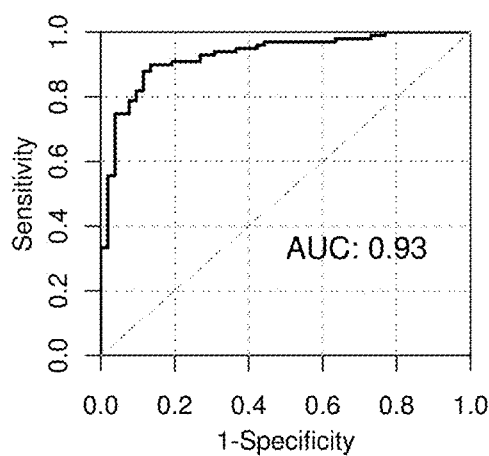
FIG. 14A shows the performance of CA19-9 plus one (HAMP) SOMAmer biomarker.
Figure 14B:
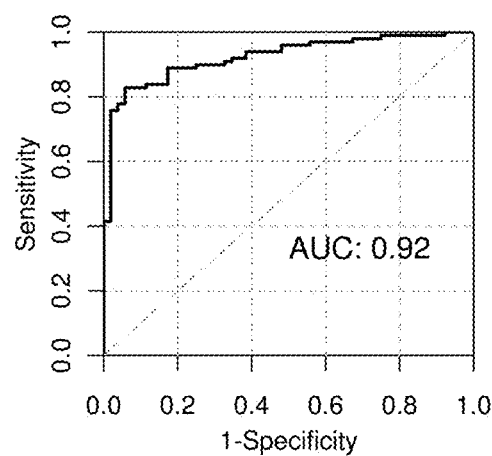
FIG. 14B shows the performance of CA19-9 plus two (HAMP and CTSB) SOMAmer biomarkers.

Further analysis revealed that when CA19-9 is included in the classifier, the number of SOMAmers required for the same relative performance is reduced. FIGS. 14A and 14B show the performance of random forest classifiers that use CA19-9 and either one or two additional SOMAmers. FIG.

14A shows the performance of a model trained using CA19-9 and HAMP and FIG. 14B shows the performance of CA19-9, HAMP, and CTSB.

Example 6

Clinical Biomarker Panel

A random forest classifier was built from a panel of biomarkers selected that may be the most appropriate for use in a clinical diagnostic test. Unlike the models selected by the naïve Bayes greedy forward algorithm, the random forest classifier does not assume that the biomarker measurements are randomly distributed. Therefore, this model can utilize biomarkers from Table 1 that are not effective in the naïve Bayes classifier.

The panel was selected using a backward elimination procedure that utilized the gini importance measure provided by the random forest classifier. The gini importance is a measure of the effectiveness of a biomarker at correctly classifying samples in the training set. This measure of biomarker importance can be used to eliminate markers that are less vital to the performance of the classifier. The backward elimination procedure was initiated by building a random forest classifier that included all 65 in Table 1. The least important biomarker was then eliminated and a new model was built with the remaining biomarkers. This procedure continued until only single biomarker remained.

Figure 15:
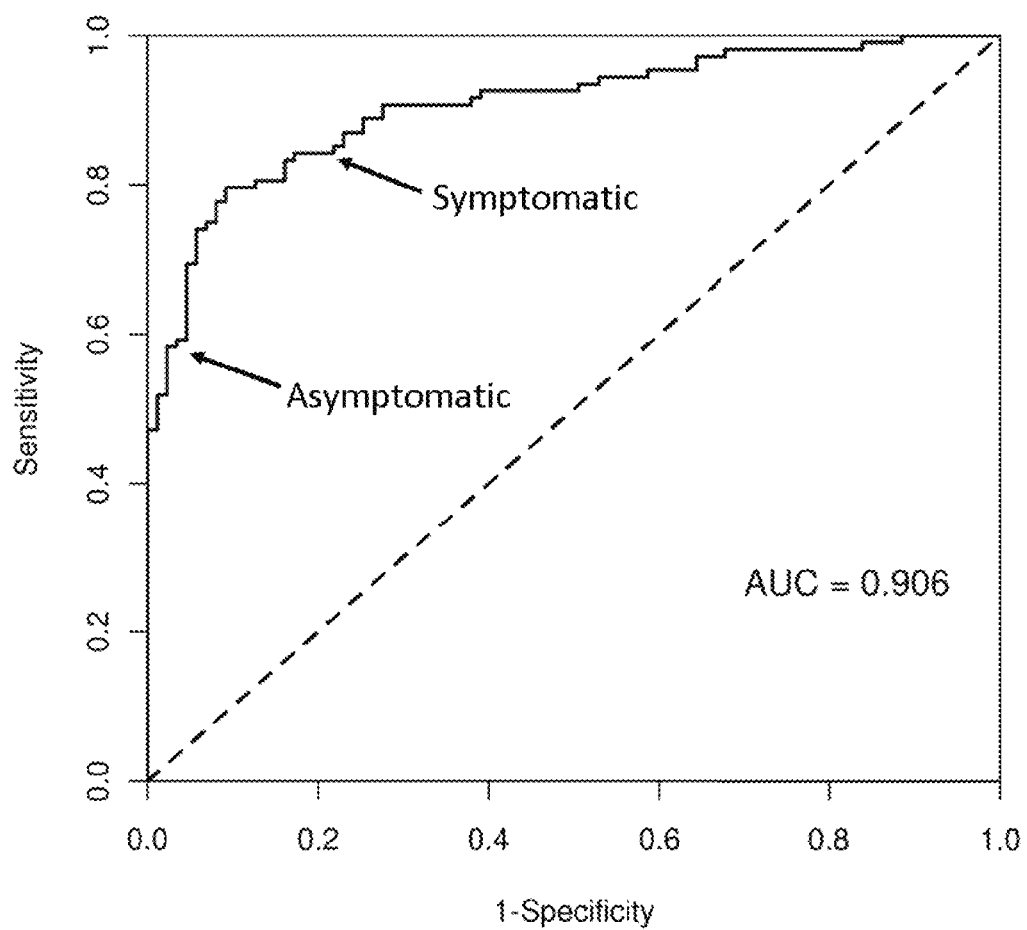
FIG. 15 shows the performance of the 10 marker random forest classifier.

The final panel that was selected provided the best balance between the greatest AUC and the lowest number of markers in the model. The panel of ten biomarkers that satisfied these criteria is composed of the following analytes, APOA1, CTSB, C2, MMP7, HAMP, TFPI, C5, c5a, SFRP1, and ETHE1. A plot of the ROC curve for this biomarker panel is shown in FIG. 15. The figure indicates two possible decision cutoffs illustrated by arrows: a symptomatic cutoff where a sensitivity of 84% or more can be obtained with at least 80% specificity; and an asymptomatic cutoff where a specificity of 97.5% can be obtained with at least 60% sensitivity.

Example 7

Biomarkers for the Diagnosis of Cancer

The identification of potential biomarkers for the general diagnosis of cancer was performed. Both case and control samples were evaluated from 3 different types of cancer (pancreatic cancer, lung cancer, and mesothelioma). Across the collection sites, inclusion criteria were at least 18 years old with signed informed consent. Both cases and controls were excluded for known malignancy other than the cancer in question.

Pancreatic Cancer. Case and control samples were obtained as described in Example 2.

Lung Cancer. Case and control samples were obtained from three academic cancer center biorepositories and one commercial biorepository to identify potential markers for the differential diagnosis of non-small cell lung cancer (NSCLC) from a control group of high risk smokers and individuals with benign pulmonary nodules. The study was composed of 978 samples collected from smokers and patients with benign nodules as well as 320 individuals diagnosed with NSCLC.

Pleural Mesothelioma. Case and control samples were obtained from an academic cancer center biorepository to identify potential markers for the differential diagnosis of malignant pleural mesothelioma from individuals with a history of asbestos exposure or benign lung disease, including suspicious radiology findings that were later diagnosed as non-malignant. The study was composed of 30 samples collected from asbestos exposed individuals and 41 samples collected from mesothelioma patients.

A final list of cancer biomarkers was identified by combining the sets of biomarkers considered for each of the 3 different cancer studies. Bayesian classifiers that used biomarker sets of increasing size were successively constructed using a greedy algorithm (as described in greater detail in Section 7.2 of this Example). The sets (or panels) of biomarkers that were useful for diagnosing cancer in general among the types of cancer were compiled as a function of set (or panel) size and analyzed for their performance. This analysis resulted in the list of 10 cancer biomarkers shown in Table 19, each of which was present in at least one of these successive marker sets, which ranged in size from three to ten markers. As an illustrative example, we describe the generation of a specific panel composed of ten cancer biomarkers, which is shown in Table 32.

7.1 Naïve Bayesian Classification for Cancer

From the list of biomarkers in Table 1, a panel of ten potential cancer biomarkers was selected using a greedy algorithm for biomarker selection, as outlined in Section 7.2 of this Example. A distinct naïve Bayes classifier was constructed for each of the 3. The class-dependent probability density functions (pdfs), $p(x_i|c)$ and $p(x_i|d)$, where $x_i$ is the log of the measured RFU value for biomarker i, and c and d refer to the control and disease populations, were modeled as log-normal distribution functions characterized by a mean $\mu$ and variance $\sigma^2$. The parameters for pdfs of the 3 models composed of the ten potential biomarkers are listed in Table 31.

The naïve Bayes classification for such a model is given by the following equation, where p(d) is the prevalence of the disease in the population, $$\ln\left(\frac{p(d|\tilde{x})}{p(c|\tilde{x})}\right) = \sum_{i=1}^{n}\ln\left(\frac{\sigma_{c,i}}{\sigma_{d_i}}\right) - \frac{1}{2}\sum_{i=1}^{n}\left[\left(\frac{x_i - \mu_{d,i}}{\sigma_{d,i}}\right)^2 - \left(\frac{x_i - \mu_{c,i}}{\sigma_{c,i}}\right)^2\right] + \ln\left(\frac{p(d)}{1 - p(d)}\right),$$

appropriate to the test and n=10. Each of the terms in the summation is a log-likelihood ratio for an individual marker and the total log-likelihood ratio of a sample $\tilde{x}$ being free from the disease interest (i.e., in this case, each particular disease from the 3 different cancer types) versus having the disease is simply the sum of these individual terms plus a term that accounts for the prevalence of the disease. For simplicity, we assume p(d)=0.5 so that $$\ln\left(\frac{p(d)}{1 - p(d)}\right) = 0.$$

Given an unknown sample measurement in log(RFU) for each of the ten biomarkers of 10.1, 8.9, 8.8, 8.8, 9.1, 7.3, 8.2, 9.5, 6.7, 7.7, the calculation of the classification is detailed in Table 32. The individual components comprising the log likelihood ratio for disease versus control class are tabulated and can be computed from the parameters in Table 31 and the values of $\tilde{x}$. The sum of the individual log likelihood ratios is −4.568, or a likelihood of being free from the disease versus having the disease of 96, where likelihood $e^{4.568}$=96. Only 1 of the biomarker values have likelihoods more consistent with the disease group (log likelihood >0) but the remaining 9 biomarkers are all consistently found to favor the control group. Multiplying the likelihoods together gives the same results as that shown above; a likelihood of 96 that the unknown sample is free from the disease. In fact, this sample came from the control population in the NSCLC training set.

7.2 Greedy Algorithm for Selecting Cancer Biomarker Panels for Classifiers

Part 1

Subsets of the biomarkers in Table 1 were selected to construct potential classifiers that could be used to determine which of the markers could be used as general cancer biomarkers to detect cancer.

Given a set of markers, a distinct model was trained for each of the 3 cancer studies, so a global measure of performance was required to select a set of biomarkers that was able to classify simultaneously many different types of cancer. The measure of classifier performance used here was the mean of the area under ROC curve across all naïve Bayes classifiers. The ROC curve is a plot of a single classifier true positive rate (sensitivity) versus the false positive rate (1-specificity). The area under the ROC curve (AUC) ranges from 0 to 1.0, where an AUC of 1.0 corresponds to perfect classification and an AUC of 0.5 corresponds to random (coin toss) classifier. One can apply other common measures of performance such as the F-measure or the sum or product of sensitivity and specificity. Specifically, one might want to treat sensitivity and specificity with differing weight, in order to select those classifiers that perform with higher specificity at the expense of some sensitivity, or to select those classifiers which perform with higher sensitivity at the expense of specificity. We chose to use the AUC because it encompasses all combinations of sensitivity and specificity in a single measure. Different applications will have different benefits for true positive and true negative findings, and will have different costs associated with false positive findings from false negative findings. Changing the performance measure may change the exact subset of markers selected for a given set of data.

For the Bayesian approach to the discrimination of cancer samples from control samples described in Section 7.1 of this Example, the classifier was completely parameterized by the distributions of biomarkers in each of the 3 cancer studies, and the list of biomarkers was chosen from Table 19. That is to say, the subset of markers chosen for inclusion determined a classifier in a one-to-one manner given a set of training data.

The greedy method employed here was used to search for the optimal subset of markers from Table 1. For small numbers of markers or classifiers with relatively few markers, every possible subset of markers was enumerated and evaluated in terms of the performance of the classifier constructed with that particular set of markers (see Example 4, Part 2). (This approach is well known in the field of statistics as "best subset selection"; see, e.g., Hastie et al). However, for the classifiers described herein, the number of combinations of multiple markers can be very large, and it was not feasible to evaluate every possible set of 10 markers, as there are 30,045,015 possible combinations that can be generated from a list of only 30 total analytes. Because of the impracticality of searching through every subset of markers, the single optimal subset may not be found; however, by using this approach, many excellent subsets were found, and, in many cases, any of these subsets may represent an optimal one.

Instead of evaluating every possible set of markers, a "greedy" forward stepwise approach may be followed (see. e.g., Dabney A R, Storey J D (2007) Optimality Driven Nearest Centroid Classification from Genomic Data. PLoS ONE 2(10): e1002. doi:10.1371/journal.pone.0001002). Using this method, a classifier is started with the best single marker (based on KS-distance for the individual markers) and is grown at each step by trying, in turn, each member of a marker list that is not currently a member of the set of markers in the classifier. The one marker that scores the best in combination with the existing classifier is added to the classifier. This is repeated until no further improvement in performance is achieved. Unfortunately, this approach may miss valuable combinations of markers for which some of the individual markers are not all chosen before the process stops.

The greedy procedure used here was an elaboration of the preceding forward stepwise approach, in that, to broaden the search, rather than keeping just a single marker subset at each step, a list of candidate marker sets was kept. The list was seeded with a list of single markers. The list was expanded in steps by deriving new marker subsets from the ones currently on the list and adding them to the list. Each marker subset currently on the list was extended by adding any marker from Table 1 not already part of that classifier, and which would not, on its addition to the subset, duplicate an existing subset (these are termed "permissible markers"). Each time a new set of markers was defined, a set of classifiers composed of one for each cancer study was trained using these markers, and the global performance was measured via the mean AUC across all 3 studies. To avoid potential over fitting, the AUC for each cancer study model was calculated via a ten-fold cross validation procedure. Every existing marker subset was extended by every permissible marker from the list. Clearly, such a process would eventually generate every possible subset, and the list would run out of space. Therefore, all the generated marker sets were kept only while the list was less than some predetermined size. Once the list reached the predetermined size limit, it became elitist; that is, only those classifier sets which showed a certain level of performance were kept on the list, and the others fell off the end of the list and were lost. This was achieved by keeping the list sorted in order of classifier set performance; new marker sets whose classifiers were globally at least as good as the worst set of classifiers currently on the list were inserted, forcing the expulsion of the current bottom underachieving classifier sets. One further implementation detail is that the list was completely replaced on each generational step; therefore, every marker set on the list had the same number of markers, and at each step the number of markers per classifier grew by one.

In one embodiment, the set. (or panel) of biomarkers useful for constructing classifiers for diagnosing general cancer from non-cancer is based on the mean AUC for the particular combination of biomarkers used in the classification scheme. We identified many combinations of biomarkers derived from the markers in Table 19 that were able to effectively classify different cancer samples from controls. Representative panels are set forth in Tables 22-29, which set forth a series of 100 different panels of 3-10 biomarkers, which have the indicated mean cross validation (CV) AUC for each panel. The total number of occurrences of each marker in each of these panels is indicated at the bottom of each table.

The biomarkers selected in Table 19 gave rise to classifiers that perform better than classifiers built with "non-markers." In FIG. 17, we display the performance of our ten biomarker classifiers compared to the performance of other possible classifiers.

Figure 17A:
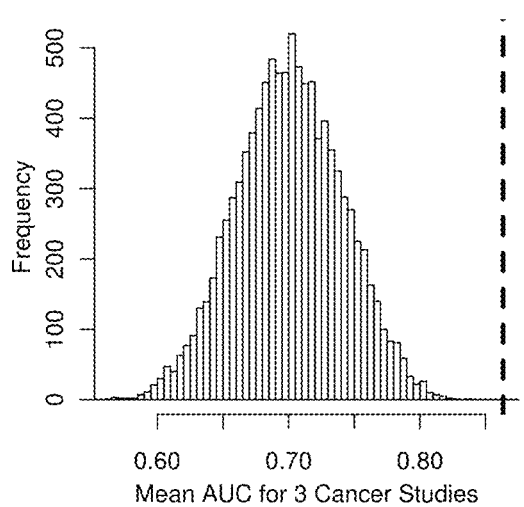
FIGS. 17A and 17B show a comparison of performance between ten biomarkers selected by a greedy selection procedure (Table 19) and 1,000 randomly sampled sets of ten "non marker" biomarkers. The mean AUC for the ten biomarkers in Table 19 is shown as a dotted vertical line.

FIG. 17A shows the distribution of mean AUCs for classifiers built from randomly sampled sets of ten "non-markers" taken from the entire set of 10 present in all 3 studies, excluding the ten markers in Table 19. The performance of the ten potential cancer biomarkers is displayed as a vertical dashed line. This plot clearly shows that the performance of the ten potential biomarkers is well beyond the distribution of other marker combinations.

Figure 17B:
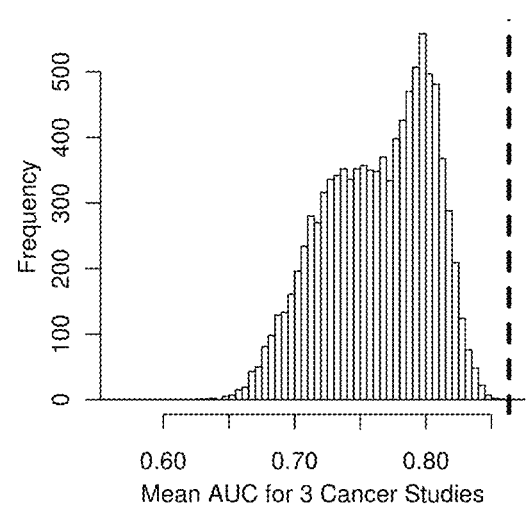

FIG. 17B displays a similar distribution as FIG. 17A, however the randomly sampled sets were restricted to the 55 biomarkers from Table 1 that were not selected by the greedy biomarker selection procedure for ten analyte classifiers. This plot demonstrates that the ten markers chosen by the greedy algorithm represent a subset of biomarkers that generalize to other types of cancer far better than classifiers built with the remaining 55 biomarkers.

Figure 18:
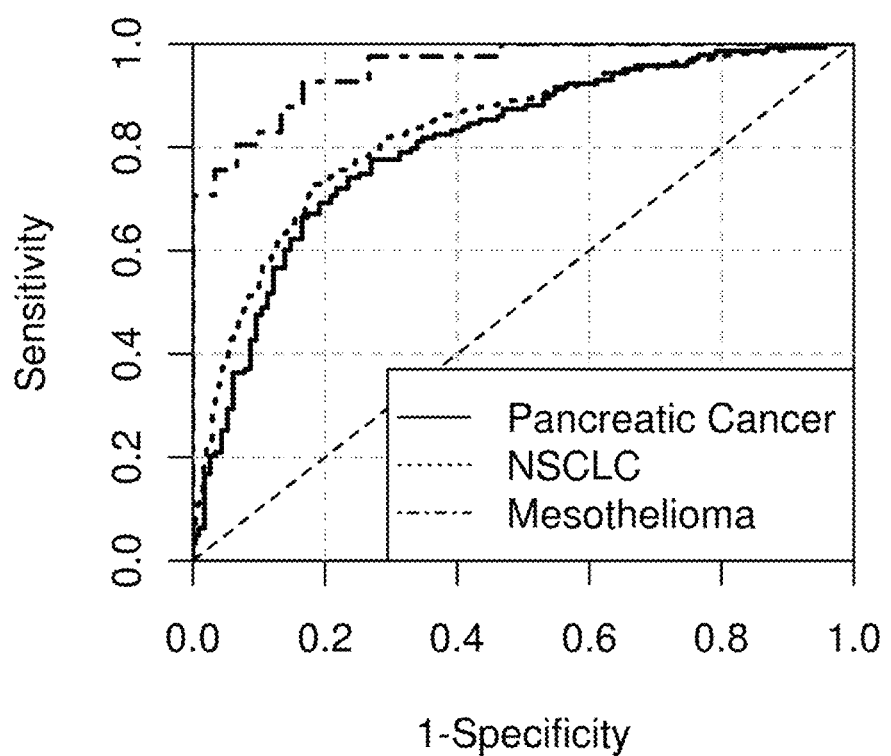
FIG. 18 shows receiver operating characteristic (ROC) curves for the 3 naïve Bayes classifiers set forth in Table 19. For each study, the area under the curve (AUC) is also displayed next to the legend.

Finally, FIG. 18 shows the classifier ROC curve for each of the 3 cancer studies classifiers. The foregoing embodiments and examples are intended only as examples. No particular embodiment, example, or element of a particular embodiment or example is to be construed as a critical, required, or essential element or feature of any of the claims. Further, no element described herein is required for the practice of the appended claims unless expressly described as "essential" or "critical." Various alterations, modifications, substitutions, and other variations can be made to the disclosed embodiments without departing from the scope of the present application, which is defined by the appended claims. The specification, including the figures and examples, is to be regarded in an illustrative manner, rather than a restrictive one, and all such modifications and substitutions are intended to be included within the scope of the application. Accordingly, the scope of the application should be determined by the appended claims and their legal equivalents, rather than by the examples given above. For example, steps recited in any of the method or process claims may be executed in any feasible order and are not limited to an order presented in any of the embodiments, the examples, or the claims. Further, in any of the aforementioned methods, one or more biomarkers of Table 1 or Table 19 can be specifically excluded either as an individual biomarker or as a biomarker from any panel.

TABLE 1

Cancer Biomarkers

| Column #1 Biomarker # | Column #2 Biomarker Designation Entrez Gene Symbol(s) | Column #3 Entrez Gene ID | Column #4 SwissProt ID | Column #5 Public Name | Column #6 Direction |
| --- | --- | --- | --- | --- | --- |
| 1 | ACP5 | 54 | P13686 | TrATPase | Up |
| 2 | ACY1 | 95 | Q03154 | Aminoacylase-1 | Up |
| 3 | AHSG | 197 | P02765 | α2-HS-Glycoprotein | Down |
| 4 | ALPL | 249 | P05186 | Alkaline phosphatase, bone | Down |
| 5 | APOA1 | 335 | P02647 | Apo A-I | Down |
| 6 | APOE | 348 | P02649 | Apo E2 | Up |
| 7 | BMP6 | 654 | P22004 | BMP-6 | Up |
| 8 | C2 | 717 | P06681 | C2 | Up |
| 9 | C5 | 727 | P01031 | C5 | Up |
| 10 | C5 | 727 | P01031 | C5a | Up |
| 11 | C5-C6 | 727; 729 | P01031; P13671 | C5b, 6 Complex | Up |
| 12 | C9 | 735 | P02748 | C9 | Up |
| 13 | CCL18 | 6362 | P55774 | MIP-4 | Up |
| 14 | CCL23 | 6368 | P55773 | MPIF-1 | Up |
| 15 | CCL23 | 6368 | P55773 | Ck-β-8-1 | Up |
| 16 | CDK5-CDK5R1 | 1020; 1775 | Q00535; Q15078 | CDK5/p35 | Up |
| 17 | CKB-CKM- | 1152; 1158 | P12277; P06732 | CK-MB | Down |
| 18 | CKM | 1158 | P06732 | CK-MM | Down |
| 19 | CRP | 1401 | P02741 | CRP | Up |
| 20 | CSF1R | 1436 | P07333 | M-CSF R | Up |
| 21 | CTSB | 1508 | P07858 | Cathepsin B | Up |
| 22 | ENTPD1 | 953 | P49961 | CD39 | Up |
| 23 | ESM1 | 11082 | Q9NQ30 | Endocan | Up |
| 24 | ETHE1 | 23474 | O95571 | ETHE1 | Up |
| 25 | FCGR3B | 2215 | O75015 | FCγ3B | Up |
| 26 | FGFR3 | 2261 | P22607 | FGFR-3 | Up |
| 27 | FSTL3 | 10272 | O95633 | FSTL3 | Up |
| 28 | GDF11 | 10220 | O95390 | GDF-11 | Down |
| 29 | GFRA1 | 2674 | P56159 | GFR α-1 | Up |
| 30 | HAMP | 57817 | P81172 | Hepcidin-25 | Up |
| 31 | HINT1 | 3094 | P49773 | HINT1 | Down |
| 32 | IDUA | 3425 | P35475 | IDUA | Up |
| 33 | IL11RA | 3590 | Q14626 | IL-11 Rα | Down |
| 34 | IL12A-IL12B | 3592; 3593 | P29459; P29460 | IL-12 | Down |
| 35 | IL18R1 | 8809 | Q13478 | IL-18 Rα | Up |
| 36 | IL1RL1 | 9173 | Q01638 | IL-1 R4 | Up |
| 37 | INSR | 3643 | P06213 | IR | Up |
| 38 | KIT | 3815 | P10721 | SCF sR | Down |
| 39 | KLK3-SERPINA3 | 354; 12 | P07288; P01011 | PSA-ACT | Up |
| 40 | KLK7 | 5650 | P49862 | Kallikrein 7 | Down |
| 41 | KLK8 | 11202 | O60259 | Kallikrein 8 | Up |
| 42 | KLKB1 | 3818 | P03952 | Prekallikrein | Down |

TABLE 1-continued

Cancer Biomarkers

| Column #1 Biomarker # | Column #2 Biomarker Designation Entrez Gene Symbol(s) | Column #3 Entrez Gene ID | Column #4 SwissProt ID | Column #5 Public Name | Column #6 Direction |
|---|---|---|---|---|---|
| 43 | LBP | 3929 | P18428 | LBP | Up |
| 44 | LTF | 4057 | P02788 | Lactoferrin | Down |
| 45 | MCM2 | 4171 | P49736 | MCM2 | Up |
| 46 | MDK | 4192 | P21741 | Midkine | Up |
| 47 | MMP7 | 4316 | P09237 | MMP-7 | Up |
| 48 | MRC1 | 4360 | P22897 | Macrophage mannose receptor | Up |
| 49 | NID1 | 4811 | P14543 | Nidogen | Up |
| 50 | NID2 | 22795 | Q14112 | Nidogen-2 | Up |
| 51 | NRP1 | 8829 | O14786 | NRP1 | Up |
| 52 | PLAT | 5327 | P00750 | tPA | Up |
| 53 | SERPINA5 | 5104 | P05154 | Protein C Inhibitor | Down |
| 54 | SERPINF2 | 5345 | P08697 | α2-Antiplasmin | Down |
| 55 | SFRP1 | 6422 | Q8N474 | FRP-1, soluble | Up |
| 56 | SGTA | 6449 | O43765 | SGTα | Down |
| 57 | TFPI | 7035 | P10646 | TFPI | Up |
| 58 | THBS2 | 7058 | P35442 | Thrombospondin-2 | Up |
| 59 | THBS4 | 7060 | P35443 | Thrombospondin-4 | Down |
| 60 | TIMP1 | 7076 | P01033 | TIMP-1 | Up |
| 61 | TNFRSF18 | 8784 | Q9Y5U5 | GITR/TNFRSF18 | Down |
| 62 | TNFRSF1B | 7133 | P20333 | TNF sR-II | Up |
| 63 | TOP1 | 7150 | P11387 | Topoisomerase I | Down |
| 64 | VEGFA | 7422 | P15692 | VEGF | Down |
| 65 | VEGFC | 7424 | P49767 | VEGF-C | Up |

TABLE 2

Panels of 1 Biomarker

| | Markers | CV AUC |
|---|---|---|
| 1 | CTSB | 0.780 |
| 2 | C2 | 0.771 |
| 3 | APOA1 | 0.754 |
| 4 | C5 | 0.745 |
| 5 | TFPI | 0.739 |
| 6 | C5a | 0.724 |
| 7 | TIMP1 | 0.720 |
| 8 | FCGR3B | 0.719 |
| 9 | HAMP | 0.718 |
| 10 | CRP | 0.717 |
| 11 | NRP1 | 0.716 |
| 12 | THBS2 | 0.715 |
| 13 | MMP7 | 0.711 |
| 14 | CCL18 | 0.709 |
| 15 | CSF1R | 0.705 |
| 16 | ACP5 | 0.704 |
| 17 | LBP | 0.703 |
| 18 | MRC1 | 0.699 |
| 19 | PLAT | 0.699 |
| 20 | GFRA1 | 0.698 |
| 21 | CCL23 | 0.696 |
| 22 | KLK7 | 0.696 |
| 23 | MDK | 0.694 |
| 24 | CKB-CKM | 0.694 |
| 25 | KLK3-SERPINA3 | 0.693 |
| 26 | CKM | 0.693 |
| 27 | GDF11 | 0.692 |
| 28 | IL11RA | 0.690 |
| 29 | IL1RL1 | 0.690 |
| 30 | ETHE1 | 0.684 |
| 31 | FSTL3 | 0.681 |
| 32 | KIT | 0.680 |
| 33 | FGFR3 | 0.677 |
| 34 | KLKB1 | 0.677 |
| 35 | THBS4 | 0.669 |
| 36 | ACY1 | 0.666 |
| 37 | C5-C6 | 0.664 |
| 38 | INSR | 0.663 |
| 39 | IL18R1 | 0.663 |
| 40 | BMP6 | 0.663 |
| 41 | TNFRSF1B | 0.660 |
| 42 | C9 | 0.657 |
| 43 | SERPINA5 | 0.655 |
| 44 | IL12A-IL12B | 0.655 |
| 45 | NID2 | 0.649 |
| 46 | TOP1 | 0.647 |
| 47 | NID1 | 0.642 |
| 48 | CCL23 | 0.641 |
| 49 | MCM2 | 0.641 |
| 50 | AHSG | 0.638 |
| 51 | VEGFC | 0.637 |
| 52 | ENTPD1 | 0.637 |
| 53 | HINT1 | 0.637 |
| 54 | ALPL | 0.635 |
| 55 | LTF | 0.632 |
| 56 | ESM1 | 0.625 |
| 57 | SERPINF2 | 0.624 |
| 58 | CDK5-CDK5R1 | 0.623 |
| 59 | SGTA | 0.603 |
| 60 | KLK8 | 0.597 |
| 61 | IDUA | 0.594 |
| 62 | SFRP1 | 0.586 |
| 63 | VEGFA | 0.585 |
| 64 | APOE | 0.574 |
| 65 | TNFRSF18 | 0.527 |

TABLE 3

Panels of 2 Biomarkers

| | Markers | | CV AUC |
|---|---|---|---|
| 1 | C5 | CTSB | 0.848 |
| 2 | C5a | CTSB | 0.841 |
| 3 | CTSB | ETHE1 | 0.833 |
| 4 | CTSB | HAMP | 0.830 |
| 5 | CTSB | THBS4 | 0.830 |
| 6 | KIT | CTSB | 0.829 |

TABLE 3-continued

Panels of 2 Biomarkers

| | Markers | | CV AUC |
|---|---|---|---|
| 7 | C9 | CTSB | 0.828 |
| 8 | CTSB | KLK7 | 0.826 |
| 9 | CTSB | C2 | 0.821 |
| 10 | C5 | APOA1 | 0.820 |
| 11 | CTSB | CRP | 0.818 |
| 12 | CCL23 | CTSB | 0.817 |
| 13 | C5-C6 | CTSB | 0.814 |
| 14 | CTSB | IL11RA | 0.812 |
| 15 | CCL18 | CTSB | 0.811 |
| 16 | APOA1 | CTSB | 0.809 |
| 17 | C5 | CSF1R | 0.808 |
| 18 | GDF11 | CTSB | 0.807 |
| 19 | C5 | C2 | 0.806 |
| 20 | C2 | TFPI | 0.806 |
| 21 | C5 | CCL18 | 0.804 |
| 22 | C2 | IL11RA | 0.803 |
| 23 | CCL23 | CTSB | 0.802 |
| 24 | TIMP1 | C5 | 0.801 |
| 25 | CTSB | LBP | 0.799 |
| 26 | CTSB | TFPI | 0.799 |
| 27 | PLAT | C5 | 0.799 |
| 28 | CTSB | AHSG | 0.799 |
| 29 | CCL18 | C2 | 0.799 |
| 30 | C5 | MRC1 | 0.799 |
| 31 | APOA1 | C2 | 0.798 |
| 32 | C5 | FCGR3B | 0.797 |
| 33 | C5 | TFPI | 0.797 |
| 34 | ALPL | CTSB | 0.796 |
| 35 | C5 | MMP7 | 0.796 |
| 36 | CTSB | KLK3-SERPINA3 | 0.795 |
| 37 | MMP7 | CTSB | 0.795 |
| 38 | MMP7 | C2 | 0.794 |
| 39 | TFPI | HAMP | 0.793 |
| 40 | CCL18 | ETHE1 | 0.793 |
| 41 | C2 | HAMP | 0.792 |
| 42 | PLAT | C2 | 0.792 |
| 43 | CTSB | NRP1 | 0.792 |
| 44 | LTF | CTSB | 0.791 |
| 45 | C5 | ACP5 | 0.790 |
| 46 | APOA1 | TFPI | 0.790 |
| 47 | C5a | TNFRSF1B | 0.789 |
| 48 | C5a | CCL18 | 0.789 |
| 49 | CKM | CTSB | 0.789 |
| 50 | C5 | THBS2 | 0.789 |
| 51 | C2 | CRP | 0.788 |
| 52 | C5a | KLK7 | 0.788 |
| 53 | C2 | THBS4 | 0.788 |
| 54 | CSF1R | THBS4 | 0.788 |
| 55 | C5a | FSTL3 | 0.788 |
| 56 | C5 | NRP1 | 0.788 |
| 57 | C5a | C2 | 0.788 |
| 58 | C5a | TFPI | 0.787 |
| 59 | CTSB | CKB-CKM | 0.787 |
| 60 | C5a | NRP1 | 0.787 |
| 61 | CSF1R | APOA1 | 0.787 |
| 62 | TFPI | CRP | 0.787 |
| 63 | MMP7 | KLK7 | 0.787 |
| 64 | C5a | FCGR3B | 0.787 |
| 65 | C2 | ETHE1 | 0.786 |
| 66 | CCL23 | C2 | 0.786 |
| 67 | PLAT | CTSB | 0.786 |
| 68 | CCL18 | TFPI | 0.786 |
| 69 | ACP5 | CRP | 0.785 |
| 70 | C2 | KLK7 | 0.785 |
| 71 | C5 | CCL23 | 0.784 |
| 72 | MMP7 | C5a | 0.784 |
| 73 | APOA1 | KLK7 | 0.784 |
| 74 | C5 | GFRA1 | 0.784 |
| 75 | C5 | HAMP | 0.784 |
| 76 | C5 | C5a | 0.784 |
| 77 | NRP1 | CRP | 0.783 |
| 78 | KIT | C2 | 0.783 |
| 79 | C5 | IL1RL1 | 0.783 |
| 80 | APOA1 | ETHE1 | 0.783 |
| 81 | CTSB | CDK5-CDK5R1 | 0.782 |
| 82 | CSF1R | CRP | 0.782 |
| 83 | TIMP1 | CTSB | 0.782 |
| 84 | IL1RL1 | CTSB | 0.782 |
| 85 | CSF1R | C5a | 0.782 |
| 86 | TIMP1 | C5a | 0.781 |
| 87 | TFPI | KLK7 | 0.781 |
| 88 | C5 | KLKB1 | 0.781 |
| 89 | CTSB | FCGR3B | 0.781 |
| 90 | APOA1 | MMP7 | 0.781 |
| 91 | IL12A-IL12B | CTSB | 0.781 |
| 92 | C5 | MDK | 0.780 |
| 93 | MDK | CTSB | 0.780 |
| 94 | C5 | TNFRSF1B | 0.780 |
| 95 | C2 | ACP5 | 0.780 |
| 96 | IL12A-IL12B | C2 | 0.780 |
| 97 | NRP1 | TFPI | 0.780 |
| 98 | C5 | KIT | 0.779 |
| 99 | FCGR3B | ETHE1 | 0.779 |
| 100 | C5-C6 | C2 | 0.779 |

TABLE 4

Panels of 3 Biomarkers

| | Markers | | | CV AUC |
|---|---|---|---|---|
| 1 | C5 | C5a | CTSB | 0.871 |
| 2 | C5 | CTSB | ETHE1 | 0.870 |
| 3 | C5 | CTSB | HAMP | 0.866 |
| 4 | C5 | CCL18 | CTSB | 0.865 |
| 5 | C5 | KIT | CTSB | 0.862 |
| 6 | C5 | CTSB | THBS4 | 0.861 |
| 7 | KIT | C5a | CTSB | 0.861 |
| 8 | C5a | CCL18 | CTSB | 0.859 |
| 9 | CTSB | HAMP | ETHE1 | 0.859 |
| 10 | CTSB | KLK7 | HAMP | 0.859 |
| 11 | C5a | CTSB | KLK7 | 0.859 |
| 12 | C9 | C5 | CTSB | 0.859 |
| 13 | C5-C6 | C5a | CTSB | 0.858 |
| 14 | C5a | CTSB | ETHE1 | 0.858 |
| 15 | C5 | ALPL | CTSB | 0.857 |
| 16 | C5a | CTSB | HAMP | 0.856 |
| 17 | KIT | CTSB | HAMP | 0.856 |
| 18 | KIT | CTSB | ETHE1 | 0.854 |
| 19 | C5 | LTF | CTSB | 0.854 |
| 20 | C5a | CTSB | THBS4 | 0.854 |
| 21 | C5 | CCL23 | CTSB | 0.854 |
| 22 | C5 | APOA1 | CTSB | 0.854 |
| 23 | CCL18 | CTSB | ETHE1 | 0.853 |
| 24 | C5 | CTSB | IL11RA | 0.853 |
| 25 | C5 | CTSB | C2 | 0.852 |
| 26 | C5a | CTSB | C2 | 0.852 |
| 27 | CTSB | THBS4 | ETHE1 | 0.852 |
| 28 | CTSB | KLK7 | ETHE1 | 0.851 |
| 29 | C5-C6 | CTSB | HAMP | 0.851 |
| 30 | C5a | CCL23 | CTSB | 0.850 |
| 31 | C9 | CTSB | ETHE1 | 0.850 |
| 32 | C5 | CTSB | KLK7 | 0.849 |
| 33 | C5-C6 | CTSB | ETHE1 | 0.849 |
| 34 | GDF11 | C5a | CTSB | 0.849 |
| 35 | CTSB | THBS4 | HAMP | 0.848 |
| 36 | CCL23 | CTSB | ETHE1 | 0.848 |
| 37 | PLAT | C5 | CTSB | 0.848 |
| 38 | C5a | CTSB | IL11RA | 0.848 |
| 39 | PLAT | C5a | CTSB | 0.848 |
| 40 | C9 | KIT | CTSB | 0.847 |
| 41 | C5 | VEGFA | CTSB | 0.847 |
| 42 | CTSB | C2 | HAMP | 0.847 |
| 43 | C5 | CCL23 | CTSB | 0.847 |
| 44 | CTSB | C2 | ETHE1 | 0.847 |
| 45 | C5 | CSF1R | APOA1 | 0.846 |
| 46 | CCL18 | CTSB | HAMP | 0.846 |
| 47 | CTSB | C2 | IL11RA | 0.846 |
| 48 | C5a | CCL23 | CTSB | 0.846 |

TABLE 4-continued

Panels of 3 Biomarkers

| | Markers | | | CV AUC |
|---|---|---|---|---|
| 49 | GDF11 | CTSB | HAMP | 0.846 |
| 50 | C9 | CTSB | THBS4 | 0.845 |
| 51 | C5a | CTSB | CDK5-CDK5R1 | 0.845 |
| 52 | APOA1 | CTSB | ETHE1 | 0.845 |
| 53 | C9 | C5a | CTSB | 0.845 |
| 54 | C9 | CCL18 | CTSB | 0.844 |
| 55 | C5 | CTSB | TFPI | 0.844 |
| 56 | CCL18 | CTSB | THBS4 | 0.844 |
| 57 | KIT | CTSB | THBS4 | 0.844 |
| 58 | C9 | CTSB | KLK7 | 0.844 |
| 59 | CTSB | C2 | THBS4 | 0.844 |
| 60 | C5-C6 | CCL18 | CTSB | 0.843 |
| 61 | C5 | CSF1R | CTSB | 0.843 |
| 62 | C9 | CTSB | HAMP | 0.843 |
| 63 | C5 | CTSB | ACP5 | 0.843 |
| 64 | C5 | CSF1R | CCL18 | 0.842 |
| 65 | C5-C6 | KIT | CTSB | 0.842 |
| 66 | C5 | MMP7 | CTSB | 0.842 |
| 67 | PLAT | C9 | CTSB | 0.842 |
| 68 | C5 | CTSB | NRP1 | 0.842 |
| 69 | MMP7 | C5a | CTSB | 0.842 |
| 70 | C5 | CTSB | LBP | 0.841 |
| 71 | CSF1R | C5a | CTSB | 0.841 |
| 72 | C5-C6 | C9 | CTSB | 0.841 |
| 73 | C5 | GDF11 | CTSB | 0.841 |
| 74 | KIT | CCL18 | CTSB | 0.840 |
| 75 | CTSB | THBS4 | CRP | 0.840 |
| 76 | C5 | CTSB | AHSG | 0.840 |
| 77 | C9 | CTSB | C2 | 0.840 |
| 78 | LTF | C5a | CTSB | 0.840 |
| 79 | C5a | CTSB | TFPI | 0.840 |
| 80 | C5a | CTSB | TNFRSF1B | 0.839 |
| 81 | ALPL | C5a | CTSB | 0.839 |
| 82 | C5a | CTSB | NRP1 | 0.839 |
| 83 | APOA1 | C5a | CTSB | 0.839 |
| 84 | CCL23 | CTSB | ETHE1 | 0.839 |
| 85 | C5a | CTSB | FCGR3B | 0.838 |
| 86 | CTSB | TFPI | ETHE1 | 0.838 |
| 87 | C5 | KLK8 | CTSB | 0.838 |
| 88 | C5-C6 | C5 | CTSB | 0.838 |
| 89 | C5a | CTSB | KLK3-SERPINA3 | 0.838 |
| 90 | CTSB | LBP | ETHE1 | 0.838 |
| 91 | CTSB | IL11RA | ETHE1 | 0.838 |
| 92 | CTSB | HAMP | IL11RA | 0.838 |
| 93 | ALPL | CTSB | KLK7 | 0.838 |
| 94 | CCL18 | CTSB | KLK7 | 0.838 |
| 95 | C5a | CTSB | INSR | 0.838 |
| 96 | CTSB | C2 | KLK7 | 0.838 |
| 97 | CTSB | AHSG | ETHE1 | 0.838 |
| 98 | C5-C6 | CTSB | THBS4 | 0.838 |
| 99 | C5 | CTSB | KLKB1 | 0.837 |
| 100 | C5a | CTSB | LBP | 0.837 |

TABLE 5

Panels of 4 Biomarkers

| | Markers | | | | CV AUC |
|---|---|---|---|---|---|
| 1 | C5 | CCL18 | CTSB | ETHE1 | 0.882 |
| 2 | C5a | CCL18 | CTSB | ETHE1 | 0.880 |
| 3 | C5 | CTSB | HAMP | ETHE1 | 0.880 |
| 4 | C5 | KIT | C5a | CTSB | 0.880 |
| 5 | C5a | CTSB | THBS4 | ETHE1 | 0.880 |
| 6 | C5 | CTSB | THBS4 | ETHE1 | 0.878 |
| 7 | C5 | LTF | CTSB | ETHE1 | 0.877 |
| 8 | C5 | CSF1R | C5a | CTSB | 0.877 |
| 9 | PLAT | C5 | C5a | CTSB | 0.876 |
| 10 | C5 | ALPL | CTSB | ETHE1 | 0.876 |
| 11 | C5 | KIT | CTSB | ETHE1 | 0.875 |
| 12 | C5a | CTSB | KLK7 | HAMP | 0.875 |
| 13 | C5 | KIT | CTSB | HAMP | 0.875 |
| 14 | C5 | CCL23 | CTSB | ETHE1 | 0.875 |
| 15 | C5a | CTSB | KLK7 | ETHE1 | 0.875 |
| 16 | PLAT | C5 | CTSB | ETHE1 | 0.875 |
| 17 | C5 | C5a | CTSB | HAMP | 0.874 |
| 18 | CTSB | KLK7 | HAMP | ETHE1 | 0.874 |
| 19 | C5 | KIT | CCL18 | CTSB | 0.874 |
| 20 | C9 | C5 | CTSB | ETHE1 | 0.874 |
| 21 | C5 | CCL18 | CTSB | THBS4 | 0.874 |
| 22 | C5-C6 | CCL18 | CTSB | ETHE1 | 0.874 |
| 23 | C5 | LTF | C5a | CTSB | 0.874 |
| 24 | C5 | ALPL | C5a | CTSB | 0.873 |
| 25 | KIT | CTSB | HAMP | ETHE1 | 0.873 |
| 26 | C5 | C5a | CTSB | KLK7 | 0.873 |
| 27 | C5 | C5a | CTSB | THBS4 | 0.872 |
| 28 | C5-C6 | C5a | CCL18 | CTSB | 0.872 |
| 29 | C5 | CTSB | KLK7 | HAMP | 0.872 |
| 30 | C5 | C5a | CTSB | ACP5 | 0.872 |
| 31 | C5 | C5a | CTSB | IL11RA | 0.872 |
| 32 | C5 | C5a | CCL23 | CTSB | 0.872 |
| 33 | C5 | CCL18 | CTSB | HAMP | 0.872 |
| 34 | C5a | CCL18 | CTSB | KLK7 | 0.872 |
| 35 | C5 | KIT | VEGFA | CTSB | 0.871 |
| 36 | KIT | C5a | CCL18 | CTSB | 0.871 |
| 37 | C5 | APOA1 | CTSB | ETHE1 | 0.871 |
| 38 | C5a | CCL18 | CTSB | ETHE1 | 0.871 |
| 39 | KIT | C5a | CTSB | ETHE1 | 0.871 |
| 40 | PLAT | C9 | C5 | CTSB | 0.871 |
| 41 | C5 | ALPL | CTSB | THBS4 | 0.870 |
| 42 | C5 | ALPL | CCL18 | CTSB | 0.870 |
| 43 | C5 | CSF1R | CTSB | ETHE1 | 0.870 |
| 44 | C5 | CTSB | THBS4 | HAMP | 0.870 |
| 45 | C5a | CCL18 | CTSB | THBS4 | 0.870 |
| 46 | C5 | CTSB | KLK7 | ETHE1 | 0.869 |
| 47 | ALPL | C5a | CTSB | KLK7 | 0.869 |
| 48 | MMP7 | C5a | CTSB | KLK7 | 0.869 |
| 49 | C5 | LTF | CCL18 | CTSB | 0.869 |
| 50 | C9 | C5 | KIT | CTSB | 0.869 |
| 51 | C5-C6 | CTSB | HAMP | ETHE1 | 0.869 |
| 52 | C5 | ALPL | CTSB | HAMP | 0.869 |
| 53 | LTF | C5a | CTSB | KLK7 | 0.869 |
| 54 | C5-C6 | KIT | C5a | CTSB | 0.869 |
| 55 | C5 | ALPL | CTSB | IL11RA | 0.868 |
| 56 | KIT | C5a | CTSB | HAMP | 0.868 |
| 57 | C9 | C5 | CCL18 | CTSB | 0.868 |
| 58 | C5 | LTF | CTSB | THBS4 | 0.868 |
| 59 | C5 | CTSB | ACP5 | ETHE1 | 0.868 |
| 60 | C5 | CCL18 | CTSB | IL11RA | 0.868 |
| 61 | CCL18 | CTSB | HAMP | ETHE1 | 0.868 |
| 62 | PLAT | KIT | C5a | CTSB | 0.868 |
| 63 | C5-C6 | C5a | CTSB | ETHE1 | 0.868 |
| 64 | C5 | C5a | CTSB | C2 | 0.868 |
| 65 | C9 | C5 | ALPL | CTSB | 0.868 |
| 66 | C5 | CTSB | IL11RA | ETHE1 | 0.868 |
| 67 | CCL18 | CTSB | KLK7 | ETHE1 | 0.868 |
| 68 | C5 | CTSB | C2 | ETHE1 | 0.868 |
| 69 | C5 | KIT | CTSB | THBS4 | 0.867 |
| 70 | CCL18 | CTSB | THBS4 | ETHE1 | 0.867 |
| 71 | CCL18 | CTSB | KLK7 | HAMP | 0.867 |
| 72 | C5 | CSF1R | CCL18 | ETHE1 | 0.867 |
| 73 | KIT | CCL18 | CTSB | ETHE1 | 0.867 |
| 74 | C5 | C5a | CTSB | CDK5-CDK5R1 | 0.867 |
| 75 | C5 | C5a | CCL23 | CTSB | 0.867 |
| 76 | C5 | KIT | ALPL | CTSB | 0.867 |
| 77 | KIT | CSF1R | C5a | CTSB | 0.867 |
| 78 | C5 | KIT | LTF | CTSB | 0.867 |
| 79 | C5 | LTF | CTSB | IL11RA | 0.867 |
| 80 | C9 | C5 | CSF1R | CTSB | 0.866 |
| 81 | C5-C6 | C5a | CTSB | KLK7 | 0.866 |
| 82 | C5 | C5a | CTSB | INSR | 0.866 |
| 83 | C5a | CCL23 | CTSB | KLK7 | 0.866 |
| 84 | C5 | GDF11 | CTSB | HAMP | 0.866 |
| 85 | C5 | GDF11 | C5a | CTSB | 0.866 |
| 86 | C5 | CSF1R | CTSB | HAMP | 0.866 |
| 87 | C5 | C5a | CTSB | TNFRSF1B | 0.866 |
| 88 | C5 | CCL23 | CTSB | ETHE1 | 0.866 |
| 89 | C9 | C5 | LTF | CTSB | 0.866 |
| 90 | C9 | C5 | CTSB | HAMP | 0.866 |

TABLE 5-continued

Panels of 4 Biomarkers

| | Markers | | | | CV AUC |
|---|---|---|---|---|---|
| 91 | C9 | C5 | CTSB | THBS4 | 0.866 |
| 92 | C5 | LTF | CTSB | HAMP | 0.866 |
| 93 | C5-C6 | C5 | C5a | CTSB | 0.865 |
| 94 | C5 | KLK8 | C5a | CTSB | 0.865 |
| 95 | C5 | VEGFA | CTSB | ETHE1 | 0.865 |
| 96 | C5a | CTSB | HAMP | ETHE1 | 0.865 |
| 97 | C5 | MMP7 | C5a | CTSB | 0.865 |
| 98 | C5 | C5a | CTSB | ESM1 | 0.865 |
| 99 | C5a | CCL18 | CTSB | IL11RA | 0.865 |
| 100 | C5a | CTSB | C2 | ETHE1 | 0.865 |

TABLE 6

Panels of 5 Biomarkers

| | Markers | | | | | CV AUC |
|---|---|---|---|---|---|---|
| 1 | C5 | CSF1R | C5a | CTSB | ETHE1 | 0.892 |
| 2 | C5 | C5a | CCL18 | CTSB | ETHE1 | 0.889 |
| 3 | C5 | CCL18 | CTSB | THBS4 | ETHE1 | 0.888 |
| 4 | C5 | CSF1R | CCL18 | CTSB | ETHE1 | 0.887 |
| 5 | PLAT | C5 | C5a | CTSB | ETHE1 | 0.886 |
| 6 | C5 | KIT | CSF1R | C5a | CTSB | 0.886 |
| 7 | C5 | KIT | CCL18 | CTSB | ETHE1 | 0.886 |
| 8 | C5 | KIT | C5a | CCL18 | CTSB | 0.886 |
| 9 | C5 | LTF | CCL18 | CTSB | ETHE1 | 0.886 |
| 10 | C5 | KIT | C5a | CTSB | ETHE1 | 0.885 |
| 11 | C5a | CCL18 | CTSB | KLK7 | ETHE1 | 0.885 |
| 12 | C5 | CSF1R | C5a | CCL18 | CTSB | 0.885 |
| 13 | C5 | C5a | CCL18 | CTSB | THBS4 | 0.885 |
| 14 | C5 | ALPL | CCL18 | CTSB | ETHE1 | 0.884 |
| 15 | C5 | C5a | CTSB | KLK7 | ETHE1 | 0.884 |
| 16 | C5 | ALPL | CTSB | THBS4 | ETHE1 | 0.884 |
| 17 | C5a | CTSB | KLK7 | HAMP | ETHE1 | 0.884 |
| 18 | C5 | CTSB | KLK7 | HAMP | ETHE1 | 0.884 |
| 19 | C5 | CCL18 | CTSB | HAMP | ETHE1 | 0.884 |
| 20 | C5 | KIT | CTSB | HAMP | ETHE1 | 0.884 |
| 21 | C5 | CSF1R | C5a | CTSB | THBS4 | 0.884 |
| 22 | C5 | LTF | CTSB | THBS4 | ETHE1 | 0.884 |
| 23 | C5 | ALPL | C5a | CTSB | ETHE1 | 0.883 |
| 24 | CCL18 | CTSB | KLK7 | HAMP | ETHE1 | 0.883 |
| 25 | C5 | KIT | LTF | C5a | CTSB | 0.883 |
| 26 | PLAT | C5 | KIT | C5a | CTSB | 0.883 |
| 27 | PLAT | C9 | C5 | CTSB | ETHE1 | 0.883 |
| 28 | C5 | LTF | C5a | CTSB | ETHE1 | 0.883 |
| 29 | C5 | CSF1R | CTSB | HAMP | ETHE1 | 0.883 |
| 30 | C9 | C5 | CSF1R | CTSB | ETHE1 | 0.882 |
| 31 | PLAT | C5 | CTSB | THBS4 | ETHE1 | 0.882 |
| 32 | C5 | C5a | CCL23 | CTSB | ETHE1 | 0.882 |
| 33 | C5 | C5a | CCL18 | CTSB | KLK7 | 0.882 |
| 34 | C5-C6 | C5a | CCL18 | CTSB | ETHE1 | 0.882 |
| 35 | C5 | CSF1R | CTSB | THBS4 | ETHE1 | 0.882 |
| 36 | C5 | C5a | CTSB | KLK7 | HAMP | 0.882 |
| 37 | C5 | LTF | C5a | CCL18 | CTSB | 0.882 |
| 38 | C5 | KIT | ALPL | C5a | CTSB | 0.882 |
| 39 | C5 | CCL23 | CCL18 | CTSB | ETHE1 | 0.881 |
| 40 | PLAT | C5 | CCL18 | CTSB | ETHE1 | 0.881 |
| 41 | C5 | C5a | CTSB | THBS4 | ETHE1 | 0.881 |
| 42 | C5 | KLK8 | CCL18 | CTSB | ETHE1 | 0.881 |
| 43 | C5 | C5a | CCL18 | CTSB | IL11RA | 0.881 |
| 44 | C5 | KIT | ALPL | CCL18 | CTSB | 0.881 |
| 45 | PLAT | C5 | C5a | CCL18 | CTSB | 0.881 |
| 46 | C5 | CCL18 | CTSB | IL11RA | ETHE1 | 0.881 |
| 47 | C5 | C5a | CTSB | INSR | ETHE1 | 0.881 |
| 48 | C5 | KIT | C5a | CTSB | HAMP | 0.881 |
| 49 | C5 | C5a | CTSB | ACP5 | ETHE1 | 0.881 |
| 50 | C5-C6 | CCL18 | CTSB | THBS4 | ETHE1 | 0.880 |
| 51 | C5 | LTF | C5a | CTSB | KLK7 | 0.880 |
| 52 | C5 | C5a | CTSB | HAMP | ETHE1 | 0.880 |
| 53 | C5 | KIT | ALPL | CTSB | ETHE1 | 0.880 |
| 54 | C5 | KIT | LTF | CTSB | ETHE1 | 0.880 |
| 55 | C5 | ALPL | CTSB | KLK7 | ETHE1 | 0.880 |
| 56 | C5-C6 | KIT | C5a | CCL18 | CTSB | 0.880 |
| 57 | C5 | CTSB | THBS4 | HAMP | ETHE1 | 0.880 |
| 58 | C5a | CCL18 | CTSB | KLK7 | HAMP | 0.880 |
| 59 | C5 | CCL18 | CTSB | KLK7 | ETHE1 | 0.880 |
| 60 | C5 | CCL18 | CTSB | ACP5 | ETHE1 | 0.880 |
| 61 | C5 | KIT | LTF | CCL18 | CTSB | 0.880 |
| 62 | MMP7 | C5a | CTSB | KLK7 | HAMP | 0.880 |
| 63 | C5 | KIT | C5a | CCL23 | CTSB | 0.880 |
| 64 | C9 | C5 | CCL18 | CTSB | ETHE1 | 0.880 |
| 65 | C5 | CSF1R | C5a | CTSB | HAMP | 0.880 |
| 66 | C5 | ALPL | C5a | CCL18 | CTSB | 0.880 |
| 67 | C5 | C5a | CCL18 | CTSB | HAMP | 0.880 |
| 68 | C5 | CSF1R | C5a | CTSB | IL11RA | 0.880 |
| 69 | C5a | CCL23 | CTSB | KLK7 | ETHE1 | 0.880 |
| 70 | C5-C6 | KIT | CCL18 | CTSB | ETHE1 | 0.879 |
| 71 | C5 | CSF1R | CCL23 | CTSB | ETHE1 | 0.879 |
| 72 | C5 | LTF | CCL23 | CTSB | ETHE1 | 0.879 |
| 73 | C5 | KLK8 | C5a | CCL18 | CTSB | 0.879 |
| 74 | LTF | C5a | CCL18 | CTSB | KLK7 | 0.879 |
| 75 | PLAT | C5 | CCL23 | CTSB | ETHE1 | 0.879 |
| 76 | C5 | KIT | CSF1R | CTSB | ETHE1 | 0.879 |
| 77 | ALPL | C5a | CCL18 | CTSB | KLK7 | 0.879 |
| 78 | KIT | C5a | CCL18 | CTSB | ETHE1 | 0.879 |
| 79 | CSF1R | C5a | CCL18 | CTSB | ETHE1 | 0.879 |
| 80 | C5 | KIT | C5a | CTSB | THBS4 | 0.879 |
| 81 | C5 | VEGFA | CCL18 | CTSB | ETHE1 | 0.879 |
| 82 | C5 | CSF1R | C5a | CTSB | KLK7 | 0.879 |
| 83 | CSF1R | C5a | CTSB | KLK7 | ETHE1 | 0.879 |
| 84 | C5-C6 | C5a | CTSB | KLK7 | ETHE1 | 0.879 |
| 85 | MMP7 | C5a | CCL18 | CTSB | KLK7 | 0.879 |
| 86 | C5-C6 | C5 | CCL18 | CTSB | ETHE1 | 0.879 |
| 87 | C5 | ALPL | CTSB | HAMP | ETHE1 | 0.879 |
| 88 | C5 | KIT | VEGFA | CTSB | ETHE1 | 0.879 |
| 89 | C5 | CCL18 | CTSB | C2 | ETHE1 | 0.879 |
| 90 | C5 | KIT | CCL18 | CTSB | HAMP | 0.879 |
| 91 | C5 | CCL23 | CTSB | THBS4 | ETHE1 | 0.879 |
| 92 | C5 | ALPL | C5a | CTSB | THBS4 | 0.879 |
| 93 | C5 | VEGFA | CTSB | THBS4 | ETHE1 | 0.879 |
| 94 | C5 | LTF | CCL18 | CTSB | THBS4 | 0.879 |
| 95 | C5 | LTF | CTSB | IL11RA | ETHE1 | 0.878 |
| 96 | MMP7 | C5a | CTSB | KLK7 | ETHE1 | 0.878 |
| 97 | C5 | KIT | VEGFA | CCL18 | CTSB | 0.878 |
| 98 | C5 | ALPL | CCL18 | CTSB | THBS4 | 0.878 |
| 99 | C5-C6 | C5a | CCL18 | CTSB | KLK7 | 0.878 |
| 100 | C5 | APOA1 | CCL18 | CTSB | ETHE1 | 0.878 |

TABLE 7

Panels of 6 Biomarkers

| | Markers | | | | | | CV AUC |
|---|---|---|---|---|---|---|---|
| 1 | C5 | CSF1R | C5a | CCL18 | CTSB | ETHE1 | 0.898 |
| 2 | C5 | CSF1R | C5a | CTSB | THBS4 | ETHE1 | 0.896 |
| 3 | C5 | KIT | CSF1R | C5a | CTSB | ETHE1 | 0.895 |
| 4 | C5 | KIT | C5a | CCL18 | CTSB | ETHE1 | 0.894 |
| 5 | PLAT | C5 | CSF1R | C5a | CTSB | ETHE1 | 0.893 |
| 6 | C5 | ALPL | CCL18 | CTSB | THBS4 | ETHE1 | 0.893 |
| 7 | C5 | CSF1R | CCL18 | CTSB | THBS4 | ETHE1 | 0.892 |
| 8 | C5 | CSF1R | C5a | CTSB | KLK7 | ETHE1 | 0.892 |
| 9 | C5 | LTF | CCL18 | CTSB | THBS4 | ETHE1 | 0.892 |
| 10 | C5 | C5a | CCL18 | CTSB | KLK7 | ETHE1 | 0.892 |
| 11 | C5 | CCL18 | CTSB | KLK7 | HAMP | ETHE1 | 0.892 |

TABLE 7-continued

Panels of 6 Biomarkers

| # | Markers | | | | | CV AUC |
|---|---|---|---|---|---|---|
| 12 | C5 | LTF | C5a | CCL18 | CTSB | 0.892 |
| 13 | ETHE1 PLAT | C5 | C5a | CCL18 | CTSB | 0.891 |
| 14 | ETHE1 C5 | KIT | CSF1R | C5a | CCL18 | 0.891 |
| 15 | CTSB C5 | CSF1R | C5a | CCL18 | CTSB | 0.891 |
| 16 | THBS4 PLAT | KIT | C5a | CCL18 | CTSB | 0.891 |
| 17 | ETHE1 C5 | KIT | LTF | CCL18 | CTSB | 0.891 |
| 18 | ETHE1 C5-C6 | C5a | CCL18 | CTSB | KLK7 | 0.890 |
| 19 | ETHE1 C5 | CSF1R | C5a | CCL23 | CTSB | 0.890 |
| 20 | ETHE1 C5 | ALPL | C5a | CCL18 | CTSB | 0.890 |
| 21 | ETHE1 C5 | LTF | CCL18 | CTSB | KLK7 | 0.890 |
| 22 | ETHE1 C5 | KIT | CCL18 | CTSB | THBS4 | 0.890 |
| 23 | ETHE1 C5 | C5a | CCL18 | CTSB | THBS4 | 0.890 |
| 24 | ETHE1 C5 | KIT | CCL18 | CTSB | HAMP | 0.890 |
| 25 | ETHE1 C5 | CSF1R | C5a | CTSB | IL11RA | 0.890 |
| 26 | ETHE1 C5 | LTF | C5a | CCL18 | CTSB | 0.890 |
| 27 | KLK7 C5 | KIT | CSF1R | CCL18 | CTSB | 0.890 |
| 28 | ETHE1 C5 | KIT | VEGFA | CCL18 | CTSB | 0.889 |
| 29 | ETHE1 C5 | KIT | ALPL | CCL18 | CTSB | 0.889 |
| 30 | ETHE1 CSF1R | C5a | CTSB | KLK7 | HAMP | 0.889 |
| 31 | ETHE1 PLAT | C5 | C5a | CTSB | KLK7 | 0.889 |
| 32 | ETHE1 C5 | KIT | LTF | C5a | CCL18 | 0.889 |
| 33 | CTSB C5 | C5a | CTSB | KLK7 | HAMP | 0.889 |
| 34 | ETHE1 PLAT | C9 | C5 | CSF1R | CTSB | 0.889 |
| 35 | ETHE1 C5 | KIT | LTF | C5a | CTSB | 0.889 |
| 36 | ETHE1 C5 | LTF | CCL18 | CTSB | IL11RA | 0.889 |
| 37 | ETHE1 LTF | C5a | CCL18 | CTSB | KLK7 | 0.889 |
| 38 | ETHE1 C5 | CSF1R | CTSB | KLK7 | HAMP | 0.889 |
| 39 | ETHE1 C5-C6 | CSF1R | C5a | CCL18 | CTSB | 0.888 |
| 40 | ETHE1 C5 | KIT | CSF1R | C5a | CTSB | 0.888 |
| 41 | THBS4 C5 | KIT | C5a | CCL18 | CTSB | 0.888 |
| 42 | THBS4 C5 | KIT | ALPL | C5a | CTSB | 0.888 |
| 43 | ETHE1 C5 | CSF1R | C5a | CCL23 | CTSB | 0.888 |
| 44 | ETHE1 C5a | CCL18 | CTSB | KLK7 | HAMP | 0.888 |
| 45 | ETHE1 C5 | ALPL | CTSB | KLK7 | HAMP | 0.888 |
| 46 | ETHE1 C5 | ALPL | C5a | CCL18 | CTSB | 0.888 |
| 47 | KLK7 C5 | ALPL | C5a | CCL18 | CTSB | 0.888 |
| 48 | ETHE1 C5 | ALPL | C5a | CCL18 | KLK7 | 0.888 |
| 49 | ETHE1 C5 | ALPL | CCL18 | CTSB | IL11RA | 0.888 |
| | ETHE1 | | | | | |
| 50 | C5 | KIT | CSF1R | CTSB | HAMP | 0.888 |
| 51 | ETHE1 C5 | CSF1R | CCL23 | CCL18 | CTSB | 0.888 |
| 52 | ETHE1 CSF1R | C5a | CCL18 | CTSB | THBS4 | 0.888 |
| 53 | ETHE1 C5 | CSF1R | C5a | CCL18 | CTSB | 0.888 |
| 54 | IL11RA C5 | C5a | CCL18 | CTSB | ACP5 | 0.888 |
| 55 | ETHE1 CSF1R | CCL18 | CTSB | KLK7 | HAMP | 0.888 |
| 56 | ETHE1 C9 | C5 | CSF1R | CCL18 | CTSB | 0.888 |
| 57 | ETHE1 PLAT | C5 | C5a | CCL23 | CTSB | 0.888 |
| 58 | ETHE1 PLAT | C5 | KIT | CSF1R | C5a | 0.888 |
| 59 | CTSB C5 | LTF | C5a | CTSB | KLK7 | 0.888 |
| 60 | ETHE1 C5-C6 | CCL18 | CTSB | KLK7 | HAMP | 0.888 |
| 61 | ETHE1 C5 | CSF1R | C5a | CTSB | ACP5 | 0.888 |
| 62 | ETHE1 C5 | CSF1R | C5a | CTSB | KLK7 | 0.888 |
| 63 | HAMP C5 | LTF | C5a | CCL18 | CTSB | 0.888 |
| 64 | IL11RA C5 | CSF1R | ALPL | C5a | CTSB | 0.888 |
| 65 | ETHE1 C5 | CSF1R | C5a | CTSB | HAMP | 0.888 |
| 66 | ETHE1 C5 | C5a | CCL23 | CTSB | KLK7 | 0.888 |
| 67 | ETHE1 CSF1R | C5a | CCL18 | CTSB | KLK7 | 0.888 |
| 68 | ETHE1 C5 | KIT | KLK8 | CCL18 | CTSB | 0.888 |
| 69 | ETHE1 C5 | C5a | CCL18 | CTSB | INSR | 0.887 |
| 70 | ETHE1 C5 | LTF | CTSB | KLK7 | HAMP | 0.887 |
| 71 | ETHE1 C5 | C5a | CCL18 | CTSB | HAMP | 0.887 |
| 72 | ETHE1 C5-C6 | KIT | CSF1R | C5a | CTSB | 0.887 |
| 73 | ETHE1 C5-C6 | KIT | C5a | CCL18 | CTSB | 0.887 |
| 74 | ETHE1 ALPL | C5a | CCL18 | CTSB | KLK7 | 0.887 |
| 75 | ETHE1 C5 | CSF1R | CCL18 | CTSB | IL11RA | 0.887 |
| 76 | ETHE1 C5 | C5a | CCL18 | CTSB | IL11RA | 0.887 |
| 77 | ETHE1 C5-C6 | C5a | CCL18 | CTSB | THBS4 | 0.887 |
| 78 | ETHE1 C5a | CCL18 | CTSB | KLK7 | INSR | 0.887 |
| 79 | ETHE1 C9 | C5 | CSF1R | CTSB | THBS4 | 0.887 |
| 80 | ETHE1 C5 | CSF1R | LTF | C5a | CTSB | 0.887 |
| 81 | ETHE1 C5 | ALPL | C5a | CCL18 | CTSB | 0.887 |
| 82 | THBS4 C5 | KIT | C5a | CCL23 | CTSB | 0.887 |
| 83 | ETHE1 C5 | C5a | CCL18 | CTSB | KLK7 | 0.887 |
| 84 | HAMP MMP7 | C5a | CTSB | KLK7 | HAMP | 0.887 |
| 85 | ETHE1 C5 | C5a | CTSB | ACP5 | KLK7 | 0.887 |
| 86 | ETHE1 C5 | MMP7 | C5a | CTSB | KLK7 | 0.887 |
| 87 | ETHE1 C5 | CCL18 | CTSB | THBS4 | HAMP | 0.887 |
| | ETHE1 | | | | | |

TABLE 7-continued

Panels of 6 Biomarkers

| | Markers | | | | | CV AUC |
|---|---|---|---|---|---|---|
| 88 | C5-C6 | LTF | C5a | CCL18 | CTSB | 0.887 |
| | KLK7 | | | | | |
| 89 | C5 | CSF1R | ALPL | CTSB | THBS4 | 0.887 |
| | ETHE1 | | | | | |
| 90 | C5 | CSF1R | CCL18 | CTSB | HAMP | 0.887 |
| | ETHE1 | | | | | |
| 91 | C5 | CSF1R | C5a | CCL18 | CTSB | 0.887 |
| | KLK7 | | | | | |
| 92 | C5-C6 | KIT | CCL18 | CTSB | HAMP | 0.887 |
| | ETHE1 | | | | | |
| 93 | C5 | KIT | C5a | CTSB | ACP5 | 0.887 |
| | ETHE1 | | | | | |
| 94 | PLAT | C5 | C5a | CTSB | THBS4 | 0.887 |
| | ETHE1 | | | | | |
| 95 | C5 | LTF | C5a | CCL18 | CTSB | 0.887 |
| | THBS4 | | | | | |
| 96 | KIT | ALPL | C5a | CCL18 | | 0.886 |
| | C5 CTSB | | | | | |
| 97 | KLK8 | C5a | CCL18 | CTSB | KLK7 | 0.886 |
| | ETHE1 | | | | | |
| 98 | C5 | VEGFA | CCL18 | CTSB | THBS4 | 0.886 |
| | ETHE1 | | | | | |
| 99 | C5 | KIT | C5a | CTSB | HAMP | 0.886 |
| | ETHE1 | | | | | |
| 100 | C5 | LTF | C5a | CCL23 | CTSB | 0.886 |
| | ETHE1 | | | | | |

TABLE 8

Panels of 7 Biomarkers

| | Markers | | | | | CV AUC |
|---|---|---|---|---|---|---|
| 1 | C5 | CSF1R | C5a | CCL18 | CTSB | 0.900 |
| | THBS4 | ETHE1 | | | | |
| 2 | C5 | KIT | CSF1R | C5a | CCL18 | 0.900 |
| | CTSB | ETHE1 | | | | |
| 3 | PLAT | C5 | KIT | CSF1R | C5a | 0.899 |
| | CTSB | ETHE1 | | | | |
| 4 | C5 | CSF1R | C5a | CCL18 | CTSB | 0.898 |
| | IL11RA | ETHE1 | | | | |
| 5 | C5 | CSF1R | C5a | CCL18 | CTSB | 0.898 |
| | KLK7 | ETHE1 | | | | |
| 6 | C5 | LTF | C5a | CCL18 | CTSB | 0.897 |
| | KLK7 | ETHE1 | | | | |
| 7 | C5-C6 | CSF1R | C5a | CCL18 | CTSB | 0.897 |
| | THBS4 | ETHE1 | | | | |
| 8 | C5 | CSF1R | C5a | CTSB | KLK7 | 0.896 |
| | HAMP | ETHE1 | | | | |
| 9 | C5 | KIT | CSF1R | C5a | CTSB | 0.896 |
| | THBS4 | ETHE1 | | | | |
| 10 | C5 | ALPL | C5a | CCL18 | CTSB | 0.896 |
| | KLK7 | ETHE1 | | | | |
| 11 | C5 | KIT | VEGFA | CSF1R | CCL18 | 0.896 |
| | CTSB | ETHE1 | | | | |
| 12 | PLAT | C5 | CSF1R | C5a | CTSB | 0.896 |
| | THBS4 | ETHE1 | | | | |
| 13 | C5 | CSF1R | ALPL | CCL18 | CTSB | 0.895 |
| | THBS4 | ETHE1 | | | | |
| 14 | PLAT | C5 | CSF1R | C5a | CCL18 | 0.895 |
| | CTSB | ETHE1 | | | | |
| 15 | C5 | KIT | CSF1R | C5a | CCL18 | 0.895 |
| | CTSB | THBS4 | | | | |
| 16 | C5 | CSF1R | C5a | CCL23 | CTSB | 0.895 |
| | THBS4 | ETHE1 | | | | |
| 17 | C5 | KIT | VEGFA | CSF1R | C5a | 0.895 |
| | CTSB | ETHE1 | | | | |
| 18 | C5 | VEGFA | CSF1R | CCL18 | CTSB | 0.895 |
| | THBS4 | ETHE1 | | | | |
| 19 | C5 | LTF | C5a | CCL23 | CTSB | 0.895 |
| | KLK7 | ETHE1 | | | | |

TABLE 8-continued

Panels of 7 Biomarkers

| | Markers | | | | | CV AUC |
|---|---|---|---|---|---|---|
| 20 | C5 | CSF1R | KLK8 | C5a | CCL18 | 0.894 |
| | CTSB | ETHE1 | | | | |
| 21 | C5-C6 | KIT | CSF1R | C5a | CCL18 | 0.894 |
| | CTSB | ETHE1 | | | | |
| 22 | C5-C6 | C5 | CSF1R | C5a | CCL18 | 0.894 |
| | CTSB | ETHE1 | | | | |
| 23 | C5 | KIT | LTF | C5a | CCL18 | 0.894 |
| | CTSB | ETHE1 | | | | |
| 24 | C5-C6 | CSF1R | C5a | CCL18 | CTSB | 0.894 |
| | KLK7 | ETHE1 | | | | |
| 25 | C5 | KIT | CSF1R | LTF | C5a | 0.894 |
| | CTSB | ETHE1 | | | | |
| 26 | PLAT | C5 | KIT | C5a | CCL18 | 0.894 |
| | CTSB | ETHE1 | | | | |
| 27 | C5 | KIT | CSF1R | ALPL | C5a | 0.894 |
| | CTSB | ETHE1 | | | | |
| 28 | C5 | KLK8 | C5a | CCL18 | CTSB | 0.894 |
| | KLK7 | ETHE1 | | | | |
| 29 | C5 | CSF1R | ALPL | C5a | CCL18 | 0.894 |
| | CTSB | ETHE1 | | | | |
| 30 | C5 | CSF1R | LTF | C5a | CCL18 | 0.894 |
| | CTSB | ETHE1 | | | | |
| 31 | C5-C6 | LTF | C5a | CCL18 | CTSB | 0.894 |
| | KLK7 | ETHE1 | | | | |
| 32 | C5 | CSF1R | C5a | CCL18 | CTSB | 0.894 |
| | CDK5-CDK5R1 | ETHE1 | | | | |
| 33 | PLAT | C5 | CSF1R | C5a | CCL23 | 0.894 |
| | CTSB | ETHE1 | | | | |
| 34 | C5 | C5a | CCL18 | CTSB | KLK7 | 0.894 |
| | HAMP | ETHE1 | | | | |
| 35 | C5 | CSF1R | CCL18 | CTSB | KLK7 | 0.894 |
| | HAMP | ETHE1 | | | | |
| 36 | C5 | KIT | KLK8 | C5a | CCL18 | 0.894 |
| | CTSB | ETHE1 | | | | |
| 37 | C5 | KIT | CSF1R | C5a | CCL23 | 0.894 |
| | CTSB | ETHE1 | | | | |
| 38 | C5 | ALPL | C5a | CCL18 | CTSB | 0.894 |
| | THBS4 | ETHE1 | | | | |
| 39 | C5 | C5a | CCL23 | CCL18 | CTSB | 0.894 |
| | KLK7 | ETHE1 | | | | |
| 40 | C5 | KIT | CSF1R | CCL18 | CTSB | 0.894 |
| | HAMP | ETHE1 | | | | |
| 41 | PLAT | C5 | CSF1R | C5a | CTSB | 0.894 |
| | KLK7 | ETHE1 | | | | |
| 42 | C5 | KIT | CSF1R | CCL18 | CTSB | 0.894 |
| | THBS4 | ETHE1 | | | | |
| 43 | C5 | KIT | C5a | CCL18 | CTSB | 0.894 |
| | THBS4 | ETHE1 | | | | |
| 44 | C5 | KIT | LTF | CCL18 | CTSB | 0.894 |
| | THBS4 | ETHE1 | | | | |
| 45 | C5 | CSF1R | MMP7 | C5a | CTSB | 0.894 |
| | KLK7 | ETHE1 | | | | |
| 46 | C5 | CSF1R | LTF | CCL18 | CTSB | 0.894 |
| | THBS4 | ETHE1 | | | | |
| 47 | C5 | KIT | CSF1R | C5a | CTSB | 0.894 |
| | ACP5 | ETHE1 | | | | |
| 48 | C5 | KIT | ALPL | C5a | CCL18 | 0.894 |
| | CTSB | ETHE1 | | | | |
| 49 | C5 | C5a | CCL18 | CTSB | ACP5 | 0.893 |
| | KLK7 | ETHE1 | | | | |
| 50 | C5 | CSF1R | ALPL | C5a | CTSB | 0.893 |
| | KLK7 | ETHE1 | | | | |
| 51 | C5 | KIT | ALPL | CCL18 | CTSB | 0.893 |
| | THBS4 | ETHE1 | | | | |
| 52 | C5-C6 | CSF1R | C5a | CTSB | KLK7 | 0.893 |
| | HAMP | ETHE1 | | | | |
| 53 | C5 | CSF1R | LTF | C5a | CTSB | 0.893 |
| | KLK7 | ETHE1 | | | | |
| 54 | C5 | CSF1R | ALPL | C5a | CTSB | 0.893 |
| | THBS4 | ETHE1 | | | | |
| 55 | C5 | CSF1R | C5a | CCL18 | CTSB | 0.893 |
| | ACP5 | ETHE1 | | | | |
| 56 | C5 | CSF1R | C5a | CCL18 | CTSB | 0.893 |
| | TFPI | ETHE1 | | | | |

TABLE 8-continued

Panels of 7 Biomarkers

| | Markers | | | | | CV AUC |
|---|---|---|---|---|---|---|
| 57 | C5 HAMP | ALPL ETHE1 | CCL18 | CTSB | KLK7 | 0.893 |
| 58 | C5 KLK7 | CSF1R ETHE1 | C5a | CTSB | ACP5 | 0.893 |
| 59 | PLAT THBS4 | C9 ETHE1 | C5 | CSF1R | CTSB | 0.893 |
| 60 | C5 CTSB | KIT ETHE1 | LTF | C5a | CCL23 | 0.893 |
| 61 | C5 FGFR3 | CSF1R ETHE1 | C5a | CCL18 | CTSB | 0.893 |
| 62 | PLAT KLK7 | C5 ETHE1 | C5a | CCL18 | CTSB | 0.893 |
| 63 | PLAT IL11RA | C5 ETHE1 | CSF1R | C5a | CTSB | 0.893 |
| 64 | C5 CTSB | CSF1R ETHE1 | C5a | CCL23 | CCL18 | 0.893 |
| 65 | C5 HAMP | KIT ETHE1 | CSF1R | C5a | CTSB | 0.893 |
| 66 | C5 CTSB | CSF1R KLK7 | ALPL | C5a | CCL18 | 0.893 |
| 67 | C5 HAMP | LTF ETHE1 | CCL18 | CTSB | KLK7 | 0.893 |
| 68 | C5 CTSB | KIT ETHE1 | CSF1R | LTF | CCL18 | 0.893 |
| 69 | PLAT CTSB | C5 ETHE1 | CSF1R | C5a | CCL23 | 0.893 |
| 70 | C5 CCL18 | KIT CTSB | CSF1R | ALPL | C5a | 0.893 |
| 71 | CSF1R HAMP | MMP7 ETHE1 | C5a | CTSB | KLK7 | 0.893 |
| 72 | C5 KLK7 | CSF1R ETHE1 | C5a | CCL23 | CTSB | 0.892 |
| 73 | C5 IL11RA | CSF1R ETHE1 | ALPL | CCL18 | CTSB | 0.892 |
| 74 | C5 KLK7 | MMP7 ETHE1 | C5a | CCL18 | CTSB | 0.892 |
| 75 | PLAT CTSB | C9 ETHE1 | C5 | CSF1R | C5a | 0.892 |
| 76 | C5 CCL18 | KIT CTSB | CSF1R | LTF | C5a | 0.892 |
| 77 | C5 CTSB | KIT ETHE1 | CSF1R | MMP7 | C5a | 0.892 |
| 78 | C5 CTSB | CSF1R KLK7 | LTF | C5a | CCL18 | 0.892 |
| 79 | C9 THBS4 | C5 ETHE1 | CSF1R | CCL18 | CTSB | 0.892 |
| 80 | C5 CTSB | CSF1R ETHE1 | GDF11 | C5a | CCL18 | 0.892 |
| 81 | C5 THBS4 | LTF ETHE1 | C5a | CCL18 | CTSB | 0.892 |
| 82 | PLAT CTSB | C9 ETHE1 | C5 | CSF1R | CCL18 | 0.892 |
| 83 | C5 CTSB | KIT ETHE1 | VEGFA | KLK8 | CCL18 | 0.892 |
| 84 | C5 THBS4 | CSF1R ETHE1 | LTF | C5a | CTSB | 0.892 |
| 85 | CSF1R HAMP | C5a ETHE1 | CCL18 | CTSB | KLK7 | 0.892 |
| 86 | C5 CTSB | CSF1R ETHE1 | LTF | C5a | CCL23 | 0.892 |
| 87 | C5-C6 KLK7 | ALPL ETHE1 | C5a | CCL18 | | 0.892 |
| 88 | KIT THBS4 | CSF1R ETHE1 | C5a | CTSB | | 0.892 |
| 89 | C5 CTSB | CSF1R THBS4 | ALPL | C5a | CCL18 | 0.892 |
| 90 | C5 INSR | C5a ETHE1 | CCL18 | CTSB | KLK7 | 0.892 |
| 91 | C5 CTSB | CSF1R IL11RA | LTF | C5a | CCL18 | 0.892 |
| 92 | C5 ESM1 | CSF1R ETHE1 | C5a | CCL18 | CTSB | 0.892 |
| 93 | C5-C6 HAMP | C5a ETHE1 | CCL18 | CTSB | KLK7 | 0.892 |
| 94 | PLAT THBS4 | C5 ETHE1 | C5a | CCL18 | CTSB | 0.892 |
| 95 | C5 HAMP | ALPL ETHE1 | C5a | CTSB | KLK7 | 0.892 |
| 96 | C5 IL11RA | LTF ETHE1 | C5a | CCL18 | CTSB | 0.892 |
| 97 | C5 CTSB | VEGFA ETHE1 | CSF1R | C5a | CCL18 | 0.892 |
| 98 | C5 HAMP | LTF ETHE1 | C5a | CTSB | KLK7 | 0.892 |
| 99 | C5 KLK7 | ALPL ETHE1 | C5a | CCL23 | CTSB | 0.892 |
| 100 | C5 CTSB | KIT THBS4 | LTF | C5a | CCL18 | 0.892 |

TABLE 9

Panels of 8 Biomarkers

| | Markers | | | | | CV AUC |
|---|---|---|---|---|---|---|
| 1 | C5 CTSB | KIT THBS4 | CSF1R ETHE1 | C5a | CCL18 | 0.902 |
| 2 | C5 CTSB | CSF1R KLK7 | LTF ETHE1 | C5a | CCL18 | 0.902 |
| 3 | PLAT CCL18 | C5 CTSB | KIT ETHE1 | CSF1R | C5a | 0.901 |
| 4 | C5 CCL18 | KIT CTSB | CSF1R ETHE1 | LTF | C5a | 0.901 |
| 5 | C5 CTSB | CSF1R KLK7 | ALPL ETHE1 | C5a | CCL18 | 0.901 |
| 6 | C5-C6 CTSB | VEGFA KLK7 | CSF1R ETHE1 | C5a | CCL18 | 0.900 |
| 7 | C5-C6 CTSB | KIT THBS4 | CSF1R ETHE1 | C5a | CCL18 | 0.900 |
| 8 | C5 CTSB | VEGFA KLK7 | CSF1R ETHE1 | C5a | CCL18 | 0.899 |
| 9 | C5 CCL18 | KIT CTSB | CSF1R ETHE1 | ALPL | C5a | 0.899 |
| 10 | C5 KLK7 | CSF1R HAMP | C5a ETHE1 | CCL18 | CTSB | 0.899 |
| 11 | C5 CTSB | KIT THBS4 | VEGFA ETHE1 | CSF1R | CCL18 | 0.899 |
| 12 | C5 CCL18 | KIT CTSB | CSF1R ETHE1 | KLK8 | C5a | 0.899 |
| 13 | C5 CTSB | CSF1R THBS4 | LTF ETHE1 | C5a | CCL18 | 0.899 |
| 14 | C5 CCL18 | KIT CTSB | VEGFA ETHE1 | CSF1R | C5a | 0.899 |
| 15 | C5 CTSB | CSF1R THBS4 | ALPL ETHE1 | C5a | CCL18 | 0.899 |
| 16 | C5-C6 CTSB | C5 THBS4 | CSF1R ETHE1 | C5a | CCL18 | 0.899 |
| 17 | C5-C6 CTSB | CSF1R KLK7 | LTF ETHE1 | C5a | CCL18 | 0.899 |
| 18 | C5 CCL18 | KIT CTSB | VEGFA ETHE1 | CSF1R | KLK8 | 0.898 |
| 19 | PLAT CTSB | C5 THBS4 | CSF1R ETHE1 | C5a | CCL18 | 0.898 |
| 20 | C5 CTSB | CSF1R IL11RA | ALPL ETHE1 | C5a | CCL18 | 0.898 |
| 21 | C5 CTSB | LTF KLK7 | C5a ETHE1 | CCL23 | CCL18 | 0.898 |
| 22 | C5-C6 CCL18 | C5 CTSB | KIT ETHE1 | CSF1R | C5a | 0.898 |
| 23 | C5 CTSB | CSF1R IL11RA | LTF ETHE1 | C5a | CCL18 | 0.898 |
| 24 | C5 CTSB | CSF1R KLK7 | MMP7 ETHE1 | C5a | CCL18 | 0.898 |
| 25 | C5 CCL23 | KIT CTSB | CSF1R ETHE1 | LTF | C5a | 0.898 |

TABLE 9-continued

Panels of 8 Biomarkers

| | Markers | | | | | CV AUC |
|---|---|---|---|---|---|---|
| 26 | C5 CTSB | ALPL KLK7 | KLK8 ETHE1 | C5a | CCL18 | 0.898 |
| 27 | C5 CTSB | LTF KLK7 | KLK8 ETHE1 | C5a | CCL18 | 0.898 |
| 28 | PLAT CCL23 | C5 CTSB | KIT ETHE1 | CSF1R | C5a | 0.898 |
| 29 | C5 CTSB | KIT ACP5 | CSF1R ETHE1 | C5a | CCL18 | 0.898 |
| 30 | C5 CCL18 | KIT CTSB | CSF1R ETHE1 | C5a | CCL23 | 0.898 |
| 31 | C5-C6 KLK7 | CSF1R HAMP | C5a ETHE1 | CCL18 | CTSB | 0.898 |
| 32 | C5 CTSB | CSF1R KLK7 | KLK8 ETHE1 | C5a | CCL18 | 0.898 |
| 33 | PLAT CTSB | C5 THBS4 | KIT ETHE1 | CSF1R | C5a | 0.898 |
| 34 | C5 CTSB | KIT THBS4 | CSF1R ETHE1 | ALPL | CCL18 | 0.898 |
| 35 | C5 CTSB | KIT THBS4 | CSF1R ETHE1 | LTF | CCL18 | 0.898 |
| 36 | C5 CTSB | CSF1R THBS4 | C5a ETHE1 | CCL23 | CCL18 | 0.898 |
| 37 | C5 CTSB | CSF1R KLK7 | LTF ETHE1 | C5a | CCL23 | 0.898 |
| 38 | C5 THBS4 | CSF1R KLK7 | C5a ETHE1 | CCL18 | CTSB | 0.898 |
| 39 | C5 CTSB | CSF1R THBS4 | KLK8 ETHE1 | C5a | CCL18 | 0.898 |
| 40 | C5 CTSB | VEGFA THBS4 | CSF1R ETHE1 | C5a | CCL18 | 0.898 |
| 41 | C5-C6 CTSB | CSF1R KLK7 | MMP7 ETHE1 | C5a | CCL18 | 0.897 |
| 42 | PLAT CTSB | C5 KLK7 | CSF1R ETHE1 | C5a | CCL18 | 0.897 |
| 43 | C5 CTSB | KIT TFPI | CSF1R ETHE1 | C5a | CCL18 | 0.897 |
| 44 | C5 CCL18 | CSF1R CTSB | GDF11 ETHE1 | LTF | C5a | 0.897 |
| 45 | C5 THBS4 | LTF KLK7 | C5a ETHE1 | CCL18 | CTSB | 0.897 |
| 46 | C5 KLK7 | KIT HAMP | CSF1R ETHE1 | C5a | CTSB | 0.897 |
| 47 | C5 CTSB | KIT THBS4 | CSF1R ETHE1 | LTF | C5a | 0.897 |
| 48 | PLAT CTSB | C5 IL11RA | CSF1R ETHE1 | C5a | CCL18 | 0.897 |
| 49 | C5 CTSB | LTF KLK7 | MMP7 ETHE1 | C5a | CCL18 | 0.897 |
| 50 | C5-C6 CCL18 | KIT CTSB | VEGFA ETHE1 | CSF1R | C5a | 0.897 |
| 51 | C5 CTSB | KIT THBS4 | CSF1R ETHE1 | ALPL | C5a | 0.897 |
| 52 | C5 CTSB | IL12A-IL12B THBS4 | C5a ETHE1 | CCL18 | | 0.896 |
| 53 | C5 CTSB | CSF1R KLK7 | C5a ETHE1 | CCL23 | CCL18 | 0.896 |
| 54 | PLAT CTSB | C5 KLK7 | CSF1R ETHE1 | MMP7 | C5a | 0.896 |
| 55 | C5 KLK7 | CSF1R HAMP | MMP7 ETHE1 | C5a | CTSB | 0.896 |
| 56 | C5 CTSB | KIT KLK7 | LTF ETHE1 | C5a | CCL18 | 0.896 |
| 57 | C5 CTSB | KIT IL11RA | CSF1R ETHE1 | C5a | CCL18 | 0.896 |
| 58 | C5 CTSB | VEGFA KLK7 | CSF1R ETHE1 | MMP7 | C5a | 0.896 |
| 59 | C5 CTSB | CSF1R THBS4 | LTF KLK7 | C5a | CCL18 | 0.896 |
| 60 | C5 THBS4 | CSF1R INSR | C5a ETHE1 | CCL18 | CTSB | 0.896 |
| 61 | C5-C6 CCL18 | KIT CTSB | CSF1R ETHE1 | C5a | CCL23 | 0.896 |
| 62 | C5 KLK7 | KIT HAMP | C5a ETHE1 | CCL18 | CTSB | 0.896 |
| 63 | C5 KLK7 | LTF INSR | C5a ETHE1 | CCL18 | CTSB | 0.896 |
| 64 | C5 CCL18 | KIT CTSB | CSF1R THBS4 | LTF | C5a | 0.896 |
| 65 | C5 CTSB | CSF1R THBS4 | LTF ETHE1 | C5a | CCL23 | 0.896 |
| 66 | C5-C6 CTSB | CSF1R KLK7 | ALPL ETHE1 | C5a | CCL18 | 0.896 |
| 67 | C5 CTSB | VEGFA IL11RA | CSF1R ETHE1 | C5a | CCL18 | 0.896 |
| 68 | C5 ACP5 | CSF1R KLK7 | C5a ETHE1 | CCL18 | CTSB | 0.896 |
| 69 | PLAT CTSB | C9 THBS4 | C5 ETHE1 | CSF1R | CCL18 | 0.896 |
| 70 | PLAT C5a | C5 CTSB | KIT ETHE1 | CSF1R | ALPL | 0.896 |
| 71 | C5 CTSB | KIT THBS4 | LTF ETHE1 | C5a | CCL18 | 0.896 |
| 72 | C5-C6 CTSB | LTF KLK7 | C5a ETHE1 | CCL23 | CCL18 | 0.896 |
| 73 | C5 THBS4 | KIT HAMP | CSF1R ETHE1 | CCL18 | CTSB | 0.896 |
| 74 | PLAT KLK7 | C5 HAMP | CSF1R ETHE1 | C5a | CTSB | 0.896 |
| 75 | C5 KLK7 | LTF HAMP | C5a ETHE1 | CCL18 | CTSB | 0.896 |
| 76 | C5 CCL18 | KIT CTSB | CSF1R IL11RA | LTF | C5a | 0.896 |
| 77 | PLAT C5a | C5 CTSB | KIT ETHE1 | VEGFA | CSF1R | 0.896 |
| 78 | C5 CTSB | KIT THBS4 | ALPL ETHE1 | C5a | CCL18 | 0.896 |
| 79 | KIT KLK7 | CSF1R HAMP | C5a ETHE1 | CCL18 | CTSB | 0.896 |
| 80 | C5 CTSB | ALPL KLK7 | C5a ETHE1 | CCL23 | CCL18 | 0.896 |
| 81 | C5 THBS4 | CSF1R ESM1 | C5a ETHE1 | CCL18 | CTSB | 0.896 |
| 82 | C5 TFPI | CSF1R THBS4 | C5a ETHE1 | CCL18 | CTSB | 0.896 |
| 83 | C5 CTSB | KIT THBS4 | KLK8 ETHE1 | C5a | CCL18 | 0.896 |
| 84 | C5-C6 THBS4 | CSF1R KLK7 | C5a ETHE1 | CCL18 | CTSB | 0.896 |
| 85 | PLAT CTSB | C5 KLK7 | CSF1R ETHE1 | C5a | CCL23 | 0.896 |
| 86 | PLAT C5a | C5 CTSB | KIT ETHE1 | CSF1R | KLK8 | 0.896 |
| 87 | C5 TFPI | CSF1R KLK7 | C5a ETHE1 | CCL18 | CTSB | 0.896 |
| 88 | C5 CTSB | KIT THBS4 | CSF1R ETHE1 | C5a | CCL23 | 0.896 |
| 89 | C5 CTSB | VEGFA KLK7 | CSF1R ETHE1 | C5a | CCL23 | 0.896 |
| 90 | PLAT CTSB | C5 KLK7 | ALPL ETHE1 | C5a | CCL18 | 0.896 |
| 91 | C5 CCL18 | KIT CTSB | CSF1R THBS4 | ALPL | C5a | 0.896 |
| 92 | PLAT CTSB | C5 KLK7 | LTF ETHE1 | C5a | CCL18 | 0.896 |
| 93 | PLAT CCL23 | C5 CTSB | KIT ETHE1 | CSF1R | C5a | 0.896 |
| 94 | PLAT CCL18 | C9 CTSB | C5 ETHE1 | KIT | CSF1R | 0.896 |
| 95 | C5 KLK7 | CSF1R HAMP | LTF ETHE1 | C5a | CTSB | 0.895 |
| 96 | C5-C6 CTSB | KIT THBS4 | VEGFA ETHE1 | CSF1R | CCL18 | 0.895 |
| 97 | C5 THBS4 | ALPL KLK7 | C5a ETHE1 | CCL18 | CTSB | 0.895 |
| 98 | CSF1R CTSB | LTF KLK7 | C5a ETHE1 | CCL23 | CCL18 | 0.895 |
| 99 | C5 CTSB | KIT THBS4 | VEGFA ETHE1 | CSF1R | C5a | 0.895 |

TABLE 9-continued

Panels of 8 Biomarkers

| | Markers | | | | CV AUC |
|---|---|---|---|---|---|
| 100 | C5 | CSF1R | C5a | CCL18 | CTSB | 0.895 |
| | THBS4 | CDK5-CDK5R1 | ETHE1 | | |

*Note: row 100 has markers C5, CSF1R, C5a, CCL18, CTSB, THBS4, CDK5-CDK5R1, ETHE1*

TABLE 10

Panels of 9 Biomarkers

| | Markers | | | | | CV AUC |
|---|---|---|---|---|---|---|
| 1 | C5 | CSF1R | LTF | C5a | CCL23 | 0.903 |
| | CCL18 | CTSB | KLK7 | ETHE1 | | |
| 2 | C5 | VEGFA | CSF1R | KLK8 | C5a | 0.902 |
| | CCL18 | CTSB | KLK7 | ETHE1 | | |
| 3 | C5-C6 | C5 | VEGFA | CSF1R | C5a | 0.902 |
| | CCL18 | CTSB | KLK7 | ETHE1 | | |
| 4 | C5 | VEGFA | CSF1R | MMP7 | C5a | 0.902 |
| | CCL18 | CTSB | KLK7 | ETHE1 | | |
| 5 | C5-C6 | VEGFA | CSF1R | MMP7 | C5a | 0.902 |
| | CCL18 | CTSB | KLK7 | ETHE1 | | |
| 6 | C5 | KIT | CSF1R | LTF | C5a | 0.902 |
| | CCL18 | CTSB | KLK7 | ETHE1 | | |
| 7 | C5 | KIT | CSF1R | ALPL | C5a | 0.902 |
| | CCL18 | CTSB | THBS4 | ETHE1 | | |
| 8 | C5 | KIT | CSF1R | LTF | C5a | 0.902 |
| | CCL18 | CTSB | THBS4 | ETHE1 | | |
| 9 | C5 | CSF1R | ALPL | KLK8 | C5a | 0.901 |
| | CCL18 | CTSB | KLK7 | ETHE1 | | |
| 10 | PLAT | C5 | KIT | CSF1R | C5a | 0.901 |
| | CCL18 | CTSB | THBS4 | ETHE1 | | |
| 11 | C5 | CSF1R | ALPL | C5a | CCL18 | 0.901 |
| | CTSB | THBS4 | KLK7 | ETHE1 | | |
| 12 | C5 | KIT | CSF1R | LTF | C5a | 0.901 |
| | CCL18 | CTSB | IL11RA | ETHE1 | | |
| 13 | C5-C6 | C5 | CSF1R | LTF | C5a | 0.901 |
| | CCL18 | CTSB | KLK7 | ETHE1 | | |
| 14 | C5 | KIT | CSF1R | KLK8 | C5a | 0.901 |
| | CCL18 | CTSB | THBS4 | ETHE1 | | |
| 15 | C5-C6 | C5 | KIT | VEGFA | CSF1R | 0.901 |
| | C5a | CCL18 | CTSB | ETHE1 | | |
| 16 | C5 | CSF1R | LTF | C5a | CCL18 | 0.901 |
| | CTSB | THBS4 | KLK7 | ETHE1 | | |
| 17 | C5 | KIT | VEGFA | CSF1R | KLK8 | 0.901 |
| | CCL18 | CTSB | THBS4 | ETHE1 | | |
| 18 | C5 | VEGFA | CSF1R | C5a | CCL18 | 0.901 |
| | CTSB | THBS4 | KLK7 | ETHE1 | | |
| 19 | C5-C6 | VEGFA | CSF1R | C5a | CCL18 | 0.901 |
| | CTSB | THBS4 | KLK7 | ETHE1 | | |
| 20 | C5 | CSF1R | ALPL | C5a | CCL18 | 0.900 |
| | CTSB | TFPI | KLK7 | ETHE1 | | |
| 21 | C5 | KIT | VEGFA | CSF1R | C5a | 0.900 |
| | CCL18 | CTSB | THBS4 | ETHE1 | | |
| 22 | C5-C6 | KIT | VEGFA | CSF1R | C5a | 0.900 |
| | CCL18 | CTSB | KLK7 | ETHE1 | | |
| 23 | C5-C6 | CSF1R | LTF | C5a | CCL23 | 0.900 |
| | CCL18 | CTSB | KLK7 | ETHE1 | | |
| 24 | PLAT | C5 | KIT | CSF1R | KLK8 | 0.900 |
| | C5a | CCL18 | CTSB | ETHE1 | | |
| 25 | C5 | CSF1R | LTF | C5a | CCL18 | 0.900 |
| | CTSB | TFPI | KLK7 | ETHE1 | | |
| 26 | C5 | CSF1R | LTF | KLK8 | C5a | 0.900 |
| | CCL18 | CTSB | KLK7 | ETHE1 | | |
| 27 | C5 | KIT | CSF1R | LTF | C5a | 0.900 |
| | CCL23 | CTSB | THBS4 | ETHE1 | | |
| 28 | C5-C6 | C5 | VEGFA | CSF1R | C5a | 0.900 |
| | CCL18 | CTSB | THBS4 | ETHE1 | | |
| 29 | C5-C6 | C5 | KIT | CSF1R | C5a | 0.900 |
| | CCL18 | CTSB | THBS4 | ETHE1 | | |
| 30 | C5 | CSF1R | LTF | C5a | CCL18 | 0.900 |
| | CTSB | KLK7 | IL11RA | ETHE1 | | |
| 31 | C5-C6 | C5 | KIT | CSF1R | LTF | 0.900 |
| | C5a | CCL18 | CTSB | ETHE1 | | |
| 32 | C5 | CSF1R | LTF | C5a | CCL18 | 0.900 |
| | CTSB | KLK7 | HAMP | ETHE1 | | |
| 33 | C5 | KIT | CSF1R | ALPL | C5a | 0.900 |
| | CCL18 | CTSB | KLK7 | ETHE1 | | |
| 34 | C5 | CSF1R | LTF | MMP7 | C5a | 0.900 |
| | CCL18 | CTSB | KLK7 | ETHE1 | | |
| 35 | C5-C6 | KIT | VEGFA | CSF1R | C5a | 0.900 |
| | CCL18 | CTSB | THBS4 | ETHE1 | | |
| 36 | C5 | KIT | CSF1R | LTF | C5a | 0.900 |
| | CCL23 | CCL18 | CTSB | ETHE1 | | |
| 37 | C5 | KIT | VEGFA | CSF1R | KLK8 | 0.900 |
| | C5a | CCL18 | CTSB | ETHE1 | | |
| 38 | C5 | LTF | C5a | CCL23 | CCL18 | 0.900 |
| | CTSB | THBS4 | KLK7 | ETHE1 | | |
| 39 | C5-C6 | VEGFA | CSF1R | KLK8 | C5a | 0.900 |
| | CCL18 | CTSB | KLK7 | ETHE1 | | |
| 40 | PLAT | C5 | CSF1R | ALPL | C5a | 0.900 |
| | CCL18 | CTSB | KLK7 | ETHE1 | | |
| 41 | C5-C6 | CSF1R | LTF | C5a | CCL18 | 0.900 |
| | CTSB | THBS4 | KLK7 | ETHE1 | | |
| 42 | C5 | KIT | LTF | C5a | CCL18 | 0.899 |
| | CTSB | KLK7 | HAMP | ETHE1 | | |
| 43 | C5 | KIT | CSF1R | C5a | CCL18 | 0.899 |
| | CTSB | THBS4 | INSR | ETHE1 | | |
| 44 | C5 | KIT | VEGFA | CSF1R | C5a | 0.899 |
| | CCL18 | CTSB | KLK7 | ETHE1 | | |
| 45 | C5 | KIT | CSF1R | ALPL | C5a | 0.899 |
| | CCL18 | CTSB | IL11RA | ETHE1 | | |
| 46 | C5 | CSF1R | ALPL | C5a | CCL23 | 0.899 |
| | CCL18 | CTSB | KLK7 | ETHE1 | | |
| 47 | C5 | CSF1R | C5a | CCL23 | CCL18 | 0.899 |
| | CTSB | THBS4 | KLK7 | ETHE1 | | |
| 48 | C5 | CSF1R | C5a | CCL18 | CTSB | 0.899 |
| | THBS4 | KLK7 | HAMP | ETHE1 | | |
| 49 | C5 | CSF1R | ALPL | C5a | CCL18 | 0.899 |
| | CTSB | KLK7 | HAMP | ETHE1 | | |
| 50 | C5 | KIT | CSF1R | LTF | CCL23 | 0.899 |
| | CCL18 | CTSB | THBS4 | ETHE1 | | |
| 51 | C5 | KIT | CSF1R | KLK8 | C5a | 0.899 |
| | CCL18 | CTSB | KLK7 | ETHE1 | | |
| 52 | C5-C6 | C5 | CSF1R | ALPL | C5a | 0.899 |
| | CCL18 | CTSB | KLK7 | ETHE1 | | |
| 53 | C5 | CSF1R | ALPL | C5a | CCL18 | 0.899 |
| | CTSB | KLK7 | IL11RA | ETHE1 | | |
| 54 | C5 | VEGFA | CSF1R | C5a | CCL23 | 0.899 |
| | CCL18 | CTSB | KLK7 | ETHE1 | | |
| 55 | C5 | CSF1R | LTF | C5a | CCL23 | 0.899 |
| | CCL18 | CTSB | THBS4 | ETHE1 | | |
| 56 | C5-C6 | CSF1R | MMP7 | C5a | CCL18 | 0.899 |
| | CTSB | KLK7 | HAMP | ETHE1 | | |
| 57 | C5 | CSF1R | MMP7 | C5a | CCL18 | 0.899 |
| | CTSB | THBS4 | KLK7 | ETHE1 | | |
| 58 | C5 | KIT | CSF1R | C5a | CCL18 | 0.899 |
| | CTSB | ACP5 | THBS4 | ETHE1 | | |
| 59 | C5 | KIT | CSF1R | MMP7 | C5a | 0.899 |
| | CCL18 | CTSB | THBS4 | ETHE1 | | |
| 60 | C5 | KIT | CSF1R | LTF | C5a | 0.899 |
| | CCL18 | CTSB | TFPI | ETHE1 | | |
| 61 | C5 | KIT | LTF | C5a | CCL23 | 0.899 |
| | CCL18 | CTSB | THBS4 | ETHE1 | | |
| 62 | C5-C6 | PLAT | C5 | KIT | CSF1R | 0.899 |
| | C5a | CCL18 | CTSB | ETHE1 | | |
| 63 | PLAT | C5 | CSF1R | LTF | C5a | 0.899 |
| | CCL18 | CTSB | KLK7 | ETHE1 | | |
| 64 | C5 | CSF1R | MMP7 | C5a | CCL18 | 0.899 |
| | CTSB | KLK7 | HAMP | ETHE1 | | |
| 65 | C5 | CSF1R | KLK8 | C5a | CCL23 | 0.899 |
| | CCL18 | CTSB | KLK7 | ETHE1 | | |
| 66 | C9 | C5 | CSF1R | LTF | C5a | 0.899 |
| | CCL18 | CTSB | KLK7 | ETHE1 | | |
| 67 | C5 | VEGFA | CSF1R | MMP7 | C5a | 0.899 |
| | CTSB | KLK7 | IL11RA | ETHE1 | | |
| 68 | C5 | KIT | CSF1R | LTF | KLK8 | 0.899 |
| | C5a | CCL18 | CTSB | ETHE1 | | |
| 69 | PLAT | C5 | KIT | VEGFA | CSF1R | 0.899 |
| | C5a | CCL23 | CTSB | ETHE1 | | |

TABLE 10-continued

Panels of 9 Biomarkers

| | Markers | | | | | CV AUC |
|---|---|---|---|---|---|---|
| 70 | C5 | KIT | CSF1R | C5a | CCL18 | 0.899 |
| | CTSB | TFPI | THBS4 | ETHE1 | | |
| 71 | C5-C6 | KIT | CSF1R | C5a | CCL23 | 0.899 |
| | CCL18 | CTSB | THBS4 | ETHE1 | | |
| 72 | PLAT | C5 | KIT | CSF1R | LTF | 0.899 |
| | C5a | CCL18 | CTSB | ETHE1 | | |
| 73 | C5-C6 | PLAT | C5 | CSF1R | C5a | 0.899 |
| | CCL18 | CTSB | THBS4 | ETHE1 | | |
| 74 | C5 | CSF1R | MMP7 | ALPL | C5a | 0.899 |
| | CCL18 | CTSB | KLK7 | ETHE1 | | |
| 75 | C5 | KIT | CSF1R | C5a | CCL18 | 0.899 |
| | CTSB | KLK7 | HAMP | ETHE1 | | |
| 76 | C5 | KIT | CSF1R | LTF | CCL18 | 0.899 |
| | CTSB | TFPI | THBS4 | ETHE1 | | |
| 77 | C5 | KIT | VEGFA | CSF1R | C5a | 0.899 |
| | CCL18 | CTSB | IL11RA | ETHE1 | | |
| 78 | C5 | CSF1R | MMP7 | KLK8 | C5a | 0.899 |
| | CCL18 | CTSB | KLK7 | ETHE1 | | |
| 79 | PLAT | C5 | CSF1R | C5a | CCL23 | 0.899 |
| | CCL18 | CTSB | KLK7 | ETHE1 | | |
| 80 | C5 | ALPL | KLK8 | C5a | CCL18 | 0.899 |
| | CTSB | THBS4 | KLK7 | ETHE1 | | |
| 81 | C5-C6 | KIT | CSF1R | LTF | C5a | 0.899 |
| | CCL18 | CTSB | KLK7 | ETHE1 | | |
| 82 | PLAT | C5 | CSF1R | MMP7 | C5a | 0.899 |
| | CCL18 | CTSB | KLK7 | ETHE1 | | |
| 83 | C5 | IL12A-IL12B | CSF1R | LTF | C5a | 0.899 |
| | CCL18 | CTSB | KLK7 | ETHE1 | | |
| 84 | C5 | KIT | CSF1R | ALPL | C5a | 0.898 |
| | CCL18 | CTSB | TFPI | ETHE1 | | |
| 85 | C5 | KIT | VEGFA | CSF1R | C5a | 0.898 |
| | CTSB | KLK7 | HAMP | ETHE1 | | |
| 86 | C5 | KIT | CSF1R | ALPL | CCL18 | 0.898 |
| | CTSB | TFPI | THBS4 | ETHE1 | | |
| 87 | PLAT | C5 | KIT | CSF1R | LTF | 0.898 |
| | C5a | CCL23 | CTSB | ETHE1 | | |
| 88 | C5-C6 | KIT | CSF1R | C5a | CCL18 | 0.898 |
| | CTSB | TFPI | THBS4 | ETHE1 | | |
| 89 | C5 | VEGFA | CSF1R | C5a | CCL18 | 0.898 |
| | CTSB | ACP5 | KLK7 | ETHE1 | | |
| 90 | C5 | VEGFA | CSF1R | LTF | C5a | 0.898 |
| | CCL18 | CTSB | KLK7 | ETHE1 | | |
| 91 | C5 | CSF1R | ALPL | C5a | CCL18 | 0.898 |
| | CTSB | TFPI | THBS4 | ETHE1 | | |
| 92 | C5 | CSF1R | KLK8 | C5a | CCL18 | 0.898 |
| | CTSB | THBS4 | KLK7 | ETHE1 | | |
| 93 | C5 | KIT | LTF | C5a | CCL23 | 0.898 |
| | CCL18 | CTSB | KLK7 | ETHE1 | | |
| 94 | PLAT | C5 | KIT | CSF1R | C5a | 0.898 |
| | CCL23 | CCL18 | CTSB | ETHE1 | | |
| 95 | C5 | VEGFA | CSF1R | C5a | CCL18 | 0.898 |
| | CTSB | KLK7 | ESM1 | ETHE1 | | |
| 96 | C5 | KIT | CSF1R | C5a | CCL23 | 0.898 |
| | CCL18 | CTSB | THBS4 | ETHE1 | | |
| 97 | C5 | VEGFA | CSF1R | C5a | CCL18 | 0.898 |
| | CTSB | KLK7 | IL11RA | ETHE1 | | |
| 98 | C5 | VEGFA | CSF1R | C5a | CCL23 | 0.898 |
| | CTSB | THBS4 | KLK7 | ETHE1 | | |
| 99 | C5-C6 | KIT | CSF1R | C5a | CCL18 | 0.898 |
| | CTSB | KLK7 | HAMP | ETHE1 | | |
| 100 | C5-C6 | CSF1R | LTF | MMP7 | C5a | 0.898 |
| | CCL18 | CTSB | KLK7 | ETHE1 | | |

TABLE 11

Panels of 10 Biomarkers

| | Markers | | | | | CV AUC |
|---|---|---|---|---|---|---|
| 1 | C5-C6 | C5 | VEGFA | CSF1R | KLK8 | 0.905 |
| | C5a | CCL18 | CTSB | KLK7 | ETHE1 | |
| 2 | C5 | CSF1R | LTF | C5a | CCL23 | 0.904 |
| | CCL18 | CTSB | THBS4 | KLK7 | ETHE1 | |
| 3 | C5 | KIT | VEGFA | CSF1R | KLK8 | 0.904 |
| | C5a | CCL18 | CTSB | KLK7 | ETHE1 | |
| 4 | C5-C6 | C5 | VEGFA | CSF1R | LTF | 0.904 |
| | C5a | CCL18 | CTSB | KLK7 | ETHE1 | |
| 5 | C5 | VEGFA | CSF1R | MMP7 | KLK8 | 0.904 |
| | C5a | CCL18 | CTSB | KLK7 | ETHE1 | |
| 6 | C5-C6 | KIT | VEGFA | CSF1R | MMP7 | 0.904 |
| | C5a | CCL18 | CTSB | KLK7 | ETHE1 | |
| 7 | C5-C6 | KIT | VEGFA | CSF1R | KLK8 | 0.903 |
| | C5a | CCL18 | CTSB | KLK7 | ETHE1 | |
| 8 | C5-C6 | VEGFA | CSF1R | MMP7 | C5a | 0.903 |
| | CCL18 | CTSB | KLK7 | IL11RA | ETHE1 | |
| 9 | C5 | VEGFA | CSF1R | KLK8 | C5a | 0.903 |
| | CCL18 | CTSB | THBS4 | KLK7 | ETHE1 | |
| 10 | C5 | KIT | VEGFA | CSF1R | MMP7 | 0.903 |
| | C5a | CCL18 | CTSB | KLK7 | ETHE1 | |
| 11 | C5 | VEGFA | CSF1R | MMP7 | C5a | 0.903 |
| | CCL18 | CTSB | THBS4 | KLK7 | ETHE1 | |
| 12 | C5 | KIT | CSF1R | LTF | C5a | 0.903 |
| | CCL23 | CCL18 | CTSB | THBS4 | ETHE1 | |
| 13 | C5 | CSF1R | ALPL | KLK8 | C5a | 0.903 |
| | CCL18 | CTSB | THBS4 | KLK7 | ETHE1 | |
| 14 | C5-C6 | KIT | VEGFA | CSF1R | LTF | 0.903 |
| | C5a | CCL18 | CTSB | KLK7 | ETHE1 | |
| 15 | C5-C6 | VEGFA | CSF1R | MMP7 | C5a | 0.903 |
| | CCL18 | CTSB | THBS4 | KLK7 | ETHE1 | |
| 16 | C5 | KIT | CSF1R | LTF | C5a | 0.903 |
| | CCL23 | CCL18 | CTSB | KLK7 | ETHE1 | |
| 17 | C5-C6 | C5 | VEGFA | CSF1R | C5a | 0.903 |
| | CCL23 | CCL18 | CTSB | KLK7 | ETHE1 | |
| 18 | C5 | VEGFA | CSF1R | MMP7 | C5a | 0.903 |
| | CCL18 | CTSB | KLK7 | IL11RA | ETHE1 | |
| 19 | C5-C6 | C5 | KIT | VEGFA | CSF1R | 0.902 |
| | C5a | CCL18 | CTSB | THBS4 | ETHE1 | |
| 20 | C5-C6 | CSF1R | LTF | C5a | CCL23 | 0.902 |
| | CCL18 | CTSB | THBS4 | KLK7 | ETHE1 | |
| 21 | C5 | KIT | CSF1R | LTF | KLK8 | 0.902 |
| | C5a | CCL18 | CTSB | THBS4 | ETHE1 | |
| 22 | C5 | KIT | CSF1R | CSF1R | KLK8 | 0.902 |
| | C5a | CCL18 | CTSB | THBS4 | ETHE1 | |
| 23 | C5 | KIT | CSF1R | ALPL | KLK8 | 0.902 |
| | C5a | CCL18 | CTSB | THBS4 | ETHE1 | |
| 24 | C5-C6 | C5 | VEGFA | CSF1R | ALPL | 0.902 |
| | C5a | CCL18 | CTSB | KLK7 | ETHE1 | |
| 25 | C5 | KIT | CSF1R | LTF | KLK8 | 0.902 |
| | C5a | CCL18 | CTSB | KLK7 | ETHE1 | |
| 26 | C5 | CSF1R | LTF | KLK8 | C5a | 0.902 |
| | CCL18 | CTSB | THBS4 | KLK7 | ETHE1 | |
| 27 | C5 | CSF1R | ALPL | C5a | CCL23 | 0.902 |
| | CCL18 | CTSB | THBS4 | KLK7 | ETHE1 | |
| 28 | C5-C6 | VEGFA | CSF1R | MMP7 | KLK8 | 0.902 |
| | C5a | CCL18 | CTSB | KLK7 | ETHE1 | |
| 29 | C5 | KIT | VEGFA | CSF1R | C5a | 0.902 |
| | CCL23 | CCL18 | CTSB | KLK7 | ETHE1 | |
| 30 | C5 | KIT | CSF1R | LTF | C5a | 0.902 |
| | CCL18 | CTSB | KLK7 | HAMP | ETHE1 | |
| 31 | C5 | KIT | CSF1R | LTF | C5a | 0.902 |
| | CCL18 | CTSB | TFPI | THBS4 | ETHE1 | |
| 32 | C5-C6 | C5 | VEGFA | CSF1R | C5a | 0.902 |
| | CCL18 | CTSB | THBS4 | KLK7 | ETHE1 | |
| 33 | C5 | VEGFA | CSF1R | KLK8 | C5a | 0.902 |
| | CCL18 | CTSB | KLK7 | ESM1 | ETHE1 | |
| 34 | PLAT | C5 | VEGFA | CSF1R | KLK8 | 0.902 |
| | C5a | CCL18 | CTSB | KLK7 | ETHE1 | |
| 35 | C5-C6 | C5 | CSF1R | LTF | C5a | 0.902 |
| | CCL18 | CTSB | THBS4 | KLK7 | ETHE1 | |
| 36 | C5 | VEGFA | CSF1R | C5a | CCL23 | 0.902 |
| | CCL18 | CTSB | THBS4 | KLK7 | ETHE1 | |
| 37 | C5 | KIT | VEGFA | CSF1R | MMP7 | 0.902 |
| | C5a | CCL18 | CTSB | IL11RA | ETHE1 | |
| 38 | C5 | CSF1R | LTF | KLK8 | C5a | 0.902 |
| | CCL23 | CCL18 | CTSB | KLK7 | ETHE1 | |
| 39 | C5 | KIT | VEGFA | CSF1R | KLK8 | 0.902 |
| | C5a | CCL18 | CTSB | IL11RA | ETHE1 | |
| 40 | C5-C6 | C5 | KIT | CSF1R | LTF | 0.902 |
| | C5a | CCL18 | CTSB | THBS4 | ETHE1 | |

TABLE 11-continued

Panels of 10 Biomarkers

| | Markers | | | | | CV AUC |
|---|---|---|---|---|---|---|
| 41 | C5 | CSF1R | LTF | MMP7 | C5a | 0.901 |
| | CCL18 | CTSB | KLK7 | IL11RA | ETHE1 | |
| 42 | C5 | VEGFA | CSF1R | KLK8 | C5a | 0.901 |
| | CCL23 | CCL18 | CTSB | KLK7 | ETHE1 | |
| 43 | C5 | KIT | CSF1R | ALPL | KLK8 | 0.901 |
| | C5a | CCL18 | CTSB | KLK7 | ETHE1 | |
| 44 | KIT | VEGFA | CSF1R | MMP7 | KLK8 | 0.901 |
| | C5a | CCL18 | CTSB | KLK7 | ETHE1 | |
| 45 | C5 | KIT | CSF1R | LTF | KLK8 | 0.901 |
| | C5a | CCL18 | CTSB | IL11RA | ETHE1 | |
| 46 | C5-C6 | C5 | CSF1R | LTF | C5a | 0.901 |
| | CCL23 | CCL18 | CTSB | KLK7 | ETHE1 | |
| 47 | C5-C6 | KIT | CSF1R | LTF | C5a | 0.901 |
| | CCL23 | CCL18 | CTSB | THBS4 | ETHE1 | |
| 48 | C5-C6 | VEGFA | CSF1R | KLK8 | C5a | 0.901 |
| | CCL18 | CTSB | THBS4 | KLK7 | ETHE1 | |
| 49 | PLAT | C5 | VEGFA | CSF1R | KIT | 0.901 |
| | KLK8 | C5a | CCL18 | CTSB | ETHE1 | |
| 50 | C5 | VEGFA | CSF1R | LTF | C5a | 0.901 |
| | CCL18 | CTSB | KLK7 | IL11RA | ETHE1 | |
| 51 | C5 | KIT | CSF1R | ALPL | C5a | 0.901 |
| | CCL18 | CTSB | TFPI | THBS4 | ETHE1 | |
| 52 | C5 | CSF1R | MMP7 | KLK8 | C5a | 0.901 |
| | CCL18 | CTSB | THBS4 | KLK7 | ETHE1 | |
| 53 | C5 | CSF1R | LTF | KLK8 | C5a | 0.901 |
| | CCL18 | CTSB | TFPI | KLK7 | ETHE1 | |
| 54 | C5 | CSF1R | LTF | MMP7 | C5a | 0.901 |
| | CCL18 | CTSB | THBS4 | KLK7 | ETHE1 | |
| 55 | C5 | CSF1R | ALPL | KLK8 | C5a | 0.901 |
| | CCL18 | CTSB | TFPI | KLK7 | ETHE1 | |
| 56 | C5 | KIT | VEGFA | CSF1R | LTF | 0.901 |
| | C5a | CCL18 | CTSB | KLK7 | ETHE1 | |
| 57 | C5-C6 | C5 | VEGFA | CSF1R | C5a | 0.901 |
| | CCL18 | CTSB | ACP5 | KLK7 | ETHE1 | |
| 58 | PLAT | C5 | KIT | CSF1R | KLK8 | 0.901 |
| | C5a | CCL18 | CTSB | THBS4 | ETHE1 | |
| 59 | C5 | CSF1R | MMP7 | C5a | CCL18 | 0.901 |
| | CTSB | THBS4 | KLK7 | HAMP | ETHE1 | |
| 60 | C5-C6 | KIT | CSF1R | LTF | C5a | 0.901 |
| | CCL18 | CTSB | KLK7 | HAMP | ETHE1 | |
| 61 | PLAT | C5 | KIT | VEGFA | CSF1R | 0.901 |
| | C5a | CCL18 | CTSB | THBS4 | ETHE1 | |
| 62 | C5-C6 | VEGFA | CSF1R | LTF | C5a | 0.901 |
| | CCL18 | CTSB | THBS4 | KLK7 | ETHE1 | |
| 63 | C5 | VEGFA | CSF1R | LTF | C5a | 0.901 |
| | CCL23 | CCL18 | CTSB | KLK7 | ETHE1 | |
| 64 | C5 | CSF1R | ALPL | C5a | CCL18 | 0.901 |
| | CTSB | TFPI | THBS4 | KLK7 | ETHE1 | |
| 65 | C5-C6 | KIT | VEGFA | CSF1R | C5a | 0.901 |
| | CCL18 | CTSB | THBS4 | KLK7 | ETHE1 | |
| 66 | C5-C6 | C5 | VEGFA | CSF1R | MMP7 | 0.901 |
| | C5a | CCL18 | CTSB | KLK7 | ETHE1 | |
| 67 | C5 | KIT | CSF1R | LTF | MMP7 | 0.901 |
| | C5a | CCL18 | CTSB | KLK7 | ETHE1 | |
| 68 | C5-C6 | C5 | VEGFA | CSF1R | C5a | 0.901 |
| | CCL23 | CCL18 | CTSB | THBS4 | ETHE1 | |
| 69 | PLAT | C9 | C5 | KIT | VEGFA | 0.901 |
| | CSF1R | KLK8 | CCL18 | CTSB | ETHE1 | |
| 70 | C5-C6 | PLAT | C5 | VEGFA | CSF1R | 0.901 |
| | C5a | CCL18 | CTSB | KLK7 | ETHE1 | |
| 71 | PLAT | C5 | VEGFA | CSF1R | MMP7 | 0.901 |
| | C5a | CCL18 | CTSB | KLK7 | ETHE1 | |
| 72 | C5-C6 | C5 | CSF1R | LTF | KLK8 | 0.901 |
| | C5a | CCL18 | CTSB | KLK7 | ETHE1 | |
| 73 | C5-C6 | C5 | KIT | VEGFA | CSF1R | 0.901 |
| | C5a | CCL18 | CTSB | KLK7 | ETHE1 | |
| 74 | C5-C6 | C5 | KIT | VEGFA | CSF1R | 0.901 |
| | C5a | CCL23 | CCL18 | CTSB | ETHE1 | |
| 75 | C5-C6 | C5 | VEGFA | CSF1R | KLK8 | 0.901 |
| | C5a | CCL18 | CTSB | THBS4 | ETHE1 | |
| 76 | C5-C6 | KIT | VEGFA | CSF1R | C5a | 0.901 |
| | CCL23 | CCL18 | CTSB | THBS4 | ETHE1 | |
| 77 | C5 | VEGFA | CSF1R | LTF | KLK8 | 0.901 |
| | C5a | CCL18 | CTSB | KLK7 | ETHE1 | |
| 78 | C5 | CSF1R | LTF | C5a | CCL18 | 0.901 |
| | CTSB | TFPI | THBS4 | KLK7 | ETHE1 | |
| 79 | C5 | KIT | CSF1R | LTF | C5a | 0.901 |
| | CCL18 | CTSB | THBS4 | KLK7 | ETHE1 | |
| 80 | C5-C6 | C5 | KIT | VEGFA | CSF1R | 0.901 |
| | KLK8 | C5a | CCL18 | CTSB | ETHE1 | |
| 81 | C5 | KIT | CSF1R | MMP7 | C5a | 0.901 |
| | CCL18 | CTSB | KLK7 | HAMP | ETHE1 | |
| 82 | C5 | CSF1R | LTF | MMP7 | C5a | 0.901 |
| | CCL18 | CTSB | KLK7 | HAMP | ETHE1 | |
| 83 | C5 | KIT | VEGFA | CSF1R | C5a | 0.901 |
| | CCL18 | CTSB | KLK7 | HAMP | ETHE1 | |
| 84 | C5 | VEGFA | CSF1R | ALPL | KLK8 | 0.901 |
| | C5a | CCL18 | CTSB | KLK7 | ETHE1 | |
| 85 | C5 | CSF1R | LTF | MMP7 | C5a | 0.900 |
| | CCL23 | CCL18 | CTSB | KLK7 | ETHE1 | |
| 86 | C5-C6 | KIT | VEGFA | CSF1R | C5a | 0.900 |
| | CCL18 | CTSB | KLK7 | HAMP | ETHE1 | |
| 87 | C5-C6 | KIT | CSF1R | LTF | C5a | 0.900 |
| | CCL23 | CCL18 | CTSB | KLK7 | ETHE1 | |
| 88 | C5-C6 | PLAT | C5 | KIT | VEGFA | 0.900 |
| | CSF1R | C5a | CCL18 | CTSB | ETHE1 | |
| 89 | C5 | VEGFA | CSF1R | KLK8 | C5a | 0.900 |
| | CCL18 | CTSB | KLK7 | IL11RA | ETHE1 | |
| 90 | C5 | CSF1R | ALPL | KLK8 | C5a | 0.900 |
| | CCL23 | CCL18 | CTSB | KLK7 | ETHE1 | |
| 91 | C5 | KIT | VEGFA | CSF1R | KLK8 | 0.900 |
| | C5a | CCL18 | CTSB | TFPI | ETHE1 | |
| 92 | C5 | KIT | VEGFA | CSF1R | C5a | 0.900 |
| | CCL18 | CTSB | ACP5 | KLK7 | ETHE1 | |
| 93 | PLAT | C5 | CSF1R | ALPL | C5a | 0.900 |
| | CCL18 | CTSB | THBS4 | KLK7 | ETHE1 | |
| 94 | C5 | KIT | VEGFA | CSF1R | C5a | 0.900 |
| | CCL23 | CCL18 | CTSB | THBS4 | ETHE1 | |
| 95 | C5 | VEGFA | CSF1R | MMP7 | ALPL | 0.900 |
| | C5a | CCL18 | CTSB | KLK7 | IL11RA | |
| 96 | PLAT | C5 | CSF1R | LTF | C5a | 0.900 |
| | CCL23 | CCL18 | CTSB | KLK7 | ETHE1 | |
| 97 | C5 | VEGFA | CSF1R | LTF | MMP7 | 0.900 |
| | C5a | CCL18 | CTSB | KLK7 | IL11RA | |
| 98 | C5 | CSF1R | LTF | C5a | CCL18 | 0.900 |
| | CTSB | KLK7 | HAMP | IL11RA | ETHE1 | |
| 99 | C5-C6 | KIT | VEGFA | CSF1R | MMP7 | 0.900 |
| | C5a | CCL18 | CTSB | IL11RA | ETHE1 | |
| 100 | C5-C6 | C5 | KIT | CSF1R | LTF | 0.900 |
| | C5a | CCL18 | CTSB | KLK7 | ETHE1 | |

TABLE 12

Counts of markers in biomarker panels

| | Panel Size | | | | | | | |
|---|---|---|---|---|---|---|---|---|
| Biomarker | 3 | 4 | 5 | 6 | 7 | 8 | 9 | 10 |
| ACP5 | 35 | 35 | 40 | 54 | 58 | 60 | 54 | 59 |
| ACY1 | 7 | 5 | 2 | 0 | 1 | 0 | 0 | 0 |
| AHSG | 18 | 15 | 3 | 0 | 0 | 0 | 0 | 0 |
| ALPL | 28 | 69 | 109 | 146 | 171 | 179 | 178 | 190 |
| APOA1 | 89 | 48 | 22 | 13 | 5 | 3 | 7 | 9 |
| APOE | 5 | 1 | 0 | 0 | 0 | 0 | 0 | 0 |
| BMP6 | 5 | 1 | 0 | 0 | 0 | 0 | 0 | 0 |
| C2 | 156 | 106 | 100 | 64 | 48 | 41 | 47 | 66 |
| C5 | 256 | 373 | 600 | 731 | 777 | 806 | 819 | 808 |
| C5a | 153 | 370 | 552 | 641 | 751 | 862 | 920 | 958 |
| C5-C6 | 45 | 92 | 103 | 114 | 134 | 175 | 217 | 287 |
| C9 | 58 | 119 | 109 | 91 | 73 | 74 | 67 | 71 |
| CCL18 | 119 | 157 | 284 | 459 | 605 | 694 | 807 | 893 |
| CCL23 | 23 | 35 | 30 | 26 | 26 | 23 | 17 | 17 |
| CCL23 | 45 | 57 | 65 | 94 | 115 | 152 | 158 | 182 |
| CDK5-CDK5R1 | 12 | 19 | 19 | 12 | 11 | 14 | 16 | 16 |
| CKB-CKM | 14 | 7 | 1 | 1 | 0 | 0 | 0 | 0 |
| CKM | 6 | 0 | 0 | 0 | 0 | 0 | 0 | 0 |
| CRP | 65 | 0 | 0 | 0 | 0 | 0 | 0 | 0 |

TABLE 12-continued

Counts of markers in biomarker panels

| Biomarker | 3 | 4 | 5 | 6 | 7 | 8 | 9 | 10 |
|---|---|---|---|---|---|---|---|---|
| CSF1R | 98 | 74 | 131 | 266 | 442 | 671 | 810 | 913 |
| CTSB | 586 | 963 | 990 | 995 | 999 | 1000 | 1000 | 1000 |
| ENTPD1 | 4 | 6 | 2 | 0 | 0 | 0 | 0 | 0 |
| ESM1 | 14 | 13 | 16 | 17 | 14 | 17 | 27 | 30 |
| ETHE1 | 118 | 237 | 403 | 613 | 778 | 870 | 923 | 955 |
| FCGR3B | 34 | 14 | 5 | 2 | 1 | 0 | 0 | 0 |
| FGFR3 | 13 | 10 | 11 | 14 | 10 | 16 | 11 | 8 |
| FSTL3 | 9 | 4 | 1 | 0 | 0 | 0 | 0 | 0 |
| GDF11 | 29 | 43 | 31 | 20 | 17 | 20 | 19 | 20 |
| GFRA1 | 10 | 4 | 0 | 0 | 0 | 0 | 0 | 0 |
| HAMP | 93 | 202 | 239 | 218 | 193 | 166 | 154 | 131 |
| HINT1 | 14 | 19 | 14 | 14 | 14 | 10 | 8 | 10 |
| IDUA | 4 | 3 | 1 | 0 | 0 | 0 | 0 | 0 |
| IL11RA | 58 | 78 | 69 | 68 | 73 | 77 | 109 | 150 |
| IL12A-IL12B | 18 | 15 | 10 | 13 | 10 | 11 | 13 | 13 |
| IL18R1 | 7 | 1 | 0 | 0 | 0 | 0 | 0 | 0 |
| IL1RL1 | 17 | 10 | 3 | 0 | 0 | 0 | 0 | 0 |
| INSR | 21 | 26 | 24 | 27 | 44 | 42 | 49 | 44 |
| KIT | 63 | 142 | 202 | 251 | 306 | 348 | 392 | 445 |
| KLK3-SERPINA3 | 18 | 12 | 2 | 0 | 0 | 0 | 0 | 0 |
| KLK7 | 89 | 127 | 231 | 317 | 410 | 511 | 606 | 714 |
| KLK8 | 19 | 27 | 40 | 59 | 90 | 137 | 205 | 294 |
| KLKB1 | 12 | 7 | 1 | 0 | 0 | 0 | 0 | 0 |
| LBP | 22 | 21 | 5 | 0 | 0 | 0 | 0 | 0 |
| LTF | 30 | 66 | 106 | 161 | 202 | 252 | 310 | 347 |
| MCM2 | 6 | 4 | 0 | 0 | 0 | 0 | 0 | 0 |
| MDK | 14 | 3 | 0 | 0 | 0 | 0 | 0 | 0 |
| MMP7 | 56 | 42 | 56 | 73 | 97 | 130 | 194 | 270 |
| MRC1 | 19 | 4 | 3 | 1 | 0 | 0 | 1 | 0 |
| NID1 | 7 | 2 | 0 | 0 | 0 | 0 | 0 | 0 |
| NID2 | 7 | 0 | 0 | 0 | 0 | 0 | 0 | 0 |
| NRP1 | 44 | 20 | 12 | 5 | 2 | 2 | 2 | 1 |
| PLAT | 48 | 54 | 92 | 123 | 143 | 145 | 165 | 177 |
| SERPINA5 | 5 | 0 | 0 | 0 | 0 | 0 | 0 | 0 |
| SERPINF2 | 5 | 3 | 3 | 0 | 0 | 0 | 0 | 0 |
| SGTA | 3 | 2 | 1 | 0 | 0 | 0 | 0 | 0 |
| TFPI | 100 | 60 | 51 | 46 | 57 | 70 | 91 | 111 |
| THBS2 | 4 | 0 | 0 | 0 | 0 | 0 | 0 | 0 |
| THBS4 | 66 | 110 | 146 | 193 | 243 | 276 | 334 | 354 |
| TIMP1 | 22 | 2 | 0 | 0 | 0 | 0 | 0 | 0 |
| TNFRSF18 | 8 | 9 | 3 | 0 | 1 | 3 | 2 | 2 |
| TNFRSF1B | 20 | 12 | 8 | 6 | 4 | 1 | 0 | 0 |
| TOP1 | 6 | 3 | 0 | 0 | 0 | 0 | 0 | 0 |
| VEGFA | 16 | 33 | 47 | 51 | 75 | 142 | 268 | 455 |
| VEGFC | 5 | 4 | 2 | 1 | 0 | 0 | 0 | 0 |

TABLE 13

Analytes in ten marker classifiers

| | |
|---|---|
| CTSB | C5a |
| ETHE1 | CSF1R |
| CCL18 | C5 |
| KLK7 | VEGFA |
| KIT | THBS4 |
| LTF | |

TABLE 14

Parameters derived from training set for naïve Bayes classifier.

| Biomarker | $\mu_c$ | $\mu_d$ | $\sigma_c$ | $\sigma_d$ |
|---|---|---|---|---|
| CSF1R | 10.712 | 10.995 | 0.398 | 0.399 |
| CTSB | 8.836 | 9.398 | 0.287 | 0.621 |
| IL1RL1 | 9.702 | 10.189 | 0.533 | 0.780 |
| GDF11 | 8.889 | 8.578 | 0.291 | 0.379 |
| ETHE1 | 7.373 | 7.443 | 0.119 | 0.121 |
| CCL23 | 8.795 | 8.975 | 0.312 | 0.329 |
| FGFR3 | 6.992 | 7.166 | 0.178 | 0.225 |
| KIT | 9.770 | 9.623 | 0.287 | 0.318 |
| FSTL3 | 8.787 | 9.029 | 0.290 | 0.374 |
| THBS2 | 7.481 | 7.922 | 0.270 | 0.633 |
| SERPINF2 | 9.264 | 9.175 | 0.115 | 0.162 |
| TNFRSF1B | 10.748 | 11.028 | 0.380 | 0.452 |
| TNFRSF18 | 12.308 | 12.279 | 0.139 | 0.168 |
| BMP6 | 7.958 | 8.138 | 0.142 | 0.239 |
| GFRA1 | 7.324 | 7.465 | 0.182 | 0.200 |
| CRP | 11.965 | 12.304 | 0.735 | 0.233 |
| SERPINA5 | 10.309 | 10.101 | 0.300 | 0.419 |
| KLKB1 | 11.802 | 11.666 | 0.159 | 0.211 |
| APOE | 8.081 | 8.314 | 0.406 | 0.656 |
| SFRP1 | 7.096 | 7.219 | 0.221 | 0.309 |
| C2 | 11.506 | 11.611 | 0.100 | 0.132 |
| CKM | 7.313 | 7.192 | 0.154 | 0.116 |
| TFPI | 10.179 | 10.490 | 0.261 | 0.352 |
| INSR | 8.480 | 8.633 | 0.224 | 0.255 |
| NID2 | 8.595 | 8.806 | 0.213 | 0.384 |
| HAMP | 10.424 | 11.079 | 0.788 | 0.617 |
| MDK | 8.034 | 8.495 | 0.570 | 0.578 |
| CDK5-CDK5R1 | 6.937 | 6.994 | 0.108 | 0.111 |
| NID1 | 9.771 | 9.941 | 0.213 | 0.357 |
| VEGFC | 7.454 | 7.540 | 0.118 | 0.126 |
| C9 | 11.911 | 12.076 | 0.234 | 0.233 |
| LTF | 10.120 | 9.870 | 0.442 | 0.419 |
| IL12A-IL12B | 7.311 | 7.273 | 0.052 | 0.057 |
| C5 | 9.485 | 9.603 | 0.119 | 0.143 |
| IL18R1 | 7.643 | 7.845 | 0.186 | 0.475 |
| CCL18 | 11.320 | 11.616 | 0.477 | 0.398 |
| VEGFA | 8.532 | 8.601 | 0.170 | 0.134 |
| IDUA | 8.428 | 8.694 | 0.366 | 0.558 |
| TOP1 | 6.892 | 6.842 | 0.088 | 0.091 |
| C5-C6 | 6.506 | 6.593 | 0.133 | 0.144 |
| TIMP1 | 9.815 | 10.148 | 0.264 | 0.430 |
| C5a | 11.354 | 11.606 | 0.254 | 0.246 |
| THBS4 | 10.013 | 9.794 | 0.359 | 0.400 |
| ENTPD1 | 7.225 | 7.299 | 0.110 | 0.103 |
| LBP | 9.102 | 9.489 | 0.439 | 0.548 |
| KLK3-SERPINA3 | 9.034 | 9.287 | 0.353 | 0.422 |
| MCM2 | 7.794 | 7.975 | 0.226 | 0.359 |
| SGTA | 5.920 | 5.883 | 0.060 | 0.079 |
| ESM1 | 9.715 | 9.919 | 0.330 | 0.476 |
| PLAT | 8.517 | 8.838 | 0.461 | 0.502 |
| KLK7 | 8.322 | 7.989 | 0.321 | 0.391 |
| CCL23 | 7.909 | 8.097 | 0.227 | 0.267 |
| ACP5 | 10.198 | 10.436 | 0.292 | 0.343 |
| NRP1 | 8.832 | 9.047 | 0.243 | 0.256 |
| MMP7 | 9.084 | 9.574 | 0.437 | 0.706 |
| ACY1 | 9.898 | 10.411 | 0.628 | 0.919 |
| ALPL | 10.577 | 10.290 | 0.377 | 0.417 |
| IL11RA | 7.312 | 7.213 | 0.110 | 0.107 |
| APOA1 | 9.701 | 9.480 | 0.171 | 0.295 |
| CKB-CKM | 7.506 | 7.025 | 0.653 | 0.479 |
| KLK8 | 7.361 | 7.421 | 0.100 | 0.178 |
| AHSG | 11.914 | 11.826 | 0.133 | 0.167 |
| HINT1 | 5.835 | 5.793 | 0.086 | 0.104 |
| MRC1 | 9.628 | 9.995 | 0.370 | 0.490 |
| FCGR3B | 10.920 | 11.145 | 0.255 | 0.269 |

TABLE 15

AUC for exemplary combinations of biomarkers

| # | | | | | | | | | | AUC |
|---|---|---|---|---|---|---|---|---|---|---|
| 1 | CTSB | | | | | | | | | 0.791 |
| 2 | CTSB | C5a | | | | | | | | 0.853 |
| 3 | CTSB | C5a | C5 | | | | | | | 0.880 |
| 4 | CTSB | C5a | C5 | CCL18 | | | | | | 0.890 |
| 5 | CTSB | C5a | C5 | CCL18 | CSF1R | | | | | 0.895 |
| 6 | CTSB | C5a | C5 | CCL18 | CSF1R | KLK7 | | | | 0.895 |
| 7 | CTSB | C5a | C5 | CCL18 | CSF1R | KLK7 | ETHE1 | | | 0.906 |
| 8 | CTSB | C5a | C5 | CCL18 | CSF1R | KLK7 | ETHE1 | C5-C6 | | 0.902 |
| 9 | CTSB | C5a | C5 | CCL18 | CSF1R | KLK7 | ETHE1 | C5-C6 | KLK8 | 0.903 |
| 10 | CTSB | C5a | C5 | CCL18 | CSF1R | KLK7 | ETHE1 | C5-C6 | KLK8 VEGFA | 0.913 |

TABLE 16

Calculations derived from training set for naïve Bayes classifier.

| Biomarker | $\mu_c$ | $\mu_d$ | $\sigma_c$ | $\sigma_d$ | $\tilde{x}$ | $p(c|\tilde{x})$ | $p(d|\tilde{x})$ | $\ln(p(d|\tilde{x})/p(c|\tilde{x}))$ |
|---|---|---|---|---|---|---|---|---|
| CSF1R | 10.712 | 10.995 | 0.398 | 0.399 | 10.751 | 0.997 | 0.831 | −0.182 |
| CTSB | 8.836 | 9.398 | 0.287 | 0.621 | 9.036 | 1.091 | 0.542 | −0.700 |
| CCL18 | 11.320 | 11.616 | 0.477 | 0.398 | 11.658 | 0.651 | 0.996 | 0.425 |
| KLK7 | 8.322 | 7.989 | 0.321 | 0.391 | 8.048 | 0.862 | 1.009 | 0.158 |
| VEGFA | 8.532 | 8.601 | 0.170 | 0.134 | 8.687 | 1.554 | 2.425 | 0.445 |
| ETHE1 | 7.373 | 7.443 | 0.119 | 0.121 | 7.313 | 2.932 | 1.845 | −0.463 |
| C5-C6 | 6.506 | 6.593 | 0.133 | 0.144 | 6.349 | 1.490 | 0.662 | −0.811 |
| C5a | 11.354 | 11.606 | 0.254 | 0.246 | 11.400 | 1.547 | 1.139 | −0.306 |
| KLK8 | 7.361 | 7.421 | 0.100 | 0.178 | 7.420 | 3.344 | 2.237 | −0.402 |
| C5 | 9.485 | 9.603 | 0.119 | 0.143 | 9.306 | 1.084 | 0.324 | −1.207 |

TABLE 17

Clinical characteristics of the training set

| Meta Data | Levels | Control | Pancreatic Cancer | p-value |
|---|---|---|---|---|
| Samples | | 115 | 143 | |
| GENDER | F | 59 | 70 | |
| | M | 56 | 73 | 8.02e−01 |
| AGE | Mean | 57.6 | 68.6 | |
| | SD | 13.7 | 9.7 | 8.98e−12 |

TABLE 18

Ten biomarker classifier proteins

| Biomarker | UniProt ID | Direction* | Biological Process (GO) |
|---|---|---|---|
| C5-C6 | P01031 P13671 | Up | immune system process regulation of immune system process proteolysis response to stress regulation of cell death signaling regulation of signaling pathway |
| C5 | P01031 | Up | immune system process regulation of immune system process proteolysis response to stress signaling regulation of signaling pathway |
| VEGFA | P15692 | Down | immune system process regulation of immune system process response to stress regulation of cell death signaling regulation of signaling pathway |
| CSF1R | P07333 | Up | cell proliferation signaling process signaling |
| KLK8 | O60259 | Up | proteolysis response to stress cell proliferation |
| C5a | P01031 | Up | immune system process regulation of immune system process proteolysis response to stress signaling regulation of signaling pathway |
| CCL18 | P55774 | Up | immune system process response to stress cell communication signaling process signaling |
| CTSB | P07858 | Up | proteolysis response to stress regulation of cell death |
| KLK7 | P49862 | Down | proteolysis |
| ETHE1 | O95571 | Up | |

TABLE 19

Biomarkers of general cancer

| | |
|---|---|
| ACY1 | APOA1 |
| C5 | CCL23 |
| CKB-CKM | CKM |
| ENTPD1 | GDF11 |
| HAMP | HINT1 |
| KIT | KLK3-SERPINA3 |

TABLE 19-continued

| Biomarkers of general cancer | |
|---|---|
| LBP | SERPINF2 |
| THBS2 | TIMP1 |
| C9 | FSTL3 |
| IL12A-IL12B | CDK5-CDK5R1 |
| CCL23 | |

TABLE 20

Panels of 1 Biomarker

| | Markers | Mean CV AUC |
|---|---|---|
| 1 | KIT | 0.753 |
| 2 | CKB-CKM | 0.750 |
| 3 | C9 | 0.740 |
| 4 | APOA1 | 0.740 |
| 5 | KLK3-SERPINA3 | 0.732 |
| 6 | CKM | 0.730 |
| 7 | CCL23 | 0.713 |
| 8 | CCL23 | 0.705 |
| 9 | TIMP1 | 0.695 |
| 10 | LBP | 0.691 |
| 11 | C5 | 0.690 |
| 12 | ACY1 | 0.676 |
| 13 | HAMP | 0.670 |
| 14 | CDK5-CDK5R1 | 0.670 |
| 15 | HINT1 | 0.669 |
| 16 | SERPINF2 | 0.663 |
| 17 | GDF11 | 0.656 |
| 18 | ENTPD1 | 0.651 |
| 19 | THBS2 | 0.650 |
| 20 | FSTL3 | 0.643 |
| 21 | IL12A-IL12B | 0.640 |

TABLE 21

Panels of 2 Biomarkers

| | Markers | | Mean CV AUC |
|---|---|---|---|
| 1 | KIT | APOA1 | 0.808 |
| 2 | APOA1 | CKB-CKM | 0.801 |
| 3 | KIT | CCL23 | 0.791 |
| 4 | C9 | KIT | 0.791 |
| 5 | KIT | CKB-CKM | 0.790 |
| 6 | C9 | CKB-CKM | 0.789 |
| 7 | C9 | APOA1 | 0.789 |
| 8 | KIT | LBP | 0.787 |
| 9 | TIMP1 | KIT | 0.787 |
| 10 | C5 | KIT | 0.787 |
| 11 | C9 | CKM | 0.786 |
| 12 | CKM | APOA1 | 0.786 |
| 13 | C5 | APOA1 | 0.785 |
| 14 | KIT | CCL23 | 0.784 |
| 15 | TIMP1 | CKB-CKM | 0.782 |
| 16 | CCL23 | CKB-CKM | 0.781 |
| 17 | KIT | CKM | 0.780 |
| 18 | KIT | ACY1 | 0.780 |
| 19 | KIT | KLK3-SERPINA3 | 0.780 |
| 20 | CKM | CCL23 | 0.778 |
| 21 | CKB-CKM | HINT1 | 0.778 |
| 22 | KIT | CDK5-CDK5R1 | 0.777 |
| 23 | SERPINF2 | CKB-CKM | 0.777 |
| 24 | APOA1 | ACY1 | 0.777 |
| 25 | KIT | SERPINF2 | 0.776 |
| 26 | LBP | CKB-CKM | 0.776 |
| 27 | CKB-CKM | KLK3-SERPINA3 | 0.776 |
| 28 | APOA1 | KLK3-SERPINA3 | 0.776 |
| 29 | APOA1 | CCL23 | 0.775 |
| 30 | TIMP1 | CKM | 0.774 |
| 31 | C9 | ACY1 | 0.774 |
| 32 | CDK5-CDK5R1 | CKB-CKM | 0.773 |
| 33 | IL12A-IL12B | CKB-CKM | 0.773 |
| 34 | TIMP1 | C9 | 0.773 |
| 35 | APOA1 | HINT1 | 0.773 |
| 36 | C5 | CCL23 | 0.772 |
| 37 | KIT | HINT1 | 0.772 |
| 38 | IL12A-IL12B | KIT | 0.771 |
| 39 | CKM | SERPINF2 | 0.771 |
| 40 | ACY1 | CKB-CKM | 0.770 |
| 41 | APOA1 | CCL23 | 0.770 |
| 42 | C9 | CDK5-CDK5R1 | 0.769 |
| 43 | C5 | CKB-CKM | 0.769 |
| 44 | C9 | HINT1 | 0.769 |
| 45 | CKM | CCL23 | 0.767 |
| 46 | CCL23 | KLK3-SERPINA3 | 0.767 |
| 47 | CKM | KLK3-SERPINA3 | 0.767 |
| 48 | C9 | FSTL3 | 0.767 |
| 49 | APOA1 | LBP | 0.766 |
| 50 | C9 | SERPINF2 | 0.766 |
| 51 | C9 | CCL23 | 0.765 |
| 52 | CKM | LBP | 0.765 |
| 53 | CCL23 | CKB-CKM | 0.764 |
| 54 | KIT | ENTPD1 | 0.764 |
| 55 | CKM | HINT1 | 0.764 |
| 56 | C9 | LBP | 0.764 |
| 57 | C9 | C5 | 0.764 |
| 58 | KIT | HAMP | 0.764 |
| 59 | FSTL3 | CKB-CKM | 0.763 |
| 60 | KIT | FSTL3 | 0.763 |
| 61 | CKM | CKB-CKM | 0.762 |
| 62 | HAMP | CKB-CKM | 0.762 |
| 63 | CKM | ACY1 | 0.762 |
| 64 | TIMP1 | APOA1 | 0.762 |
| 65 | APOA1 | CDK5-CDK5R1 | 0.761 |
| 66 | C5 | KLK3-SERPINA3 | 0.761 |
| 67 | C5 | HINT1 | 0.760 |
| 68 | C9 | GDF11 | 0.760 |
| 69 | C9 | THBS2 | 0.760 |
| 70 | CKM | CDK5-CDK5R1 | 0.760 |
| 71 | ENTPD1 | CKB-CKM | 0.759 |
| 72 | C5 | CCL23 | 0.759 |
| 73 | CCL23 | ACY1 | 0.758 |
| 74 | CCL23 | ACY1 | 0.758 |
| 75 | C5 | CDK5-CDK5R1 | 0.757 |
| 76 | C5 | CKM | 0.757 |
| 77 | TIMP1 | KLK3-SERPINA3 | 0.757 |
| 78 | CKM | HAMP | 0.757 |
| 79 | C9 | HAMP | 0.757 |
| 80 | C9 | CCL23 | 0.757 |
| 81 | C9 | IL12A-IL12B | 0.756 |
| 82 | LBP | ACY1 | 0.756 |
| 83 | C9 | ENTPD1 | 0.754 |
| 84 | CKM | ENTPD1 | 0.754 |
| 85 | APOA1 | SERPINF2 | 0.754 |
| 86 | LBP | HINT1 | 0.754 |
| 87 | CDK5-CDK5R1 | KLK3-SERPINA3 | 0.754 |
| 88 | APOA1 | ENTPD1 | 0.753 |
| 89 | TIMP1 | CCL23 | 0.753 |
| 90 | KIT | GDF11 | 0.753 |
| 91 | GDF11 | KLK3-SERPINA3 | 0.753 |
| 92 | IL12A-IL12B | CKM | 0.753 |
| 93 | C5 | SERPINF2 | 0.752 |
| 94 | APOA1 | GDF11 | 0.752 |
| 95 | CCL23 | KLK3-SERPINA3 | 0.751 |
| 96 | CCL23 | CDK5-CDK5R1 | 0.751 |
| 97 | ACY1 | KLK3-SERPINA3 | 0.749 |
| 98 | C9 | KLK3-SERPINA3 | 0.749 |
| 99 | LBP | CDK5-CDK5R1 | 0.749 |
| 100 | APOA1 | HAMP | 0.748 |

TABLE 22

Panels of 3 Biomarkers

| | Markers | | | Mean CV AUC |
|---|---|---|---|---|
| 1 | C5 | KIT | APOA1 | 0.830 |
| 2 | KIT | APOA1 | CKB-CKM | 0.826 |
| 3 | C9 | KIT | APOA1 | 0.822 |
| 4 | KIT | APOA1 | ACY1 | 0.820 |
| 5 | KIT | APOA1 | CDK5-CDK5R1 | 0.819 |
| 6 | APOA1 | CCL23 | CKB-CKM | 0.819 |
| 7 | APOA1 | ACY1 | CKB-CKM | 0.818 |
| 8 | C9 | KIT | CKB-CKM | 0.817 |
| 9 | C9 | KIT | ACY1 | 0.816 |
| 10 | KIT | APOA1 | LBP | 0.816 |
| 11 | C5 | KIT | CCL23 | 0.816 |
| 12 | C5 | APOA1 | CKB-CKM | 0.816 |
| 13 | TIMP1 | C9 | KIT | 0.815 |
| 14 | C9 | APOA1 | CKB-CKM | 0.815 |
| 15 | C5 | KIT | CDK5-CDK5R1 | 0.815 |
| 16 | APOA1 | CKB-CKM | HINT1 | 0.815 |
| 17 | KIT | CKM | APOA1 | 0.815 |
| 18 | KIT | APOA1 | CCL23 | 0.815 |
| 19 | TIMP1 | KIT | APOA1 | 0.814 |
| 20 | APOA1 | LBP | CKB-CKM | 0.813 |
| 21 | C9 | KIT | CKM | 0.813 |
| 22 | APOA1 | CDK5-CDK5R1 | CKB-CKM | 0.812 |
| 23 | KIT | APOA1 | CCL23 | 0.812 |
| 24 | C9 | CKM | APOA1 | 0.812 |
| 25 | TIMP1 | KIT | CDK5-CDK5R1 | 0.812 |
| 26 | C5 | KIT | CKB-CKM | 0.812 |
| 27 | TIMP1 | APOA1 | CKB-CKM | 0.812 |
| 28 | KIT | APOA1 | HINT1 | 0.812 |
| 29 | C9 | KIT | HINT1 | 0.811 |
| 30 | KIT | CDK5-CDK5R1 | CKB-CKM | 0.811 |
| 31 | KIT | LBP | CKB-CKM | 0.811 |
| 32 | IL12A-IL12B | KIT | APOA1 | 0.811 |
| 33 | C9 | C5 | KIT | 0.811 |
| 34 | C5 | KIT | CCL23 | 0.811 |
| 35 | C5 | KIT | HINT1 | 0.811 |
| 36 | KIT | CCL23 | ACY1 | 0.809 |
| 37 | C9 | KIT | CCL23 | 0.809 |
| 38 | APOA1 | CKB-CKM | KLK3-SERPINA3 | 0.809 |
| 39 | KIT | CCL23 | ACY1 | 0.809 |
| 40 | APOA1 | SERPINF2 | CKB-CKM | 0.808 |
| 41 | C9 | ACY1 | CKB-CKM | 0.808 |
| 42 | TIMP1 | KIT | CKB-CKM | 0.808 |
| 43 | KIT | APOA1 | KLK3-SERPINA3 | 0.808 |
| 44 | IL12A-IL12B | APOA1 | CKB-CKM | 0.808 |
| 45 | KIT | CCL23 | CKB-CKM | 0.807 |
| 46 | C5 | APOA1 | CDK5-CDK5R1 | 0.807 |
| 47 | C5 | APOA1 | CCL23 | 0.807 |
| 48 | KIT | ACY1 | CKB-CKM | 0.807 |
| 49 | C5 | KIT | ACY1 | 0.807 |
| 50 | TIMP1 | C5 | KIT | 0.807 |
| 51 | C9 | C5 | CKB-CKM | 0.806 |
| 52 | C5 | APOA1 | HINT1 | 0.806 |
| 53 | C9 | CDK5-CDK5R1 | CKB-CKM | 0.806 |
| 54 | C9 | CKB-CKM | HINT1 | 0.806 |
| 55 | C5 | CCL23 | CKB-CKM | 0.806 |
| 56 | C5 | KIT | SERPINF2 | 0.806 |
| 57 | KIT | CCL23 | CKB-CKM | 0.806 |
| 58 | C5 | CKM | APOA1 | 0.806 |
| 59 | CKM | APOA1 | CCL23 | 0.806 |
| 60 | APOA1 | CCL23 | CKB-CKM | 0.806 |
| 61 | C5 | CKB-CKM | HINT1 | 0.806 |
| 62 | APOA1 | HAMP | CKB-CKM | 0.806 |
| 63 | KIT | LBP | CDK5-CDK5R1 | 0.805 |
| 64 | TIMP1 | KIT | CCL23 | 0.805 |
| 65 | KIT | APOA1 | ENTPD1 | 0.805 |
| 66 | TIMP1 | C9 | CKB-CKM | 0.805 |
| 67 | C5 | APOA1 | ACY1 | 0.804 |
| 68 | C9 | KIT | CDK5-CDK5R1 | 0.804 |
| 69 | TIMP1 | KIT | CKM | 0.804 |
| 70 | C9 | APOA1 | CDK5-CDK5R1 | 0.804 |
| 71 | C9 | CCL23 | CKB-CKM | 0.804 |
| 72 | KIT | CKB-CKM | HINT1 | 0.804 |
| 73 | TIMP1 | CDK5-CDK5R1 | CKB-CKM | 0.804 |
| 74 | KIT | APOA1 | SERPINF2 | 0.804 |
| 75 | KIT | CKM | LBP | 0.803 |
| 76 | CKM | APOA1 | ACY1 | 0.803 |
| 77 | C5 | CDK5-CDK5R1 | CKB-CKM | 0.803 |
| 78 | KIT | APOA1 | HAMP | 0.803 |
| 79 | TIMP1 | C9 | CKM | 0.803 |
| 80 | KIT | LBP | ACY1 | 0.803 |
| 81 | C9 | CKM | ACY1 | 0.803 |
| 82 | C5 | IL12A-IL12B | KIT | 0.803 |
| 83 | LBP | CKB-CKM | HINT1 | 0.803 |
| 84 | C9 | CKM | CDK5-CDK5R1 | 0.803 |
| 85 | C9 | KIT | FSTL3 | 0.802 |
| 86 | LBP | CDK5-CDK5R1 | CKB-CKM | 0.802 |
| 87 | C9 | KIT | SERPINF2 | 0.802 |
| 88 | APOA1 | FSTL3 | CKB-CKM | 0.802 |
| 89 | C5 | KIT | CKM | 0.802 |
| 90 | KIT | CKM | CDK5-CDK5R1 | 0.802 |
| 91 | TIMP1 | KIT | ACY1 | 0.802 |
| 92 | C9 | IL12A-IL12B | CKB-CKM | 0.801 |
| 93 | KIT | CCL23 | CDK5-CDK5R1 | 0.801 |
| 94 | KIT | CCL23 | LBP | 0.801 |
| 95 | C9 | KIT | LBP | 0.801 |
| 96 | CCL23 | CDK5-CDK5R1 | CKB-CKM | 0.801 |
| 97 | KIT | SERPINF2 | LBP | 0.801 |
| 98 | C5 | KIT | ENTPD1 | 0.801 |
| 99 | APOA1 | ENTPD1 | CKB-CKM | 0.800 |
| 100 | KIT | CKM | ACY1 | 0.800 |

TABLE 23

Panels of 4 Biomarkers

| | Markers | | | | Mean CV AUC |
|---|---|---|---|---|---|
| 1 | C5 | KIT | APOA1 | CDK5-CDK5R1 | 0.845 |
| 2 | C5 | KIT | APOA1 | CKB-CKM | 0.839 |
| 3 | KIT | APOA1 | CDK5-CDK5R1 | CKB-CKM | 0.839 |
| 4 | KIT | APOA1 | ACY1 | CKB-CKM | 0.838 |
| 5 | C5 | KIT | APOA1 | ACY1 | 0.837 |
| 6 | C9 | KIT | APOA1 | CKB-CKM | 0.835 |
| 7 | C5 | KIT | APOA1 | HINT1 | 0.835 |
| 8 | C5 | APOA1 | CKB-CKM | HINT1 | 0.835 |
| 9 | KIT | APOA1 | CCL23 | CKB-CKM | 0.834 |
| 10 | C5 | KIT | APOA1 | CCL23 | 0.834 |
| 11 | KIT | APOA1 | CCL23 | CKB-CKM | 0.833 |
| 12 | C9 | KIT | APOA1 | ACY1 | 0.833 |
| 13 | KIT | APOA1 | LBP | CKB-CKM | 0.833 |
| 14 | C5 | KIT | APOA1 | CCL23 | 0.833 |

TABLE 23-continued

Panels of 4 Biomarkers

| | Markers | | | | Mean CV AUC |
|---|---|---|---|---|---|
| 15 | C9 | KIT | CKM | APOA1 | 0.833 |
| 16 | C5 | APOA1 | CDK5-CDK5R1 | CKB-CKM | 0.833 |
| 17 | IL12A-IL12B | KIT | APOA1 | CKB-CKM | 0.832 |
| 18 | C5 | KIT | CDK5-CDK5R1 | CKB-CKM | 0.832 |
| 19 | C5 | KIT | CKM | APOA1 | 0.832 |
| 20 | TIMP1 | KIT | CDK5-CDK5R1 | CKB-CKM | 0.832 |
| 21 | C9 | C5 | KIT | CKB-CKM | 0.832 |
| 22 | TIMP1 | KIT | APOA1 | CKB-CKM | 0.832 |
| 23 | TIMP1 | C5 | KIT | CDK5-CDK5R1 | 0.831 |
| 24 | C9 | KIT | APOA1 | CDK5-CDK5R1 | 0.831 |
| 25 | C5 | KIT | CCL23 | ACY1 | 0.831 |
| 26 | C5 | IL12A-IL12B | KIT | APOA1 | 0.831 |
| 27 | C5 | APOA1 | ACY1 | CKB-CKM | 0.830 |
| 28 | C9 | C5 | KIT | APOA1 | 0.830 |
| 29 | KIT | APOA1 | CKB-CKM | HINT1 | 0.830 |
| 30 | C9 | KIT | ACY1 | CKB-CKM | 0.830 |
| 31 | C5 | KIT | CCL23 | CKB-CKM | 0.830 |
| 32 | C5 | APOA1 | CCL23 | CKB-CKM | 0.829 |
| 33 | C9 | KIT | CCL23 | ACY1 | 0.829 |
| 34 | C9 | KIT | APOA1 | CCL23 | 0.829 |
| 35 | C5 | KIT | CCL23 | CKB-CKM | 0.829 |
| 36 | C5 | KIT | APOA1 | SERPINF2 | 0.829 |
| 37 | APOA1 | CCL23 | ACY1 | CKB-CKM | 0.829 |
| 38 | C5 | KIT | APOA1 | ENTPD1 | 0.829 |
| 39 | KIT | APOA1 | LBP | CDK5-CDK5R1 | 0.829 |
| 40 | KIT | APOA1 | CCL23 | ACY1 | 0.829 |
| 41 | C9 | KIT | APOA1 | HINT1 | 0.829 |
| 42 | KIT | LBP | CDK5-CDK5R1 | CKB-CKM | 0.829 |
| 43 | KIT | APOA1 | ACY1 | CDK5-CDK5R1 | 0.828 |
| 44 | TIMP1 | KIT | APOA1 | ACY1 | 0.828 |
| 45 | C5 | KIT | CCL23 | CDK5-CDK5R1 | 0.828 |
| 46 | KIT | APOA1 | CCL23 | ACY1 | 0.828 |
| 47 | TIMP1 | C9 | KIT | CDK5-CDK5R1 | 0.828 |
| 48 | C5 | APOA1 | CCL23 | CKB-CKM | 0.828 |
| 49 | KIT | CKM | APOA1 | ACY1 | 0.828 |
| 50 | TIMP1 | C5 | KIT | APOA1 | 0.828 |
| 51 | C5 | KIT | CCL23 | ACY1 | 0.828 |
| 52 | C9 | KIT | CCL23 | CKB-CKM | 0.828 |
| 53 | APOA1 | LBP | ACY1 | CKB-CKM | 0.827 |
| 54 | TIMP1 | C9 | KIT | CKB-CKM | 0.827 |
| 55 | C9 | KIT | CDK5-CDK5R1 | CKB-CKM | 0.827 |
| 56 | KIT | APOA1 | LBP | ACY1 | 0.827 |
| 57 | KIT | APOA1 | SERPINF2 | CKB-CKM | 0.827 |
| 58 | APOA1 | ACY1 | CDK5-CDK5R1 | CKB-CKM | 0.827 |
| 59 | C5 | KIT | CCL23 | CDK5-CDK5R1 | 0.827 |
| 60 | C9 | KIT | CKM | ACY1 | 0.827 |
| 61 | TIMP1 | APOA1 | ACY1 | CKB-CKM | 0.827 |
| 62 | C5 | KIT | APOA1 | LBP | 0.827 |
| 63 | TIMP1 | KIT | APOA1 | CDK5-CDK5R1 | 0.827 |
| 64 | KIT | CKM | APOA1 | CDK5-CDK5R1 | 0.826 |
| 65 | KIT | APOA1 | HAMP | CKB-CKM | 0.826 |
| 66 | C5 | KIT | ACY1 | CDK5-CDK5R1 | 0.826 |
| 67 | TIMP1 | C9 | KIT | APOA1 | 0.826 |
| 68 | C9 | KIT | CKB-CKM | HINT1 | 0.826 |
| 69 | APOA1 | LBP | CKB-CKM | HINT1 | 0.826 |
| 70 | C9 | KIT | ACY1 | CDK5-CDK5R1 | 0.826 |
| 71 | TIMP1 | APOA1 | CDK5-CDK5R1 | CKB-CKM | 0.826 |
| 72 | KIT | APOA1 | CCL23 | CDK5-CDK5R1 | 0.826 |
| 73 | C9 | CKM | APOA1 | CDK5-CDK5R1 | 0.826 |
| 74 | C5 | KIT | CKB-CKM | HINT1 | 0.825 |
| 75 | C5 | KIT | SERPINF2 | CDK5-CDK5R1 | 0.825 |
| 76 | C9 | KIT | CKM | CDK5-CDK5R1 | 0.825 |
| 77 | TIMP1 | C9 | KIT | ACY1 | 0.825 |
| 78 | C5 | CCL23 | CDK5-CDK5R1 | CKB-CKM | 0.825 |
| 79 | KIT | APOA1 | ENTPD1 | CKB-CKM | 0.825 |
| 80 | C9 | KIT | APOA1 | LBP | 0.825 |
| 81 | C5 | KIT | APOA1 | KLK3-SERPINA3 | 0.825 |
| 82 | C9 | KIT | CKM | HINT1 | 0.825 |
| 83 | C5 | APOA1 | LBP | CKB-CKM | 0.825 |
| 84 | KIT | LBP | ACY1 | CKB-CKM | 0.825 |
| 85 | APOA1 | CCL23 | CDK5-CDK5R1 | CKB-CKM | 0.825 |
| 86 | C9 | CKM | APOA1 | ACY1 | 0.824 |
| 87 | KIT | CKM | APOA1 | LBP | 0.824 |
| 88 | C9 | KIT | CKM | CCL23 | 0.824 |
| 89 | TIMP1 | C5 | KIT | ACY1 | 0.824 |
| 90 | C9 | APOA1 | CDK5-CDK5R1 | CKB-CKM | 0.824 |

TABLE 23-continued

Panels of 4 Biomarkers

| | | Markers | | | Mean CV AUC |
|---|---|---|---|---|---|
| 91 | KIT | ACY1 | CDK5-CDK5R1 | CKB-CKM | 0.824 |
| 92 | C5 | KIT | ACY1 | CKB-CKM | 0.824 |
| 93 | KIT | CCL23 | CDK5-CDK5R1 | CKB-CKM | 0.824 |
| 94 | APOA1 | ACY1 | FSTL3 | CKB-CKM | 0.824 |
| 95 | C9 | C5 | KIT | CKM | 0.824 |
| 96 | C5 | KIT | CKM | CDK5-CDK5R1 | 0.824 |
| 97 | KIT | CCL23 | CDK5-CDK5R1 | CKB-CKM | 0.824 |
| 98 | C5 | APOA1 | SERPINF2 | CKB-CKM | 0.824 |
| 99 | C5 | KIT | APOA1 | HAMP | 0.824 |
| 100 | C9 | APOA1 | CKB-CKM | HINT1 | 0.824 |

TABLE 24

Panels of 5 Biomarkers

| | | | Markers | | | Mean CV AUC |
|---|---|---|---|---|---|---|
| 1 | C5 | KIT | APOA1 | CDK5-CDK5R1 | CKB-CKM | 0.854 |
| 2 | C5 | KIT | APOA1 | ACY1 | CKB-CKM | 0.851 |
| 3 | C5 | KIT | APOA1 | CCL23 | CKB-CKM | 0.849 |
| 4 | C5 | KIT | APOA1 | CCL23 | CKB-CKM | 0.847 |
| 5 | KIT | APOA1 | ACY1 | CDK5-CDK5R1 | CKB-CKM | 0.847 |
| 6 | KIT | APOA1 | LBP | ACY1 | CKB-CKM | 0.847 |
| 7 | C5 | KIT | APOA1 | CKB-CKM | HINT1 | 0.847 |
| 8 | TIMP1 | KIT | APOA1 | ACY1 | CKB-CKM | 0.847 |
| 9 | C5 | KIT | APOA1 | ACY1 | CDK5-CDK5R1 | 0.846 |
| 10 | C5 | KIT | APOA1 | CCL23 | CDK5-CDK5R1 | 0.846 |
| 11 | KIT | APOA1 | LBP | CDK5-CDK5R1 | CKB-CKM | 0.845 |
| 12 | C5 | KIT | CCL23 | CDK5-CDK5R1 | CKB-CKM | 0.845 |
| 13 | C5 | KIT | APOA1 | CCL23 | CDK5-CDK5R1 | 0.845 |
| 14 | TIMP1 | C5 | KIT | APOA1 | CDK5-CDK5R1 | 0.845 |
| 15 | TIMP1 | KIT | APOA1 | CDK5-CDK5R1 | CKB-CKM | 0.844 |
| 16 | KIT | APOA1 | CCL23 | ACY1 | CKB-CKM | 0.844 |
| 17 | KIT | APOA1 | CCL23 | CDK5-CDK5R1 | CKB-CKM | 0.844 |
| 18 | C5 | KIT | CCL23 | CDK5-CDK5R1 | CKB-CKM | 0.844 |
| 19 | C5 | KIT | CKM | APOA1 | CDK5-CDK5R1 | 0.844 |
| 20 | C5 | KIT | APOA1 | LBP | CDK5-CDK5R1 | 0.844 |
| 21 | C5 | IL12A-IL12B | KIT | APOA1 | CKB-CKM | 0.844 |
| 22 | KIT | APOA1 | CCL23 | ACY1 | CKB-CKM | 0.843 |
| 23 | C5 | KIT | APOA1 | CCL23 | ACY1 | 0.843 |
| 24 | KIT | APOA1 | CCL23 | CDK5-CDK5R1 | CKB-CKM | 0.843 |
| 25 | C9 | KIT | CKM | APOA1 | CDK5-CDK5R1 | 0.843 |
| 26 | C5 | KIT | APOA1 | CCL23 | ACY1 | 0.843 |
| 27 | C9 | KIT | APOA1 | CDK5-CDK5R1 | CKB-CKM | 0.843 |
| 28 | C5 | KIT | APOA1 | LBP | CKB-CKM | 0.843 |
| 29 | IL12A-IL12B | KIT | APOA1 | CDK5-CDK5R1 | CKB-CKM | 0.843 |
| 30 | C9 | C5 | KIT | APOA1 | CKB-CKM | 0.843 |
| 31 | C9 | KIT | APOA1 | ACY1 | CKB-CKM | 0.843 |
| 32 | TIMP1 | C5 | KIT | CDK5-CDK5R1 | CKB-CKM | 0.843 |
| 33 | C5 | APOA1 | CCL23 | CDK5-CDK5R1 | CKB-CKM | 0.843 |
| 34 | C9 | KIT | CKM | APOA1 | ACY1 | 0.843 |
| 35 | TIMP1 | C5 | KIT | APOA1 | ACY1 | 0.842 |
| 36 | C5 | KIT | ACY1 | CDK5-CDK5R1 | CKB-CKM | 0.842 |
| 37 | C5 | KIT | APOA1 | SERPINF2 | CKB-CKM | 0.842 |
| 38 | C5 | IL12A-IL12B | KIT | APOA1 | CDK5-CDK5R1 | 0.841 |
| 39 | KIT | APOA1 | CDK5-CDK5R1 | HAMP | CKB-CKM | 0.841 |
| 40 | C5 | APOA1 | CCL23 | CKB-CKM | HINT1 | 0.841 |
| 41 | C5 | APOA1 | CDK5-CDK5R1 | CKB-CKM | HINT1 | 0.841 |
| 42 | C9 | KIT | APOA1 | CCL23 | CKB-CKM | 0.841 |
| 43 | C5 | APOA1 | ACY1 | CDK5-CDK5R1 | CKB-CKM | 0.841 |
| 44 | TIMP1 | C5 | KIT | APOA1 | CKB-CKM | 0.841 |
| 45 | C9 | KIT | APOA1 | CKB-CKM | HINT1 | 0.841 |
| 46 | C5 | APOA1 | ACY1 | CKB-CKM | HINT1 | 0.840 |
| 47 | TIMP1 | KIT | ACY1 | CDK5-CDK5R1 | CKB-CKM | 0.840 |
| 48 | C9 | IL12A-IL12B | KIT | APOA1 | CKB-CKM | 0.840 |
| 49 | C5 | KIT | APOA1 | CDK5-CDK5R1 | FSTL3 | 0.840 |
| 50 | C9 | KIT | CKM | APOA1 | HINT1 | 0.840 |
| 51 | C9 | C5 | KIT | ACY1 | CKB-CKM | 0.840 |
| 52 | C9 | C5 | KIT | CKM | APOA1 | 0.840 |
| 53 | C5 | KIT | CKM | APOA1 | ACY1 | 0.840 |
| 54 | C5 | KIT | CCL23 | ACY1 | CKB-CKM | 0.840 |
| 55 | IL12A-IL12B | KIT | APOA1 | LBP | CKB-CKM | 0.840 |
| 56 | C5 | KIT | CCL23 | ACY1 | CKB-CKM | 0.840 |

TABLE 24-continued

Panels of 5 Biomarkers

| | Markers | | | | | Mean CV AUC |
|---|---|---|---|---|---|---|
| 57 | C5 | KIT | APOA1 | SERPINF2 | CDK5-CDK5R1 | 0.840 |
| 58 | C9 | KIT | CCL23 | ACY1 | CKB-CKM | 0.839 |
| 59 | KIT | APOA1 | LBP | CKB-CKM | HINT1 | 0.839 |
| 60 | IL12A-IL12B | KIT | APOA1 | ACY1 | CKB-CKM | 0.839 |
| 61 | C5 | KIT | APOA1 | CDK5-CDK5R1 | HAMP | 0.839 |
| 62 | C5 | KIT | APOA1 | CDK5-CDK5R1 | HINT1 | 0.839 |
| 63 | C9 | KIT | CKM | APOA1 | CCL23 | 0.839 |
| 64 | C9 | C5 | KIT | APOA1 | CDK5-CDK5R1 | 0.839 |
| 65 | C5 | KIT | LBP | CDK5-CDK5R1 | CKB-CKM | 0.839 |
| 66 | KIT | APOA1 | CCL23 | LBP | CKB-CKM | 0.839 |
| 67 | KIT | APOA1 | CCL23 | LBP | CKB-CKM | 0.839 |
| 68 | KIT | APOA1 | SERPINF2 | ACY1 | CKB-CKM | 0.838 |
| 69 | C5 | KIT | APOA1 | ACY1 | FSTL3 | 0.838 |
| 70 | C5 | IL12A-IL12B | KIT | APOA1 | CCL23 | 0.838 |
| 71 | KIT | APOA1 | ACY1 | FSTL3 | CKB-CKM | 0.838 |
| 72 | C5 | KIT | APOA1 | ENTPD1 | CKB-CKM | 0.838 |
| 73 | C9 | C5 | KIT | CCL23 | CKB-CKM | 0.838 |
| 74 | C5 | APOA1 | SERPINF2 | CDK5-CDK5R1 | CKB-CKM | 0.838 |
| 75 | C9 | C5 | KIT | CKB-CKM | HINT1 | 0.838 |
| 76 | KIT | CKM | APOA1 | LBP | CDK5-CDK5R1 | 0.838 |
| 77 | C9 | KIT | APOA1 | CCL23 | ACY1 | 0.838 |
| 78 | KIT | APOA1 | ACY1 | CKB-CKM | HINT1 | 0.838 |
| 79 | TIMP1 | C9 | C5 | KIT | CKB-CKM | 0.838 |
| 80 | C5 | KIT | SERPINF2 | CDK5-CDK5R1 | CKB-CKM | 0.838 |
| 81 | C5 | KIT | CCL23 | CKB-CKM | HINT1 | 0.838 |
| 82 | C5 | KIT | CCL23 | ACY1 | CDK5-CDK5R1 | 0.838 |
| 83 | C5 | KIT | CCL23 | ACY1 | CDK5-CDK5R1 | 0.838 |
| 84 | C5 | KIT | APOA1 | LBP | ACY1 | 0.838 |
| 85 | TIMP1 | C5 | APOA1 | CDK5-CDK5R1 | CKB-CKM | 0.838 |
| 86 | IL12A-IL12B | KIT | APOA1 | CCL23 | CKB-CKM | 0.838 |
| 87 | TIMP1 | C5 | KIT | ACY1 | CDK5-CDK5R1 | 0.838 |
| 88 | C9 | KIT | APOA1 | LBP | CKB-CKM | 0.838 |
| 89 | KIT | APOA1 | SERPINF2 | CDK5-CDK5R1 | CKB-CKM | 0.838 |
| 90 | TIMP1 | KIT | APOA1 | CCL23 | CKB-CKM | 0.838 |
| 91 | TIMP1 | KIT | LBP | CDK5-CDK5R1 | CKB-CKM | 0.838 |
| 92 | C5 | KIT | APOA1 | CCL23 | HINT1 | 0.838 |
| 93 | KIT | APOA1 | CCL23 | CKB-CKM | HINT1 | 0.838 |
| 94 | C9 | C5 | KIT | APOA1 | CCL23 | 0.837 |
| 95 | C9 | C5 | KIT | APOA1 | ACY1 | 0.837 |
| 96 | C5 | KIT | LBP | ACY1 | CKB-CKM | 0.837 |
| 97 | C5 | KIT | CKM | APOA1 | CCL23 | 0.837 |
| 98 | C5 | KIT | CDK5-CDK5R1 | CKB-CKM | HINT1 | 0.837 |
| 99 | C5 | APOA1 | CCL23 | ACY1 | CKB-CKM | 0.837 |
| 100 | C5 | KIT | APOA1 | FSTL3 | CKB-CKM | 0.837 |

TABLE 25

Panels of 6 Biomarkers

| | Markers | | | | | | Mean CV AUC |
|---|---|---|---|---|---|---|---|
| 1 | C5 CKB-CKM | KIT | APOA1 | ACY1 | CDK5-CDK5R1 | | 0.860 |
| 2 | C5 CKB-CKM | KIT | APOA1 | CCL23 | CDK5-CDK5R1 | | 0.859 |
| 3 | C5 CKB-CKM | KIT | APOA1 | CCL23 | CDK5-CDK5R1 | | 0.858 |
| 4 | C5 CKB-CKM | KIT | APOA1 | CCL23 | ACY1 | | 0.857 |
| 5 | C5 CKB-CKM | KIT | APOA1 | CCL23 | ACY1 | | 0.856 |
| 6 | TIMP1 CKB-CKM | C5 | KIT | APOA1 | CDK5-CDK5R1 | | 0.856 |
| 7 | C5 CKB-CKM | IL12A-IL12B | KIT | APOA1 | CDK5-CDK5R1 | | 0.855 |
| 8 | C5 CKB-CKM | KIT | APOA1 | LBP | CDK5-CDK5R1 | | 0.855 |
| 9 | C5 CKB-CKM | KIT | APOA1 | LBP | ACY1 | | 0.855 |
| 10 | TIMP1 CKB-CKM | KIT | APOA1 | ACY1 | CDK5-CDK5R1 | | 0.854 |
| 11 | C5 HINT1 | KIT | APOA1 | CDK5-CDK5R1 | CKB-CKM | | 0.854 |

TABLE 25-continued

Panels of 6 Biomarkers

| | | Markers | | | | Mean CV AUC |
|---|---|---|---|---|---|---|
| 12 | C5 HINT1 | KIT | APOA1 | CCL23 | CKB-CKM | 0.853 |
| 13 | C5 CDK5-CDK5R1 | KIT | CKM | APOA1 | CCL23 | 0.853 |
| 14 | C5 CKB-CKM | KIT | APOA1 | SERPINF2 | CDK5-CDK5R1 | 0.853 |
| 15 | C5 HINT1 | KIT | APOA1 | ACY1 | CKB-CKM | 0.852 |
| 16 | KIT CKB-CKM | APOA1 | LBP | ACY1 | CDK5-CDK5R1 | 0.852 |
| 17 | C5 CKB-CKM | IL12A-IL12B | KIT | APOA1 | ACY1 | 0.852 |
| 18 | C9 CDK5-CDK5R1 | C5 | KIT | CKM | APOA1 | 0.852 |
| 19 | C5 CKB-CKM | IL12A-IL12B | KIT | APOA1 | CCL23 | 0.852 |
| 20 | C5 CKB-CKM | KIT | APOA1 | SERPINF2 | ACY1 | 0.851 |
| 21 | C5 CKB-CKM | KIT | APOA1 | CDK5-CDK5R1 | FSTL3 | 0.851 |
| 22 | KIT CKB-CKM | APOA1 | CCL23 | ACY1 | CDK5-CDK5R1 | 0.851 |
| 23 | C9 CKB-CKM | KIT | APOA1 | CCL23 | ACY1 | 0.851 |
| 24 | TIMP1 CKB-CKM | C5 | KIT | APOA1 | ACY1 | 0.851 |
| 25 | C5 CDK5-CDK5R1 | KIT | APOA1 | CCL23 | ACY1 | 0.851 |
| 26 | KIT CKB-CKM | APOA1 | CCL23 | ACY1 | CDK5-CDK5R1 | 0.851 |
| 27 | C5 CKB-CKM | KIT | APOA1 | CDK5-CDK5R1 | HAMP | 0.851 |
| 28 | C9 CKB-CKM | KIT | APOA1 | ACY1 | CDK5-CDK5R1 | 0.850 |
| 29 | TIMP1 CKB-CKM | C5 | KIT | ACY1 | CDK5-CDK5R1 | 0.850 |
| 30 | C5 CKB-CKM | KIT | APOA1 | CCL23 | LBP | 0.850 |
| 31 | C9 ACY1 | KIT | CKM | APOA1 | CCL23 | 0.850 |
| 32 | TIMP1 CDK5-CDK5R1 | C5 | KIT | APOA1 | ACY1 | 0.850 |
| 33 | C5 CDK5-CDK5R1 | KIT | APOA1 | CCL23 | ACY1 | 0.850 |
| 34 | KIT CKB-CKM | APOA1 | CCL23 | LBP | ACY1 | 0.850 |
| 35 | C5 CKB-CKM | APOA1 | CCL23 | ACY1 | CDK5-CDK5R1 | 0.850 |
| 36 | C5 CDK5-CDK5R1 | KIT | CKM | APOA1 | CCL23 | 0.849 |
| 37 | C5 CKB-CKM | KIT | LBP | ACY1 | CDK5-CDK5R1 | 0.849 |
| 38 | IL12A-IL12B CKB-CKM | KIT | APOA1 | ACY1 | CDK5-CDK5R1 | 0.849 |
| 39 | C5 CKB-CKM | KIT | CCL23 | ACY1 | CDK5-CDK5R1 | 0.849 |
| 40 | IL12A-IL12B CKB-CKM | KIT | APOA1 | LBP | CDK5-CDK5R1 | 0.849 |
| 41 | C5 CKB-CKM | KIT | APOA1 | ACY1 | FSTL3 | 0.849 |
| 42 | C9 CKB-CKM | KIT | APOA1 | CCL23 | CDK5-CDK5R1 | 0.849 |
| 43 | KIT CKB-CKM | APOA1 | CCL23 | LBP | CDK5-CDK5R1 | 0.849 |
| 44 | C9 CKB-CKM | C5 | KIT | APOA1 | ACY1 | 0.849 |
| 45 | C5 CDK5-CDK5R1 | KIT | CKM | APOA1 | LBP | 0.849 |
| 46 | C5 CKB-CKM | KIT | CCL23 | ACY1 | CDK5-CDK5R1 | 0.849 |
| 47 | C5 CKB-CKM | KIT | APOA1 | SERPINF2 | CCL23 | 0.848 |
| 48 | C9 CKB-CKM | C5 | KIT | APOA1 | CDK5-CDK5R1 | 0.848 |
| 49 | C5 HINT1 | KIT | APOA1 | LBP | CKB-CKM | 0.848 |

TABLE 25-continued

Panels of 6 Biomarkers

| | | Markers | | | | Mean CV AUC |
|---|---|---|---|---|---|---|
| 50 | C5<br>CDK5-CDK5R1 | KIT | CKM | APOA1 | SERPINF2 | 0.848 |
| 51 | KIT<br>CKB-CKM | APOA1 | ACY1 | CDK5-CDK5R1 | HAMP | 0.848 |
| 52 | TIMP1<br>CKB-CKM | C5 | KIT | CCL23 | CDK5-CDK5R1 | 0.848 |
| 53 | C5<br>CKB-CKM | IL12A-IL12B | KIT | APOA1 | LBP | 0.848 |
| 54 | C5<br>CKB-CKM | KIT | APOA1 | CCL23 | LBP | 0.848 |
| 55 | TIMP1<br>HINT1 | C5 | KIT | APOA1 | CKB-CKM | 0.848 |
| 56 | C9<br>CKB-CKM | C5 | KIT | APOA1 | CCL23 | 0.848 |
| 57 | KIT<br>CKB-CKM | APOA1 | CCL23 | LBP | ACY1 | 0.848 |
| 58 | KIT<br>CKB-CKM | APOA1 | SERPINF2 | ACY1 | CDK5-CDK5R1 | 0.848 |
| 59 | TIMP1<br>CKB-CKM | C5 | KIT | CCL23 | CDK5-CDK5R1 | 0.848 |
| 60 | C9<br>CDK5-CDK5R1 | KIT | CKM | APOA1 | ACY1 | 0.848 |
| 61 | C9<br>CKB-CKM | C5 | KIT | CCL23 | ACY1 | 0.847 |
| 62 | TIMP1<br>CKB-CKM | KIT | APOA1 | CCL23 | CDK5-CDK5R1 | 0.847 |
| 63 | KIT<br>CKB-CKM | APOA1 | CCL23 | LBP | CDK5-CDK5R1 | 0.847 |
| 64 | C5<br>CKB-CKM | IL12A-IL12B | KIT | APOA1 | CCL23 | 0.847 |
| 65 | C5<br>CKB-CKM | IL12A-IL12B | KIT | CCL23 | CDK5-CDK5R1 | 0.847 |
| 66 | KIT<br>CKB-CKM | APOA1 | ACY1 | CDK5-CDK5R1 | FSTL3 | 0.847 |
| 67 | C5<br>HINT1 | KIT | APOA1 | CCL23 | CKB-CKM | 0.847 |
| 68 | C5<br>CDK5-CDK5R1 | KIT | CKM | APOA1 | ACY1 | 0.847 |
| 69 | C5<br>CDK5-CDK5R1 | IL12A-IL12B | KIT | APOA1 | CCL23 | 0.847 |
| 70 | TIMP1<br>CKB-CKM | KIT | APOA1 | LBP | CDK5-CDK5R1 | 0.847 |
| 71 | C5<br>CDK5-CDK5R1 | KIT | APOA1 | LBP | ACY1 | 0.847 |
| 72 | TIMP1<br>CKB-CKM | KIT | APOA1 | CDK5-CDK5R1 | HAMP | 0.847 |
| 73 | TIMP1<br>CKB-CKM | IL12A-IL12B | KIT | APOA1 | CDK5-CDK5R1 | 0.847 |
| 74 | C5<br>CKB-CKM | KIT | SERPINF2 | ACY1 | CDK5-CDK5R1 | 0.847 |
| 75 | TIMP1<br>CDK5-CDK5R1 | C5 | KIT | APOA1 | CCL23 | 0.847 |
| 76 | C5<br>CDK5-CDK5R1 | KIT | APOA1 | CCL23 | LBP | 0.847 |
| 77 | C9<br>CDK5-CDK5R1 | KIT | CKM | APOA1 | CCL23 | 0.847 |
| 78 | TIMP1<br>CKB-CKM | KIT | APOA1 | LBP | ACY1 | 0.847 |
| 79 | C5<br>ACY1 | KIT | CKM | APOA1 | CCL23 | 0.847 |
| 80 | TIMP1<br>CKB-CKM | C5 | KIT | APOA1 | CCL23 | 0.847 |
| 81 | C5<br>HINT1 | APOA1 | CCL23 | CDK5-CDK5R1 | CKB-CKM | 0.847 |
| 82 | C9<br>HINT1 | C5 | KIT | CKM | APOA1 | 0.847 |
| 83 | TIMP1<br>CKB-CKM | C9 | KIT | APOA1 | CDK5-CDK5R1 | 0.847 |
| 84 | TIMP1<br>CDK5-CDK5R1 | C5 | KIT | APOA1 | CCL23 | 0.846 |
| 85 | C9<br>CKB-CKM | KIT | APOA1 | CDK5-CDK5R1 | HAMP | 0.846 |
| 86 | C5<br>CKB-CKM | KIT | CCL23 | LBP | CDK5-CDK5R1 | 0.846 |
| 87 | TIMP1<br>CKB-CKM | C5 | KIT | LBP | CDK5-CDK5R1 | 0.846 |

TABLE 25-continued

Panels of 6 Biomarkers

| | Markers | | | | | Mean CV AUC |
|---|---|---|---|---|---|---|
| 88 | IL12A-IL12B CKB-CKM | KIT | APOA1 | CCL23 | CDK5-CDK5R1 | 0.846 |
| 89 | TIMP1 CDK5-CDK5R1 | C5 | KIT | CKM | APOA1 | 0.846 |
| 90 | C5 CKB-CKM | KIT | APOA1 | ACY1 | HAMP | 0.846 |
| 91 | TIMP1 CKB-CKM | C5 | KIT | APOA1 | CCL23 | 0.846 |
| 92 | C9 HINT1 | C5 | KIT | APOA1 | CKB-CKM | 0.846 |
| 93 | C5 HINT1 | IL12A-IL12B | KIT | APOA1 | CKB-CKM | 0.846 |
| 94 | C5 FSTL3 | KIT | APOA1 | ACY1 | CDK5-CDK5R1 | 0.846 |
| 95 | C9 CDK5-CDK5R1 | C5 | KIT | APOA1 | CCL23 | 0.846 |
| 96 | C5 ACY1 | KIT | CKM | APOA1 | LBP | 0.846 |
| 97 | C9 CDK5-CDK5R1 | KIT | CKM | APOA1 | LBP | 0.846 |
| 98 | KIT CKB-CKM | APOA1 | LBP | CDK5-CDK5R1 | HAMP | 0.846 |
| 99 | C5 CKB-CKM | KIT | APOA1 | CCL23 | SERPINF2 | 0.846 |
| 100 | C9 CKB-CKM | C5 | IL12A-IL12B | KIT | APOA1 | 0.846 |

TABLE 26

Panels of 7 Biomarkers

| | Markers | | | | | Mean CV AUC |
|---|---|---|---|---|---|---|
| 1 | C5 CDK5-CDK5R1 | KIT CKB-CKM | APOA1 | CCL23 | ACY1 | 0.864 |
| 2 | C5 CDK5-CDK5R1 | KIT CKB-CKM | APOA1 | CCL23 | ACY1 | 0.863 |
| 3 | TIMP1 CDK5-CDK5R1 | C5 CKB-CKM | KIT | APOA1 | ACY1 | 0.863 |
| 4 | C5 FSTL3 | KIT CKB-CKM | APOA1 | ACY1 | CDK5-CDK5R1 | 0.861 |
| 5 | C5 CDK5-CDK5R1 | KIT CKB-CKM | APOA1 | LBP | ACY1 | 0.861 |
| 6 | C5 CDK5-CDK5R1 | KIT CKB-CKM | APOA1 | SERPINF2 | ACY1 | 0.860 |
| 7 | C5 CDK5-CDK5R1 | IL12A-IL12B CKB-CKM | KIT | APOA1 | ACY1 | 0.860 |
| 8 | C5 CDK5-CDK5R1 | IL12A-IL12B CKB-CKM | KIT | APOA1 | CCL23 | 0.860 |
| 9 | C5 CDK5-CDK5R1 | KIT CKB-CKM | APOA1 | CCL23 | LBP | 0.859 |
| 10 | C5 CDK5-CDK5R1 | IL12A-IL12B CKB-CKM | KIT | APOA1 | LBP | 0.859 |
| 11 | C5 CDK5-CDK5R1 | KIT CKB-CKM | APOA1 | CCL23 | LBP | 0.859 |
| 12 | C5 CKB-CKM | KIT HINT1 | APOA1 | CCL23 | CDK5-CDK5R1 | 0.859 |
| 13 | TIMP1 CDK5-CDK5R1 | C5 CKB-CKM | KIT | APOA1 | CCL23 | 0.859 |
| 14 | C5 ACY1 | KIT CKB-CKM | APOA1 | CCL23 | LBP | 0.859 |
| 15 | C5 CDK5-CDK5R1 | IL12A-IL12B CKB-CKM | KIT | APOA1 | CCL23 | 0.858 |
| 16 | TIMP1 CDK5-CDK5R1 | C5 CKB-CKM | KIT | APOA1 | CCL23 | 0.858 |
| 17 | C5 CKB-CKM | KIT HINT1 | APOA1 | CCL23 | ACY1 | 0.858 |
| 18 | C5 ACY1 | IL12A-IL12B CKB-CKM | KIT | APOA1 | CCL23 | 0.858 |
| 19 | C5 CDK5-CDK5R1 | KIT CKB-CKM | APOA1 | SERPINF2 | CCL23 | 0.858 |
| 20 | C5 HAMP | KIT CKB-CKM | APOA1 | ACY1 | CDK5-CDK5R1 | 0.857 |

TABLE 26-continued

| | | Panels of 7 Biomarkers | | | | |
|---|---|---|---|---|---|---|
| | | | Markers | | | Mean CV AUC |
| 21 | C9<br>CDK5-CDK5R1 | KIT<br>CKB-CKM | APOA1 | CCL23 | ACY1 | 0.857 |
| 22 | C5<br>ACY1 | KIT<br>CDK5-CDK5R1 | CKM | APOA1 | CCL23 | 0.857 |
| 23 | TIMP1<br>CDK5-CDK5R1 | C5<br>CKB-CKM | IL12A-IL12B | KIT | APOA1 | 0.856 |
| 24 | TIMP1<br>ACY1 | C5<br>CKB-CKM | KIT | APOA1 | CCL23 | 0.856 |
| 25 | C5<br>ACY1 | KIT<br>CKB-CKM | APOA1 | SERPINF2 | CCL23 | 0.856 |
| 26 | C5<br>ACY1 | KIT<br>CKB-CKM | APOA1 | CCL23 | SERPINF2 | 0.856 |
| 27 | C9<br>CCL23 | C5<br>CDK5-CDK5R1 | KIT | CKM | APOA1 | 0.856 |
| 28 | IL12A-IL12B<br>CDK5-CDK5R1 | KIT<br>CKB-CKM | APOA1 | LBP | ACY1 | 0.856 |
| 29 | C5<br>ACY1 | IL12A-IL12B<br>CKB-CKM | KIT | APOA1 | CCL23 | 0.856 |
| 30 | C5<br>ACY1 | KIT<br>CKB-CKM | APOA1 | CCL23 | LBP | 0.856 |
| 31 | C5<br>CDK5-CDK5R1 | KIT<br>CKB-CKM | APOA1 | CCL23 | SERPINF2 | 0.856 |
| 32 | C5<br>ACY1 | KIT<br>CDK5-CDK5R1 | CKM | APOA1 | CCL23 | 0.856 |
| 33 | C5<br>CKB-CKM | KIT<br>HINT1 | APOA1 | ACY1 | CDK5-CDK5R1 | 0.855 |
| 34 | C9<br>CDK5-CDK5R1 | C5<br>CKB-CKM | KIT | APOA1 | CCL23 | 0.855 |
| 35 | TIMP1<br>CDK5-CDK5R1 | KIT<br>CKB-CKM | APOA1 | LBP | ACY1 | 0.855 |
| 36 | KIT<br>CDK5-CDK5R1 | APOA1<br>CKB-CKM | CCL23 | LBP | ACY1 | 0.855 |
| 37 | C5<br>ACY1 | KIT<br>CKB-CKM | APOA1 | SERPINF2 | LBP | 0.855 |
| 38 | C5<br>CKB-CKM | KIT<br>HINT1 | APOA1 | CCL23 | CDK5-CDK5R1 | 0.855 |
| 39 | C9<br>ACY1 | C5<br>CKB-CKM | KIT | APOA1 | CCL23 | 0.855 |
| 40 | C5<br>CDK5-CDK5R1 | KIT<br>CKB-CKM | APOA1 | CCL23 | CCL23 | 0.855 |
| 41 | TIMP1<br>CDK5-CDK5R1 | C5<br>CKB-CKM | KIT | APOA1 | SERPINF2 | 0.855 |
| 42 | TIMP1<br>CDK5-CDK5R1 | C5<br>CKB-CKM | KIT | APOA1 | LBP | 0.854 |
| 43 | C5<br>ACY1 | KIT<br>CKB-CKM | APOA1 | CCL23 | CCL23 | 0.854 |
| 44 | C5<br>CKB-CKM | KIT<br>HINT1 | APOA1 | LBP | CDK5-CDK5R1 | 0.854 |
| 45 | C5<br>CKB-CKM | KIT<br>HINT1 | APOA1 | CCL23 | LBP | 0.854 |
| 46 | C5<br>ACY1 | IL12A-IL12B<br>CKB-CKM | KIT | APOA1 | LBP | 0.854 |
| 47 | C9<br>ACY1 | KIT<br>CDK5-CDK5R1 | CKM | APOA1 | CCL23 | 0.854 |
| 48 | C5<br>SERPINF2 | KIT<br>CDK5-CDK5R1 | CKM | APOA1 | CCL23 | 0.854 |
| 49 | TIMP1<br>ACY1 | C5<br>CKB-CKM | KIT | APOA1 | CCL23 | 0.854 |
| 50 | C5<br>FSTL3 | KIT<br>CKB-CKM | APOA1 | CCL23 | ACY1 | 0.854 |
| 51 | C5<br>HAMP | IL12A-IL12B<br>CKB-CKM | KIT | APOA1 | CDK5-CDK5R1 | 0.854 |
| 52 | TIMP1<br>CDK5-CDK5R1 | IL12A-IL12B<br>CKB-CKM | KIT | APOA1 | ACY1 | 0.854 |
| 53 | C5<br>FSTL3 | KIT<br>CKB-CKM | APOA1 | CCL23 | CDK5-CDK5R1 | 0.854 |
| 54 | C5<br>LBP | KIT<br>CDK5-CDK5R1 | CKM | APOA1 | CCL23 | 0.854 |
| 55 | C5<br>HAMP | KIT<br>CKB-CKM | APOA1 | CCL23 | CDK5-CDK5R1 | 0.854 |
| 56 | TIMP1<br>HAMP | KIT<br>CKB-CKM | APOA1 | ACY1 | CDK5-CDK5R1 | 0.854 |
| 57 | TIMP1<br>CDK5-CDK5R1 | KIT<br>CKB-CKM | APOA1 | CCL23 | ACY1 | 0.854 |
| 58 | C9<br>CDK5-CDK5R1 | C5<br>CKB-CKM | KIT | APOA1 | ACY1 | 0.854 |

TABLE 26-continued

Panels of 7 Biomarkers

| # | Markers | | | | | | | Mean CV AUC |
|---|---|---|---|---|---|---|---|---|
| 59 | C5 | IL12A-IL12B | KIT | APOA1 | SERPINF2 | CDK5-CDK5R1 | CKB-CKM | 0.854 |
| 60 | C5 | KIT | APOA1 | CCL23 | CDK5-CDK5R1 | HAMP | CKB-CKM | 0.854 |
| 61 | KIT | APOA1 | CCL23 | LBP | ACY1 | CDK5-CDK5R1 | CKB-CKM | 0.854 |
| 62 | C9 | C5 | KIT | CKM | APOA1 | CDK5-CDK5R1 | HINT1 | 0.854 |
| 63 | TIMP1 | C5 | KIT | APOA1 | CDK5-CDK5R1 | CKB-CKM | HINT1 | 0.854 |
| 64 | C5 | KIT | CKM | APOA1 | LBP | ACY1 | CDK5-CDK5R1 | 0.854 |
| 65 | TIMP1 | C5 | KIT | CKM | APOA1 | CCL23 | CDK5-CDK5R1 | 0.853 |
| 66 | C5 | KIT | APOA1 | LBP | CDK5-CDK5R1 | FSTL3 | CKB-CKM | 0.853 |
| 67 | C9 | C5 | KIT | CKM | APOA1 | ACY1 | CDK5-CDK5R1 | 0.853 |
| 68 | C5 | IL12A-IL12B | KIT | APOA1 | CCL23 | LBP | CKB-CKM | 0.853 |
| 69 | C9 | KIT | APOA1 | LBP | ACY1 | CDK5-CDK5R1 | CKB-CKM | 0.853 |
| 70 | C5 | KIT | CCL23 | LBP | ACY1 | CDK5-CDK5R1 | CKB-CKM | 0.853 |
| 71 | C5 | KIT | APOA1 | LBP | ACY1 | CKB-CKM | HINT1 | 0.853 |
| 72 | KIT | APOA1 | LBP | ACY1 | CDK5-CDK5R1 | FSTL3 | CKB-CKM | 0.853 |
| 73 | C5 | KIT | CKM | APOA1 | LBP | CDK5-CDK5R1 | HINT1 | 0.853 |
| 74 | C9 | C5 | KIT | APOA1 | CDK5-CDK5R1 | CKB-CKM | HINT1 | 0.853 |
| 75 | C5 | KIT | APOA1 | SERPINF2 | LBP | CDK5-CDK5R1 | CKB-CKM | 0.853 |
| 76 | C9 | C5 | KIT | CKM | APOA1 | CCL23 | ACY1 | 0.853 |
| 77 | IL12A-IL12B | KIT | APOA1 | CCL23 | ACY1 | CDK5-CDK5R1 | CKB-CKM | 0.853 |
| 78 | TIMP1 | C5 | KIT | APOA1 | CDK5-CDK5R1 | HAMP | CKB-CKM | 0.853 |
| 79 | C5 | KIT | APOA1 | LBP | ACY1 | FSTL3 | CKB-CKM | 0.853 |
| 80 | C5 | KIT | CKM | APOA1 | SERPINF2 | ACY1 | CDK5-CDK5R1 | 0.853 |
| 81 | TIMP1 | C5 | KIT | APOA1 | ACY1 | CKB-CKM | HINT1 | 0.853 |
| 82 | KIT | APOA1 | LBP | ACY1 | CDK5-CDK5R1 | HAMP | CKB-CKM | 0.852 |
| 83 | C5 | IL12A-IL12B | KIT | APOA1 | CDK5-CDK5R1 | FSTL3 | CKB-CKM | 0.852 |
| 84 | C5 | KIT | CKM | APOA1 | SERPINF2 | CCL23 | CDK5-CDK5R1 | 0.852 |
| 85 | C5 | KIT | CCL23 | LBP | ACY1 | CDK5-CDK5R1 | CKB-CKM | 0.852 |
| 86 | C9 | C5 | KIT | CKM | APOA1 | CCL23 | CDK5-CDK5R1 | 0.852 |
| 87 | C5 | KIT | APOA1 | CCL23 | ACY1 | FSTL3 | CKB-CKM | 0.852 |
| 88 | C5 | KIT | APOA1 | CCL23 | CDK5-CDK5R1 | FSTL3 | CKB-CKM | 0.852 |
| 89 | TIMP1 | C5 | KIT | LBP | ACY1 | CDK5-CDK5R1 | CKB-CKM | 0.852 |
| 90 | C5 | KIT | CKM | APOA1 | CCL23 | LBP | CDK5-CDK5R1 | 0.852 |
| 91 | C5 | KIT | APOA1 | SERPINF2 | CDK5-CDK5R1 | CKB-CKM | HINT1 | 0.852 |
| 92 | IL12A-IL12B | KIT | APOA1 | CCL23 | LBP | CDK5-CDK5R1 | CKB-CKM | 0.852 |
| 93 | C5 | KIT | APOA1 | LBP | CDK5-CDK5R1 | HAMP | CKB-CKM | 0.852 |
| 94 | IL12A-IL12B | KIT | APOA1 | CCL23 | ACY1 | CDK5-CDK5R1 | CKB-CKM | 0.852 |
| 95 | C5 | KIT | APOA1 | CCL23 | ACY1 | CKB-CKM | HINT1 | 0.852 |
| 96 | C5 | KIT | CKM | APOA1 | CCL23 | CDK5-CDK5R1 | HINT1 | 0.852 |

TABLE 26-continued

Panels of 7 Biomarkers

| | Markers | | | | | Mean CV AUC |
|---|---|---|---|---|---|---|
| 97 | C5<br>CDK5-CDK5R1 | IL12A-IL12B<br>CKB-CKM | KIT | LBP | ACY1 | 0.852 |
| 98 | TIMP1<br>ACY1 | C5<br>CKB-CKM | KIT | APOA1 | LBP | 0.852 |
| 99 | TIMP1<br>ACY1 | C5<br>CDK5-CDK5R1 | KIT | CKM | APOA1 | 0.852 |
| 100 | TIMP1<br>CDK5-CDK5R1 | KIT<br>CKB-CKM | APOA1 | CCL23 | ACY1 | 0.852 |

TABLE 27

Panels of 8 Biomarkers

| | Markers | | | | | Mean CV AUC |
|---|---|---|---|---|---|---|
| 1 | C5<br>ACY1 | KIT<br>CDK5-CDK5R1 | APOA1<br>CKB-CKM | CCL23 | LBP | 0.864 |
| 2 | C5<br>ACY1 | IL12A-IL12B<br>CDK5-CDK5R1 | KIT<br>CKB-CKM | APOA1 | CCL23 | 0.864 |
| 3 | C5<br>ACY1 | KIT<br>CDK5-CDK5R1 | APOA1<br>CKB-CKM | CCL23 | LBP | 0.864 |
| 4 | TIMP1<br>ACY1 | C5<br>CDK5-CDK5R1 | KIT<br>CKB-CKM | APOA1 | CCL23 | 0.863 |
| 5 | TIMP1<br>ACY1 | C5<br>CDK5-CDK5R1 | IL12A-IL12B<br>CKB-CKM | KIT | APOA1 | 0.863 |
| 6 | TIMP1<br>ACY1 | C5<br>CDK5-CDK5R1 | KIT<br>CKB-CKM | APOA1 | CCL23 | 0.863 |
| 7 | C5<br>ACY1 | IL12A-IL12B<br>CDK5-CDK5R1 | KIT<br>CKB-CKM | APOA1 | LBP | 0.862 |
| 8 | TIMP1<br>ACY1 | C5<br>CDK5-CDK5R1 | KIT<br>CKB-CKM | APOA1 | SERPINF2 | 0.862 |
| 9 | C5<br>ACY1 | IL12A-IL12B<br>CDK5-CDK5R1 | KIT<br>CKB-CKM | APOA1 | CCL23 | 0.862 |
| 10 | C5<br>ACY1 | KIT<br>CDK5-CDK5R1 | APOA1<br>CKB-CKM | SERPINF2 | CCL23 | 0.862 |
| 11 | C5<br>ACY1 | KIT<br>CDK5-CDK5R1 | APOA1<br>CKB-CKM | CCL23 | SERPINF2 | 0.861 |
| 12 | TIMP1<br>ACY1 | C5<br>CDK5-CDK5R1 | KIT<br>CKB-CKM | APOA1 | LBP | 0.861 |
| 13 | C5<br>CDK5-CDK5R1 | KIT<br>FSTL3 | APOA1<br>CKB-CKM | LBP | ACY1 | 0.861 |
| 14 | C5<br>LBP | IL12A-IL12B<br>CDK5-CDK5R1 | KIT<br>CKB-CKM | APOA1 | CCL23 | 0.861 |
| 15 | C5<br>CDK5-CDK5R1 | KIT<br>CKB-CKM | APOA1<br>HINT1 | CCL23 | LBP | 0.860 |
| 16 | C5<br>CDK5-CDK5R1 | KIT<br>CKB-CKM | APOA1<br>HINT1 | CCL23 | ACY1 | 0.860 |
| 17 | C5<br>CDK5-CDK5R1 | IL12A-IL12B<br>FSTL3 | KIT<br>CKB-CKM | APOA1 | ACY1 | 0.860 |
| 18 | C5<br>ACY1 | IL12A-IL12B<br>CDK5-CDK5R1 | KIT<br>CKB-CKM | APOA1 | SERPINF2 | 0.860 |
| 19 | C5<br>LBP | KIT<br>ACY1 | CKM<br>CDK5-CDK5R1 | APOA1 | CCL23 | 0.860 |
| 20 | C5<br>ACY1 | KIT<br>CDK5-CDK5R1 | APOA1<br>CKB-CKM | CCL23 | CCL23 | 0.859 |
| 21 | C5<br>CDK5-CDK5R1 | KIT<br>HAMP | APOA1<br>CKB-CKM | CCL23 | ACY1 | 0.859 |
| 22 | C5<br>ACY1 | KIT<br>CDK5-CDK5R1 | APOA1<br>CKB-CKM | SERPINF2 | LBP | 0.859 |
| 23 | C5<br>CDK5-CDK5R1 | KIT<br>FSTL3 | APOA1<br>CKB-CKM | CCL23 | ACY1 | 0.859 |
| 24 | TIMP1<br>CCL23 | C5<br>CDK5-CDK5R1 | IL12A-IL12B<br>CKB-CKM | KIT | APOA1 | 0.859 |
| 25 | C5<br>CDK5-CDK5R1 | KIT<br>HAMP | APOA1<br>CKB-CKM | CCL23 | ACY1 | 0.859 |
| 26 | C5<br>LBP | IL12A-IL12B<br>CDK5-CDK5R1 | KIT<br>CKB-CKM | APOA1 | CCL23 | 0.859 |
| 27 | C5<br>CDK5-CDK5R1 | KIT<br>FSTL3 | APOA1<br>CKB-CKM | CCL23 | ACY1 | 0.859 |
| 28 | TIMP1<br>CDK5-CDK5R1 | C5<br>HAMP | KIT<br>CKB-CKM | APOA1 | ACY1 | 0.859 |
| 29 | C5<br>CCL23 | IL12A-IL12B<br>CDK5-CDK5R1 | KIT<br>CKB-CKM | APOA1 | SERPINF2 | 0.859 |

TABLE 27-continued

| Panels of 8 Biomarkers | | | | | | |
|---|---|---|---|---|---|---|
| | | Markers | | | | Mean CV AUC |
| 30 | C5 | KIT | APOA1 | CCL23 | LBP | 0.859 |
| | ACY1 | CKB-CKM | HINT1 | | | |
| 31 | C9 | C5 | KIT | CKM | APOA1 | 0.859 |
| | CCL23 | ACY1 | CDK5-CDK5R1 | | | |
| 32 | C9 | KIT | APOA1 | CCL23 | LBP | 0.859 |
| | ACY1 | CDK5-CDK5R1 | CKB-CKM | | | |
| 33 | C9 | C5 | KIT | APOA1 | CCL23 | 0.859 |
| | ACY1 | CDK5-CDK5R1 | CKB-CKM | | | |
| 34 | C5 | KIT | APOA1 | ACY1 | CDK5-CDK5R1 | 0.858 |
| | FSTL3 | HAMP | CKB-CKM | | | |
| 35 | TIMP1 | C5 | KIT | APOA1 | CCL23 | 0.858 |
| | LBP | CDK5-CDK5R1 | CKB-CKM | | | |
| 36 | C5 | KIT | APOA1 | LBP | ACY1 | 0.858 |
| | CDK5-CDK5R1 | CKB-CKM | HINT1 | | | |
| 37 | C5 | IL12A-IL12B | KIT | APOA1 | ACY1 | 0.858 |
| | CDK5-CDK5R1 | HAMP | CKB-CKM | | | |
| 38 | TIMP1 | C5 | KIT | APOA1 | SERPINF2 | 0.858 |
| | CCL23 | CDK5-CDK5R1 | CKB-CKM | | | |
| 39 | TIMP1 | C5 | IL12A-IL12B | KIT | APOA1 | 0.858 |
| | CCL23 | CDK5-CDK5R1 | CKB-CKM | | | |
| 40 | C5 | KIT | APOA1 | SERPINF2 | CCL23 | 0.858 |
| | CDK5-CDK5R1 | CKB-CKM | HINT1 | | | |
| 41 | TIMP1 | C5 | KIT | APOA1 | CCL23 | 0.858 |
| | LBP | CDK5-CDK5R1 | CKB-CKM | | | |
| 42 | C5 | IL12A-IL12B | KIT | APOA1 | CCL23 | 0.858 |
| | LBP | ACY1 | CKB-CKM | | | |
| 43 | C5 | KIT | APOA1 | SERPINF2 | CCL23 | 0.858 |
| | LBP | CDK5-CDK5R1 | CKB-CKM | | | |
| 44 | C5 | KIT | CKM | APOA1 | SERPINF2 | 0.857 |
| | LBP | ACY1 | CDK5-CDK5R1 | | | |
| 45 | TIMP1 | C5 | KIT | APOA1 | CCL23 | 0.857 |
| | CDK5-CDK5R1 | CKB-CKM | HINT1 | | | |
| 46 | C5 | KIT | APOA1 | CCL23 | SERPINF2 | 0.857 |
| | LBP | ACY1 | CKB-CKM | | | |
| 47 | TIMP1 | C5 | KIT | APOA1 | ACY1 | 0.857 |
| | CDK5-CDK5R1 | CKB-CKM | HINT1 | | | |
| 48 | C5 | IL12A-IL12B | KIT | APOA1 | CCL23 | 0.857 |
| | CDK5-CDK5R1 | CKB-CKM | HINT1 | | | |
| 49 | C5 | KIT | APOA1 | CCL23 | ACY1 | 0.857 |
| | CDK5-CDK5R1 | CKB-CKM | HINT1 | | | |
| 50 | C5 | KIT | CKM | APOA1 | CCL23 | 0.857 |
| | SERPINF2 | ACY1 | CDK5-CDK5R1 | | | |
| 51 | C5 | KIT | APOA1 | SERPINF2 | ACY1 | 0.857 |
| | CDK5-CDK5R1 | HAMP | CKB-CKM | | | |
| 52 | C5 | KIT | APOA1 | GDF11 | CCL23 | 0.857 |
| | ACY1 | CDK5-CDK5R1 | CKB-CKM | | | |
| 53 | TIMP1 | C5 | IL12A-IL12B | KIT | APOA1 | 0.857 |
| | LBP | CDK5-CDK5R1 | CKB-CKM | | | |
| 54 | C9 | C5 | KIT | APOA1 | CCL23 | 0.857 |
| | ACY1 | CKB-CKM | HINT1 | | | |
| 55 | TIMP1 | C5 | KIT | APOA1 | ACY1 | 0.857 |
| | CDK5-CDK5R1 | FSTL3 | CKB-CKM | | | |
| 56 | TIMP1 | C5 | KIT | APOA1 | CCL23 | 0.857 |
| | LBP | ACY1 | CKB-CKM | | | |
| 57 | C9 | C5 | KIT | CKM | APOA1 | 0.857 |
| | CCL23 | CDK5-CDK5R1 | HINT1 | | | |
| 58 | C5 | KIT | APOA1 | SERPINF2 | ACY1 | 0.857 |
| | CDK5-CDK5R1 | FSTL3 | CKB-CKM | | | |
| 59 | C5 | KIT | CKM | APOA1 | CCL23 | 0.857 |
| | LBP | ACY1 | CDK5-CDK5R1 | | | |
| 60 | C5 | KIT | APOA1 | LBP | ACY1 | 0.857 |
| | CDK5-CDK5R1 | HAMP | CKB-CKM | | | |
| 61 | IL12A-IL12B | KIT | APOA1 | CCL23 | LBP | 0.857 |
| | ACY1 | CDK5-CDK5R1 | CKB-CKM | | | |
| 62 | C5 | KIT | APOA1 | SERPINF2 | CCL23 | 0.857 |
| | LBP | ACY1 | CKB-CKM | | | |
| 63 | C9 | C5 | KIT | APOA1 | CCL23 | 0.857 |
| | LBP | CDK5-CDK5R1 | CKB-CKM | | | |
| 64 | TIMP1 | C9 | KIT | APOA1 | CCL23 | 0.856 |
| | ACY1 | CDK5-CDK5R1 | CKB-CKM | | | |
| 65 | TIMP1 | C5 | KIT | CKM | APOA1 | 0.856 |
| | CCL23 | ACY1 | CDK5-CDK5R1 | | | |
| 66 | C9 | C5 | KIT | CKM | APOA1 | 0.856 |
| | CCL23 | CCL23 | CDK5-CDK5R1 | | | |
| 67 | C5 | IL12A-IL12B | KIT | APOA1 | SERPINF2 | 0.856 |
| | LBP | CDK5-CDK5R1 | CKB-CKM | | | |

TABLE 27-continued

Panels of 8 Biomarkers

| # | Markers | | | | | Mean CV AUC |
|---|---|---|---|---|---|---|
| 68 | C5 | IL12A-IL12B | KIT | APOA1 | LBP | 0.856 |
| | CDK5-CDK5R1 | HAMP | CKB-CKM | | | |
| 69 | TIMP1 | IL12A-IL12B | KIT | APOA1 | LBP | 0.856 |
| | ACY1 | CDK5-CDK5R1 | CKB-CKM | | | |
| 70 | C5 | IL12A-IL12B | KIT | APOA1 | CCL23 | 0.856 |
| | CDK5-CDK5R1 | HAMP | CKB-CKM | | | |
| 71 | TIMP1 | C5 | KIT | APOA1 | GDF11 | 0.856 |
| | ACY1 | CDK5-CDK5R1 | CKB-CKM | | | |
| 72 | C9 | C5 | KIT | CKM | APOA1 | 0.856 |
| | CCL23 | ACY1 | HINT1 | | | |
| 73 | C9 | C5 | KIT | CKM | APOA1 | 0.856 |
| | CCL23 | ACY1 | CDK5-CDK5R1 | | | |
| 74 | TIMP1 | C5 | KIT | APOA1 | CCL23 | 0.856 |
| | ACY1 | CKB-CKM | HINT1 | | | |
| 75 | C5 | IL12A-IL12B | KIT | APOA1 | LBP | 0.856 |
| | CDK5-CDK5R1 | FSTL3 | CKB-CKM | | | |
| 76 | TIMP1 | KIT | APOA1 | CCL23 | LBP | 0.856 |
| | ACY1 | CDK5-CDK5R1 | CKB-CKM | | | |
| 77 | TIMP1 | C9 | C5 | KIT | CKM | 0.856 |
| | APOA1 | CCL23 | CDK5-CDK5R1 | | | |
| 78 | C5 | KIT | CKM | APOA1 | CCL23 | 0.856 |
| | LBP | CDK5-CDK5R1 | HINT1 | | | |
| 79 | C9 | C5 | KIT | CKM | APOA1 | 0.856 |
| | LBP | ACY1 | CDK5-CDK5R1 | | | |
| 80 | C5 | KIT | CKM | APOA1 | CCL23 | 0.856 |
| | SERPINF2 | LBP | CDK5-CDK5R1 | | | |
| 81 | C9 | KIT | CKM | APOA1 | CCL23 | 0.856 |
| | LBP | ACY1 | CDK5-CDK5R1 | | | |
| 82 | C5 | IL12A-IL12B | KIT | APOA1 | CCL23 | 0.856 |
| | LBP | ACY1 | CKB-CKM | | | |
| 83 | C5 | KIT | APOA1 | CCL23 | LBP | 0.856 |
| | CDK5-CDK5R1 | CKB-CKM | HINT1 | | | |
| 84 | C5 | KIT | APOA1 | CCL23 | LBP | 0.856 |
| | CDK5-CDK5R1 | FSTL3 | CKB-CKM | | | |
| 85 | C5 | IL12A-IL12B | KIT | APOA1 | SERPINF2 | 0.856 |
| | CCL23 | ACY1 | CKB-CKM | | | |
| 86 | TIMP1 | C5 | KIT | APOA1 | CCL23 | 0.856 |
| | CDK5-CDK5R1 | CKB-CKM | HINT1 | | | |
| 87 | IL12A-IL12B | KIT | APOA1 | LBP | ACY1 | 0.856 |
| | CDK5-CDK5R1 | HAMP | CKB-CKM | | | |
| 88 | TIMP1 | C9 | KIT | CKM | APOA1 | 0.856 |
| | CCL23 | ACY1 | CDK5-CDK5R1 | | | |
| 89 | C9 | C5 | KIT | CKM | APOA1 | 0.856 |
| | ACY1 | CDK5-CDK5R1 | HINT1 | | | |
| 90 | C5 | IL12A-IL12B | KIT | CKM | APOA1 | 0.855 |
| | CCL23 | ACY1 | CDK5-CDK5R1 | | | |
| 91 | C9 | C5 | KIT | APOA1 | LBP | 0.855 |
| | ACY1 | CDK5-CDK5R1 | CKB-CKM | | | |
| 92 | C5 | KIT | CKM | APOA1 | SERPINF2 | 0.855 |
| | CCL23 | ACY1 | CDK5-CDK5R1 | | | |
| 93 | C9 | C5 | IL12A-IL12B | KIT | CKM | 0.855 |
| | APOA1 | CCL23 | CDK5-CDK5R1 | | | |
| 94 | TIMP1 | C5 | KIT | APOA1 | CCL23 | 0.855 |
| | CDK5-CDK5R1 | HAMP | CKB-CKM | | | |
| 95 | C5 | KIT | CKM | APOA1 | CCL23 | 0.855 |
| | ACY1 | CDK5-CDK5R1 | FSTL3 | | | |
| 96 | TIMP1 | C5 | IL12A-IL12B | KIT | APOA1 | 0.855 |
| | CDK5-CDK5R1 | HAMP | CKB-CKM | | | |
| 97 | C9 | C5 | KIT | APOA1 | CCL23 | 0.855 |
| | LBP | ACY1 | CKB-CKM | | | |
| 98 | C9 | C5 | KIT | APOA1 | CCL23 | 0.855 |
| | ACY1 | CDK5-CDK5R1 | CKB-CKM | | | |
| 99 | C9 | C5 | KIT | CKM | APOA1 | 0.855 |
| | CCL23 | LBP | CDK5-CDK5R1 | | | |
| 100 | C9 | KIT | APOA1 | CCL23 | ACY1 | 0.855 |
| | CDK5-CDK5R1 | HAMP | CKB-CKM | | | |

TABLE 28

| | | Panels of 9 Biomarkers | | | | |
|---|---|---|---|---|---|---|
| | | | Markers | | | Mean CV AUC |
| 1 | C5 | IL12A-IL12B | KIT | APOA1 | CCL23 | 0.864 |
| | LBP | ACY1 | CDK5-CDK5R1 | CKB-CKM | | |
| 2 | C5 | IL12A-IL12B | KIT | APOA1 | CCL23 | 0.864 |
| | LBP | ACY1 | CDK5-CDK5R1 | CKB-CKM | | |
| 3 | C5 | KIT | APOA1 | SERPINF2 | CCL23 | 0.863 |
| | LBP | ACY1 | CDK5-CDK5R1 | CKB-CKM | | |
| 4 | TIMP1 | C5 | KIT | APOA1 | CCL23 | 0.863 |
| | LBP | ACY1 | CDK5-CDK5R1 | CKB-CKM | | |
| 5 | TIMP1 | C5 | IL12A-IL12B | KIT | APOA1 | 0.863 |
| | CCL23 | ACY1 | CDK5-CDK5R1 | CKB-CKM | | |
| 6 | TIMP1 | C5 | IL12A-IL12B | KIT | APOA1 | 0.862 |
| | LBP | ACY1 | CDK5-CDK5R1 | CKB-CKM | | |
| 7 | C5 | KIT | APOA1 | CCL23 | LBP | 0.862 |
| | ACY1 | CDK5-CDK5R1 | CKB-CKM | HINT1 | | |
| 8 | C5 | KIT | APOA1 | CCL23 | SERPINF2 | 0.862 |
| | LBP | ACY1 | CDK5-CDK5R1 | CKB-CKM | | |
| 9 | TIMP1 | C5 | IL12A-IL12B | KIT | APOA1 | 0.862 |
| | CCL23 | ACY1 | CDK5-CDK5R1 | CKB-CKM | | |
| 10 | TIMP1 | C5 | KIT | APOA1 | SERPINF2 | 0.861 |
| | CCL23 | ACY1 | CDK5-CDK5R1 | CKB-CKM | | |
| 11 | TIMP1 | C5 | KIT | APOA1 | SERPINF2 | 0.861 |
| | LBP | ACY1 | CDK5-CDK5R1 | CKB-CKM | | |
| 12 | TIMP1 | C5 | IL12A-IL12B | KIT | APOA1 | 0.861 |
| | SERPINF2 | ACY1 | CDK5-CDK5R1 | CKB-CKM | | |
| 13 | C5 | IL12A-IL12B | KIT | APOA1 | SERPINF2 | 0.861 |
| | CCL23 | ACY1 | CDK5-CDK5R1 | CKB-CKM | | |
| 14 | TIMP1 | C5 | KIT | APOA1 | CCL23 | 0.861 |
| | LBP | ACY1 | CDK5-CDK5R1 | CKB-CKM | | |
| 15 | TIMP1 | C5 | KIT | APOA1 | CCL23 | 0.861 |
| | ACY1 | CDK5-CDK5R1 | CKB-CKM | HINT1 | | |
| 16 | C9 | C5 | KIT | APOA1 | CCL23 | 0.861 |
| | LBP | ACY1 | CDK5-CDK5R1 | CKB-CKM | | |
| 17 | C5 | IL12A-IL12B | KIT | APOA1 | SERPINF2 | 0.861 |
| | CCL23 | LBP | CDK5-CDK5R1 | CKB-CKM | | |
| 18 | TIMP1 | C5 | IL12A-IL12B | KIT | APOA1 | 0.861 |
| | ACY1 | CDK5-CDK5R1 | HAMP | CKB-CKM | | |
| 19 | C5 | KIT | APOA1 | CCL23 | LBP | 0.861 |
| | ACY1 | CDK5-CDK5R1 | FSTL3 | CKB-CKM | | |
| 20 | TIMP1 | C5 | KIT | APOA1 | CCL23 | 0.861 |
| | ACY1 | CDK5-CDK5R1 | HAMP | CKB-CKM | | |
| 21 | TIMP1 | C5 | KIT | APOA1 | CCL23 | 0.860 |
| | SERPINF2 | ACY1 | CDK5-CDK5R1 | CKB-CKM | | |
| 22 | C5 | KIT | CKM | APOA1 | CCL23 | 0.860 |
| | SERPINF2 | LBP | ACY1 | CDK5-CDK5R1 | | |
| 23 | C5 | IL12A-IL12B | KIT | APOA1 | LBP | 0.860 |
| | ACY1 | CDK5-CDK5R1 | FSTL3 | CKB-CKM | | |
| 24 | C5 | KIT | APOA1 | CCL23 | LBP | 0.860 |
| | ACY1 | CDK5-CDK5R1 | HAMP | CKB-CKM | | |
| 25 | C5 | IL12A-IL12B | KIT | APOA1 | SERPINF2 | 0.860 |
| | LBP | ACY1 | CDK5-CDK5R1 | CKB-CKM | | |
| 26 | C5 | IL12A-IL12B | KIT | APOA1 | CCL23 | 0.860 |
| | SERPINF2 | ACY1 | CDK5-CDK5R1 | CKB-CKM | | |
| 27 | C5 | KIT | APOA1 | CCL23 | LBP | 0.860 |
| | ACY1 | CDK5-CDK5R1 | FSTL3 | CKB-CKM | | |
| 28 | TIMP1 | C5 | KIT | APOA1 | CCL23 | 0.860 |
| | CCL23 | ACY1 | CDK5-CDK5R1 | CKB-CKM | | |
| 29 | C5 | KIT | APOA1 | CCL23 | CCL23 | 0.860 |
| | LBP | ACY1 | CDK5-CDK5R1 | CKB-CKM | | |
| 30 | TIMP1 | C5 | IL12A-IL12B | KIT | APOA1 | 0.860 |
| | CCL23 | LBP | CDK5-CDK5R1 | CKB-CKM | | |
| 31 | C9 | C5 | KIT | CKM | APOA1 | 0.860 |
| | CCL23 | ACY1 | CDK5-CDK5R1 | HINT1 | | |
| 32 | TIMP1 | C5 | KIT | APOA1 | SERPINF2 | 0.860 |
| | ACY1 | CDK5-CDK5R1 | HAMP | CKB-CKM | | |
| 33 | C9 | C5 | KIT | CKM | APOA1 | 0.859 |
| | SERPINF2 | CCL23 | ACY1 | CDK5-CDK5R1 | | |
| 34 | TIMP1 | C9 | C5 | KIT | APOA1 | 0.859 |
| | CCL23 | ACY1 | CDK5-CDK5R1 | CKB-CKM | | |
| 35 | C5 | KIT | APOA1 | SERPINF2 | CCL23 | 0.859 |
| | LBP | CDK5-CDK5R1 | CKB-CKM | HINT1 | | |
| 36 | TIMP1 | C5 | C9 | C5 | KIT | CKM | 0.859 |
| | APOA1 | CCL23 | ACY1 | CDK5-CDK5R1 | | |
| 37 | C5 | IL12A-IL12B | KIT | APOA1 | CCL23 | 0.859 |
| | LBP | CDK5-CDK5R1 | CKB-CKM | HINT1 | | |
| 38 | C5 | KIT | APOA1 | CCL23 | SERPINF2 | 0.859 |
| | CCL23 | ACY1 | CDK5-CDK5R1 | CKB-CKM | | |

TABLE 28-continued

Panels of 9 Biomarkers

| | Markers | | | | | Mean CV AUC |
|---|---|---|---|---|---|---|
| 39 | C5 | IL12A-IL12B | KIT | APOA1 | CCL23 | 0.859 |
| | ACY1 | CDK5-CDK5R1 | HAMP | CKB-CKM | | |
| 40 | TIMP1 | C5 | KIT | APOA1 | CCL23 | 0.859 |
| | LBP | CDK5-CDK5R1 | CKB-CKM | HINT1 | | |
| 41 | C5 | KIT | APOA1 | SERPINF2 | CCL23 | 0.859 |
| | ACY1 | CDK5-CDK5R1 | CKB-CKM | HINT1 | | |
| 42 | C5 | KIT | APOA1 | GDF11 | CCL23 | 0.859 |
| | LBP | ACY1 | CDK5-CDK5R1 | CKB-CKM | | |
| 43 | C5 | KIT | APOA1 | SERPINF2 | LBP | 0.859 |
| | ACY1 | CDK5-CDK5R1 | FSTL3 | CKB-CKM | | |
| 44 | C5 | KIT | CKM | APOA1 | CCL23 | 0.859 |
| | LBP | ACY1 | CDK5-CDK5R1 | HINT1 | | |
| 45 | C5 | IL12A-IL12B | KIT | APOA1 | CCL23 | 0.859 |
| | ACY1 | CDK5-CDK5R1 | FSTL3 | CKB-CKM | | |
| 46 | C5 | KIT | APOA1 | CCL23 | LBP | 0.859 |
| | ACY1 | CDK5-CDK5R1 | CKB-CKM | HINT1 | | |
| 47 | C9 | C5 | KIT | CKM | APOA1 | 0.859 |
| | CCL23 | LBP | ACY1 | CDK5-CDK5R1 | | |
| 48 | C5 | IL12A-IL12B | KIT | APOA1 | CCL23 | 0.859 |
| | CCL23 | ACY1 | CDK5-CDK5R1 | CKB-CKM | | |
| 49 | C9 | C5 | KIT | APOA1 | CCL23 | 0.858 |
| | ACY1 | CDK5-CDK5R1 | CKB-CKM | HINT1 | | |
| 50 | C9 | C5 | IL12A-IL12B | KIT | CKM | 0.858 |
| | APOA1 | CCL23 | ACY1 | CDK5-CDK5R1 | | |
| 51 | C5 | KIT | APOA1 | CCL23 | ACY1 | 0.858 |
| | CDK5-CDK5R1 | FSTL3 | HAMP | CKB-CKM | | |
| 52 | C5 | IL12A-IL12B | KIT | APOA1 | CCL23 | 0.858 |
| | ACY1 | CDK5-CDK5R1 | HAMP | CKB-CKM | | |
| 53 | C5 | KIT | APOA1 | CCL23 | LBP | 0.858 |
| | ACY1 | CDK5-CDK5R1 | HAMP | CKB-CKM | | |
| 54 | C5 | IL12A-IL12B | KIT | APOA1 | CCL23 | 0.858 |
| | ACY1 | CDK5-CDK5R1 | FSTL3 | CKB-CKM | | |
| 55 | TIMP1 | C9 | KIT | APOA1 | CCL23 | 0.858 |
| | LBP | ACY1 | CDK5-CDK5R1 | CKB-CKM | | |
| 56 | C9 | C5 | KIT | CKM | APOA1 | 0.858 |
| | CCL23 | CCL23 | ACY1 | CDK5-CDK5R1 | | |
| 57 | TIMP1 | C5 | KIT | APOA1 | LBP | 0.858 |
| | ACY1 | CDK5-CDK5R1 | FSTL3 | CKB-CKM | | |
| 58 | C5 | KIT | APOA1 | GDF11 | CCL23 | 0.858 |
| | SERPINF2 | ACY1 | CDK5-CDK5R1 | CKB-CKM | | |
| 59 | TIMP1 | C5 | IL12A-IL12B | KIT | APOA1 | 0.858 |
| | SERPINF2 | CCL23 | CDK5-CDK5R1 | CKB-CKM | | |
| 60 | C5 | KIT | APOA1 | SERPINF2 | CCL23 | 0.858 |
| | ACY1 | CDK5-CDK5R1 | HAMP | CKB-CKM | | |
| 61 | C5 | IL12A-IL12B | KIT | CKM | APOA1 | 0.858 |
| | CCL23 | LBP | ACY1 | CDK5-CDK5R1 | | |
| 62 | TIMP1 | C5 | KIT | APOA1 | CCL23 | 0.858 |
| | ACY1 | CDK5-CDK5R1 | HAMP | CKB-CKM | | |
| 63 | C5 | KIT | APOA1 | SERPINF2 | CCL23 | 0.858 |
| | ACY1 | CDK5-CDK5R1 | FSTL3 | CKB-CKM | | |
| 64 | TIMP1 | C5 | KIT | CKM | APOA1 | 0.858 |
| | CCL23 | SERPINF2 | ACY1 | CDK5-CDK5R1 | | |
| 65 | C5 | KIT | APOA1 | LBP | ACY1 | 0.858 |
| | CDK5-CDK5R1 | FSTL3 | HAMP | CKB-CKM | | |
| 66 | TIMP1 | C5 | KIT | APOA1 | CCL23 | 0.858 |
| | ACY1 | CDK5-CDK5R1 | CKB-CKM | HINT1 | | |
| 67 | TIMP1 | C9 | KIT | APOA1 | CCL23 | 0.858 |
| | ACY1 | CDK5-CDK5R1 | HAMP | CKB-CKM | | |
| 68 | TIMP1 | C5 | IL12A-IL12B | KIT | APOA1 | 0.858 |
| | CCL23 | LBP | CDK5-CDK5R1 | CKB-CKM | | |
| 69 | C5 | KIT | APOA1 | GDF11 | CCL23 | 0.858 |
| | ACY1 | CDK5-CDK5R1 | CKB-CKM | HINT1 | | |
| 70 | C5 | IL12A-IL12B | KIT | APOA1 | ACY1 | 0.858 |
| | CDK5-CDK5R1 | FSTL3 | HAMP | CKB-CKM | | |
| 71 | TIMP1 | C5 | KIT | APOA1 | LBP | 0.858 |
| | ACY1 | CDK5-CDK5R1 | HAMP | CKB-CKM | | |
| 72 | C9 | C5 | KIT | APOA1 | LBP | 0.858 |
| | ACY1 | CDK5-CDK5R1 | CKB-CKM | HINT1 | | |
| 73 | TIMP1 | C5 | KIT | APOA1 | CCL23 | 0.858 |
| | ACY1 | CDK5-CDK5R1 | FSTL3 | CKB-CKM | | |
| 74 | C5 | IL12A-IL12B | KIT | APOA1 | LBP | 0.858 |
| | ACY1 | CDK5-CDK5R1 | HAMP | CKB-CKM | | |
| 75 | TIMP1 | C5 | KIT | APOA1 | LBP | 0.858 |
| | ACY1 | CDK5-CDK5R1 | CKB-CKM | HINT1 | | |
| 76 | TIMP1 | C5 | KIT | APOA1 | GDF11 | 0.858 |
| | CCL23 | ACY1 | CDK5-CDK5R1 | CKB-CKM | | |

TABLE 28-continued

Panels of 9 Biomarkers

| # | Markers | | | | | Mean CV AUC |
|---|---|---|---|---|---|---|
| 77 | C9 | C5 | KIT | APOA1 | CCL23 | 0.858 |
|    | LBP | CDK5-CDK5R1 | CKB-CKM | HINT1 | | |
| 78 | C5 | KIT | CKM | APOA1 | SERPINF2 | 0.858 |
|    | CCL23 | LBP | ACY1 | CDK5-CDK5R1 | | |
| 79 | C9 | IL12A-IL12B | KIT | APOA1 | CCL23 | 0.858 |
|    | LBP | ACY1 | CDK5-CDK5R1 | CKB-CKM | | |
| 80 | TIMP1 | C5 | IL12A-IL12B | KIT | APOA1 | 0.858 |
|    | CCL23 | CDK5-CDK5R1 | HAMP | CKB-CKM | | |
| 81 | C5 | KIT | APOA1 | GDF11 | CCL23 | 0.858 |
|    | LBP | ACY1 | CDK5-CDK5R1 | CKB-CKM | | |
| 82 | C9 | C5 | KIT | CKM | APOA1 | 0.858 |
|    | CCL23 | ACY1 | CDK5-CDK5R1 | HAMP | | |
| 83 | C5 | IL12A-IL12B | KIT | APOA1 | GDF11 | 0.858 |
|    | CCL23 | ACY1 | CDK5-CDK5R1 | CKB-CKM | | |
| 84 | C9 | C5 | KIT | APOA1 | CCL23 | 0.857 |
|    | ACY1 | CDK5-CDK5R1 | HAMP | CKB-CKM | | |
| 85 | C9 | C5 | KIT | APOA1 | SERPINF2 | 0.857 |
|    | CCL23 | ACY1 | CDK5-CDK5R1 | CKB-CKM | | |
| 86 | C5 | IL12A-IL12B | KIT | APOA1 | CCL23 | 0.857 |
|    | LBP | ACY1 | CKB-CKM | HINT1 | | |
| 87 | C5 | IL12A-IL12B | KIT | APOA1 | SERPINF2 | 0.857 |
|    | CCL23 | LBP | ACY1 | CKB-CKM | | |
| 88 | C5 | IL12A-IL12B | KIT | APOA1 | CCL23 | 0.857 |
|    | CCL23 | LBP | CDK5-CDK5R1 | CKB-CKM | | |
| 89 | C5 | KIT | APOA1 | CCL23 | ACY1 | 0.857 |
|    | CDK5-CDK5R1 | FSTL3 | CKB-CKM | HINT1 | | |
| 90 | TIMP1 | IL12A-IL12B | KIT | APOA1 | LBP | 0.857 |
|    | ACY1 | CDK5-CDK5R1 | HAMP | CKB-CKM | | |
| 91 | C5 | IL12A-IL12B | KIT | APOA1 | SERPINF2 | 0.857 |
|    | ACY1 | CDK5-CDK5R1 | FSTL3 | CKB-CKM | | |
| 92 | TIMP1 | C5 | KIT | APOA1 | GDF11 | 0.857 |
|    | SERPINF2 | ACY1 | CDK5-CDK5R1 | CKB-CKM | | |
| 93 | C9 | KIT | CKM | APOA1 | CCL23 | 0.857 |
|    | LBP | ACY1 | CDK5-CDK5R1 | HINT1 | | |
| 94 | TIMP1 | C5 | KIT | APOA1 | SERPINF2 | 0.857 |
|    | CCL23 | LBP | CDK5-CDK5R1 | CKB-CKM | | |
| 95 | TIMP1 | C5 | IL12A-IL12B | KIT | CKM | 0.857 |
|    | APOA1 | CCL23 | ACY1 | CDK5-CDK5R1 | | |
| 96 | C9 | C5 | KIT | CKM | APOA1 | 0.857 |
|    | LBP | ACY1 | CDK5-CDK5R1 | HINT1 | | |
| 97 | C5 | KIT | APOA1 | CCL23 | SERPINF2 | 0.857 |
|    | ACY1 | CDK5-CDK5R1 | HAMP | CKB-CKM | | |
| 98 | C5 | IL12A-IL12B | KIT | APOA1 | GDF11 | 0.857 |
|    | CCL23 | ACY1 | CDK5-CDK5R1 | CKB-CKM | | |
| 99 | C9 | C5 | KIT | CKM | APOA1 | 0.857 |
|    | CCL23 | LBP | ACY1 | CDK5-CDK5R1 | | |
| 100 | TIMP1 | C5 | KIT | APOA1 | ACY1 | 0.857 |
|    | CDK5-CDK5R1 | FSTL3 | HAMP | CKB-CKM | | |

TABLE 29

Panels of 10 Biomarkers

| # | Markers | | | | | Mean CV AUC |
|---|---|---|---|---|---|---|
| 1 | C5 | IL12A-IL12B | KIT | APOA1 | SERPINF2 | 0.863 |
|   | CCL23 | LBP | ACY1 | CDK5-CDK5R1 | CKB-CKM | |
| 2 | TIMP1 | C5 | IL12A-IL12B | KIT | APOA1 | 0.863 |
|   | CCL23 | LBP | ACY1 | CDK5-CDK5R1 | CKB-CKM | |
| 3 | TIMP1 | C5 | IL12A-IL12B | KIT | APOA1 | 0.862 |
|   | CCL23 | LBP | ACY1 | CDK5-CDK5R1 | CKB-CKM | |
| 4 | TIMP1 | C5 | IL12A-IL12B | KIT | APOA1 | 0.862 |
|   | SERPINF2 | LBP | ACY1 | CDK5-CDK5R1 | CKB-CKM | |
| 5 | C5 | KIT | APOA1 | SERPINF2 | CCL23 | 0.862 |
|   | LBP | ACY1 | CDK5-CDK5R1 | CKB-CKM | HINT1 | |
| 6 | C5 | IL12A-IL12B | KIT | APOA1 | CCL23 | 0.862 |
|   | SERPINF2 | LBP | ACY1 | CDK5-CDK5R1 | CKB-CKM | |
| 7 | TIMP1 | C5 | KIT | APOA1 | CCL23 | 0.862 |
|   | SERPINF2 | LBP | ACY1 | CDK5-CDK5R1 | CKB-CKM | |
| 8 | TIMP1 | C5 | KIT | APOA1 | CCL23 | 0.862 |
|   | LBP | ACY1 | CDK5-CDK5R1 | CKB-CKM | HINT1 | |
| 9 | TIMP1 | C5 | KIT | APOA1 | SERPINF2 | 0.861 |
|   | CCL23 | LBP | ACY1 | CDK5-CDK5R1 | CKB-CKM | |

TABLE 29-continued

| Panels of 10 Biomarkers | | | | | |
|---|---|---|---|---|---|
| | Markers | | | | Mean CV AUC |
| 10 | C9 | C5 | KIT | APOA1 | CCL23 | 0.861 |
| | LBP | ACY1 | CDK5-CDK5R1 | HAMP | CKB-CKM | |
| 11 | C9 | C5 | KIT | CKM | APOA1 | 0.861 |
| | SERPINF2 | CCL23 | ACY1 | CDK5-CDK5R1 | HINT1 | |
| 12 | C5 | IL12A-IL12B | KIT | APOA1 | CCL23 | 0.861 |
| | CCL23 | LBP | ACY1 | CDK5-CDK5R1 | CKB-CKM | |
| 13 | C5 | IL12A-IL12B | KIT | APOA1 | CCL23 | 0.861 |
| | LBP | ACY1 | CDK5-CDK5R1 | CKB-CKM | HINT1 | |
| 14 | C9 | C5 | KIT | APOA1 | CCL23 | 0.861 |
| | LBP | ACY1 | CDK5-CDK5R1 | CKB-CKM | HINT1 | |
| 15 | TIMP1 | C5 | IL12A-IL12B | KIT | APOA1 | 0.861 |
| | SERPINF2 | CCL23 | ACY1 | CDK5-CDK5R1 | CKB-CKM | |
| 16 | TIMP1 | C9 | C5 | KIT | APOA1 | 0.860 |
| | CCL23 | LBP | ACY1 | CDK5-CDK5R1 | CKB-CKM | |
| 17 | TIMP1 | C5 | IL12A-IL12B | KIT | APOA1 | 0.860 |
| | CCL23 | ACY1 | CDK5-CDK5R1 | HAMP | CKB-CKM | |
| 18 | C9 | C5 | KIT | CKM | APOA1 | 0.860 |
| | SERPINF2 | CCL23 | LBP | ACY1 | CDK5-CDK5R1 | |
| 19 | TIMP1 | C5 | KIT | APOA1 | SERPINF2 | 0.860 |
| | CCL23 | ACY1 | CDK5-CDK5R1 | CKB-CKM | HINT1 | |
| 20 | C5 | KIT | APOA1 | GDF11 | CCL23 | 0.860 |
| | LBP | ACY1 | CDK5-CDK5R1 | CKB-CKM | HINT1 | |
| 21 | C5 | IL12A-IL12B | KIT | APOA1 | CCL23 | 0.860 |
| | LBP | ACY1 | CDK5-CDK5R1 | FSTL3 | CKB-CKM | |
| 22 | C9 | C5 | KIT | CKM | APOA1 | 0.860 |
| | CCL23 | LBP | ACY1 | CDK5-CDK5R1 | HINT1 | |
| 23 | C9 | C5 | IL12A-IL12B | KIT | CKM | 0.860 |
| | APOA1 | CCL23 | LBP | ACY1 | CDK5-CDK5R1 | |
| 24 | C5 | IL12A-IL12B | KIT | APOA1 | CCL23 | 0.860 |
| | LBP | ACY1 | CDK5-CDK5R1 | HAMP | CKB-CKM | |
| 25 | C9 | C5 | KIT | CKM | APOA1 | 0.860 |
| | CCL23 | ACY1 | CDK5-CDK5R1 | CKB-CKM | HINT1 | |
| 26 | C5 | IL12A-IL12B | KIT | APOA1 | CCL23 | 0.860 |
| | LBP | ACY1 | CDK5-CDK5R1 | HAMP | CKB-CKM | |
| 27 | C9 | C5 | KIT | CKM | APOA1 | 0.860 |
| | CCL23 | LBP | CDK5-CDK5R1 | CKB-CKM | HINT1 | |
| 28 | C5 | KIT | APOA1 | SERPINF2 | CCL23 | 0.860 |
| | LBP | ACY1 | CDK5-CDK5R1 | HAMP | CKB-CKM | |
| 29 | TIMP1 | C9 | C5 | KIT | APOA1 | 0.860 |
| | CCL23 | ACY1 | CDK5-CDK5R1 | CKB-CKM | HINT1 | |
| 30 | TIMP1 | C5 | IL12A-IL12B | KIT | APOA1 | 0.860 |
| | CCL23 | ACY1 | CDK5-CDK5R1 | HAMP | CKB-CKM | |
| 31 | C9 | C5 | KIT | APOA1 | SERPINF2 | 0.860 |
| | CCL23 | LBP | ACY1 | CDK5-CDK5R1 | CKB-CKM | |
| 32 | TIMP1 | C5 | IL12A-IL12B | KIT | APOA1 | 0.860 |
| | SERPINF2 | ACY1 | CDK5-CDK5R1 | HAMP | CKB-CKM | |
| 33 | C5 | IL12A-IL12B | KIT | APOA1 | CCL23 | 0.859 |
| | LBP | ACY1 | CDK5-CDK5R1 | FSTL3 | CKB-CKM | |
| 34 | C5 | KIT | APOA1 | CCL23 | SERPINF2 | 0.859 |
| | CCL23 | LBP | ACY1 | CDK5-CDK5R1 | CKB-CKM | |
| 35 | C9 | C5 | IL12A-IL12B | KIT | APOA1 | 0.859 |
| | CCL23 | LBP | ACY1 | CDK5-CDK5R1 | CKB-CKM | |
| 36 | TIMP1 | C9 | C5 | KIT | CKM | 0.859 |
| | APOA1 | CCL23 | ACY1 | CDK5-CDK5R1 | HINT1 | |
| 37 | TIMP1 | C5 | IL12A-IL12B | KIT | APOA1 | 0.859 |
| | LBP | ACY1 | CDK5-CDK5R1 | HAMP | CKB-CKM | |
| 38 | TIMP1 | C5 | IL12A-IL12B | KIT | APOA1 | 0.859 |
| | CCL23 | SERPINF2 | ACY1 | CDK5-CDK5R1 | CKB-CKM | |
| 39 | TIMP1 | C5 | KIT | APOA1 | GDF11 | 0.859 |
| | CCL23 | LBP | ACY1 | CDK5-CDK5R1 | CKB-CKM | |
| 40 | C9 | C5 | KIT | CKM | APOA1 | 0.859 |
| | CCL23 | CCL23 | LBP | ACY1 | CDK5-CDK5R1 | |
| 41 | TIMP1 | C5 | KIT | APOA1 | CCL23 | 0.859 |
| | LBP | ACY1 | CDK5-CDK5R1 | HAMP | CKB-CKM | |
| 42 | C5 | KIT | APOA1 | CCL23 | LBP | 0.859 |
| | ACY1 | CDK5-CDK5R1 | FSTL3 | CKB-CKM | HINT1 | |
| 43 | TIMP1 | C5 | KIT | APOA1 | CCL23 | 0.859 |
| | LBP | ACY1 | CDK5-CDK5R1 | CKB-CKM | HINT1 | |
| 44 | C5 | KIT | APOA1 | SERPINF2 | CCL23 | 0.859 |
| | LBP | ACY1 | CDK5-CDK5R1 | FSTL3 | CKB-CKM | |
| 45 | TIMP1 | C9 | C5 | KIT | APOA1 | 0.859 |
| | SERPINF2 | CCL23 | ACY1 | CDK5-CDK5R1 | CKB-CKM | |
| 46 | TIMP1 | C9 | C5 | IL12A-IL12B | KIT | 0.859 |
| | CKM | APOA1 | CCL23 | ACY1 | CDK5-CDK5R1 | |
| 47 | TIMP1 | C5 | KIT | APOA1 | CCL23 | 0.859 |
| | SERPINF2 | ACY1 | CDK5-CDK5R1 | HAMP | CKB-CKM | |

TABLE 29-continued

| | Panels of 10 Biomarkers | | | | | |
|---|---|---|---|---|---|---|
| | | Markers | | | | Mean CV AUC |
| 48 | C5 | IL12A-IL12B | KIT | APOA1 | SERPINF2 | 0.859 |
| | CCL23 | LBP | CDK5-CDK5R1 | CKB-CKM | HINT1 | |
| 49 | TIMP1 | C5 | KIT | APOA1 | CCL23 | 0.859 |
| | LBP | ACY1 | CDK5-CDK5R1 | HAMP | CKB-CKM | |
| 50 | TIMP1 | C5 | KIT | APOA1 | CCL23 | 0.859 |
| | CCL23 | LBP | ACY1 | CDK5-CDK5R1 | CKB-CKM | |
| 51 | C9 | C5 | KIT | CKM | APOA1 | 0.859 |
| | CCL23 | LBP | ACY1 | CDK5-CDK5R1 | HAMP | |
| 52 | C5 | KIT | APOA1 | CCL23 | SERPINF2 | 0.859 |
| | LBP | ACY1 | CDK5-CDK5R1 | FSTL3 | CKB-CKM | |
| 53 | TIMP1 | C9 | C5 | KIT | APOA1 | 0.859 |
| | CCL23 | ACY1 | CDK5-CDK5R1 | HAMP | CKB-CKM | |
| 54 | TIMP1 | C5 | IL12A-IL12B | KIT | APOA1 | 0.859 |
| | CCL23 | CCL23 | ACY1 | CDK5-CDK5R1 | CKB-CKM | |
| 55 | C9 | C5 | KIT | CKM | APOA1 | 0.859 |
| | CCL23 | CCL23 | ACY1 | CDK5-CDK5R1 | HINT1 | |
| 56 | TIMP1 | C5 | IL12A-IL12B | KIT | APOA1 | 0.859 |
| | GDF11 | CCL23 | ACY1 | CDK5-CDK5R1 | CKB-CKM | |
| 57 | TIMP1 | C5 | KIT | APOA1 | SERPINF2 | 0.858 |
| | CCL23 | LBP | CDK5-CDK5R1 | CKB-CKM | HINT1 | |
| 58 | C5 | IL12A-IL12B | KIT | APOA1 | GDF11 | 0.858 |
| | CCL23 | LBP | ACY1 | CDK5-CDK5R1 | CKB-CKM | |
| 59 | C5 | KIT | APOA1 | CCL23 | LBP | 0.858 |
| | ACY1 | CDK5-CDK5R1 | HAMP | CKB-CKM | HINT1 | |
| 60 | TIMP1 | C5 | KIT | APOA1 | GDF11 | 0.858 |
| | CCL23 | ACY1 | CDK5-CDK5R1 | HAMP | CKB-CKM | |
| 61 | TIMP1 | C9 | C5 | KIT | CKM | 0.858 |
| | APOA1 | CCL23 | LBP | ACY1 | CDK5-CDK5R1 | |
| 62 | C5 | IL12A-IL12B | KIT | APOA1 | CCL23 | 0.858 |
| | SERPINF2 | CCL23 | ACY1 | CDK5-CDK5R1 | CKB-CKM | |
| 63 | C9 | C5 | KIT | APOA1 | CCL23 | 0.858 |
| | LBP | ACY1 | CDK5-CDK5R1 | FSTL3 | CKB-CKM | |
| 64 | C9 | C5 | KIT | CKM | APOA1 | 0.858 |
| | CCL23 | LBP | ACY1 | CDK5-CDK5R1 | CKB-CKM | |
| 65 | TIMP1 | C5 | KIT | APOA1 | CCL23 | 0.858 |
| | ACY1 | CDK5-CDK5R1 | HAMP | CKB-CKM | HINT1 | |
| 66 | C5 | KIT | APOA1 | CCL23 | CCL23 | 0.858 |
| | LBP | ACY1 | CDK5-CDK5R1 | CKB-CKM | HINT1 | |
| 67 | C5 | KIT | APOA1 | CCL23 | SERPINF2 | 0.858 |
| | LBP | ACY1 | CDK5-CDK5R1 | HAMP | CKB-CKM | |
| 68 | C5 | KIT | APOA1 | GDF11 | CCL23 | 0.858 |
| | LBP | ACY1 | CDK5-CDK5R1 | HAMP | CKB-CKM | |
| 69 | TIMP1 | C5 | KIT | APOA1 | SERPINF2 | 0.858 |
| | LBP | ACY1 | CDK5-CDK5R1 | HAMP | CKB-CKM | |
| 70 | C5 | KIT | APOA1 | CCL23 | SERPINF2 | 0.858 |
| | LBP | ACY1 | CDK5-CDK5R1 | CKB-CKM | HINT1 | |
| 71 | C5 | IL12A-IL12B | KIT | APOA1 | GDF11 | 0.858 |
| | CCL23 | ACY1 | CDK5-CDK5R1 | HAMP | CKB-CKM | |
| 72 | C5 | KIT | APOA1 | GDF11 | SERPINF2 | 0.858 |
| | CCL23 | LBP | ACY1 | CDK5-CDK5R1 | CKB-CKM | |
| 73 | TIMP1 | C5 | IL12A-IL12B | KIT | APOA1 | 0.858 |
| | CCL23 | ACY1 | CDK5-CDK5R1 | CKB-CKM | HINT1 | |
| 74 | C9 | C5 | IL12A-IL12B | KIT | CKM | 0.858 |
| | APOA1 | CCL23 | ACY1 | CDK5-CDK5R1 | HINT1 | |
| 75 | TIMP1 | C5 | KIT | APOA1 | GDF11 | 0.858 |
| | CCL23 | ACY1 | CDK5-CDK5R1 | CKB-CKM | HINT1 | |
| 76 | TIMP1 | C9 | C5 | IL12A-IL12B | KIT | 0.858 |
| | APOA1 | CCL23 | ACY1 | CDK5-CDK5R1 | CKB-CKM | |
| 77 | TIMP1 | C9 | KIT | APOA1 | CCL23 | 0.858 |
| | LBP | ACY1 | CDK5-CDK5R1 | HAMP | CKB-CKM | |
| 78 | TIMP1 | C5 | IL12A-IL12B | KIT | APOA1 | 0.858 |
| | LBP | ACY1 | CDK5-CDK5R1 | FSTL3 | CKB-CKM | |
| 79 | C9 | C5 | KIT | APOA1 | CCL23 | 0.858 |
| | CCL23 | LBP | ACY1 | CDK5-CDK5R1 | CKB-CKM | |
| 80 | TIMP1 | C9 | C5 | KIT | APOA1 | 0.858 |
| | CCL23 | CCL23 | ACY1 | CDK5-CDK5R1 | CKB-CKM | |
| 81 | TIMP1 | C9 | IL12A-IL12B | KIT | APOA1 | 0.858 |
| | CCL23 | LBP | ACY1 | CDK5-CDK5R1 | CKB-CKM | |
| 82 | C9 | C5 | KIT | CKM | APOA1 | 0.858 |
| | CCL23 | SERPINF2 | CCL23 | ACY1 | CDK5-CDK5R1 | |
| 83 | C5 | KIT | APOA1 | GDF11 | CCL23 | 0.858 |
| | SERPINF2 | LBP | ACY1 | CDK5-CDK5R1 | CKB-CKM | |
| 84 | C9 | KIT | CKM | APOA1 | CCL23 | 0.858 |
| | LBP | ACY1 | CDK5-CDK5R1 | CKB-CKM | HINT1 | |
| 85 | C5 | IL12A-IL12B | KIT | APOA1 | GDF11 | 0.858 |
| | CCL23 | LBP | ACY1 | CDK5-CDK5R1 | CKB-CKM | |

TABLE 29-continued

Panels of 10 Biomarkers

| | Markers | | | | | Mean CV AUC |
|---|---|---|---|---|---|---|
| 86 | C5 | IL12A-IL12B | KIT | APOA1 | SERPINF2 | 0.858 |
| | LBP | ACY1 | CDK5-CDK5R1 | HAMP | CKB-CKM | |
| 87 | C5 | IL12A-IL12B | KIT | APOA1 | SERPINF2 | 0.858 |
| | LBP | ACY1 | CDK5-CDK5R1 | FSTL3 | CKB-CKM | |
| 88 | C5 | KIT | APOA1 | SERPINF2 | CCL23 | 0.858 |
| | ACY1 | CDK5-CDK5R1 | HAMP | CKB-CKM | HINT1 | |
| 89 | C5 | KIT | CKM | APOA1 | SERPINF2 | 0.858 |
| | CCL23 | LBP | ACY1 | CDK5-CDK5R1 | HINT1 | |
| 90 | TIMP1 | C5 | KIT | APOA1 | CCL23 | 0.858 |
| | CCL23 | ACY1 | CDK5-CDK5R1 | CKB-CKM | HINT1 | |
| 91 | C5 | KIT | APOA1 | CCL23 | LBP | 0.858 |
| | ACY1 | CDK5-CDK5R1 | FSTL3 | HAMP | CKB-CKM | |
| 92 | TIMP1 | C9 | C5 | KIT | CKM | 0.858 |
| | APOA1 | CCL23 | ACY1 | CDK5-CDK5R1 | CKB-CKM | |
| 93 | C9 | C5 | KIT | CKM | APOA1 | 0.858 |
| | CCL23 | ACY1 | CDK5-CDK5R1 | HAMP | HINT1 | |
| 94 | TIMP1 | C5 | IL12A-IL12B | KIT | APOA1 | 0.858 |
| | GDF11 | CCL23 | ACY1 | CDK5-CDK5R1 | CKB-CKM | |
| 95 | TIMP1 | C5 | IL12A-IL12B | KIT | APOA1 | 0.858 |
| | SERPINF2 | CCL23 | LBP | CDK5-CDK5R1 | CKB-CKM | |
| 96 | C5 | IL12A-IL12B | KIT | APOA1 | SERPINF2 | 0.858 |
| | CCL23 | ACY1 | CDK5-CDK5R1 | HAMP | CKB-CKM | |
| 97 | C5 | IL12A-IL12B | KIT | APOA1 | GDF11 | 0.858 |
| | ACY1 | CDK5-CDK5R1 | FSTL3 | HAMP | CKB-CKM | |
| 98 | C5 | IL12A-IL12B | KIT | CKM | APOA1 | 0.858 |
| | SERPINF2 | CCL23 | LBP | ACY1 | CDK5-CDK5R1 | |
| 99 | TIMP1 | C9 | C5 | KIT | CKM | 0.858 |
| | APOA1 | SERPINF2 | CCL23 | ACY1 | CDK5-CDK5R1 | |
| 100 | TIMP1 | C5 | KIT | CKM | APOA1 | 0.858 |
| | CCL23 | LBP | ACY1 | CDK5-CDK5R1 | HINT1 | |

TABLE 30

Counts of markers in biomarker panels

| | Panel Size | | | | | | | |
|---|---|---|---|---|---|---|---|---|
| Biomarker | 3 | 4 | 5 | 6 | 7 | 8 | 9 | 10 |
| ACY1 | 141 | 192 | 308 | 399 | 489 | 590 | 658 | 759 |
| APOA1 | 180 | 395 | 598 | 728 | 833 | 919 | 962 | 981 |
| C5 | 163 | 285 | 437 | 559 | 644 | 693 | 773 | 834 |
| C9 | 190 | 314 | 340 | 341 | 359 | 395 | 436 | 511 |
| CCL23 | 151 | 168 | 191 | 202 | 238 | 273 | 308 | 363 |
| CCL23 | 150 | 160 | 195 | 260 | 332 | 412 | 502 | 587 |
| CDK5-CDK5R1 | 147 | 230 | 359 | 512 | 660 | 785 | 893 | 943 |
| CKB-CKM | 187 | 391 | 473 | 563 | 623 | 654 | 680 | 685 |
| CKM | 174 | 227 | 224 | 254 | 298 | 350 | 407 | 476 |
| ENTPD1 | 107 | 57 | 38 | 31 | 27 | 12 | 8 | 14 |
| FSTL3 | 112 | 89 | 87 | 101 | 107 | 136 | 170 | 190 |
| GDF11 | 112 | 62 | 52 | 53 | 73 | 116 | 156 | 228 |
| HAMP | 107 | 67 | 73 | 96 | 134 | 199 | 265 | 322 |
| HINT1 | 129 | 156 | 182 | 205 | 240 | 276 | 336 | 421 |
| IL12A-IL12B | 116 | 120 | 132 | 169 | 208 | 268 | 320 | 355 |
| KIT | 188 | 523 | 728 | 862 | 928 | 977 | 995 | 999 |
| KLK3-SERPINA3 | 166 | 71 | 40 | 28 | 23 | 22 | 21 | 13 |
| LBP | 146 | 177 | 208 | 250 | 326 | 383 | 471 | 565 |
| SERPINF2 | 126 | 134 | 139 | 161 | 206 | 241 | 300 | 351 |
| THBS2 | 72 | 7 | 0 | 0 | 0 | 0 | 0 | 0 |
| TIMP1 | 136 | 175 | 196 | 226 | 252 | 299 | 339 | 403 |

TABLE 31

Parameters derived from cancer datasets set for naive Bayes classifiers

| | | Pancreatic Cancer | | NSCLC | | Mesothelioma | |
|---|---|---|---|---|---|---|---|
| | | Control | Cancer | Control | Cancer | Control | Cancer |
| ACY1 | Mean | 9.90 | 10.41 | 9.70 | 9.43 | 9.29 | 8.67 |
| | SD | 0.63 | 0.92 | 0.45 | 0.46 | 0.57 | 0.65 |
| APOA1 | Mean | 9.70 | 9.48 | 8.77 | 8.65 | 9.22 | 8.97 |
| | SD | 0.17 | 0.30 | 0.21 | 0.23 | 0.13 | 0.24 |
| C5 | Mean | 9.49 | 9.60 | 10.13 | 10.20 | 10.05 | 10.19 |
| | SD | 0.12 | 0.14 | 0.12 | 0.14 | 0.11 | 0.16 |
| CCL23 | Mean | 7.91 | 8.10 | 7.38 | 7.45 | 6.76 | 6.97 |
| | SD | 0.23 | 0.27 | 0.15 | 0.20 | 0.08 | 0.23 |
| CDK5-CDK5R1 | Mean | 6.94 | 6.99 | 6.85 | 6.93 | 6.72 | 6.88 |
| | SD | 0.11 | 0.11 | 0.12 | 0.15 | 0.11 | 0.12 |

TABLE 31-continued

Parameters derived from cancer datasets set for naive Bayes classifiers

| | | Pancreatic Cancer | | NSCLC | | Mesothelioma | |
|---|---|---|---|---|---|---|---|
| | | Control | Cancer | Control | Cancer | Control | Cancer |
| CKB-CKM | Mean | 7.51 | 7.02 | 7.45 | 7.06 | 8.25 | 7.41 |
| | SD | 0.65 | 0.48 | 0.49 | 0.49 | 0.61 | 0.49 |
| IL12A-IL12B | Mean | 7.31 | 7.27 | 8.86 | 8.80 | 7.76 | 7.71 |
| | SD | 0.05 | 0.06 | 0.11 | 0.13 | 0.05 | 0.07 |
| KIT | Mean | 9.77 | 9.62 | 8.67 | 8.46 | 8.62 | 8.34 |
| | SD | 0.29 | 0.32 | 0.22 | 0.27 | 0.22 | 0.17 |
| LBP | Mean | 9.10 | 9.49 | 8.32 | 8.47 | 9.19 | 9.51 |
| | SD | 0.44 | 0.55 | 0.32 | 0.50 | 0.26 | 0.68 |
| SERPINF2 | Mean | 9.26 | 9.18 | 8.97 | 8.85 | 8.80 | 8.67 |
| | SD | 0.12 | 0.16 | 0.21 | 0.19 | 0.21 | 0.26 |

TABLE 32

Calculations derived from training set for naïve Bayes classifier.

| Biomarker | $\mu_c$ | $\mu_d$ | $\sigma_c$ | $\sigma_d$ | $\tilde{x}$ | $p(c|\tilde{x})$ | $p(d|\tilde{x})$ | $\ln(p(d|\tilde{x})/p(c|\tilde{x}))$ |
|---|---|---|---|---|---|---|---|---|
| KIT | 8.671 | 8.462 | 0.222 | 0.270 | 8.763 | 1.652 | 0.794 | −0.732 |
| SERPINF2 | 8.971 | 8.852 | 0.208 | 0.194 | 9.085 | 1.649 | 0.998 | −0.503 |
| CCL23 | 7.382 | 7.452 | 0.146 | 0.204 | 7.327 | 2.539 | 1.626 | −0.445 |
| IL12A-IL12B | 8.857 | 8.798 | 0.115 | 0.131 | 8.863 | 3.478 | 2.691 | −0.257 |
| CDK5-CDK5R1 | 6.852 | 6.931 | 0.122 | 0.149 | 6.688 | 1.321 | 0.712 | −0.618 |
| ACY1 | 9.701 | 9.435 | 0.449 | 0.459 | 9.526 | 0.823 | 0.853 | 0.035 |
| APOA1 | 8.772 | 8.648 | 0.210 | 0.230 | 8.805 | 1.875 | 1.378 | −0.308 |
| CKB-CKM | 7.449 | 7.062 | 0.495 | 0.487 | 7.742 | 0.676 | 0.309 | −0.782 |
| LBP | 8.322 | 8.472 | 0.317 | 0.504 | 8.215 | 1.187 | 0.695 | −0.536 |
| C5 | 10.127 | 10.201 | 0.123 | 0.144 | 10.086 | 3.077 | 2.017 | −0.422 |

What is claimed is:

1. A method for detecting protein levels of a set of proteins in a human, the method comprising:
contacting a biological sample from the human with a set of N capture reagents,
wherein each capture reagent specifically binds to a different protein of a set of N proteins, wherein N=4 to 65, and wherein the set of proteins comprises at least HAMP, CTSB, THBS4, CCL23, and measuring the level of each protein of the set of proteins based on measurement of the capture reagents;
wherein, the biological sample is selected from the group consisting of whole blood, plasma, and serum, and wherein the measuring of the capture reagents is performed with a capture reagent-based assay; and
analyzing the level of each protein measured with an algorithm to determine risk of pancreatic cancer in the human.

2. The method of claim 1, wherein the set of proteins, in addition to HAMP, CTSB, THBS4 and CCL23, comprises one or more proteins selected from the group consisting of C5, MMP-7, C2, CRP, PSA-ACT and GDF-11.

3. The method of claim 1, wherein the human is high risk for pancreatic cancer due to smoking, alcohol consumption or family history of pancreatic cancer.

4. The method of claim 1, wherein the capture reagent is selected from the group consisting of an aptamer and an antibody.

5. The method of claim 1, wherein the capture reagent is an aptamer.

6. The method of claim 1, wherein the capture reagent-based assay is an aptamer-based assay.

7. The method of claim 1, wherein said analyzing the level of each protein measured with an algorithm comprises application of a classification algorithm.

8. The method of claim 1, wherein said analyzing the level of each protein measured with an algorithm comprises application of a naïve Bayes classification.

* * * * *